(12) United States Patent
Fairhurst et al.

(10) Patent No.: US 8,318,750 B2
(45) Date of Patent: Nov. 27, 2012

(54) ORGANIC COMPOUNDS

(75) Inventors: Robin Alec Fairhurst, Horsham (GB);
Roger John Taylor, Horsham (GB);
Brian Cox, Horsham (GB)

(73) Assignee: Novartis AG, Basel (NL)

( * ) Notice: Subject to any disclaimer, the term of this patent is extended or adjusted under 35 U.S.C. 154(b) by 0 days.

(21) Appl. No.: 13/218,865

(22) Filed: Aug. 26, 2011

(65) Prior Publication Data

US 2012/0004212 A1 Jan. 5, 2012

Related U.S. Application Data

(63) Continuation of application No. 12/297,291, filed as application No. PCT/EP2007/003435 on Apr. 19, 2007.

(30) Foreign Application Priority Data

Apr. 21, 2006 (GB) .................................. 0607947.9
Jan. 31, 2007 (EP) .................................. 07101483

(51) Int. Cl.
*C07D 473/16* (2006.01)
*A61K 31/52* (2006.01)
*C07D 401/14* (2006.01)
*C07D 233/64* (2006.01)
*C07D 473/40* (2006.01)
*C07D 413/12* (2006.01)
*A61P 11/06* (2006.01)
*A61P 11/08* (2006.01)
*A61P 11/00* (2006.01)
*A61P 27/02* (2006.01)

(52) U.S. Cl. .................. 514/263.22; 514/46; 514/234.2; 514/252.16; 514/263.21; 514/263.2; 514/263.24; 514/263.4; 544/118; 544/277; 546/187; 546/279.1; 546/309; 548/518; 548/334.1; 548/248

(58) Field of Classification Search .................... 514/46, 514/234.2, 252.16, 263.21, 263.2, 263.22, 514/263.24, 263.4; 544/118, 277; 536/27.22, 536/27.62
See application file for complete search history.

(56) References Cited

U.S. PATENT DOCUMENTS

| | | | |
|---|---|---|---|
| 4,008,125 A | 2/1977 | Kurozumi et al. | |
| 4,738,954 A | 4/1988 | Hamilton et al. | |
| 4,873,360 A | 10/1989 | Johnson et al. | |
| 4,954,504 A | 9/1990 | Chen et al. | |
| 5,688,774 A | 11/1997 | Jacobson et al. | |
| 6,307,054 B1 | 10/2001 | Truesdale et al. | |
| 6,376,472 B1 | 4/2002 | Myers et al. | |
| 6,403,567 B1 | 6/2002 | Zablocki et al. | |
| 6,429,315 B1 | 8/2002 | Sledeski et al. | |
| 6,492,348 B1 | 12/2002 | Bays et al. | |
| 6,559,313 B2 | 5/2003 | Myers et al. | |
| 6,677,316 B2 | 1/2004 | Bays et al. | |
| 7,553,823 B2 | 6/2009 | Zablocki et al. | |
| 7,737,126 B2 | 6/2010 | Blatcher et al. | |
| 2003/0092668 A1 | 5/2003 | Liang et al. | |
| 2003/0176390 A1 | 9/2003 | Herling et al. | |
| 2004/0106572 A1 | 6/2004 | Fishman et al. | |
| 2004/0162422 A1 | 8/2004 | Hall et al. | |
| 2005/0101551 A1 | 5/2005 | Sevillano et al. | |
| 2005/0182018 A1 | 8/2005 | Linden et al. | |
| 2006/0142237 A1 | 6/2006 | Fishman et al. | |
| 2006/0189636 A1 | 8/2006 | Critchley et al. | |
| 2007/0099865 A1 | 5/2007 | Fishman et al. | |
| 2007/0191293 A1 | 8/2007 | Langston et al. | |
| 2007/0232626 A1 | 10/2007 | Jacobson et al. | |
| 2008/0027022 A1 | 1/2008 | Linden et al. | |
| 2008/0051364 A1 | 2/2008 | Fishman et al. | |
| 2008/0051404 A1 | 2/2008 | Claiborne et al. | |
| 2008/0200483 A1 | 8/2008 | Fairhurst et al. | |
| 2008/0207648 A1 | 8/2008 | Fairhurst et al. | |
| 2008/0214581 A1 | 9/2008 | Allen et al. | |
| 2008/0242683 A1 | 10/2008 | Fairhurst et al. | |
| 2008/0262001 A1 | 10/2008 | Kranenburg et al. | |
| 2008/0300213 A1 | 12/2008 | Fishman | |
| 2008/0312160 A1 | 12/2008 | Guerrant et al. | |

(Continued)

FOREIGN PATENT DOCUMENTS

EP 0 267 878 A1 5/1988

(Continued)

OTHER PUBLICATIONS

Baraldi et al., "Recent improvements in the field of A3 adenosine receptor ligands", Expert Opinion on Therapeutic Patents, vol. 15, No. 11 (2005), pp. 1507-1519.

(Continued)

*Primary Examiner* — Mark Berch

(74) *Attorney, Agent, or Firm* — Paul D. Strain, Esq.; Strain & Strain PLLC

(57) ABSTRACT

A compound of formula (I) or stereoisomers or pharmaceutically acceptable salts thereof, and their preparation and use as pharmaceuticals

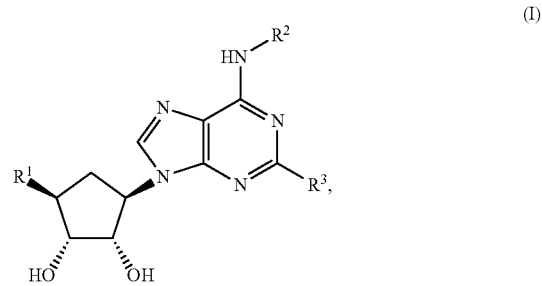

(I)

wherein $R^1$, $R^2$ and $R^3$ are as defined herein.

11 Claims, No Drawings

U.S. PATENT DOCUMENTS

| | | | |
|---|---|---|---|
| 2009/0012035 A1 | 1/2009 | Jacobson et al. | |
| 2009/0054476 A1 | 2/2009 | Goblyos et al. | |
| 2009/0081764 A1 | 3/2009 | Pausch et al. | |
| 2009/0093633 A1 | 4/2009 | Fairhurst et al. | |
| 2009/0099214 A1 | 4/2009 | Fairhurst et al. | |
| 2009/0105476 A1 | 4/2009 | Fairhurst et al. | |
| 2009/0123510 A1 | 5/2009 | Cronstein et al. | |
| 2009/0181920 A1 | 7/2009 | Watkins et al. | |
| 2009/0181934 A1 | 7/2009 | Fairhurst | |
| 2009/0240045 A1 | 9/2009 | Fairhurst et al. | |
| 2009/0281126 A1 | 11/2009 | Fairhurst et al. | |
| 2009/0281127 A1 | 11/2009 | Fairhurst et al. | |
| 2009/0325967 A1 | 12/2009 | Fairhurst et al. | |
| 2010/0041918 A1 | 2/2010 | Laumen | |
| 2010/0190784 A1 | 7/2010 | Fairhurst et al. | |
| 2010/0197914 A1 | 8/2010 | Fairhurst et al. | |
| 2010/0240680 A1 | 9/2010 | Fairhurst et al. | |
| 2010/0286126 A1 | 11/2010 | Fairhurst et al. | |
| 2012/0004247 A1* | 1/2012 | Fairhurst et al. | 514/263.22 |

FOREIGN PATENT DOCUMENTS

| | | |
|---|---|---|
| JP | 63-219387 | 9/1988 |
| WO | WO 92/05177 A1 | 4/1992 |
| WO | WO 93/22328 A1 | 11/1993 |
| WO | WO 98/50047 A1 | 11/1998 |
| WO | WO 99/67263 A1 | 12/1999 |
| WO | WO 99/67265 A1 | 12/1999 |
| WO | WO 99/67266 A1 | 12/1999 |
| WO | WO 00/23457 A1 | 4/2000 |
| WO | WO 00/78774 A2 | 12/2000 |
| WO | WO 00/78779 A2 | 12/2000 |
| WO | WO 01/60835 A1 | 8/2001 |
| WO | WO 02/22630 A1 | 3/2002 |
| WO | WO 02/055085 A2 | 7/2002 |
| WO | WO 02/070534 A1 | 9/2002 |
| WO | WO 03/029264 A2 | 4/2003 |
| WO | WO 03/086408 A1 | 10/2003 |
| WO | WO 2005/063246 A1 | 7/2005 |
| WO | WO 2005/084653 A2 | 9/2005 |
| WO | WO 2005/107463 A1 | 11/2005 |
| WO | WO 2005/116037 A1 | 12/2005 |
| WO | WO 2006/011130 A1 | 2/2006 |
| WO | WO 2006/045552 A1 | 5/2006 |
| WO | WO 2006/074925 A1 | 7/2006 |
| WO | WO 2006/097260 A1 | 9/2006 |
| WO | WO 2007/121917 A2 | 11/2007 |
| WO | WO 2007/121919 A1 | 11/2007 |
| WO | WO 2007/121920 A2 | 11/2007 |
| WO | WO 2007/121921 A2 | 11/2007 |
| WO | WO 2007/121923 A1 | 11/2007 |
| WO | WO 2007/121924 A2 | 11/2007 |
| WO | WO 2007/147659 A1 | 12/2007 |
| WO | WO 2008/006563 A1 | 1/2008 |

OTHER PUBLICATIONS

Barnard et al., "Inhibition of measles virus replication by 5'-nor carbocyclic adenosine analogues", Antiviral Chemistry & Chemotherapy, vol. 12, No. 4 (2001), pp. 241-250.

Bressi et al., "Adenosine Analogues as Inhibitors of Trypanosoma brucei Phosphoglycerate Kinase: Elucidation of a Novel Binding Mode for a 2-Amino-N6-Substituted Adenosine", Journal of Medicinal Chemistry, vol. 43, No. 22 (2000), pp. 4135-4150.

Broadley et al., "Drugs Modulating Adenosine Receptors as Potential Therapeutic Agents for Cardiovascular Diseases", Expert Opinion on Therapeutic Patents, vol. 10, No. 11 (2000), pp. 1669-1692.

Cowart et al., "Synthesis of Novel Carbocyclic Adenosine Analogues as Inhibitors of Adenosine Kinase", J. Org. Chem., vol. 64, No. 7 (1999), pp. 2240-2249.

Curran et al., "The Preparation of Optically Active 2, Cyclopenten-1,4-Diol Derivatives from Furfuryl Alcohol", Tetrahedron, vol. 53, No. 6 (1997), pp. 1983-2004.

Duhamel et al., "Acylation Enatioselective D'un Diol, Meso: Le Cis-Cyclopenthen-2 Diol-1,4", Tetrahedron Letters, vol. 26, No. 26 (1985), pp. 3099-3102.

Edwards et al., "Nonpeptidic Inhibitors of Human Neutrophil Elastase. 7. Design, Synthesis, and in Vitro Activity of a Series of Pyridopyrimidine Trifluoromethyl Ketones", J. Med. Chem., vol. 39 (1996), pp. 1112-1124.

Fairhurst et al., U.S. PTO Office Action, U.S. Appl. No. 12/297,727, Oct. 4, 2010, 13 pgs.

Fairhurst, U.S. PTO Notice of Allowance, U.S. Appl. No. 11/576,607, Jun. 9, 2011, 7 pgs.

Fairhurst, U.S. PTO Notice of Allowance, U.S. Appl. No. 11/722,835, May 27, 2011, 7 pgs.

Fairhurst, U.S. PTO Office Action, U.S. Appl. No. 11/576,607, Jan. 11, 2010, 39 pgs.

Fairhurst, U.S. PTO Office Action, U.S. Appl. No. 11/576,607, Feb. 17, 2011, 12 pgs.

Fairhurst, U.S. PTO Office Action, U.S. Appl. No. 11/576,607, Jul. 16, 2010, 40 pgs.

Fairhurst, U.S. PTO Office Action, U.S. Appl. No. 11/576,607, Dec. 23, 2009, 43 pgs.

Fairhurst, U.S. PTO Office Action, U.S. Appl. No. 11/722,835, Jan. 3, 2011, 12 pgs.

Fairhurst, U.S. PTO Office Action, U.S. Appl. No. 11/722,835, Jul. 16, 2010, 32 pgs.

Fairhurst, U.S. PTO Office Action, U.S. Appl. No. 11/722,835, Dec. 22, 2009, 37 pgs.

Fairhurst, U.S. PTO Office Action, U.S. Appl. No. 12/296,714, Jan. 3, 2011, 16 pgs.

Fairhurst, U.S. PTO Office Action, U.S. Appl. No. 12/296,714, Jan. 5, 2010, 4 pgs.

Fairhurst, U.S. PTO Office Action, U.S. Appl. No. 12/296,714, Apr. 28, 2011, 7 pgs.

Fairhurst, U.S. PTO Office Action, U.S. Appl. No. 12/296,714, May 19, 2010, 63 pgs.

Fairhurst, U.S. PTO Office Action, U.S. Appl. No. 12/296,714, Dec. 23, 2009, 12 pgs.

Fairhurst, U.S. PTO Office Action, U.S. Appl. No. 12/296,714, Dec. 30, 2009, 10 pgs.

Fairhurst, U.S. PTO Office Action, U.S. Appl. No. 12/297,007, Jul. 15, 2010, 32 pgs.

Fairhurst, U.S. PTO Office Action, U.S. Appl. No. 12/297,007, Dec. 23, 2009, 11 pgs.

Fairhurst, U.S. PTO Office Action, U.S. Appl. No. 12/297,291, Mar. 21, 2011, 41 pgs.

Fairhurst, U.S. PTO Office Action, U.S. Appl. No. 12/297,291, Dec. 1, 2010, 21 pgs.

Fairhurst, U.S. PTO Office Action, U.S. Appl. No. 12/297,373, Jul. 15, 2010, 8 pgs.

Fairhurst, U.S. PTO Office Action, U.S. Appl. No. 12/297,373, Dec. 22, 2009, 8 pgs.

Fairhurst, U.S. PTO Office Action, U.S. Appl. No. 12/297,404, Jul. 15, 2010, 38 pgs.

Fairhurst, U.S. PTO Office Action, U.S. Appl. No. 12/297,404, Dec. 30, 2009, 18 pgs.

Fairhurst, U.S. PTO Office Action, U.S. Appl. No. 12/297,491, Mar. 24, 2011, 20 pgs.

Fairhurst, U.S. PTO Office Action, U.S. Appl. No. 12/297,940, Jan. 22, 2010, 15 pgs.

Fairhurst, U.S. PTO Office Action, U.S. Appl. No. 12/308,637, Feb. 24, 2011, 23 pgs.

Fairhurst, U.S. PTO Office Action, U.S. Appl. No. 12/310,254, Mar. 24, 2011, 18 pgs.

Fairhurst, U.S. PTO Office Action, U.S. Appl. No. 12/679,663, Feb. 28, 2011, 21 pgs.

Fairhurst, U.S. PTO Restriction Requirement, U.S. Appl. No. 12/247,764, Jul. 15, 2011, 14 pgs.

Fairhurst, U.S. PTO Supplemental Notice of Allowance, U.S. Appl. No. 11/576,607, Jun. 15, 2011, 3 pgs.

Fourie et al., "Percutaneous delivery of carbamazepine and selected N-alkyl and N-hydroxyalkyl analogues", International Journal of Pharmaceutics, vol. 279, Issues 1-2 (2004), pp. 59-66.

Galkina et al., "Studies on an Oixdative, 1,4-Addition to s-trans-1,3-Dienes, a Key Reaction in a Strigol Total Synthesis", Eur. J. Org. Chem., (2003), pp. 4640-4653.

Ghosh et al. "Synthesis of Enantiomerically Pure 5'-Aza Noraristeromycin Analogs", J. Org. Chem., vol. 60, No. 18 (1995), pp. 5808-5813.

Ghosh et al., "Synthesis and Biological Evaluation of a Carbocyclic Azanoraristeromycin Siderophore Conjugate", Nucleosides & Nucleotides, vol. 18, No. 2 (1999), pp. 217-225.

Goosen et al., "Physicochemical Characterization and Solubility Analysis of Thalidomide and Its N-Alkyl Analogs", Pharmaceutical Research, vol. 19, No. 1 (2002), pp. 13-19.

Hegde et al., "5'-Amino-5'-deoxy-5'-noraristeromycin", Chemical Abstracts Index entry for Journal of Organic Chemistry, vol. 63, No. 20 (1998), pp. 7092-7094.

Hegde et al., "5'-Amino-5'-deoxy-5'noraristeromycin", J. Org. Chem., vol. 63, No. 20 (1998), pp. 7092-7094.

International Search Report, PCT/EP2007/006156, Oct. 12, 2007, 3 pgs.

International Search Report, PCT/EP2007/059666, Jan. 18, 2008, 3 pgs.

International Search Report, PCT/EP2008/063869, Jul. 21, 2009, 7 pgs.

Kerns et al., "Drug-like Properties: Concepts, Structure Design and Methods: from ADME to Toxicity Optimization", Elsevier (2008), pp. 92-93.

Kikugawa et al., "Platelet Aggregation Inhibitors. 6. 12-Thioadenosine Derivatives", Journal of Medicinal Chemistry, vol. 16, No. 12 (1973), pp. 1381-1388.

Laumen, U.S. PTO Office Action, U.S. Appl. No. 12/312,311, Aug. 9, 2011, 20 pgs.

Marlene A Jacobsen, "Adenosine receptor agonists", Expert Opinion Therapeutic Targets, vol. 12, No. 4 (2002), pp. 489-501.

Marumoto et al., "Synthesis and Coronary Vasodilating Activity of 2-Substituted Adenosines", Chemical and Pharmaceutical Bulletin, vol. 23, No. 4 (1975), pp. 759-774.

Oriyama et al., "Catalytic Asymmetrization of CIS-2-Cyclopentene-1,4-Diol. Highly Efficient and Practical Synthesis . . . ", Heterocycles, vol. 52, No. 3 (2000), pp. 1055-1069.

Palle et al., "Structure-Affinity Relationships of the Affinity of 2-Pyrazolyl Adenosine Analogues for the Adenosine A2A Receptor", Bioorganic & Medicinal Chemistry Letters, vol. 12, No. 20 (2002), pp. 2935-2939.

Rautio et al., "Piperazinylalkyl prodrugs of naproxen improve in vitro skin permeation", European Journal of Pharmaceutical Sciences, vol. 11 (2000), pp. 157-163.

Siddiqi et al., "Enantiospecific Synthesis of the Fluoro and Epimeric Derivatives of 5'-Noraristeromycin", J. Chem. Soc., Chem. Commun., 1993, pp. 708-709.

Silverman J, Rheumatol, vol. 35, No. 4 (2008), pp. 1-8.

Terashima et al., "Novel Use of Meso-Compound for the Preparation of Optically Active Compounds . . . ", Tetrahedron Letters, vol. 11 (1977), pp. 1001-1004.

Wanner et al., "Synthesis and properties of 2-nitrosoadenosine", J. Chem. Soc., Perkin Trans., vol. 1 (2001), pp. 1908-1915.

Yang et al., "Amino substituted derivatives of 5'-amino-5'-deoxy-5'-noraristeromycin", Bioorganic & Medicinal Chemistry, vol. 13, No. 3 (2005), pp. 877-882.

Fairhurst, U.S. Notice of Allowance, U.S. Appl. No. 12/297,291, Jul. 14, 2011, 9 pgs.

Pending U.S. Appl. No. 13/218,887, Robin Alec Fairhurst et al., filed Aug. 26, 2011.

Fairhurst, U.S. PTO Notice of Allowance, U.S. Appl. No. 11/722,835, Oct. 21, 2011, 10 pgs.

Fairhurst, U.S. PTO Notice of Allowance, U.S. Appl. No. 12/308,637, Sep. 26, 2011, 13 pgs.

Fairhurst, U.S. PTO Office Action, U.S. Appl. No. 12/297,491, Oct. 12, 2011, 11 pgs.

Fairhurst, U.S. PTO Office Action, U.S. Appl. No. 12/310,254, Oct. 12, 2011, 11 pgs.

Fairhurst, U.S. PTO Office Action, U.S. Appl. No. 12/247,764, Oct. 26, 2011, 17 pgs.

"Clinical Data, Inc. Reports Results of Phase I Studies of Stedivaze(TM) Demonstrating Safety and Tolerability in Patients with Asthma and COPD", http://www.lifescience-online.com/ClinicaLData_Inc_Reports_Results_of_Phase_Studies_of_Stedivaze . . . , downloaded Jan. 25, 2012, 3 pgs.

"Lexiscan(R) (Regadenoson) Injection Study in Subjects With Asthma or Chronic Obstructive Pulmonary Disease (COPD) Presented as Late-Breaker at American Society of Nuclear Cardiology 2010", Astellas Leading Light for Life (Sep. 25, 2010), http://www.astellas.us/docs/us/FINAL_LEXISCAN_INJECTION_STUDY_IN_SUBJECTS_WITH_ASTHMA_OR_COPD_20100925, 3 pgs.

Fairhurst, U.S. Notice of Allowance, U.S. Appl. No. 12/297,291, Nov. 10, 2011, 9 pgs.

Fairhurst, U.S. Notice of Allowance, U.S. Appl. No. 12/297,291, May 7, 2012, 17 pgs.

Fairhurst, U.S. PTO Notice of Allowance, U.S. Appl. No. 11/576,607, Nov. 14, 2011, 9 pgs.

Fairhurst, U.S. PTO Notice of Allowance, U.S. Appl. No. 12/297,491, Feb. 1, 2012, 7 pgs.

Fairhurst, U.S. PTO Notice of Allowance, U.S. Appl. No. 12/310,254, Feb. 2, 2012, 7 pgs.

Fairhurst, U.S. PTO Office Action, U.S. Appl. No. 12/297,291, Apr. 17, 2012, 47 pgs.

Fairhurst, U.S. PTO Office Action, U.S. Appl. No. 13/218,887, Feb. 1, 2012, 21 pgs.

Fairhurst, U.S.PTO Advisory Action, U.S. Appl. No. 12/297,491, Jan. 18, 2012, 15 pgs.

Fairhurst, U.S.PTO Advisory Action, U.S. Appl. No. 12/310,254, Jan. 18, 2012, 10 pgs.

Gao et al., "Emerging adenosine receptor agonists—an update", Expert Opinion, Emerging Drugs, vol. 16, No. 4 (2011), pp. 597-602.

Luijk et al., "[Poster: K64] The Effects of the Adenosine A2a Agonist UK-432,097 on Lung Function and AMP Airway Hyperresponsiveness in Mild Asthmatic Patients", (2005) http://www.mindcull.com/data/american-thoracic-society/ats-2005-american-thoracic-society/poster-k64-the-effects-of-the-adenosine-a2a-agonist-uk-432-097-on-lung-function-and-amp-airway-hyperresponsiveness-in-mild-asthmatic-patients/# downloaded Jan. 25, 2012.

Luijk et al., "Effect of an inhaled adenosine A2A agonist on the allergen-induced late asthmatic response", Allergy, vol. 63 (2008), pp. 75-80.

Murray et al., "Safety of Binodenoson, a Selective Adenosine A2A Receptor Agonist Vasodilator Pharmacological Stress Agent, in Healthy Subjects With Mild Intermittent Asthma", Circulation Cardiovascular Imaging, vol. 2 (2009), pp. 492-498.

* cited by examiner

ORGANIC COMPOUNDS

CROSS-REFERENCE TO RELATED PATENT APPLICATIONS

This application is a Continuation of U.S. application Ser. No. 12/297,291, filed Oct. 15, 2008, which is the National Stage of International Application No. PCT/EP2007/003435, filed Apr. 19, 2007, which is based upon and claims the benefit of priority from prior European Patent Application No. 07101483.1, filed Jan. 31, 2007 and United Kingdom Patent Application No. 0607947.9, filed Apr. 21, 2006, the entire contents of all of which are incorporated herein by reference in their entirety.

This invention relates to organic compounds, their preparation and use as pharmaceuticals.

An aspect of the present invention provides compounds of formula (I) or stereoisomers or pharmaceutically acceptable salts thereof,

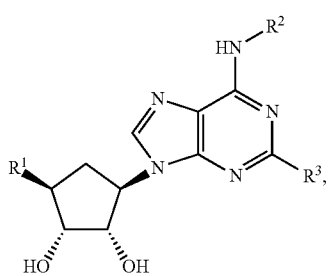

(I)

wherein
$R^1$ is selected from NH—$C_1$-$C_8$-alkyl, NHC(O)$C_1$-$C_8$ hydroxyalkyl, NHC(O)$C_1$-$C_8$ aminoalkyl, NHCO$_2$$C_1$-$C_8$-alkyl, NHCO$_2$$C_2$-$C_8$ hydroxyalkyl, NHC(O)-3- to 12-membered heterocyclic group containing from 1 to 4 heteroatoms selected from the group consisting of oxygen, nitrogen and sulfur, that group being optionally substituted, by $C_1$-$C_8$-alkyl, NHC(O)—$C_6$-$C_{10}$-aryl optionally substituted by $C_1$-$C_8$-alkyl or O—$C_1$-$C_8$-alkyl, NH—$C_1$-$C_8$-alkoxycarbonyl optionally substituted by $C_6$-$C_{10}$-aryl, and NHC(O)—$C_1$-$C_8$-alkyl optionally substituted by halo, OH, $C_1$-$C_8$-alkyl, COOH or $C_1$-$C_8$-alkoxycarbonyl;

$R^2$ is $C_1$-$C_8$-alkyl substituted by OH, halogen $C_6$-$C_{10}$-aryl optionally substituted by OH, $SO_2R^{10}$, $SC_1$-$C_8$-alkyl, CN, halogen, O—$C_7$-$C_{14}$-aralkyl, or O—$C_1$-$C_8$-alkyl, a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, $C_2$-$C_8$-alkenyl, $C_2$-$C_8$-alkynyl or $C_1$-$C_8$-alkyl, O—$C_1$-$C_8$-alkyl, —$SO_2$—$C_1$-$C_8$-alkyl, a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur, $C_7$-$C_{14}$ aralkyl, or $C_6$-$C_{14}$-aryl optionally substituted by O—$C_7$-$C_{14}$ aralkyl, or $R^2$ is a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, or $C_1$-$C_8$-alkyl, or $R^2$ is a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur, $C_7$-$C_{14}$ aralkyl, or $C_6$-$C_{14}$-aryl optionally substituted by O—$C_7$-$C_{14}$ aralkyl;

$R^3$ is hydrogen, halo, $C_2$-$C_8$-alkenyl, $C_2$-$C_8$-alkynyl or $C_1$-$C_8$-alkoxycarbonyl, or $R^3$ is amino optionally substituted by $C_3$-$C_8$-cycloalkyl optionally substituted by amino, hydroxy, $C_7$-$C_{14}$-aralkyloxy, —$SO_2$—$C_6$-$C_{10}$-aryl or —NH—C(=O)—NH—$R^{3c}$, or $R^3$ is amino substituted by $R^{3a}$, —$R^{3a}$—$C_7$-$C_{14}$-aralkyl or a $C_5$-$C_{15}$-carbocyclic group optionally substituted by OH, $C_1$-$C_8$-alkyl or $C_1$-$C_8$-alkoxycarbonyl, or $R^3$ is aminocarbonyl optionally substituted by $R^{3b}$, or $R^3$ is $C_1$-$C_8$-alkylamino optionally substituted by OH, $R^{3b}$, amino, di($C_1$-$C_8$-alkyl)amino, —NH—C(=O)—$C_1$-$C_8$-alkyl, —NH—$SO_2$—$C_1$-$C_8$-alkyl, —NH—C(=O)—NH—$R^{3c}$, —NH—C(=O)—NH—$C_1$-$C_8$-alkyl-$R^{3b}$, a $C_5$-$C_{15}$-carbocyclic group or by $C_6$-$C_{10}$-aryl optionally substituted by $C_6$-$C_{10}$-aryloxy, or $R^3$ is $C_1$-$C_8$-alkylaminocarbonyl or $C_3$-$C_8$-cycloalkylaminocarbonyl optionally substituted by amino, $C_1$-$C_8$-alkylamino, di($C_1$-$C_8$-alkyl)amino or —NH—C(=O)—NH—$R^{3d}$, or $R^3$ is a 3- to 12-membered heterocyclic group containing from 1 to 4 ring nitrogen atoms and optionally containing from 1 to 4 other heteroatoms selected from the group consisting of oxygen and sulfur, that group being optionally substituted by 0-3$R^4$;

$R^{3a}$ and $R^{3b}$ are each independently a 3- to 12-membered heterocyclic group containing at least one ring heteroatom selected from the group consisting of nitrogen, oxygen and sulfur; optionally substituted by halo, cyano, oxo, OH, carboxy, nitro, $C_1$-$C_8$-alkyl, $C_1$-$C_8$-alkylcarbonyl, OH—$C_1$-$C_8$-alkyl, $C_1$-$C_8$-haloalkyl, amino-$C_1$-$C_8$-alkyl, amino(OH)$C_1$-$C_8$-alkyl and $C_1$-$C_8$-alkoxy optionally substituted by aminocarbonyl;

$R^{3c}$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur;

$R^{3d}$ are independently a 5- or 6-membered heterocyclic ring containing at least one ring heteroatom selected from the group consisting of nitrogen, oxygen and sulfur, said 5- or 6-membered heterocyclic ring being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl, or a 5- or 6-membered heterocyclic ring containing at least one ring heteroatom selected from the group consisting of nitrogen, oxygen and sulfur, said ring also being optionally substituted by halo, cyano, oxo, OH, carboxy, amino, nitro, $C_1$-$C_8$-alkyl, $C_1$-$C_8$-alkylsulfonyl, aminocarbonyl, $C_1$-$C_8$-alkylcarbonyl, $C_1$-$C_8$-alkoxy optionally substituted by aminocarbonyl;

$R^4$ is selected from OH, $C_1$-$C_8$-alkyl optionally substituted by OH, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl or -halogen, O—$C_6$-$C_{10}$-aryl optionally substituted by OH, $C_1$-$C_8$-alkyl, O—$C_1$-$C_8$-alkyl or -halogen, $NR^{4a}R^{4b}$, NHC(O)

$R^{4c}$, NHS(O)$_2$R$^{4d}$, NHS(O)$_2$R$^{4e}$, NR$^{4f}$C(O)NR$^{4e}$R$^{4h}$, NR$^{4f}$C(O)OR$^{4g}$R$^{4h}$, NR$^{4i}$C(O)OR$_4j$, C$_1$-C$_8$-alkylcarbonyl, C$_1$-C$_8$-alkoxycarbonyl, di(C$_1$-C$_8$-alkyl)aminocarbonyl, COOR$^{4k}$, C(O)R$^{4l}$, NHC(O)R$^{4q}$, NHC(=NR$^{4m}$)N(R$^{4n}$) R$^{4o}$, and a 3- to 12-membered heterocyclic group containing at least one ring heteroatom selected from the group consisting of nitrogen, oxygen and sulfur optionally substituted by COOR$^{4p}$;

R$^{4a}$, R$^{4c}$, R$^{4f}$, R$^{4h}$ and R$^{4i}$ are, independently, H, or C$_1$-C$_8$-alkyl;

R$^{4b}$ is H, C$_1$-C$_8$-alkyl a 3- to 12-membered heterocyclic group containing at least one ring heteroatom selected from the group consisting of nitrogen, oxygen and sulfur, optionally substituted by 0-3R$^5$ or C$_6$-C$_{10}$-aryl;

R$^{4d}$, and R$^{4e}$, R$^{4j}$ are, independently, C$_1$-C$_8$-alkyl or a 3- to 12-membered heterocyclic group containing at least one ring heteroatom selected from the group consisting of nitrogen, oxygen and sulfur, optionally substituted by 0-3R$^5$;

R$^{4g}$ is C$_1$-C$_8$-alkyl optionally substituted by a 3- to 12-membered heterocyclic group containing at least one ring heteroatom selected from the group consisting of nitrogen, oxygen and sulfur, optionally substituted with SO$_2$R$^{10}$, CN, or 0-3R$^5$, or R$^{4g}$ is a C$_6$-C$_{10}$-aryl optionally substituted by OH, C$_1$-C$_8$-alkyl, O—C$_1$-C$_8$-alkyl, SO$_2$R$^{10}$ or -halogen, or R$^{4g}$ is a C$_7$-C$_{14}$-aralkyl optionally substituted by OH, O—C$_1$-C$_8$-alkyl, halogen, C$_6$-C$_{10}$-aryl, SO$_2$R$^{10}$, CN, —C(=NH)NH2, or O—C$_6$-C$_{10}$-aryl, or R$^{4g}$ is a 3- to 12-membered heterocyclic group containing at least one ring heteroatom selected from the group consisting of nitrogen, oxygen and sulfur, optionally substituted by 0-3R$^5$;

R$^{4k}$ is H, C$_1$-C$_8$-alkyl, C$_6$-C$_{10}$-aryl or a 3- to 12-membered heterocyclic group containing at least one ring heteroatom selected from the group consisting of nitrogen, oxygen and sulfur;

R$^{4l}$ is C$_1$-C$_8$-alkyl, C$_6$-C$_{10}$-aryl, NHR$^6$ or a 3- to 12-membered heterocyclic group containing at least one ring heteroatom selected from the group consisting of nitrogen, oxygen and sulfur;

R$^{4m}$ is H or CN;

R$^{4n}$ is H or C$_1$-C$_8$ alkyl;

R$^{4o}$ is H, C$_1$-C$_8$-alkyl optionally substituted by OH or by a 3- to 12-membered heterocyclic group containing at least one ring heteroatom selected from the group consisting of nitrogen, oxygen and sulfur, optionally substituted with SO$_2$R$^{10}$, CN, or 0-3R$^5$, C$_1$-C$_8$-alkoxy, C$_7$-C$_{14}$-aralkyl optionally substituted with OH, O—C$_1$-C$_8$-alkyl, halogen C$_6$-C$_{10}$-aryl, or O—C$_6$-C$_{10}$-aryl, C$_1$-C$_8$-alkoxy, C$_6$-C$_{10}$-aryl optionally substituted by OH, C$_1$-C$_8$-alkyl, O—C$_1$-C$_8$-alkyl SO$_2$R$^{10}$ or -halogen;

R$^{4p}$ is H, C$_1$-C$_8$-alkyl or C$_7$-C$_{14}$-aralkyl;

R$^{4q}$ is C$_6$-C$_{10}$-aryl optionally substituted by OH, C(=NH)NH$_2$, or SO$_2$NH$_2$, or a 3- to 12-membered heterocyclic group containing at least one ring heteroatom selected from the group consisting of nitrogen, oxygen and sulfur optionally substituted by 0-3R$^5$ or a 3- to 12-membered heterocyclic group containing at least one ring heteroatom selected from the group consisting of nitrogen, oxygen and sulfur, optionally substituted by 0-3R$^5$;

R$^5$ is selected from OH, C$_1$-C$_8$-alkyl optionally substituted by OH, CN, SO$_2$R$^{10}$ or halogen, C$_7$-C$_{14}$-aralkyl optionally substituted with OH, O—C$_1$-C$_8$-alkyl, C$_6$-C$_{10}$-aryl, or O—C$_6$-C$_{10}$-aryl, C$_1$-C$_8$-alkoxy, C$_6$-C$_{10}$-aryl optionally substituted by OH, C$_1$-C$_8$-alkyl, O—C$_1$-C$_8$-alkyl or -halogen, O—C$_6$-C$_{10}$-aryl optionally substituted by OH, C$_1$-C$_8$-alkyl, O—C$_1$-C$_8$-alkyl optionally substituted by halogen, NR$^{5a}$R$^{5b}$, NHC(O)R$^{5c}$, NHS(O)$_2$R$^{5d}$, NHS(O)$_2$R$^{5e}$, NR$^{5f}$C(O)NR$^{5g}$R$^{5h}$, NR$^{5i}$C(O)OR$^{5j}$, C$_1$-C$_8$-alkylcarbonyl, C$_1$-C$_8$-alkoxycarbonyl, di(C$_1$-C$_8$-alkyl)aminocarbonyl, COOR$^{5k}$, C(O)R$^{5l}$, a C(O)—C$_6$-C$_{10}$-aryl optionally substituted by OH, —COOH, C$_1$-C$_8$-alkyl, O—C$_1$-C$_8$-alkyl, -halogen, or SO$_2$R$^{10}$, C(O)NHR$^{5m}$ or a 3-12-membered heterocyclic group containing at least one ring heteroatom selected from the group consisting of nitrogen, oxygen and sulfur, optionally substituted by 0-3R$^7$;

R$^{5a}$, R$^{5b}$, R$^{5c}$, R$^{5f}$, R$^{5h}$ and R$^{5i}$ are, independently, H, C$_1$-C$_8$-alkyl or C$_6$-C$_{10}$-aryl;

R$^{5d}$, R$^{5e}$, R$^{5g}$, R$^{5j}$ and R$^{5m}$ are, independently, C$_1$-C$_8$-alkyl or a 3- to 12-membered heterocyclic group containing at least one ring heteroatom selected from the group consisting of nitrogen, oxygen and sulfur, optionally substituted by COOR$^8$;

R$^{5k}$ is H, C$_1$-C$_8$-alkyl, C$_6$-C$_{10}$-aryl or a 3- to 12-membered heterocyclic group containing at least one ring heteroatom selected from the group consisting of nitrogen, oxygen and sulfur;

R$^{5l}$ is C$_1$-C$_8$-alkyl, C$_6$-C$_{10}$-aryl or a 3- to 12-membered heterocyclic group containing at least one ring heteroatom selected from the group consisting of nitrogen, oxygen and sulfur, optionally substituted by COOR$^9$;

R$^6$ is COOR$^{6a}$ or a 3- to 12-membered heterocyclic group containing at least one ring heteroatom selected from the group consisting of nitrogen, oxygen and sulfur, optionally substituted by COOR$^{6b}$;

R$^{6a}$, R$^{6b}$, R$^7$, R$^8$ and R$^9$ are selected from H, C$_1$-C$_8$-alkyl and C$_7$-C$_{14}$-aralkyl; and R$^{10}$ is C$_1$-C$_8$-alkyl optionally substituted by halogen, C$_6$-C$_{10}$-aryl optionally substituted by OH, C$_1$-C$_8$-alkyl, O—C$_1$-C$_8$-alkyl or -halogen, or NR$^{4a}$R$^{4b}$.

According to formula (I) R$^1$ is suitably NHC(O)C$_1$-C$_8$ hydroxyalkyl. R$^1$ is preferably NHC(O)C$_1$-C$_2$ hydroxyalkyl (e.g. a 2-hydroxy-acetamide group, a 2-hydroxy-propionamide group, or a 3-hydroxy-propionamide group).

According to formula (I), R$^1$ is also suitably NHCO$_2$C$_1$-C$_8$-alkyl, R$^1$ is preferably NHCO$_2$CH$_3$.

According to formula (I), R$^2$ is suitably selected from C$_1$-C$_8$-alkyl optionally substituted by OH, halogen or C$_6$-C$_{10}$-aryl optionally substituted by OH or O—C$_1$-C$_8$ alkyl, preferably C$_6$-C$_{10}$-aryl is phenyl substituted by one OCH$_3$ or one OH.

According to formula (I), R$^3$ is suitably a N-bonded 3- to 12-membered heterocyclic group containing at least one ring heteroatom selected from the group consisting of nitrogen, oxygen and sulfur. This heterocyclic group is preferably a pyrrolidine, or pyrazole. The heterocyclic group is optionally substituted by NR$^{4f}$C(O)NR$^{4g}$R$^{4h}$, NR$^{4a}$R$^{4b}$, NHC(O)R$^{4q}$ and NHC(=NR$^{4m}$)N(R$^{4n}$)R$^{4o}$, where R$^{4a}$ is preferably H or C$_1$-C$_8$ alkyl (e.g. methyl) and R$^{4f}$ and R$^{4h}$ are preferably H. R$^{4b}$ is selected from H and 3- to 12-membered heterocyclic group containing at least one ring heteroatom selected from the group consisting of nitrogen, oxygen and sulfur, optionally substituted by 0-3R$^5$. R$^{4b}$ is preferably H or a 4,5 dihydro-1H imidazole.

According to formula (I), R$^{4g}$ is suitably C$_1$-C$_8$-alkyl optionally substituted by a 3- to 12-membered heterocyclic group containing at least one ring heteroatom selected from the group consisting of nitrogen, oxygen and sulfur, optionally substituted with SO$_2$R$^{10}$, CN, or 0-3R$^5$. R$^{4g}$ is preferably a methylene substituted by a pyridine where the pyridine is optionally substituted by one CN.

According to formula (I), R$^{4g}$ is also suitably C$_6$-C$_{10}$-aryl optionally substituted by OH, C$_1$-C$_8$-alkyl, O—C$_1$-C$_8$-alkyl, $SO_2R^{10}$, or -halogen, $R^{4g}$ is preferably a phenyl that is optionally substituted by one OH or one $SO_2NH_2$.

According to formula (I), $R^{4g}$ is also suitably $C_7$-$C_{14}$-aralkyl optionally substituted by OH, O—$C_1$-$C_8$-alkyl, halogen, $C_6$-$C_{10}$-aryl, $SO_2R^{10}$, CN, —C(=NH)$NH_2$, or O—$C_6$-$C_{10}$-aryl. $R^{4g}$ is preferably a benzyl group optionally substituted by one OH or one —C(=NH)$NH_2$.

According to formula (I), $R^{4g}$ is also suitably 3- to 12-membered heterocyclic group containing at least one ring heteroatom selected from the group consisting of nitrogen, oxygen and sulfur, optionally substituted by 0-3$R^5$; $R^{4g}$ is preferably a pyridine optionally substituted by CN or pyrrolidine substituted by a C(O)—$C_6$-$C_{10}$-aryl optionally substituted by OH, —COOH, $C_1$-$C_8$-alkyl, O—$C_1$-$C_8$-alkyl, -halogen, or $SO_2R^{10}$. Preferably the C(O)—$C_6$-$C_{10}$-aryl is C(O)-benzoic acid.

According to formula (I), $R^{4m}$ is CN.

According to formula (I) $R^{4n}$ is H or $C_1$-$C_8$ alkyl. Preferably, $R^{4n}$ is H.

According to formula (I), $R^{4o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with $SO_2R^{10}$, CN, or 0-3$R^5$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^{10}$ or -halogen. $R^{4o}$ is preferably a methylene substituted by an unsubstituted pyridine or phenyl optionally substituted by $SO_2NH_2$.

According to formula (I), $R^{4q}$ is suitably phenyl substituted by OH, C(=NH)$NH_2$, or $SO_2NH_2$.

According to formula (I), $R^{4q}$ is also suitably 3- to 12-membered heterocyclic group containing at least one ring heteroatom selected from the group consisting of nitrogen, oxygen and sulfur optionally substituted by a 3- to 12-membered heterocyclic group containing at least one ring heteroatom selected from the group consisting of nitrogen, oxygen and sulfur, optionally substituted by 0-3$R^5$. Preferably $R^{4q}$ is a 6 membered heterocyclic group (e.g. pyridine) substituted by a 6 membered heterocyclic group (e.g. morpholine).

Another aspect of the invention is compounds of formula Ia

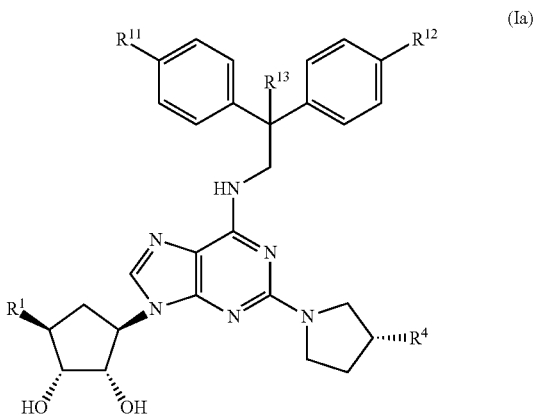

(Ia)

where
$R^1$ is NHCO$_2$$C_1$-$C_8$-alkyl or NH C(O)$C_1$-$C_8$ hydroxylalkyl;
$R^4$ is NR$^{4f}$C(O)NR$^{4g}$R$^{4h}$, NR$^{4a}$R$^{4b}$, NHC(O)R$^{4q}$ and NHC(=NR$^{4m}$)N(R$^{4n}$)R$^{4o}$;
$R^{4a}$ is selected from H and $C_1$-$C_8$ alkyl;

$R^{4b}$ is selected from H, $C_1$-$C_8$ alkyl and 3- to 12-membered heterocyclic group containing at least one ring heteroatom selected from the group consisting of nitrogen, oxygen and sulfur, optionally substituted by 0-3$R^5$;
$R^{4f}$ and $R^{4h}$ are H;
$R^{4g}$ is $C_1$-$C_8$-alkyl optionally substituted by a 3- to 12-membered heterocyclic group containing at least one ring heteroatom selected from the group consisting of nitrogen, oxygen and sulfur, optionally substituted with CN, or
$R^{4g}$ is a $C_6$-$C_{10}$-aryl optionally substituted by OH or $SO_2R^{10}$, or
$R^{4g}$ is a $C_7$-$C_{14}$-aralkyl optionally substituted by OH —C(=NH)$NH_2$, or
$R^{4g}$ is a 3- to 12-membered heterocyclic group containing at least one ring heteroatom selected from the group consisting of nitrogen, oxygen and sulfur, optionally substituted by 0-3$R^5$;
$R^{4m}$ is CN;
$R^{4n}$ is H;
$R^{4o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with $SO_2R^{10}$, a $C_7$-$C_{14}$-aralkyl optionally substituted with OH, O—$C_1$-$C_8$-alkyl, halogen, $C_6$-$C_{10}$-aryl, or O—$C_6$-$C_{10}$-aryl;
$R^{4q}$ is $C_6$-$C_{10}$-aryl optionally substituted by OH, C(=NH)$NH_2$, or $SO_2NH_2$, or a 3- to 12-membered heterocyclic group containing at least one ring heteroatom selected from the group consisting of nitrogen, oxygen and sulfur optionally substituted by a 3- to 12-membered heterocyclic group containing at least one ring heteroatom selected from the group consisting of nitrogen, oxygen and sulfur;
$R^5$ is C(O)—$C_6$-$C_{10}$-aryl optionally substituted by OH, —COOH, $C_1$-$C_8$-alkyl, O—$C_1$-$C_8$-alkyl, -halogen, or $SO_2R^{10}$;
$R^{10}$ is $NH_2$;
$R^{11}$ and $R^{12}$ are, independently, selected from H, OH, halogen and O—$C_1$-$C_8$-alkyl; and
$R^{13}$ is selected from H or OH.

An aspect of the present invention provides compounds of formula (II) or stereoisomers or pharmaceutically acceptable salts thereof,

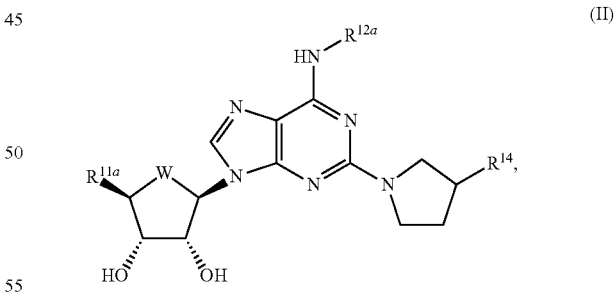

(II)

wherein
W is $CH_2$ or O, with the proviso that when W is O, then $R^{11a}$ is not a N-bonded substituent;
$R^{11a}$ is —$NH_2$, —NH—$C_1$-$C_8$-alkylcarbonyl, —NH—$C_3$-$C_8$-cycloalkylcarbonyl, —NHSO$_2$—$C_1$-$C_8$-alkyl, —NH—$C_7$-$C_{14}$-aralkylcarbonyl or —NHC(=O)—C(=O)—NH—$C_1$-$C_8$-alkyl optionally substituted by $R^{11b}$, or
$R^{11a}$ is selected from $CH_2OH$, $CH_2$—O—$C_1$-$C_8$-alkyl, C(O)—O—$C_1$-$C_8$-alkyl, C(O)$NH_2$, and C(O)—NH—$C_1$-$C_8$-alkyl;

$R^{11b}$ is a 3- to 12-membered heterocyclic ring containing at least one ring heteroatom selected from the group consisting of nitrogen, oxygen and sulfur, said 3- to 12-membered heterocyclic ring being optionally substituted by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl or $C_1$-$C_8$-alkoxy optionally substituted by aminocarbonyl;

$R^{12a}$ is $C_1$-$C_8$-alkyl substituted by OH, halogen $C_6$-$C_{10}$-aryl optionally substituted by OH, $SO_2R^{10}$, $SC_1$-$C_8$-alkyl, CN, halogen, O—$C_7$-$C_{14}$-aralkyl, or O—$C_1$-$C_8$-alkyl, a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, $C_2$-$C_8$-alkenyl, $C_2$-$C_8$-alkynyl or $C_1$-$C_8$-alkyl, O—$C_1$-$C_8$-alkyl, —$SO_2$—$C_1$-$C_8$-alkyl, a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur, $C_7$-$C_{14}$ aralkyl, or $C_6$-$C_{14}$-aryl optionally substituted by O—$C_7$-$C_{14}$ aralkyl, or $R^{12a}$ is a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, or $C_1$-$C_8$-alkyl, or $R^{12a}$ is a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur, $C_7$-$C_{14}$ aralkyl, or $C_6$-$C_{14}$-aryl optionally substituted by O—$C_7$-$C_{14}$ aralkyl;

$R^{14}$ is selected from $NR^{14a}R^{14b}$, $NR^{14f}C(O)NR^{14g}R^{14h}$, NHC(O)$R^{14q}$, and NHC(=$NR^{14m}$)N($R^{14n}$)$R^{14o}$;

$R^{14a}$, $R^{14c}$, $R^{14f}$, $R^{14h}$ and $R^{14i}$ are, independently, H, $C_1$-$C_8$-alkyl or $C_6$-$C_{10}$-aryl;

$R^{14b}$ is H, $C_1$-$C_8$-alkyl a 3- to 10-membered heterocyclic group containing at least one ring heteroatom selected from the group consisting of nitrogen, oxygen and sulfur, optionally substituted by 0-3$R^{15}$ or $C_6$-$C_{10}$-aryl;

$R^{14g}$ is $C_1$-$C_8$-alkyl optionally substituted by a 3- to 10-membered heterocyclic group containing at least one ring heteroatom selected from the group consisting of nitrogen, oxygen and sulfur, optionally substituted with $SO_2R^{16}$, CN, or 0-3$R^{15}$, or $R^{14g}$ is a $C_6$-$C_{10}$-aryl optionally substituted by OH, $C_1$-$C_8$-alkyl, O—$C_1$-$C_8$-alkyl, $SO_2R^{16}$ or -halogen, or $R^{14g}$ is a $C_7$-$C_{14}$-aralkyl optionally substituted by OH, O—$C_1$-$C_8$-alkyl, halogen, $C_6$-$C_{10}$-aryl, $SO_2R^{16}$, CN, —C(=NH)$NH_2$, or O—$C_6$-$C_{10}$-aryl, or $R^{14g}$ is a 3- to 10-membered heterocyclic group containing at least one ring heteroatom selected from the group consisting of nitrogen, oxygen and sulfur, optionally substituted by 0-3$R^{15}$;

$R^{14m}$ is CN;

$R^{14n}$ is H or $C_1$-$C_8$ alkyl;

$R^{14o}$ is H, $C_1$-$C_8$-alkyl optionally substituted by OH or by a 3- to 10-membered heterocyclic group containing at least one ring heteroatom selected from the group consisting of nitrogen, oxygen and sulfur, optionally substituted with $SO_2R^{16}$, CN, or 0-3$R^{15}$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^{16}$ or -halogen;

$R^{14p}$ is H, $C_1$-$C_8$-alkyl or $C_7$-$C_{14}$-aralkyl;

$R^{14q}$ is a 3- to 10-membered heterocyclic group containing at least one ring heteroatom selected from the group consisting of nitrogen, oxygen and sulfur optionally substituted by 0-3$R^{15}$ or a 3- to 10-membered heterocyclic group containing at least one ring heteroatom selected from the group consisting of nitrogen, oxygen and sulfur, optionally substituted by 0-3$R^{15}$;

$R^{15}$ is selected from CN, or halogen, O—$C_1$-$C_8$-alkyl optionally substituted by halogen, a C(O)—$C_6$-$C_{10}$-aryl optionally substituted by OH, —COOH, $C_1$-$C_8$-alkyl, O—$C_1$-$C_8$-alkyl, -halogen, or $SO_2R^{16}$; and $R^{16}$ is $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or -halogen, or $NR^{14a}R^{14b}$.

According to formula (II), $R^{11a}$ is suitably a 3- to 10-membered heterocyclic group containing from 1 to 4 ring nitrogen atoms and optionally containing from 1 to 4 other heteroatoms selected from the group consisting of oxygen and sulfur, that group being optionally substituted by oxo, $C_1$-$C_8$-alkoxy, $C_6$-$C_{10}$-aryl, $R^{11b}$ or by $C_1$-$C_8$-alkyl optionally substituted by hydroxyl. $R^{11a}$ is preferably tetrazole substituted by an ethyl group or a triazole substituted by an ethanol group.

According to formula (II), $R^{11a}$ is also suitably —NH—$C_1$-$C_8$-alkylcarbonyl or —NH—$C_3$-$C_8$-cycloalkylcarbonyl. The —NH—$C_1$-$C_8$-alkylcarbonyl group is preferably a acetamide group or a propionamide group. The —NH—$C_3$-$C_8$-cycloalkylcarbonyl is preferably a cyclobutane carboxylic acid amide group.

According to formula (II), $R^{11a}$ is also suitably C(O)—NH—$C_1$-$C_8$-alkyl, preferably C(O)—NH-ethyl.

According to formula (II), $R^{12a}$ is suitably selected from $C_1$-$C_8$-alkyl optionally substituted by OH, halogen or $C_6$-$C_{10}$-aryl optionally substituted by OH or O—$C_1$-$C_8$ alkyl, preferably $C_6$-$C_{10}$-aryl is phenyl substituted by $OCH_3$ or OH.

According to formula (II), $R^{14}$ is suitably $NR^{14f}C(O)NR^{14g}R^{14h}$, $NR^{14a}NR^{14b}$, NHC(O)$R^{14q}$ and NHC(=$NR^{14m}$)N($R^{14n}$)$R^{14o}$, where $R^{14a}$ is preferably H or $C_1$-$C_8$ alkyl (e.g. methyl) and $R^{14f}$ and $R^{14h}$ are preferably H. $R^{14b}$ is selected from H and 3- to 10-membered heterocyclic group containing at least one ring heteroatom selected from the group consisting of nitrogen, oxygen and sulfur, optionally substituted by 0-3$R^{15}$. $R^{14b}$ is preferably H or a 4,5 dihydro-1H imidazole.

According to formula (II), $R^{14g}$ is $C_1$-$C_8$-alkyl optionally substituted by a 3- to 10-membered heterocyclic group containing at least one ring heteroatom selected from the group consisting of nitrogen, oxygen and sulfur, optionally substituted with $SO_2R^{16}$, CN, or 0-3$R^{15}$. $R^{14g}$ is preferably a methylene substituted by a pyridine where the pyridine is optionally substituted by CN.

According to formula (II), $R^{14g}$ is also suitably $C_6$-$C_{10}$-aryl optionally substituted by OH, $C_1$-$C_8$-alkyl, O—$C_1$-$C_8$-alkyl, $SO_2R^{16}$, or -halogen, $R^{14g}$ is preferably a phenyl that is optionally substituted by OH or $SO_2NH_2$.

According to formula (II), $R^{14g}$ is also suitably $C_7$-$C_{14}$-aralkyl optionally substituted by OH, O—$C_1$-$C_8$-alkyl, halogen, $C_6$-$C_{10}$-aryl, $SO_2R^{16}$, CN, —C(=NH)$NH_2$, or O—$C_6$-$C_{10}$-aryl. $R^{14g}$ is preferably a benzyl group optionally substituted by OH or —C(=NH)$NH_2$.

According to formula (II), $R^{14g}$ is also suitably 3- to 10-membered heterocyclic group containing at least one ring heteroatom selected from the group consisting of nitrogen, substituted by OH, —COOH, $C_1$-$C_8$-alkyl, O—$C_1$-$C_8$-alkyl, -halogen, or $SO_2R^{16}$. Preferably the C(O)—$C_6$-$C_{10}$-aryl is C(O)-benzoic acid.

According to formula (II), $R^{14m}$ is CN.

According to formula (II) $R^{14n}$ is H or $C_1$-$C_8$ alkyl. Preferably, $R^{14n}$ is H.

According to formula (II), $R^{14o}$ is H, $C_1$-$C_8$-alkyl optionally substituted by OH or by a 3- to 10-membered heterocyclic group containing at least one ring heteroatom selected from the group consisting of nitrogen, oxygen and sulfur, optionally substituted with $SO_2R^{16}$, CN, or 0-3$R^{15}$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^{16}$ or -halogen. $R^{14o}$ is preferably a methylene substituted by an unsubstituted pyridine or phenyl optionally substituted by $SO_2NH_2$.

According to formula (II) $R^{14q}$ is a 3- to 10-membered heterocyclic group containing at least one ring heteroatom selected from the group consisting of nitrogen, oxygen and sulfur optionally substituted by a 3- to 10-membered heterocyclic group containing at least one ring heteroatom selected from the group consisting of nitrogen, oxygen and sulfur, optionally substituted by 0-3$R^{15}$. Preferably $R^{14q}$ is a 6 membered heterocyclic group (e.g. pyridine) substituted by a 6 membered heterocyclic group (e.g. morpholine).

Definitions

Terms used in the specification have the following meanings:

"Optionally substituted" means the group referred to can be substituted at one or more positions by any one or any combination of the radicals listed thereafter.

"Halo" or "halogen", as used herein, may be fluorine, chlorine, bromine or iodine. Preferably halo is chlorine.

"$C_1$-$C_8$-alkyl", as used herein, denotes straight chain or branched alkyl having 1-8 carbon atoms. Preferably $C_1$-$C_8$-alkyl is $C_1$-$C_4$-alkyl.

"$C_1$-$C_8$-alkoxy", or as used herein, denotes straight chain or branched alkoxy having 1-8 carbon atoms. Preferably, $C_1$-$C_8$-alkoxy is $C_1$-$C_4$-alkoxy.

"$C_3$-$C_8$-cycloalkyl", as used herein, denotes cycloalkyl having 3-8 ring carbon atoms, e.g., a monocyclic group, such as a cyclopropyl, cyclobutyl, cyclopentyl, cyclohexyl, cycloheptyl or cyclooctyl, any of which can be substituted by one or more, usually one or two, $C_1$-$C_4$-alkyl groups; or a bicyclic group, such as bicycloheptyl or bicyclooctyl.

"$C_1$-$C_8$-alkylamino" and "di($C_1$-$C_8$-alkyl)amino", as used herein, denote amino substituted respectively by one or two $C_1$-$C_8$-alkyl groups as hereinbefore defined, which may be the same or different.

"$C_1$-$C_8$-alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined attached by a carbon atom to a carbonyl group.

"$C_6$-$C_{10}$-aryl", as used herein, denotes a monovalent carbocyclic aromatic group that contains 6-10 carbon atoms and which may be, e.g., a monocyclic group, such as phenyl; or a bicyclic group, such as naphthyl.

"$C_7$-$C_{14}$-aralkyl", as used herein, denotes alkyl, e.g., $C_1$-$C_4$-alkyl, as hereinbefore defined, substituted by $C_6$-$C_{10}$-aryl as hereinbefore defined. Preferably, $C_7$-$C_{14}$-aralkyl is $C_7$-$C_{10}$-aralkyl, such as phenyl-$C_1$-$C_4$-alkyl.

"$C_1$-$C_8$-alkylaminocarbonyl" and "$C_3$-$C_8$-cycloalkylaminocarbonyl" as used herein denote $C_1$-$C_8$-alkylamino and $C_3$-$C_8$-cycloalkylamino respectively as hereinbefore defined attached by a carbon atom to a carbonyl group. Preferably $C_1$-$C_8$-alkylaminocarbonyl and $C_3$-$C_8$-cycloalkyl-aminocarbonyl are $C_1$-$C_4$-alkylaminocarbonyl and $C_3$-$C_8$-cycloalkylaminocarbonyl respectively.

"$C_5$-$C_{15}$-carbocyclic group" as used herein denotes a carbocyclic group having 5 to 15 ring carbon atoms, for example a monocyclic group, either aromatic or non-aromatic, such as a cyclopentyl, cyclohexyl, cycloheptyl, cyclooctyl or phenyl, or a bicyclic group such as bicyclooctyl, bicyclononyl, bicyclodecyl, indanyl or indenyl, again any of which can be substituted by one or more, usually one or two, $C_1$-$C_4$-alkyl groups. Preferably the $C_5$-$C_{15}$-carbocyclic group is a $C_5$-$C_{10}$-carbocyclic group, especially phenyl, cyclohexyl or indanyl. The $C_5$-$C_{15}$-carbocyclic group can unsubstituted or substituted. Preferred substituents on the heterocyclic ring include halo, cyano, OH, carboxy, amino, aminocarbonyl, nitro, $C_1$-$C_{10}$-alkyl, $C_1$-$C_{10}$-alkoxy and $C_3$-$C_{10}$-cycloalkyl, especially OH or amino.

"$C_3$-$C_{15}$-carbocyclic group", as used herein, denotes a carbocyclic group having 3-15 ring carbon atoms, e.g., a monocyclic group, either aromatic or non-aromatic, such as a cyclopentyl, cyclohexyl, cycloheptyl, cyclooctyl or phenyl; or a bicyclic group, such as bicyclooctyl, bicyclononyl, bicyclodecyl, indanyl or indenyl, again any of which can be substituted by one or more, usually one or two, $C_1$-$C_4$-alkyl groups. Preferably the $C_3$-$C_{15}$-carbocyclic group is a $C_5$-$C_{10}$-carbocyclic group, especially phenyl, cyclohexyl or indanyl. The $C_5$-$C_{15}$-carbocyclic group can unsubstituted or substituted. Substituents on the heterocyclic ring include halo, cyano, OH, carboxy, amino, aminocarbonyl, nitro, $C_1$-$C_{10}$-alkyl, $C_1$-$C_{10}$-alkoxy and $C_3$-$C_{10}$-cycloalkyl.

"3- to 12-membered heterocyclic ring containing at least one ring heteroatom selected from the group consisting of nitrogen, oxygen and sulfur", as used herein, may be, e.g., furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, morpholino, triazine, oxazine or thiazole. Preferred heterocyclic rings include piperazine, pyrrolidine, morpholino, imidazole, isotriazole, pyrazole, tetrazole, thiazole, triazole, thiadiazole, pyridine, piperidine, pyrazine, furan, oxazole, isoxazole, oxadiazole and azetidine. The 3-to-12-membered heterocyclic ring can be unsubstituted or substituted.

"5- or 6-membered heterocyclic group containing at least one ring heteroatom selected from the group consisting of nitrogen, oxygen and sulfur" as used herein may be, for example, a saturated or unsaturated heterocyclic group such as furanyl, pyrrolyl, pyrrolidinyl, pyrazolyl, imidazolyl, triazolyl, isotriazolyl, tetrazolyl, thiadiazolyl, isothiazolyl, oxadiazolyl, pyridinyl, piperidinyl, pyrazinyl, oxazolyl, isoxazolyl, pyrazinyl, pyridazinyl, pyrimidinyl, piperazinyl, pyrrolidinyl, morpholinyl, triazinyl, oxazinyl or thiazolyl. Preferred 5- or 6-membered heterocyclic groups include pyrazolyl, imidazolyl, pyrrolidinyl, pyridinyl and piperidinyl. The 5- or 6-membered heterocyclic group can be unsubstituted or substituted. Preferred substituents include halo, cyano, oxo, OH, carboxy, amino, nitro, $C_1$-$C_8$-alkyl (optionally substituted by hydroxy), $C_1$-$C_8$-alkylsulfonyl, aminocarbonyl, $C_1$-$C_8$-alkylcarbonyl, $C_1$-$C_8$-alkoxycarbonyl, and $C_1$-$C_8$-alkoxy optionally substituted by aminocarbonyl. Especially preferred substituents include chloro, cyano, carboxy, amino, $C_1$-$C_8$-alkoxycarbonyl, $C_1$-$C_4$-alkoxy and $C_1$-$C_4$-alkyl optionally substituted by OH.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps. As understood by one skilled in the art only combinations of substituents that are chemically possible are embodiments of the invention.

Especially preferred specific compounds of formula (I) and formula (II) are those described hereinafter in the Examples.

Stereoisomers are those compounds where there is an asymmetric carbon atom. The compounds exist in individual optically active isomeric forms or as mixtures thereof, e.g., as diastereomeric mixtures. The present invention embraces both individual optically active R and S isomers, as well as mixtures thereof. Individual isomers can be separated by methods well known to those skilled in the art, e.g. chiral high performance liquid chromatography (HPLC).

Tautomers are one of two or more structural isomers that exist in equilibrium and are readily converted from one isomeric form to another.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Synthesis

Another embodiment of the present invention provides a process for the preparation of compounds of formula (I) in free or pharmaceutically acceptable salt form, which comprises the steps of:

(i) reacting a compound of formula (Ib)

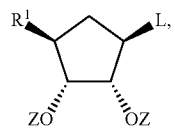

(Ib)

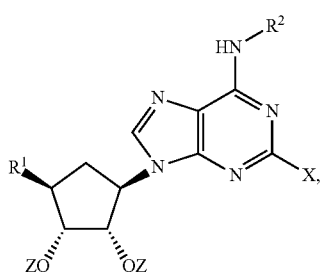

wherein
$R^1$, and $R^2$ are as defined in claim 1;
Z is H or a protecting group; and
X is a leaving group,
with a compound of formula (Ic)

H—R³     (Ic), wherein
$R^3$ is as defined in claim 1; and
removing any protecting groups and recovering the resultant compound of formula (I), in free or pharmaceutically acceptable salt form.

The compound of formula (Ic) may be prepared by reacting a compound of formula (Id)

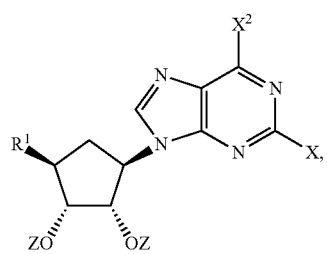

(Id)

wherein
$R^1$ and Z are as defined in claim 1; and
L represents a leaving group or a protected derivative thereof with a 2,6-dihalopurine, e.g., 2,6-dichloropurine,
to provide a compound of formula (Ie)

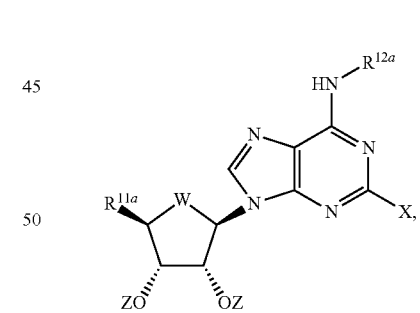

(Ie)

wherein
$R^1$ and Z are defined in claim 1; and
X and $X^2$ are halogen.

Compound of formula (Ie) can be reacted with $R^2NH_2$ under conventional conditions to provide compound of formula (Ib).

Another embodiment of the present invention provides a process for the preparation of compounds of formula (II) in free or pharmaceutically acceptable salt form, which comprises the steps of:

(i) reacting a compound of formula (IIa)

(IIa)

wherein
$R^{11a}$, W and $R^{12a}$ are as defined in claim 4;
Z is H or a protecting group; and
X is a leaving group,
with a compound of formula (IIb)

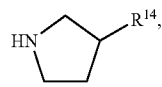

(IIb)

wherein
R[14] is as defined in claim 1; and
removing any protecting groups and recovering the resultant compound of formula (I), in free or pharmaceutically acceptable salt form.

The compound of formula (IIb) may be prepared by reacting a compound of formula (IIc)

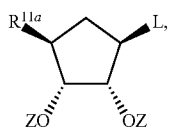

(IIc)

wherein
R[11a] and Z are as defined hereinbefore; and
L represents a leaving group or a protected derivative thereof with a 2,6-dihalopurine, e.g., 2,6-dichloropurine,
to provide a compound of formula (IId)

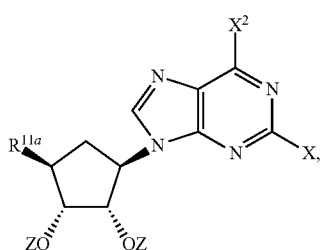

(IId)

wherein
R[11a] and Z are defined hereinbefore; and
X and X[2] are halogen.

Compound of formula (IId) can be reacted with R[2]NH$_2$ under conventional conditions to provide compound of formula (IIa).

The compounds of formula (I) and formula (II) can be prepared, for example, using the reactions and techniques described below and in the Examples. The compounds of formula (I) and formula (II) can be prepared analogously to the preparations described in Applicant's patent applications WO 2006/045552, and WO 2006/074925. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I) or one compound of formula (II) into another compound of formula (II). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is T. W. Greene and P. G. M. Wuts, *Protective Groups In Organic Synthesis*, Wiley and Sons, 1999. It is understood by those skilled in the art that only combinations of substituents that are chemically possible are embodiments of the present invention.

Compounds of formula (I) and formula (II) in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as stereoisomers, may be obtained in a conventional manner, e.g. by fractional crystallisation or asymmetric synthesis from correspondingly asymmetrically substituted, e.g. optically active, starting materials.

Compounds of formula (I) and formula (II) and their pharmaceutically acceptable salts are useful as pharmaceuticals. In particular, they activate the adenosine $A_{2A}$ receptor, i.e. they act as $A_{2A}$ receptor agonists. Their properties as $A_{2A}$ agonists may be demonstrated using the method described by L. J. Murphree et al in *Molecular Pharmacology* 61, 455-462 (2002).

Compounds of the Examples hereinbelow have $K_i$ values below 1.0 μM in the above assay. For example, the compounds of Examples 1, 14, 20, 36, 69, and 178 have K[i] values of 0.0083, 0.0025, 0.0016, 0.0030, 0.0043, and 0.0080 μM respectively.

Having regard to their activation of the adenosine $A_{2A}$ receptor, compounds of formula I in free or pharmaceutically acceptable salt form, hereinafter alternately referred to as "agents of the invention", are useful in the treatment of conditions which respond to the activation of the adenosine $A_{2A}$ receptor, particularly inflammatory or allergic conditions. Treatment in accordance with the invention may be symptomatic or prophylactic. Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include bronchiectasis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Other inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. cortico-steroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunct-ivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Further, agents of the invention may also be used for the treatment of cystic fibrosis, pulmonary hypertension, pulmonary fibrosis, inflammatory bowel syndrome, wound healing, diabetic nephropathy as described in WO 05/107463, reduction of inflammation in transplanted tissue as described in US 2005/182018, inflammatory diseases caused by pathogenic organisms as described in WO 03/086408, and cardiovascular conditions as described in WO 03/029264.

Also, the agents of the invention may be used to assess the severity of coronary artery stenosis as described in WO 00/078774 and useful in conjunction with radioactive imaging agents to image coronary activity and useful in adjunctive therapy with angioplasty as described in WO 00/78779.

Agents of the invention are also useful in combination with a protease inhibitor for prevention of organ ischaemia and reperfusion injury as described in WO 05/003150, and in combination with an integrin antagonist for treating platelet aggregation as described in WO 03/090733.

Agents of the invention are also useful in promoting wound healing in bronchial epithelial cells as described in *AJP-Lung* 290: 849-855.

Other diseases or conditions which may be treated with agents of the invention include diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, conditions characterised by elevated intraocular pressure or secretion of ocular aqueous humor, such as glaucoma, ischemic tissue/organ damage from reperfusion, bedsores, as agents for promoting sleep, as agents for treating demyelinating diseases, eg multiple sclerosis and as neuroprotective agents for eg, cerebral haemorrhagic injury and spinal cord ischaemi-reperfusion injury.

The effectiveness of an agent of the invention in inhibiting inflammatory conditions, for example in inflammatory airways diseases, may be demonstrated in an animal model, e.g.

a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; Cernadas et al (1999) *Am. J. Respir. Cell Mol. Biol.* 20:1-8; and Fozard et al (2002) *European Journal of Pharmacological* 438, 183-188.

The agents of the invention are also useful as co-therapeutic agents for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance.

Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine $A_{2B}$ receptor antagonists such as those described in WO 02/42298; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 0075114, which document is incorporated herein by reference, preferably compounds of the Examples thereof, especially a compound of formula

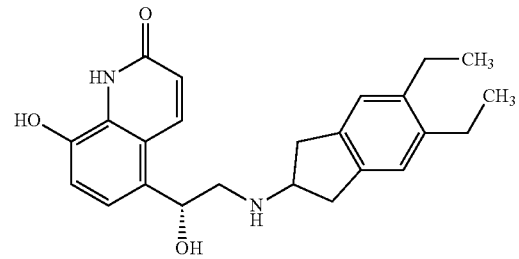

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103, WO 05/044787, WO 05/058867, WO 05/065650, WO 05/066140 and WO 05/07908.

Suitable bronchodilatory drugs include anticholinergic or antimuscarinic agents, in particular
ipratropium bromide, oxitropium bromide, tiotropium salts and CHF 4226 (Chiesi), and glycopyrrolate, but also those described in EP 424021, U.S. Pat. Nos. 3,714,357, 5,171, 744, US 2005/171147, US 2005/182091, WO 01/04118, WO 02/00652, WO 02/51841, WO 02/53564, WO 03/00840, WO 03/33495, WO 03/53966, WO 03/87094, WO 04/018422, WO 04/05285 and WO 05/077361.

Suitable dual anti-inflammatory and bronchodilatory drugs include dual beta-2 adrenoceptor agonist/muscarinic antagonists such as those disclosed in US 2004/0167167, US 2004/0242622, US 2005/182092, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

In accordance with the foregoing, the invention also provides a method for the treatment of a condition responsive to activation of the adenosine $A_{2A}$ receptor, for example an inflammatory or allergic condition, particularly an inflammatory or obstructive airways disease, which comprises administering to a subject, particularly a human subject, in need thereof a compound of formula (I) or formula (II) in free form or in the form of a pharmaceutically acceptable salt. In another aspect the invention provides a compound of formula (I) or formula (II), in free form or in the form of a pharmaceutically acceptable salt, for use in the manufacture of a medicament for the treatment of a condition responsive to activation of the adenosine $A_{2A}$ receptor, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising a compounds of formula (I) and formula (II) in free form or in the form of a pharmaceutically acceptable salt, optionally together with a pharmaceutically acceptable diluent or carrier therefor. The composition may contain a co-therapeutic agent such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compounds of formula (I) or formula (II) having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it preferably contains, for example, the compound of formula (I) or formula (II) either dissolved, or suspended, in a vehicle containing water, a co-solvent such as ethanol or propylene glycol and a stabiliser, which may be a surfactant.

The invention includes (A) a compounds of formula (I) or formula (II) in inhalable form, e.g. in an aerosol or other atomisable composition or in inhalable particulate, e.g. micronised, form, (B) an inhalable medicament comprising a compounds of formula (I) or formula (II) in inhalable form; (C) a pharmaceutical product comprising a compounds of formula (I) or formula (II) in inhalable form in association with an inhalation device; and (D) an inhalation device containing a compounds of formula (I) or formula (II) in inhalable form.

Dosages of compounds of formula (I) or formula (II) employed in practising the present invention will of course vary depending, for example, on the particular condition to be treated, the effect desired and the mode of administration. In general, suitable daily dosages for administration by inhalation are of the order of 0.005 to 10 mg, while for oral administration suitable daily doses are of the order of 0.05 to 100 mg.

The invention is illustrated by the following Examples.

EXAMPLES

Preferred compounds of formula I

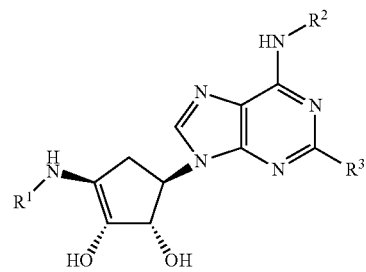

are shown in Table 1 below.

TABLE 1

| Ex. | R¹ | R² | R³ |
|---|---|---|---|
| 1 | | | |

TABLE 1-continued
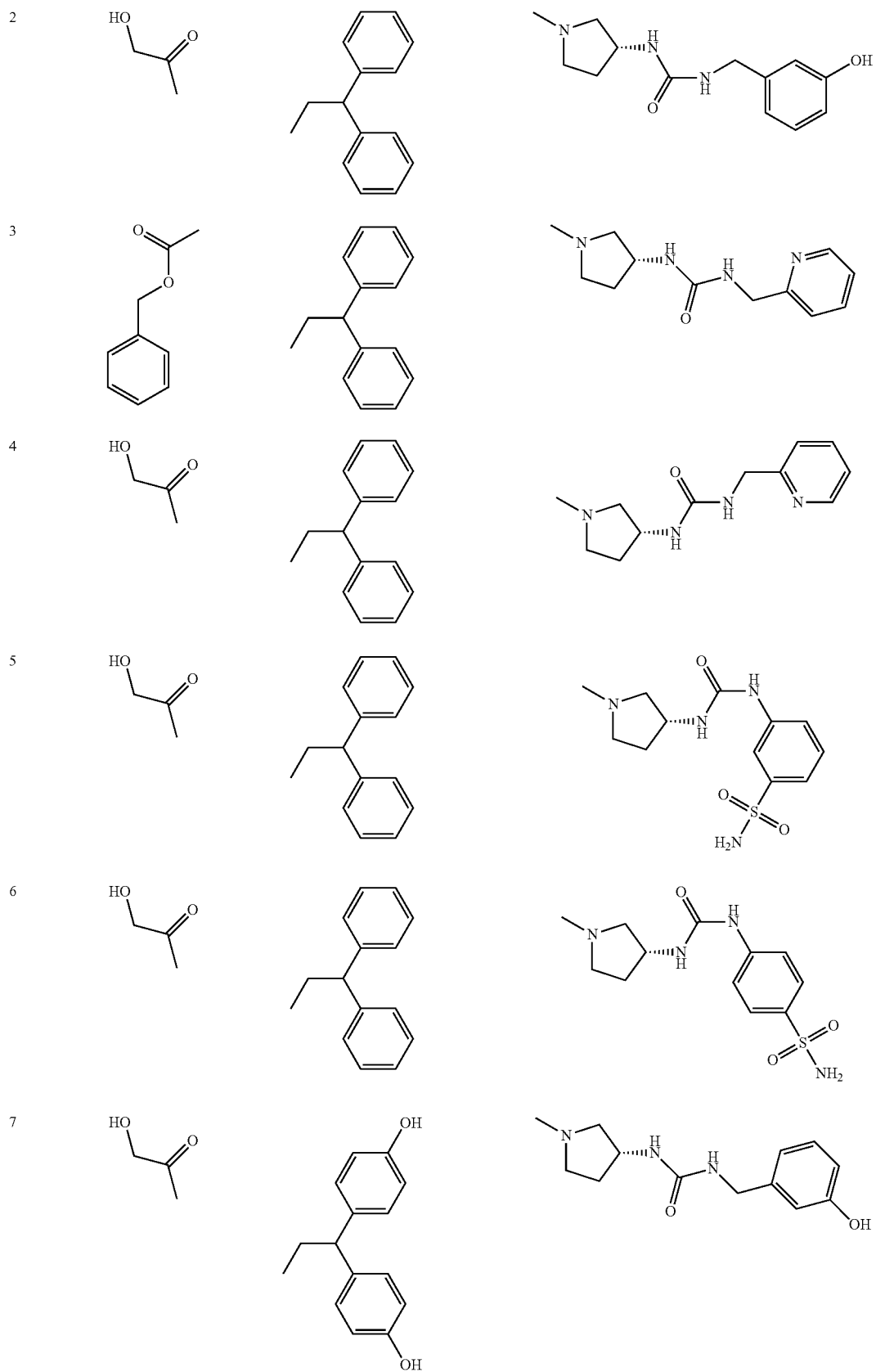

TABLE 1-continued
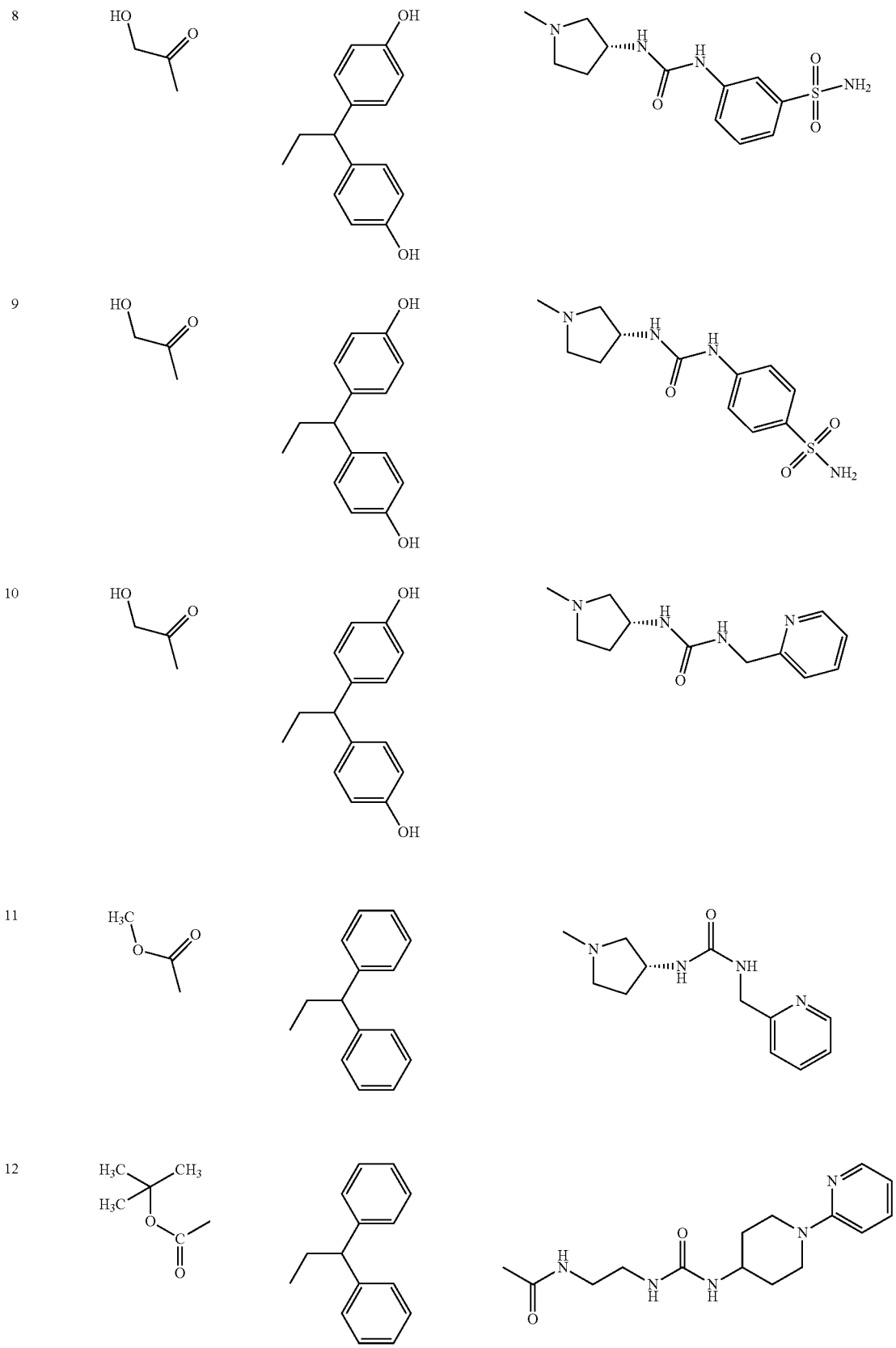

TABLE 1-continued
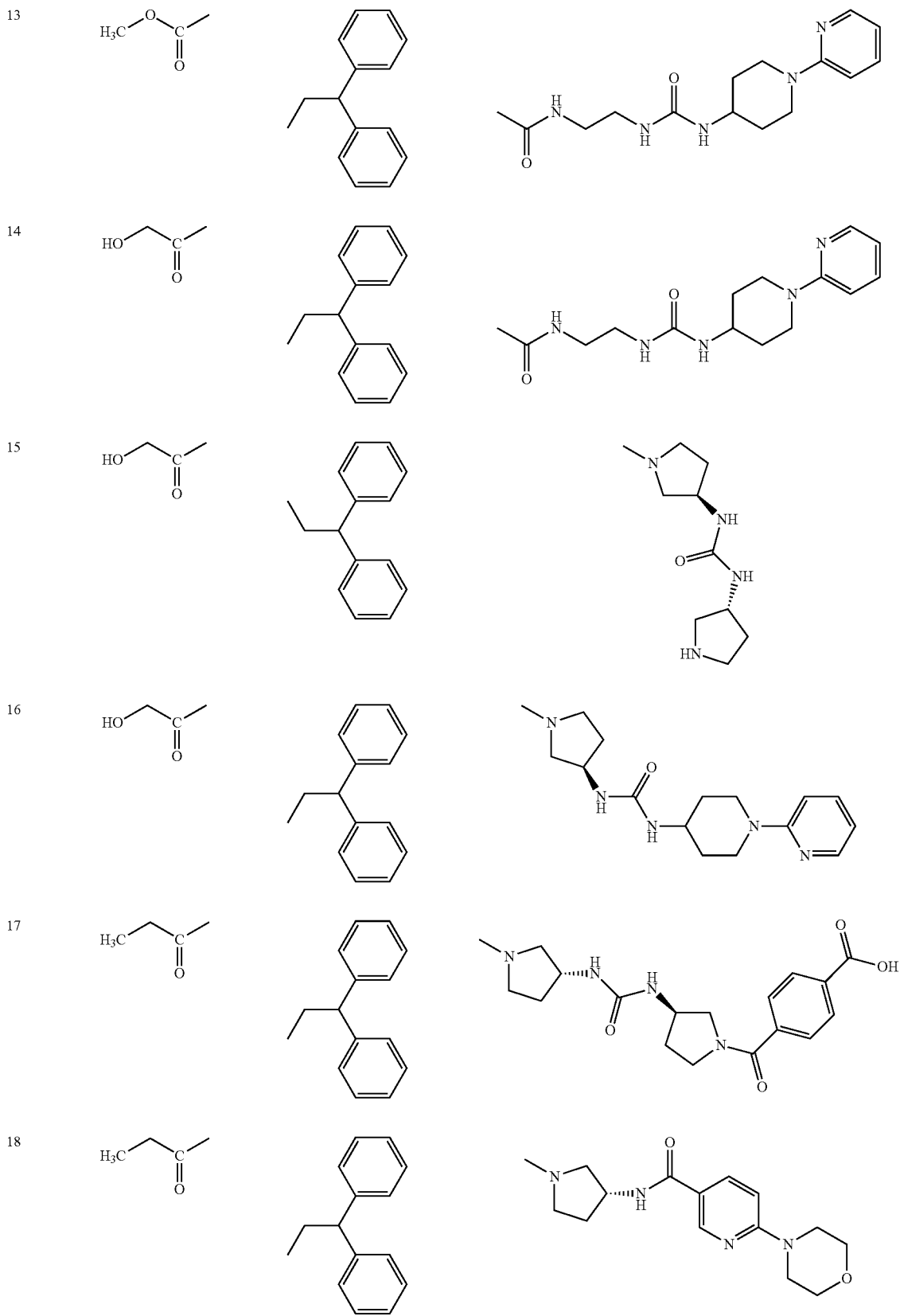

TABLE 1-continued
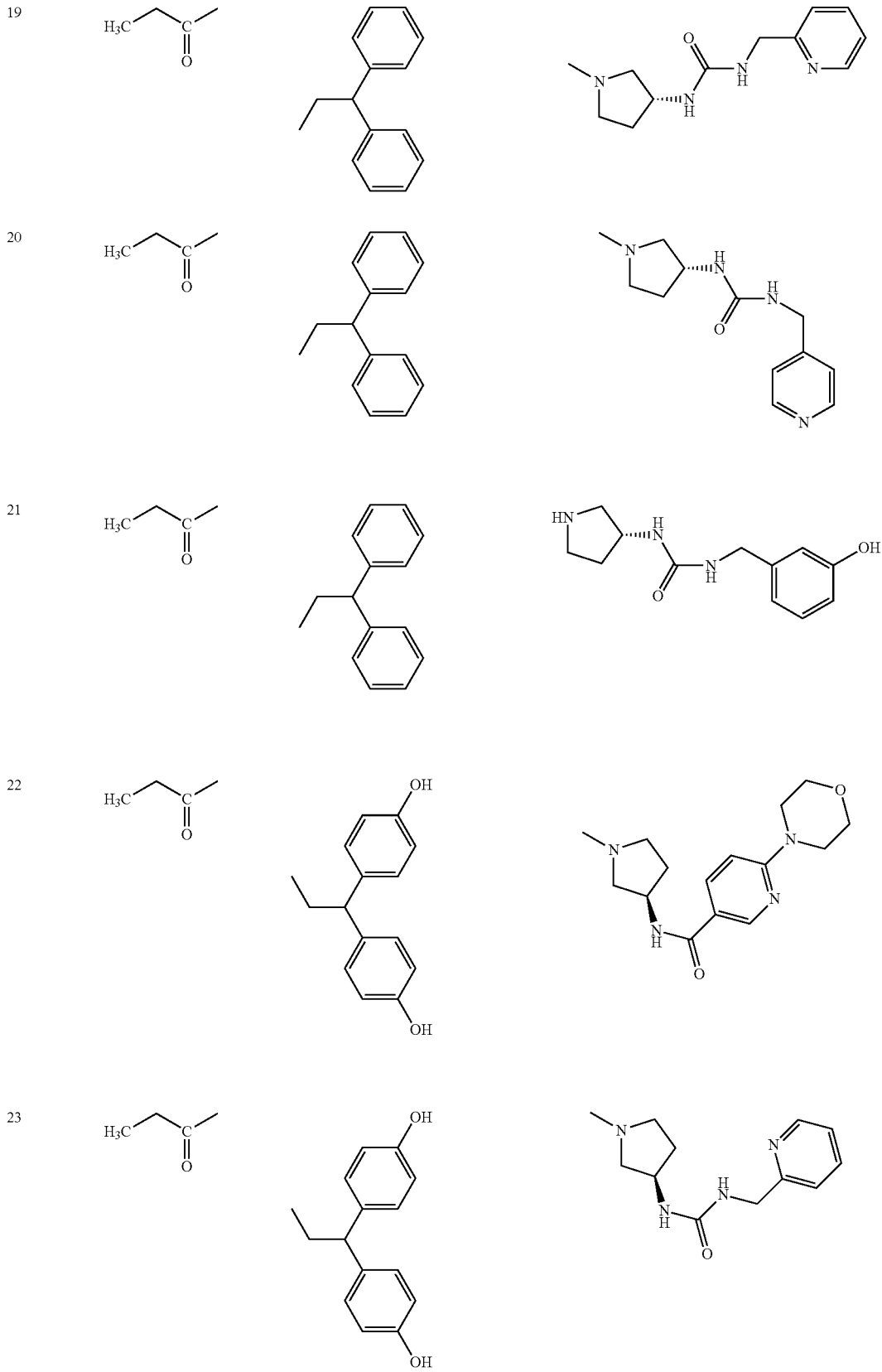

TABLE 1-continued

| | | | |
|---|---|---|---|
| 24 | H₃C–C(=O)–CH₃ (methyl ethyl ketone-like) | 1,1-bis(4-hydroxyphenyl)propane | (3S)-1-methyl-N-[(3-hydroxybenzyl)carbamoyl]pyrrolidin-3-amine |
| 25 | HO–CH₂–C(=O)– | 1,1-diphenylpropane | 1-(1-methylpyrrolidin-3-yl)-3-(pyridin-3-yl)urea |
| 26 | H₃C–O–C(=O)–CH₃ | 1,1-diphenylpropane | 1-(1-methylpyrrolidin-3-yl)-3-(pyridin-3-yl)urea |
| 27 | H₃C–C(=O)– | 1,1-diphenylpropane | 3-sulfamoylphenyl urea derivative of 1-methylpyrrolidin-3-amine |
| 28 | H₃C–C(=O)– | 1,1-diphenylpropane | 4-sulfamoylphenyl urea derivative of 1-methylpyrrolidin-3-amine |
| 29 | H— | 1,1-diphenylpropane | 1-(1-methylpyrrolidin-3-yl)-3-(pyridin-2-ylmethyl)urea |

TABLE 1-continued
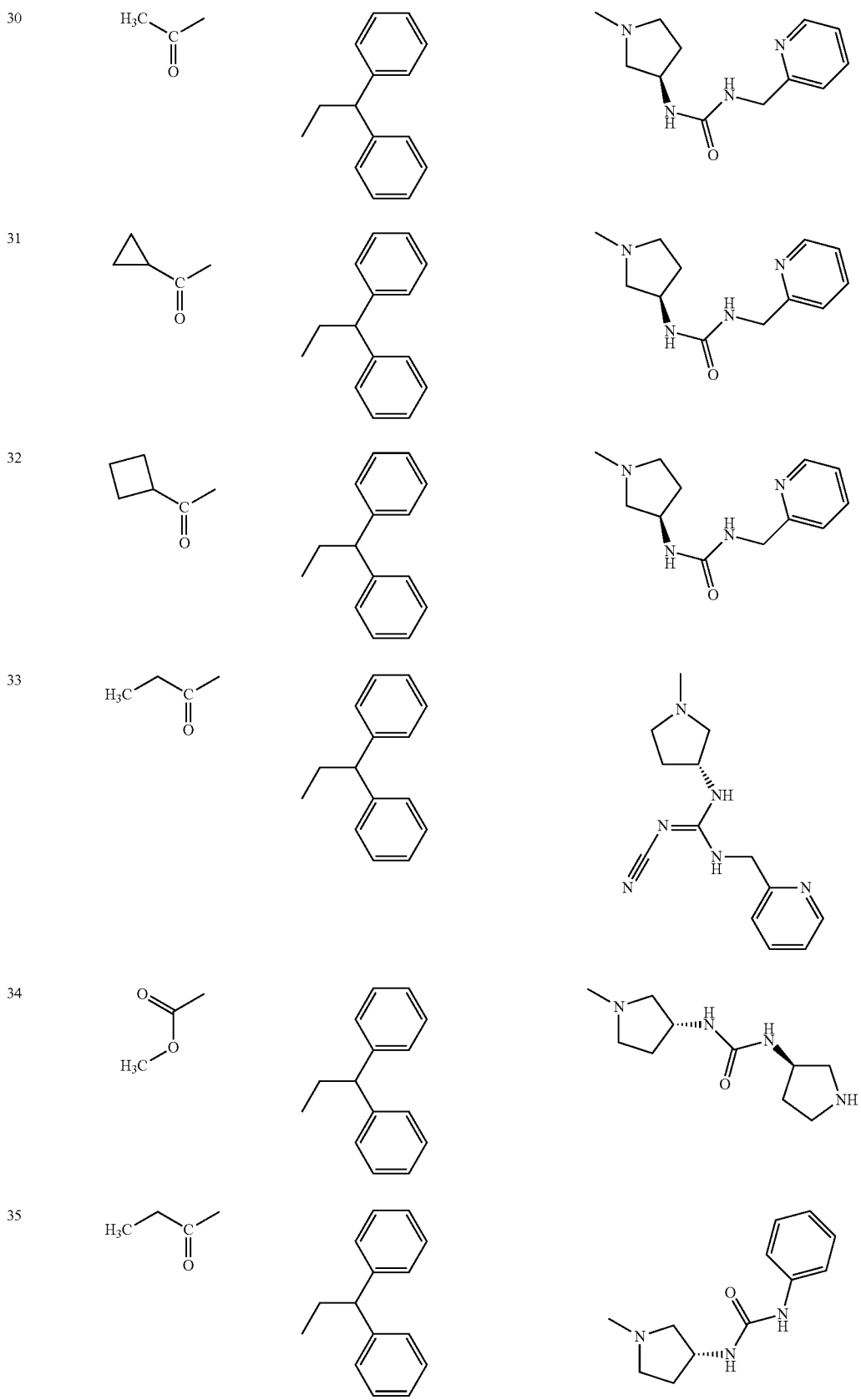

TABLE 1-continued
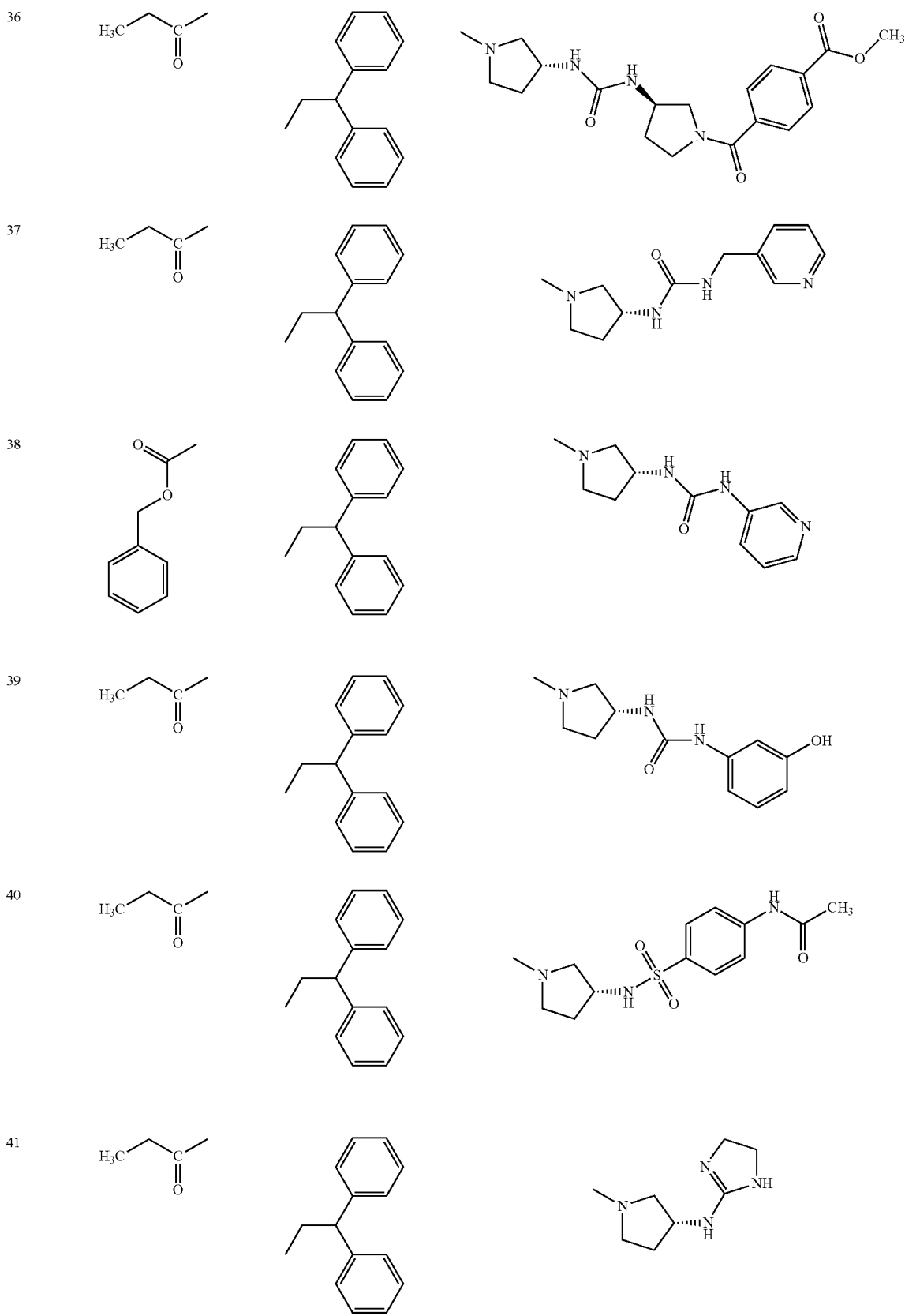

TABLE 1-continued

| 42 | (ethyl methyl ketone) | (1,1-diphenylpropyl) | (cyclohexanone N-methylhydrazone) |
| 43 | (butyl) | (1,1-diphenylpropyl) | (1-methylpyrrolidin-3-yl urea pyridin-3-yl) |
| 44 | (ethyl methyl ketone) | —H | (cyclohexanone N-methylhydrazone) |
| 45 | (ethyl methyl ketone) | (1,1-diphenylpropyl) | (bis-pyrrolidinyl urea/carboxamide pyridin-3-yl) |
| 46 | (N,N-dimethylacetamide) | (1,1-diphenylpropyl) | (acetamidoethyl urea piperidinyl pyridin-2-yl) |
| 47 | (acetoxyacetone) | (1,1-diphenylpropyl) | (acetamidoethyl urea piperidinyl pyridin-2-yl) |
| 48 | (ethyl methyl ketone) | (1,1-diphenylpropyl) | (acetamidoethyl methanesulfonamide) |

TABLE 1-continued
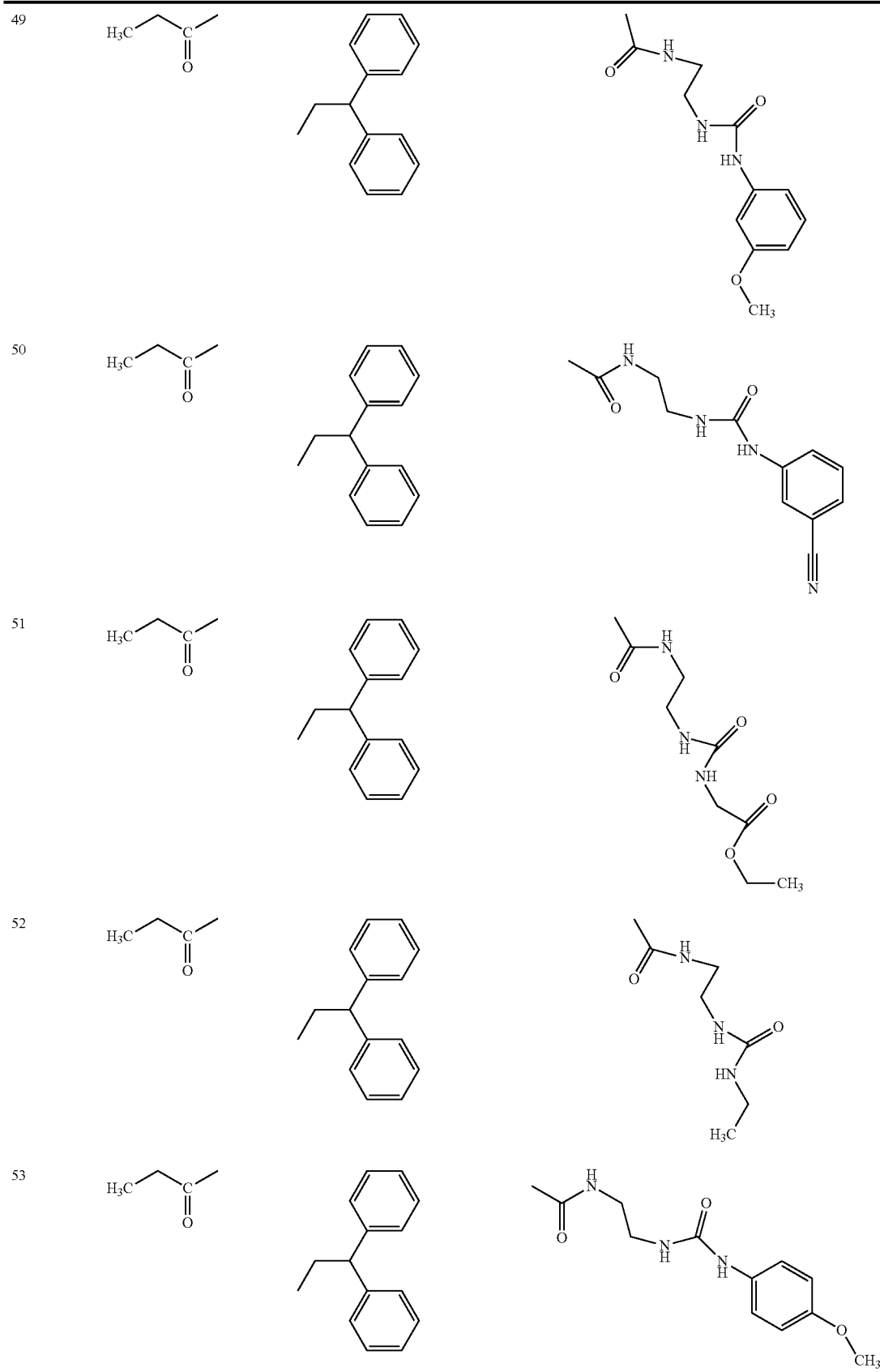

TABLE 1-continued
| 54 | 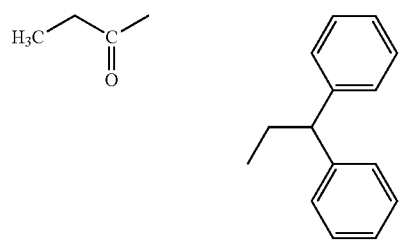 | | |
| 55 | | 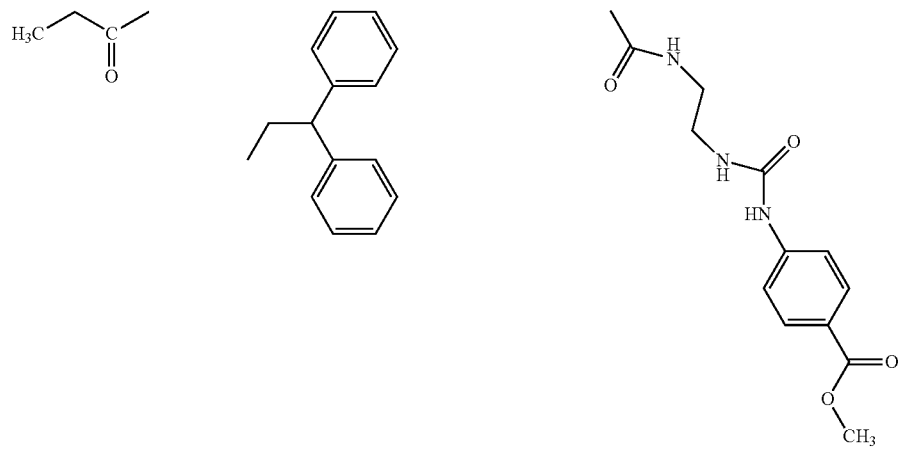 | |
| 56 | | | 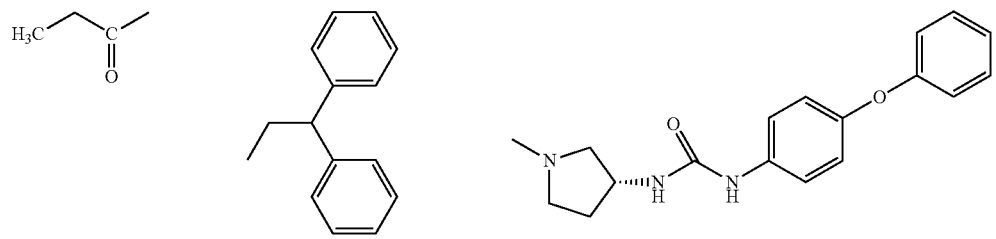 |
| 57 | | | 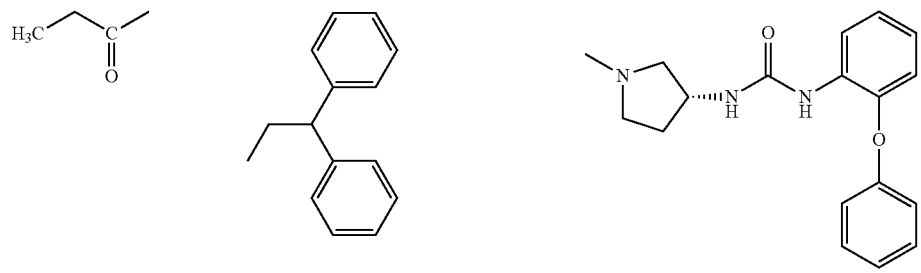 |
| 58 | | | 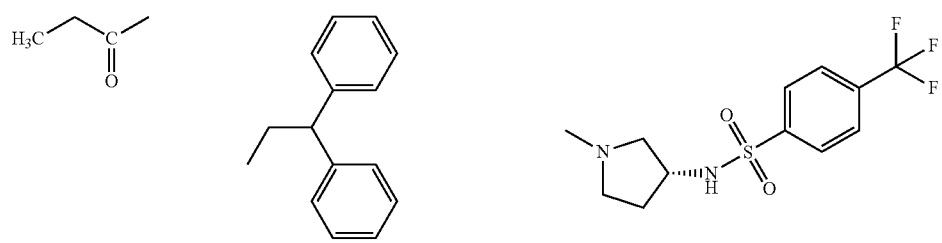 |

TABLE 1-continued
| 59 | 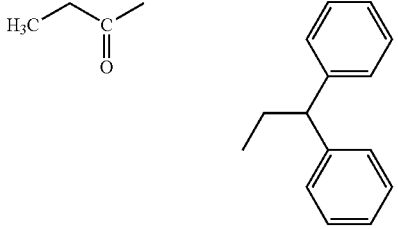 | 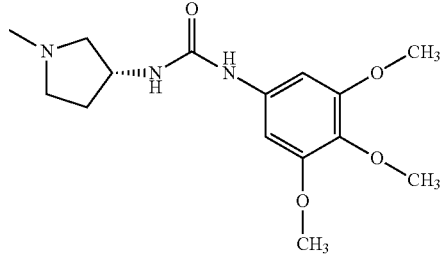 | 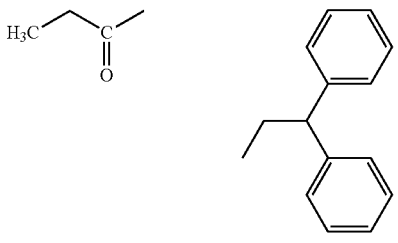 |
| 60 | 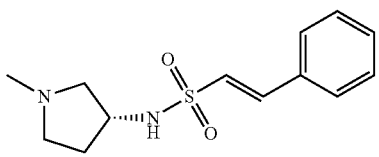 | 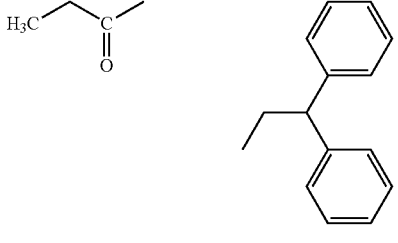 | 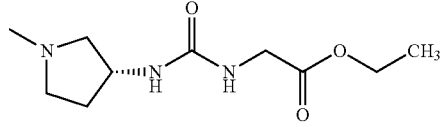 |
| 61 | 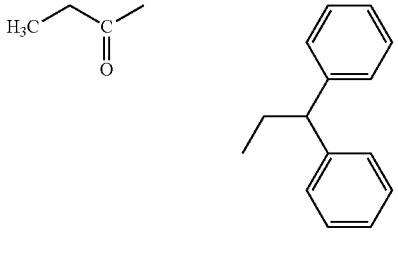 | 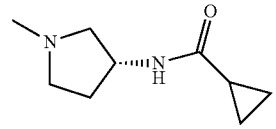 | 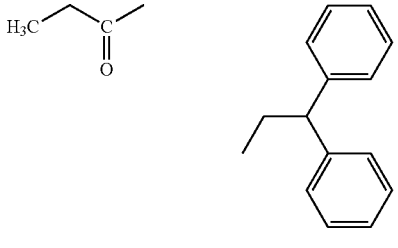 |
| 62 | 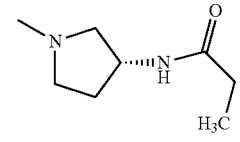 | | |
| 63 | 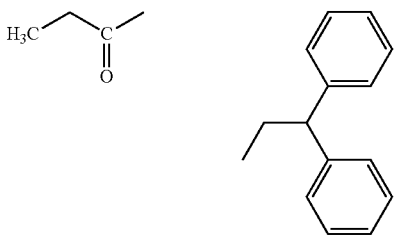 | | |
| 64 | 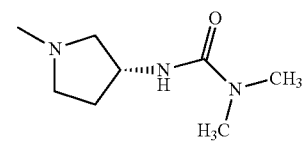 | | |

TABLE 1-continued
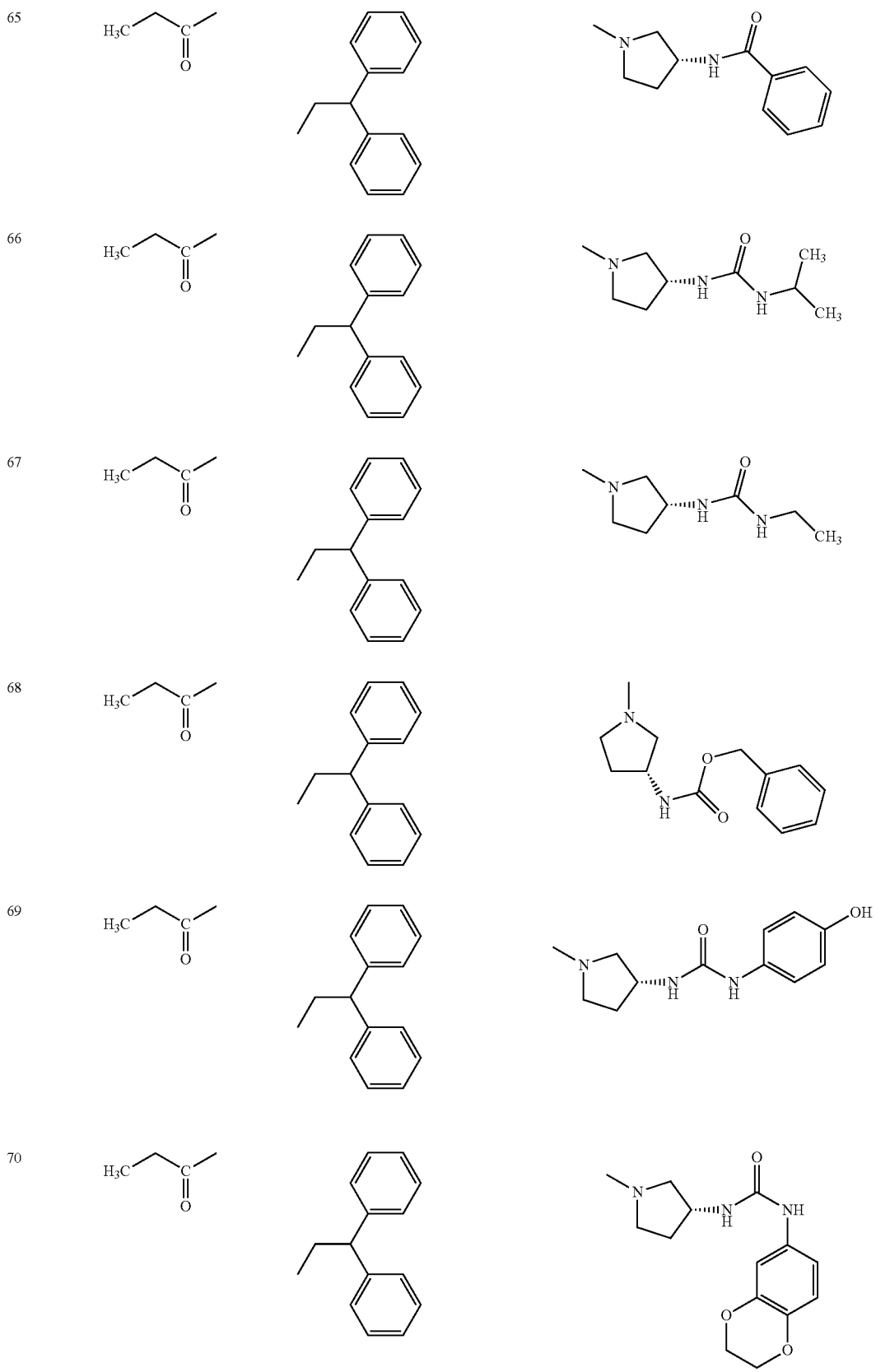

TABLE 1-continued
| 71 | 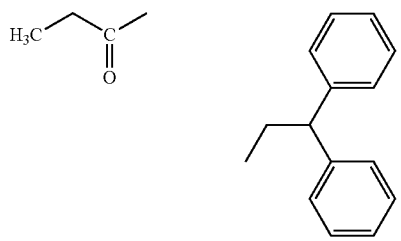 | 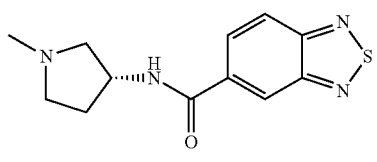 | 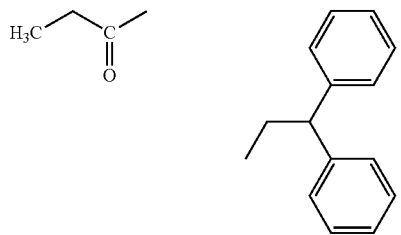 |
| 72 | 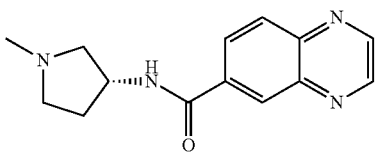 | | 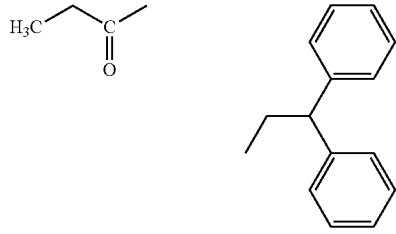 |
| 73 | 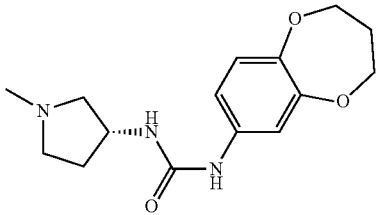 | | 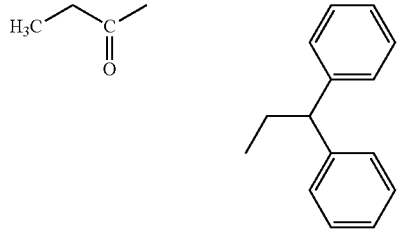 |
| 74 | | 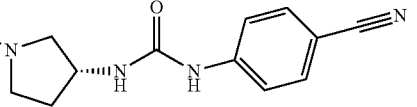 | 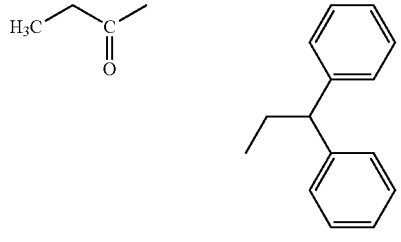 |
| 75 | | 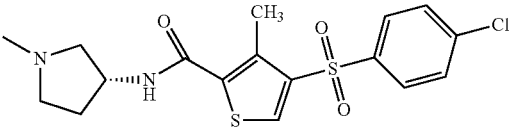 | 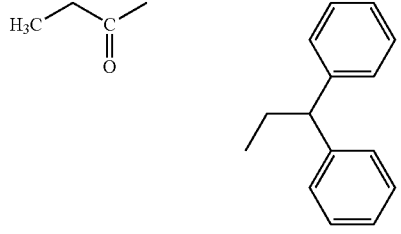 |
| 76 | | | 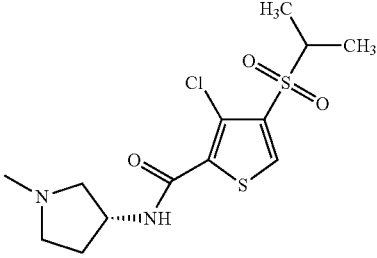 |

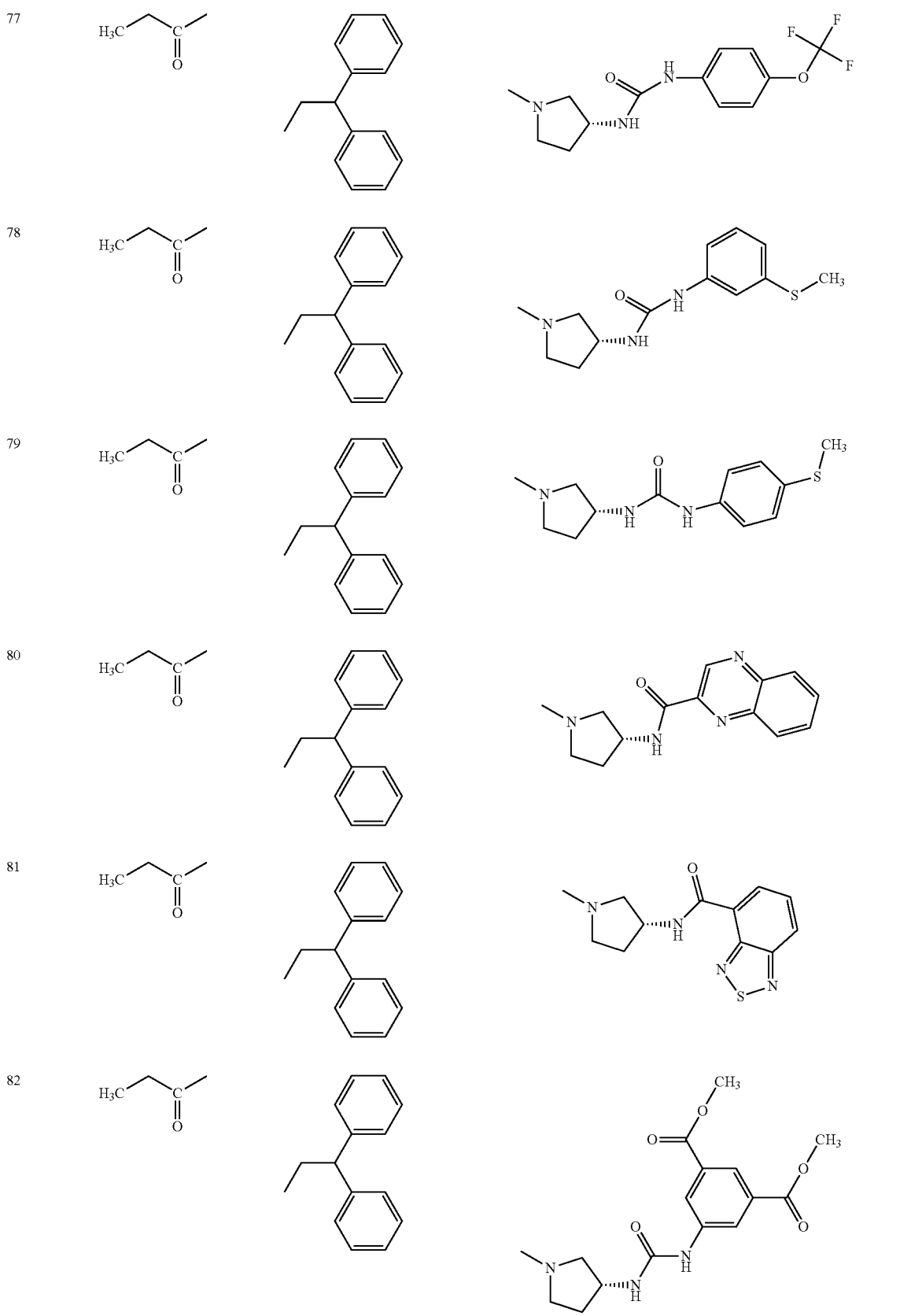

TABLE 1-continued

| 83 | (structure: ethyl ketone) | (structure: 1,1-diphenylpropyl) | (structure: (S)-1-methylpyrrolidin-3-yl amide of 2-(1H-indol-3-yl)-2-oxoacetic acid) |
| 84 | (structure: ethyl ketone) | (structure: 1,1-diphenylpropyl) | (structure: (S)-1-methylpyrrolidin-3-yl pyridine-2-carboxamide) |
| 85 | (structure: ethyl ketone) | (structure: 1,1-diphenylpropyl) | (structure: (S)-1-methylpyrrolidin-3-yl 5-methyl-1-(4-methoxyphenyl)-1H-pyrazole-4-carboxamide) |
| 86 | (structure: ethyl ketone) | (structure: 1,1-diphenylpropyl) | (structure: (S)-1-methylpyrrolidin-3-yl 1-benzyloxycarbonyl-piperidine-3-carboxamide) |
| 87 | (structure: ethyl ketone) | (structure: 1,1-diphenylpropyl) | (structure: (S)-1-methylpyrrolidin-3-yl 4-(N,N-dipropylsulfamoyl)benzamide) |

TABLE 1-continued
| 88 | 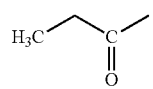 | 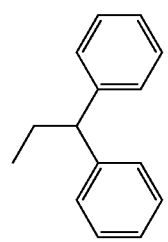 | 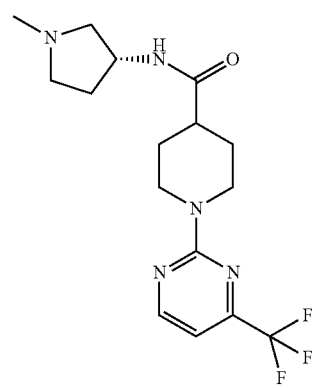 |
| 89 | 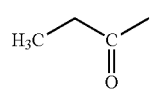 | 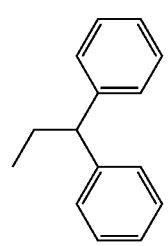 | 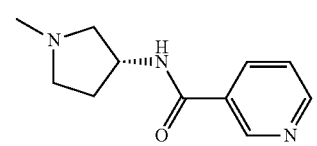 |
| 90 | 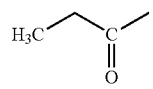 | 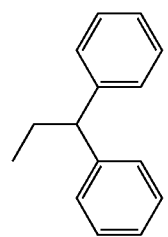 | 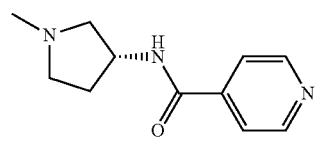 |
| 91 | 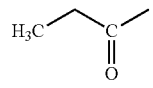 | 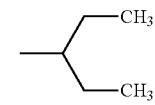 | 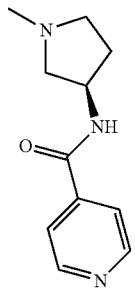 |
| 92 | 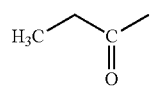 | 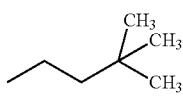 | 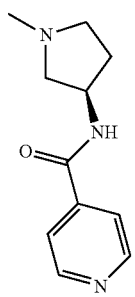 |

TABLE 1-continued

| | | | |
|---|---|---|---|
| 93 | ethyl methyl ketone | isobutyl (2-methylpropyl) | (3S)-1-methyl-N-(5-methylisoxazole-3-carbonyl)pyrrolidin-3-amine |
| 94 | cyclobutyl methyl ketone | 1,1-diphenylpropyl | (3S)-1-benzyl-N-methylpyrrolidin-3-amine |
| 95 | ethyl methyl ketone | 1,1-diphenylpropyl | N-acetyl-N'-(2-(diisopropylamino)ethyl)-urea derivative |
| 96 | ethyl methyl ketone | 1,1-diphenylpropyl | (3S)-1-benzyl-N-methylpyrrolidin-3-amine |
| 97 | ethyl methyl ketone | 1,1-diphenylpropyl | tert-butyl ((3S)-1-methylpyrrolidin-3-yl)carbamate |
| 98 | ethyl methyl ketone | 1,1-diphenylpropyl | tert-butyl (3S)-3-(methylamino)pyrrolidine-1-carboxylate |

TABLE 1-continued
| | | | |
|---|---|---|---|
| 99 | 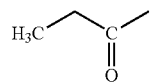 | 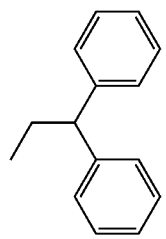 | 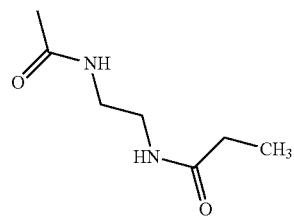 |
| 100 | 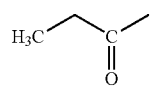 | 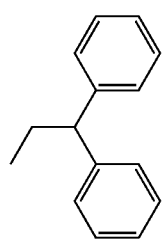 | 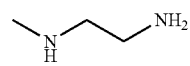 |
| 101 | 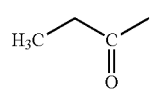 | 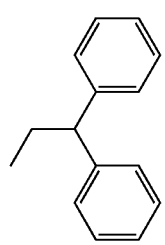 | 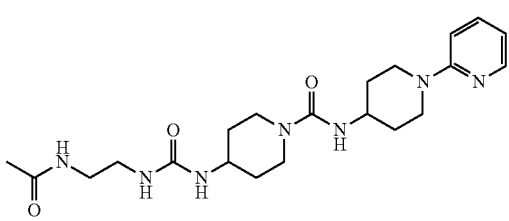 |
| 102 | 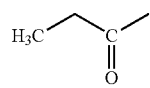 | 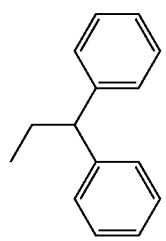 | 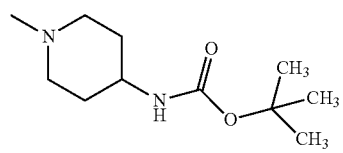 |
| 103 | 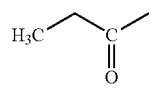 | 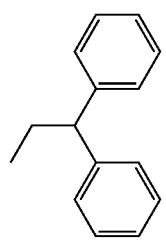 | 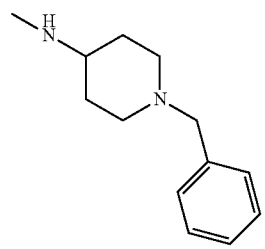 |
| 104 | 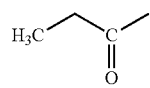 | 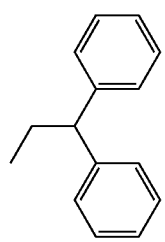 | 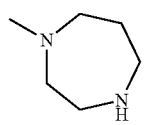 |

TABLE 1-continued
| 105 | 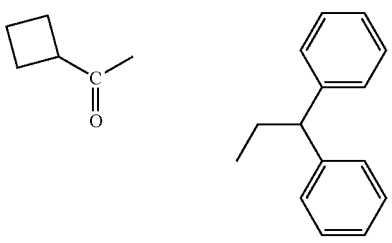 | | |
| 106 | | | |
| 107 | | 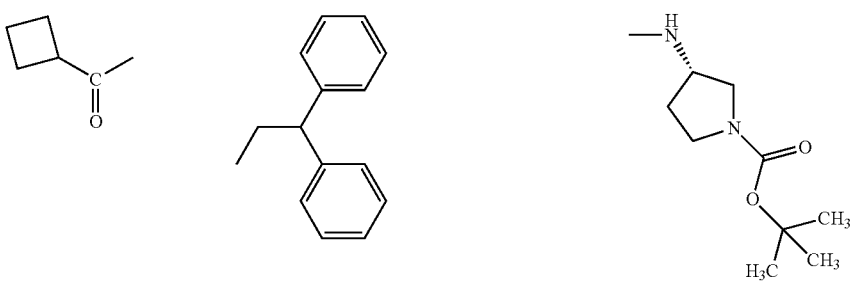 | |
| 108 | | 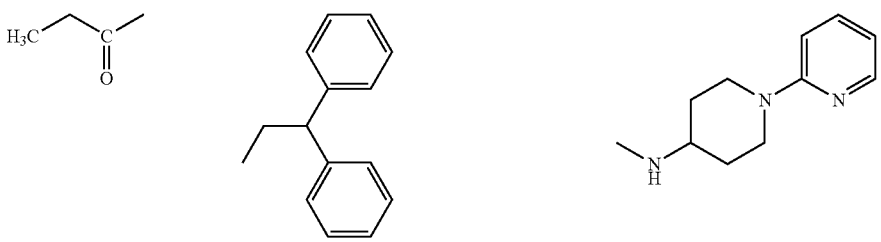 | |
| 109 | | 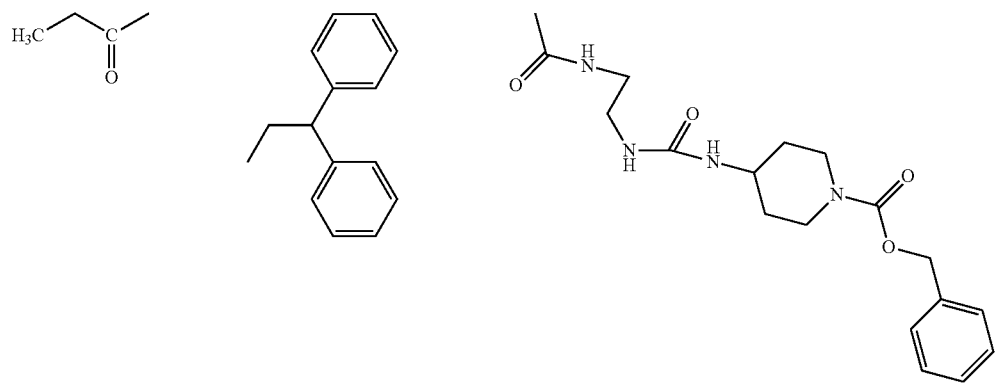 | |
|     | | 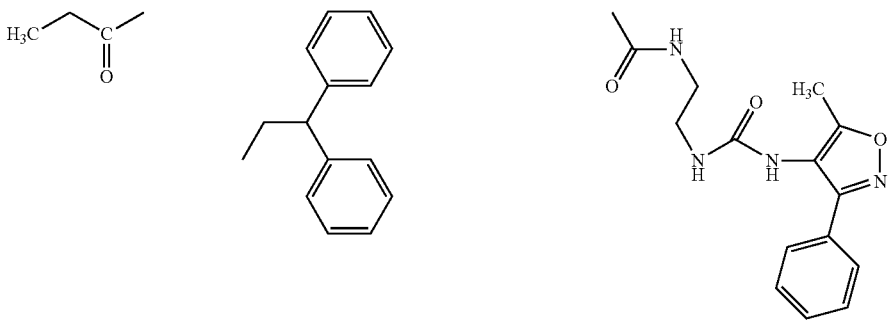 | |

TABLE 1-continued
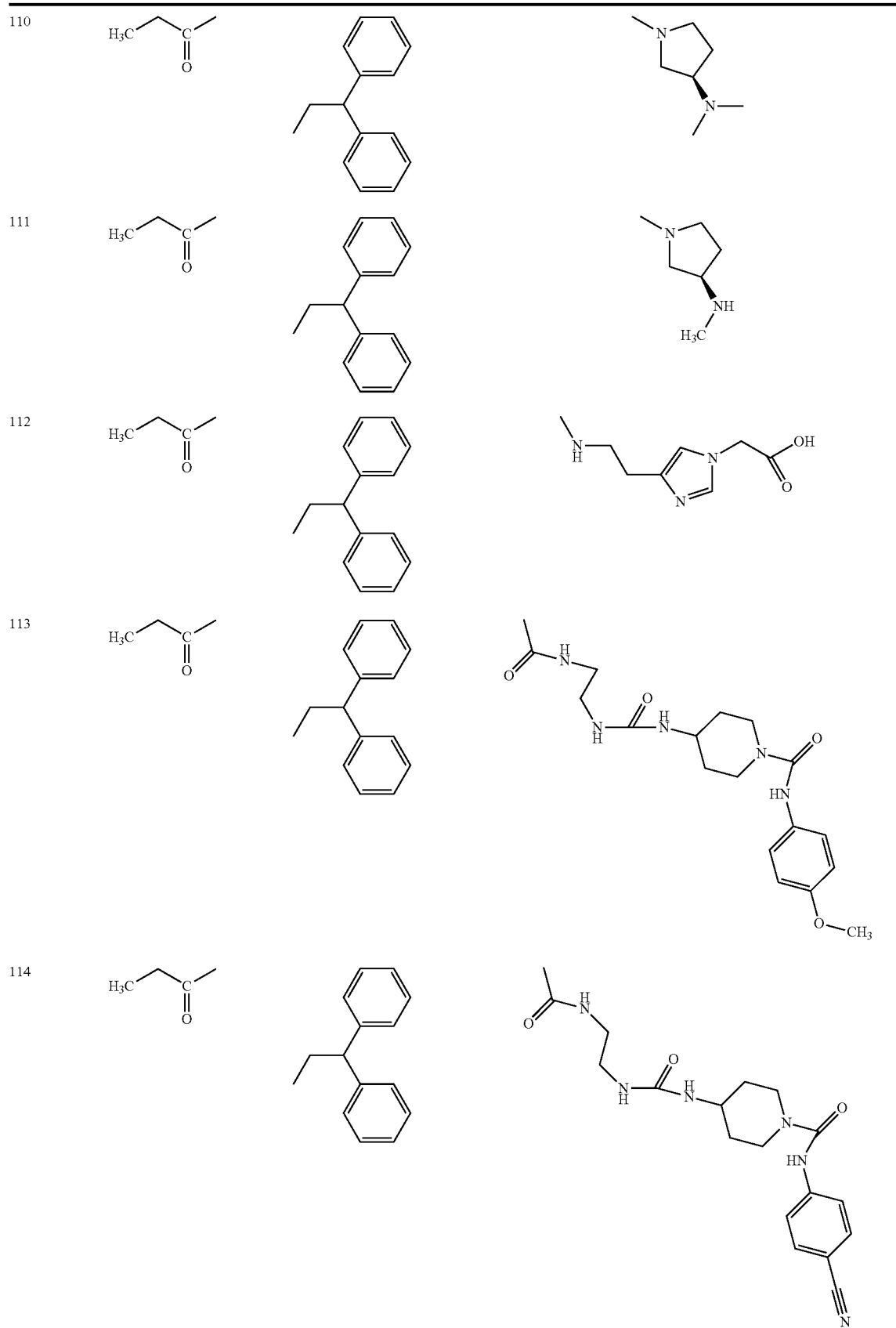

TABLE 1-continued
| | | | |
|---|---|---|---|
| 115 | 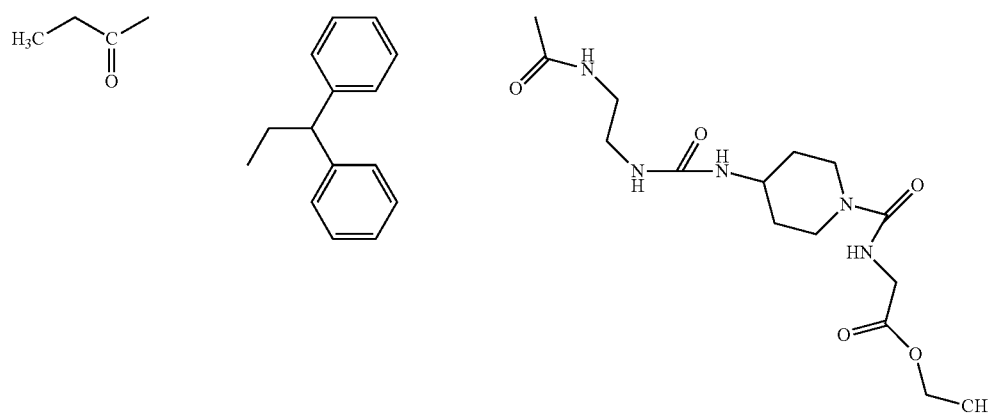 | | |
| 116 | 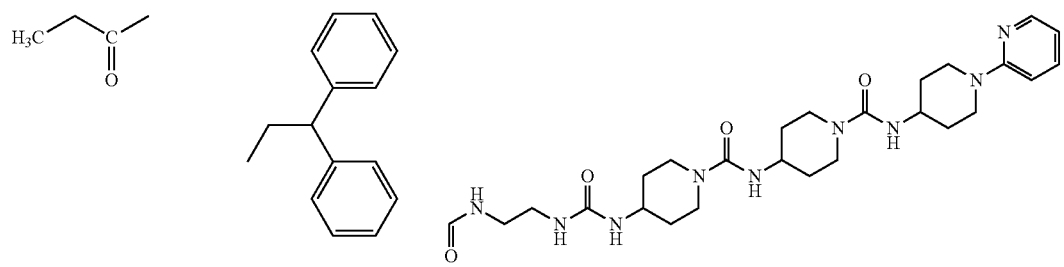 | | |
| 117 | 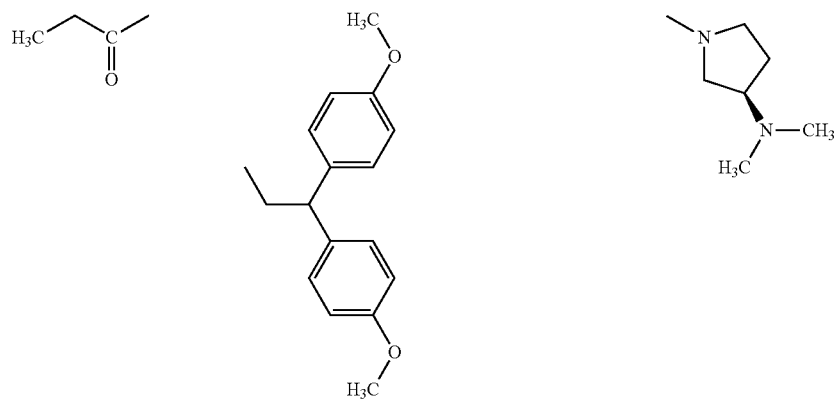 | | |
| 118 | 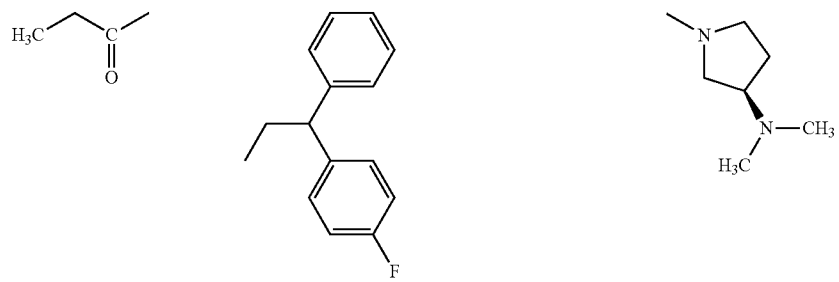 | | |
| 119 | 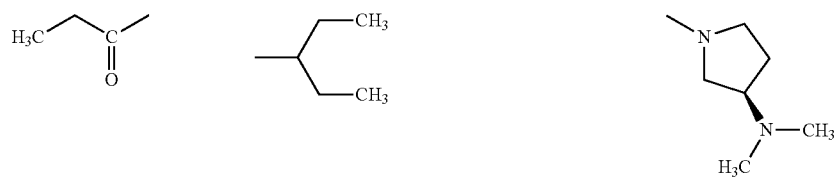 | | |

TABLE 1-continued
| | | | |
|---|---|---|---|
| 120 | 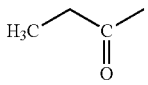 | 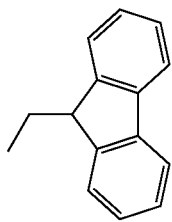 | 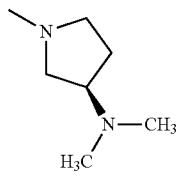 |
| 121 | 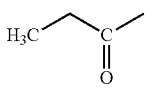 | 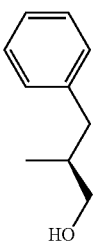 | 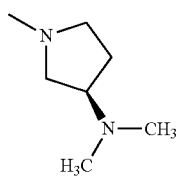 |
| 122 | 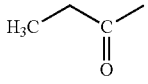 | 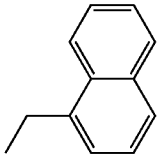 | 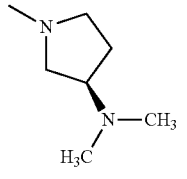 |
| 123 | 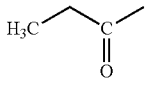 | 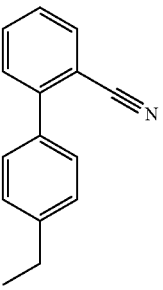 | 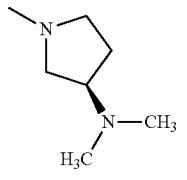 |
| 124 | 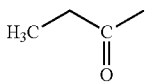 | 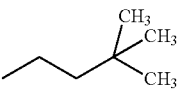 | 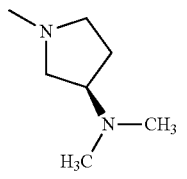 |
| 125 | 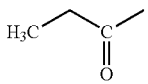 | 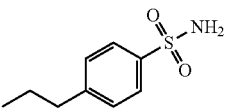 | 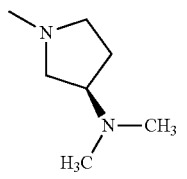 |
| 126 | 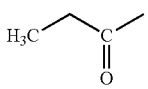 | 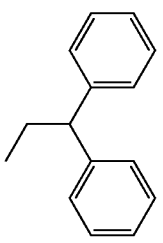 | 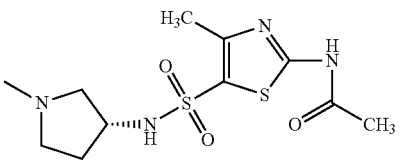 |

TABLE 1-continued
| 127 | 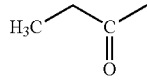 | 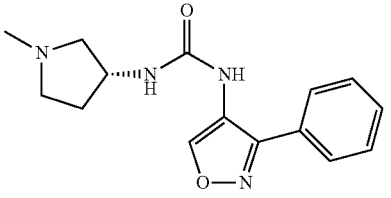 | 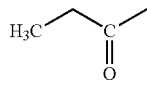 |
| 128 | 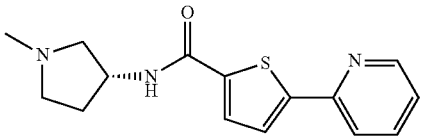 | 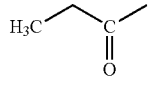 | 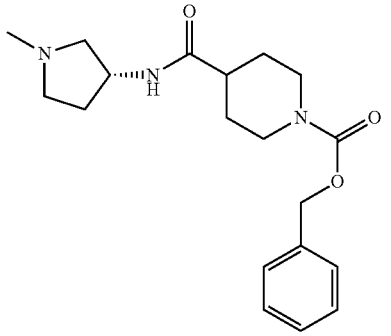 |
| 129 | 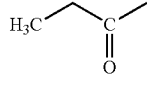 | 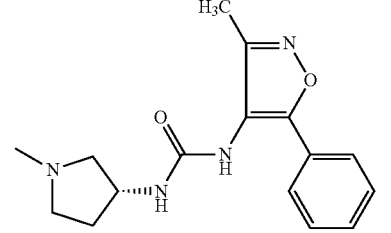 | 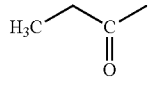 |
| 130 | 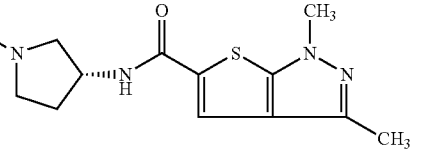 | 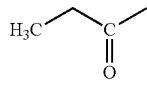 | 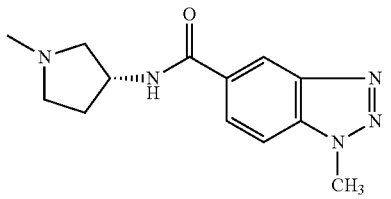 |
| 131 | | | |
| 132 | | | |

TABLE 1-continued

TABLE 1-continued
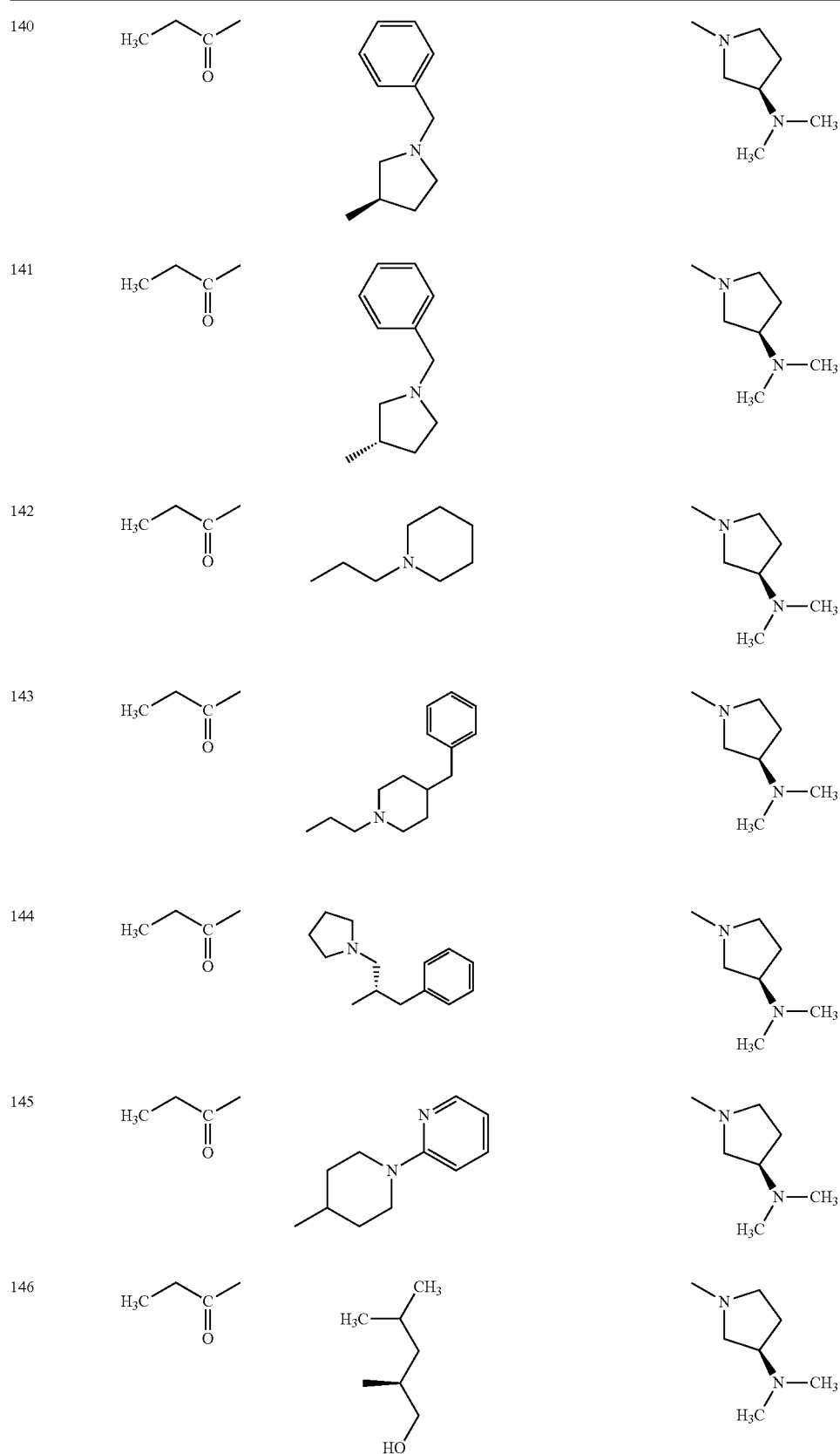

TABLE 1-continued
| | | | |
|---|---|---|---|
| 147 | 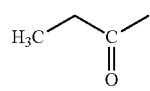 | 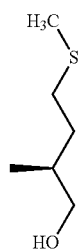 | 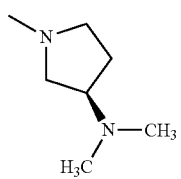 |
| 148 | 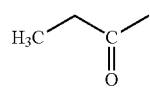 | 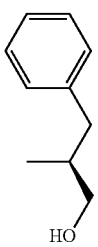 | 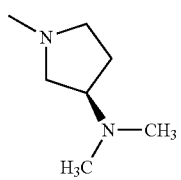 |
| 149 | 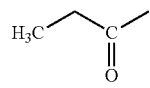 | 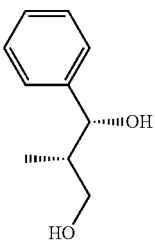 | 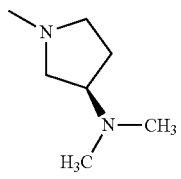 |
| 150 | 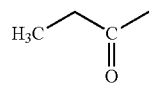 | 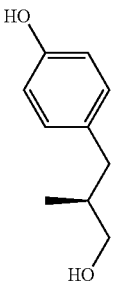 | 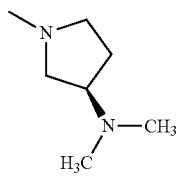 |
| 151 | 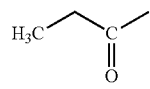 |  | 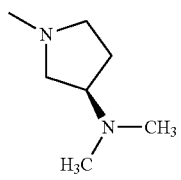 |
| 152 | 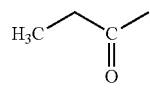 | 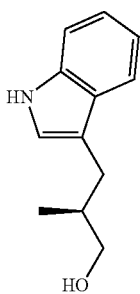 | 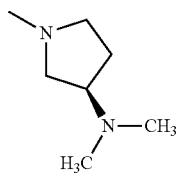 |

TABLE 1-continued
| | | | |
|---|---|---|---|
| 153 | 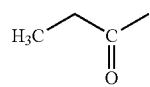 | 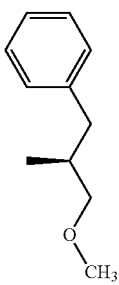 | 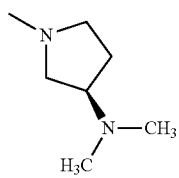 |
| 154 | 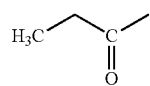 | 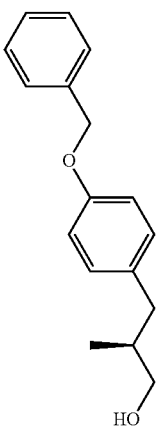 | 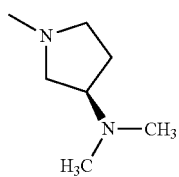 |
| 155 | 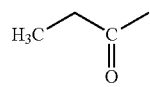 | 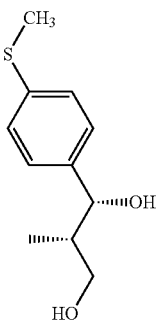 | 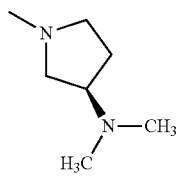 |
| 156 | 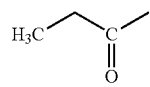 | 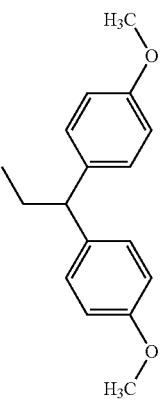 | 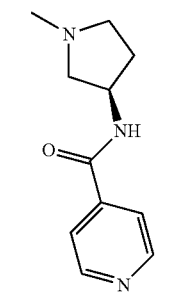 |

TABLE 1-continued
| 157 | 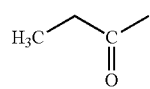 | 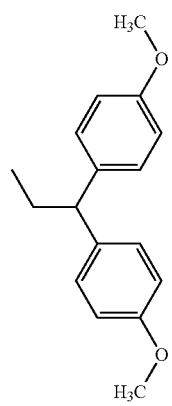 | 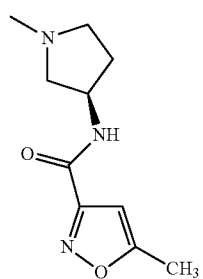 |
| 158 | 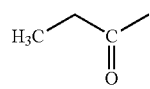 | 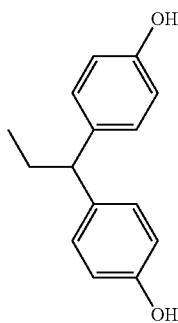 | 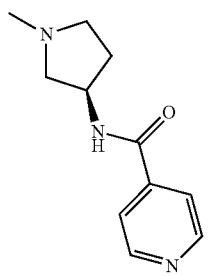 |
| 159 | 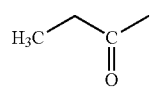 | 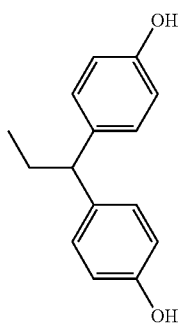 | 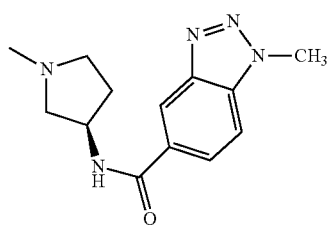 |
| 160 | 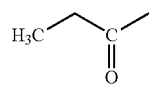 | 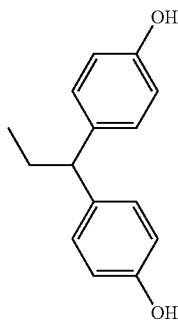 | 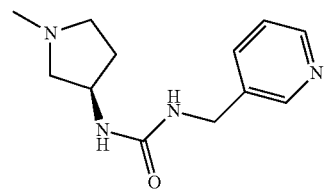 |

TABLE 1-continued

| | | | |
|---|---|---|---|
| 161 | (structure) | (structure) | (structure) |
| 162 | (structure) | (structure) | (structure) |
| 163 | (structure) | (structure) | (structure) |
| 164 | (structure) | (structure) | (structure) |
| 165 | (structure) | (structure) | (structure) |
| 166 | (structure) | (structure) | (structure) |

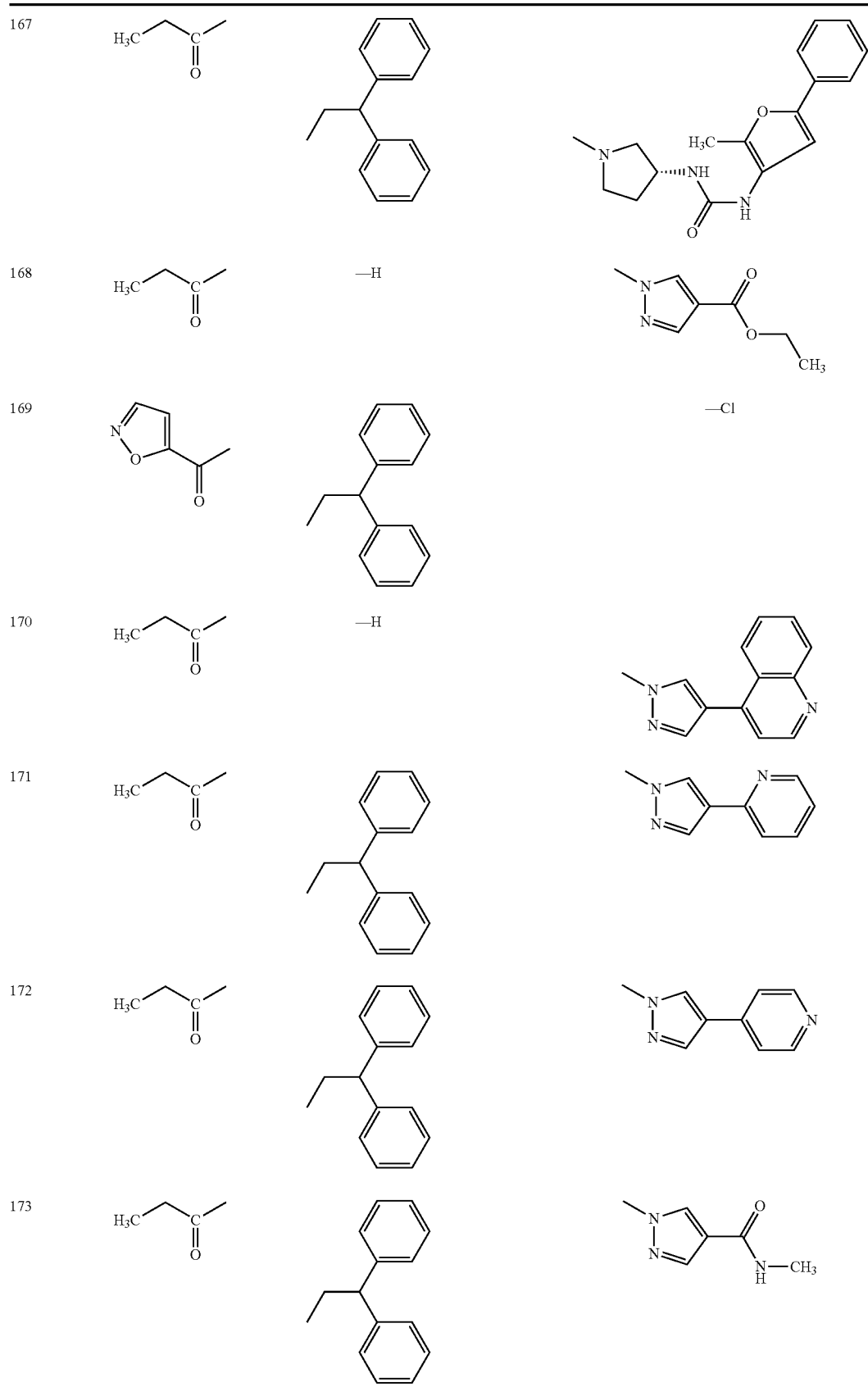

TABLE 1-continued

| 174 | | —H | |
| 175 | | | |
| 176 | | | |
| 177 | | | |
| 178 | | | |

TABLE 1-continued
| | | | |
|---|---|---|---|
| 179 | 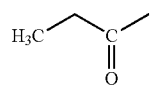 | 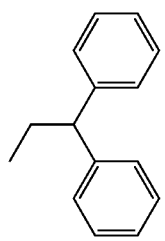 | 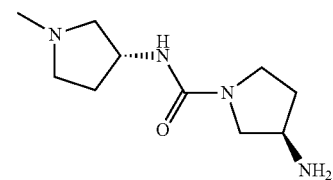 |
| 180 | 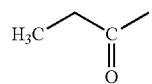 | 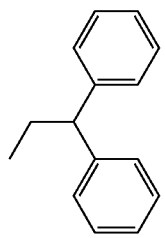 | 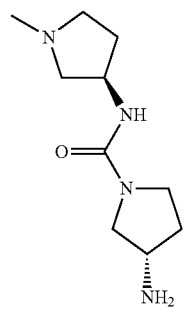 |
| 181 | 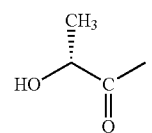 | 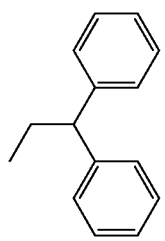 | 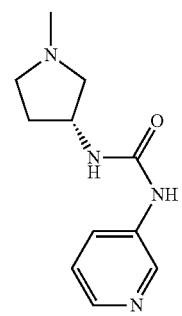 |
| 182 | 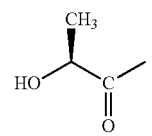 | 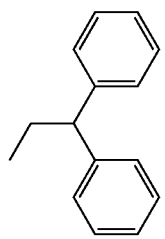 | 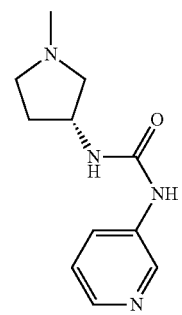 |
| 183 | 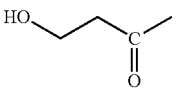 | 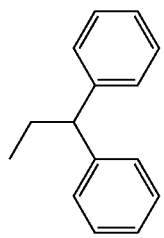 | 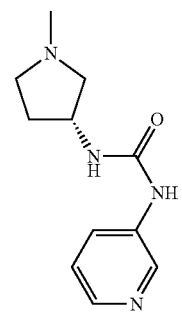 |

TABLE 1-continued
| 184 | 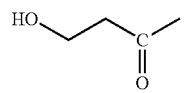 | 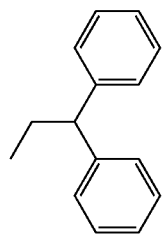 | 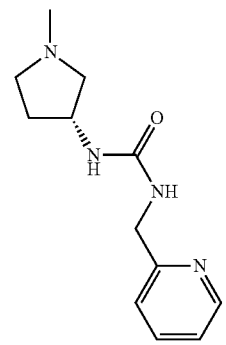 |
| 185 | 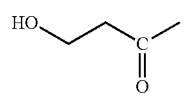 | 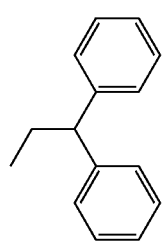 | 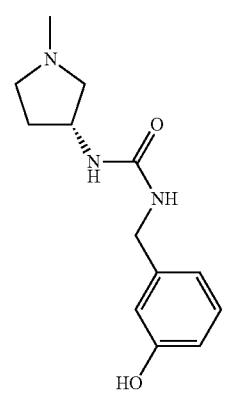 |
| 186 | 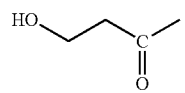 | 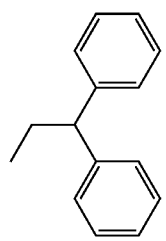 | 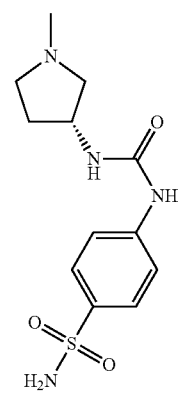 |
| 187 | 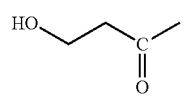 | 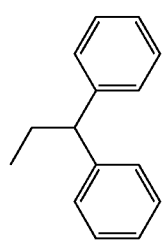 | 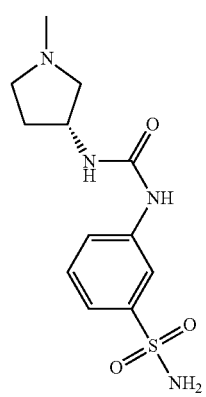 |

TABLE 1-continued
| 188 | 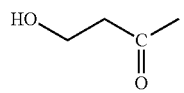 | 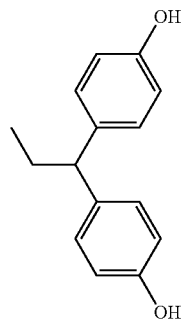 | 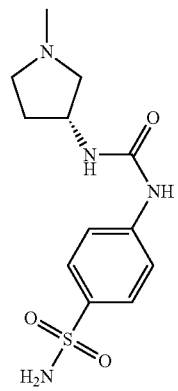 |
| 189 | 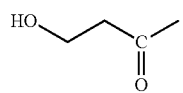 | 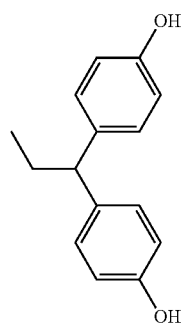 | 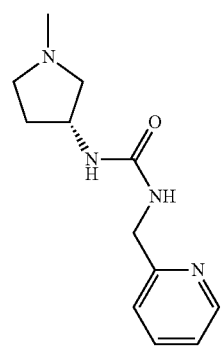 |
| 190 | 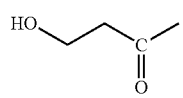 | 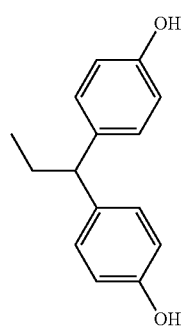 | 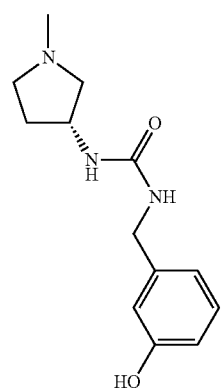 |
| 191 | 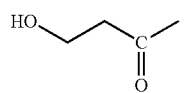 | 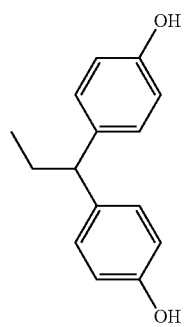 | 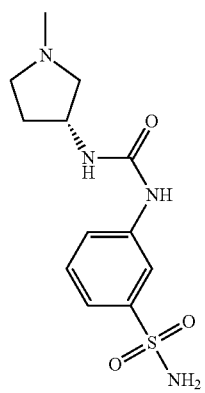 |

TABLE 1-continued
| 192 | 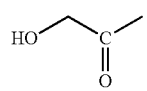 | 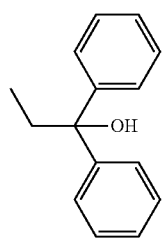 | 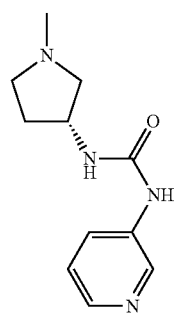 |
| --- | --- | --- | --- |
| 193 | 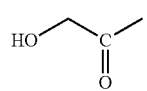 | 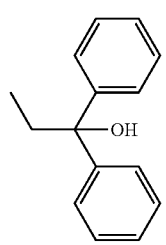 | 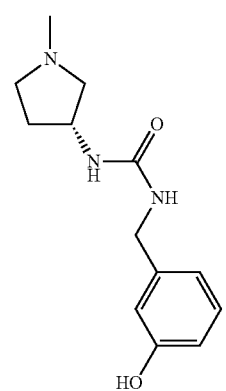 |
| 194 | 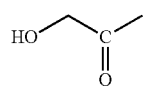 | 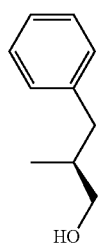 | 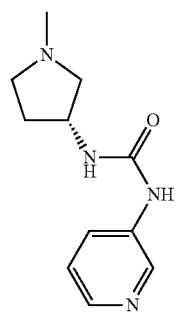 |
| 195 | 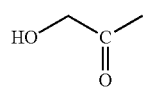 | 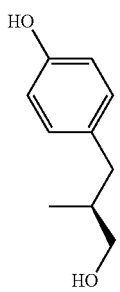 | 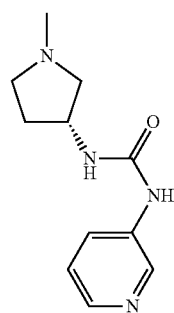 |

TABLE 1-continued
| 196 | 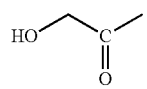 | 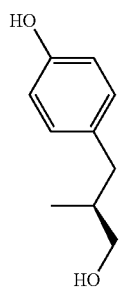 | 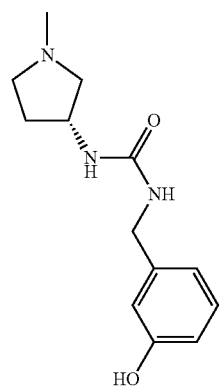 |
| 197 | 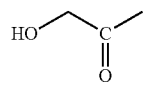 | 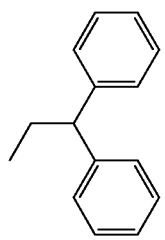 | 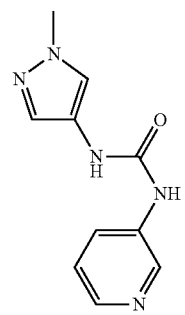 |
| 198 | 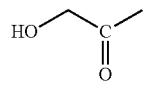 | 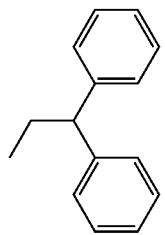 | 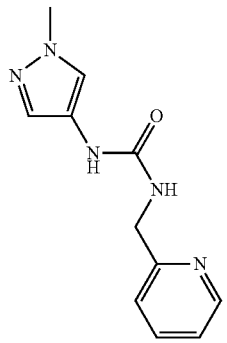 |
| 199 | 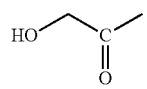 | 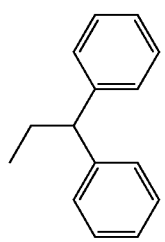 | 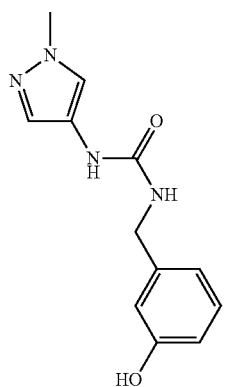 |

TABLE 1-continued
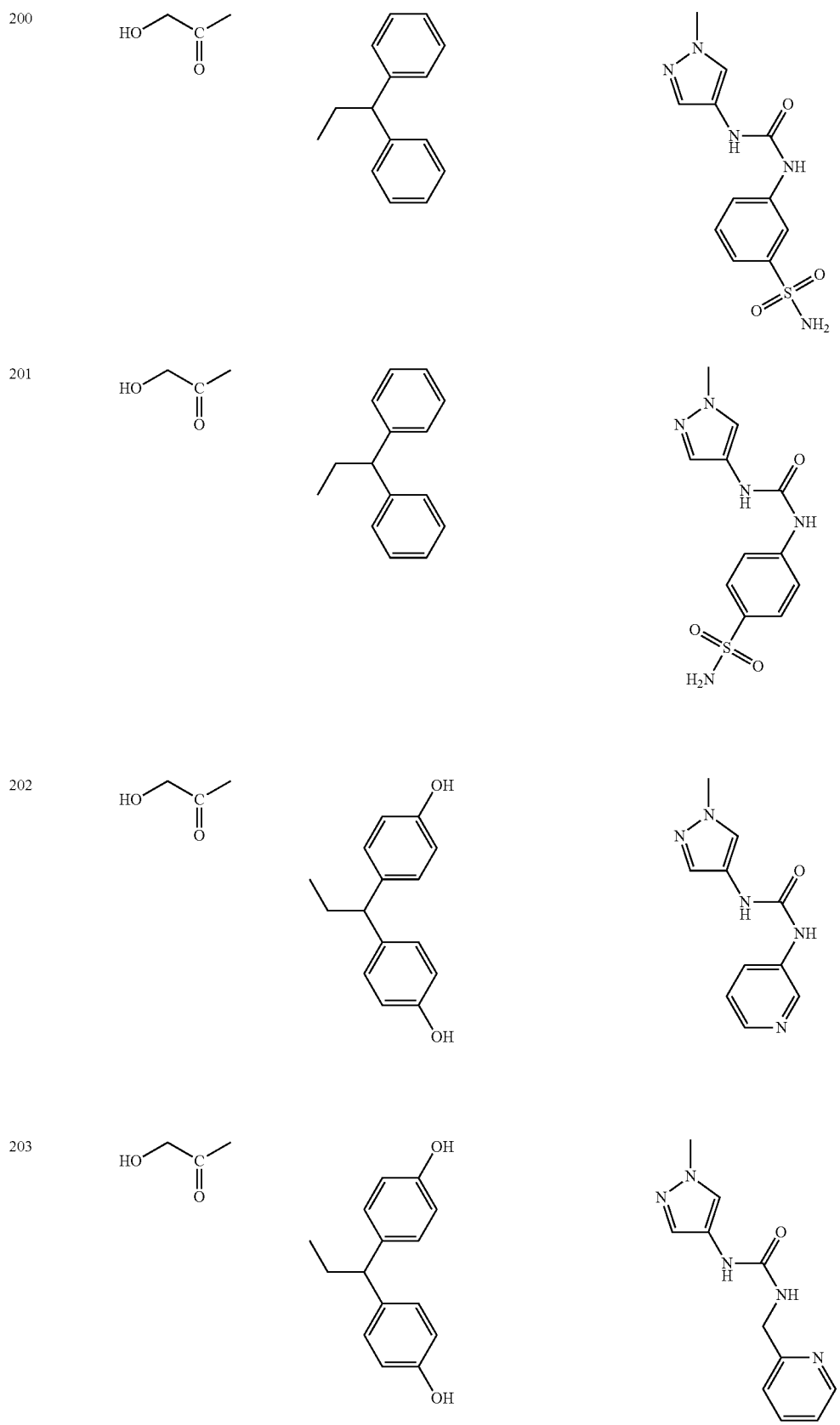

TABLE 1-continued
| 204 | 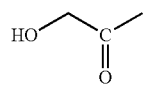 | 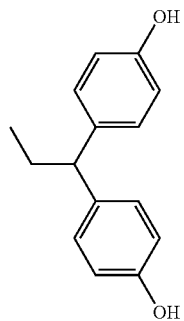 | 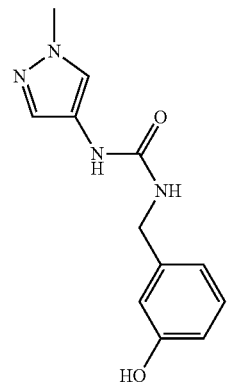 |
| 205 | 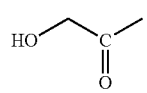 | 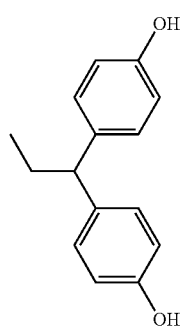 | 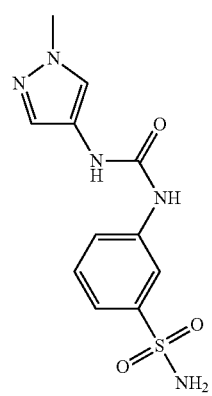 |
| 206 | 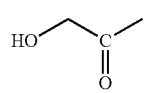 | 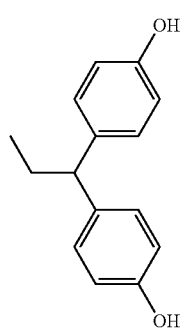 | 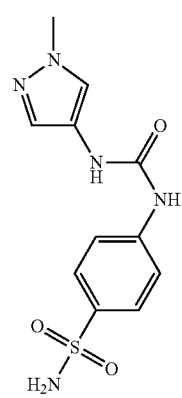 |
| 207 | 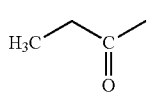 | 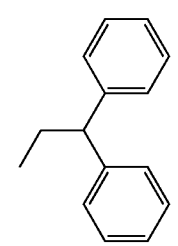 | 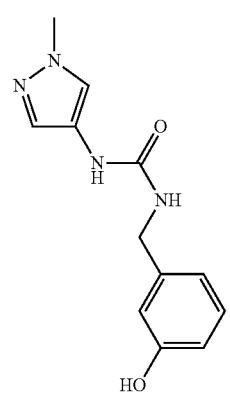 |

TABLE 1-continued
| | | | |
|---|---|---|---|
| 208 | 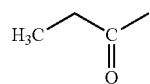 | 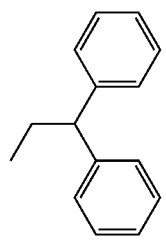 | 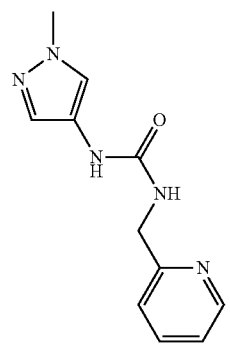 |
| 209 | 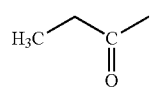 | 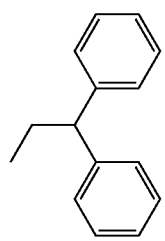 | 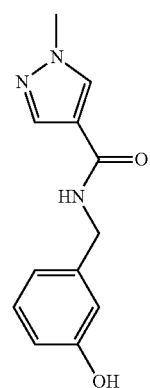 |
| 210 | 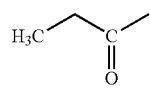 | 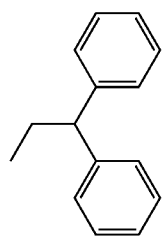 | 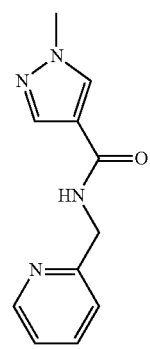 |
| 211 | 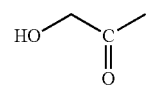 | 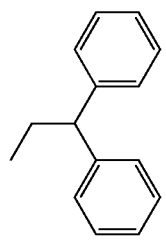 | 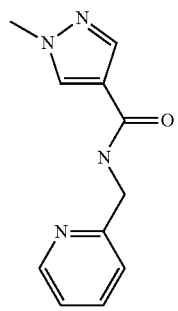 |

TABLE 1-continued
| 212 | 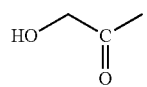 | 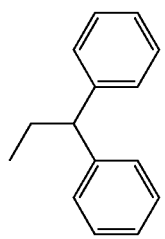 | 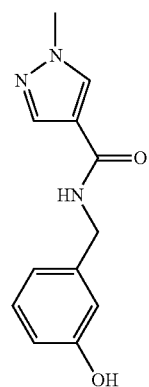 |
| 213 | 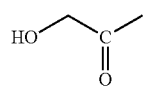 | 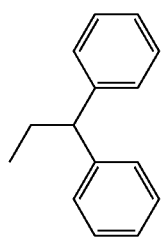 | 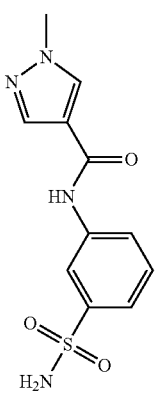 |
| 214 | 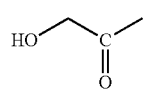 | 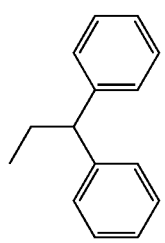 | 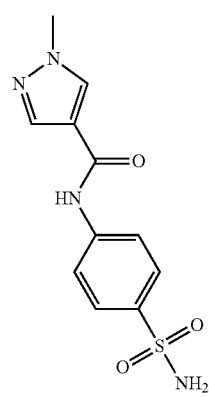 |
| 215 | 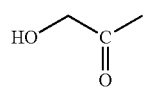 | 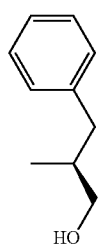 | 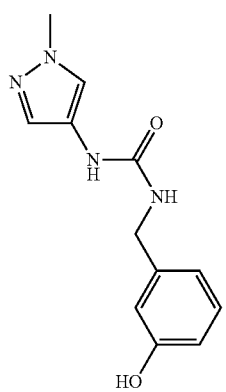 |

TABLE 1-continued
| | | | |
|---|---|---|---|
| 216 | 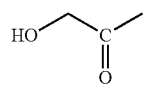 | 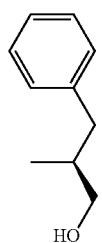 | 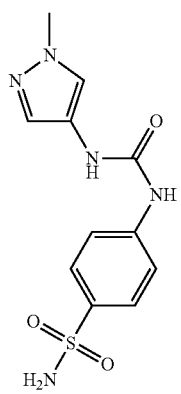 |
| 217 | 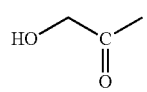 | 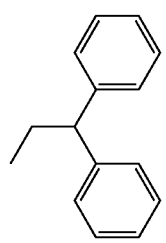 | 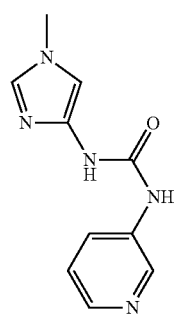 |
| 218 | 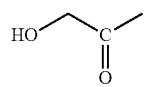 | 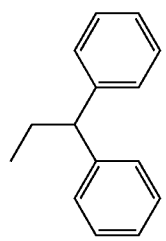 | 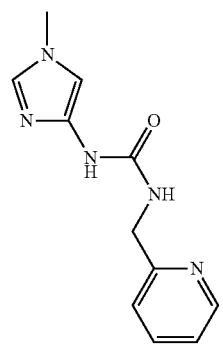 |
| 219 | 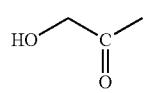 | 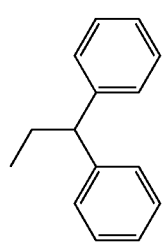 | 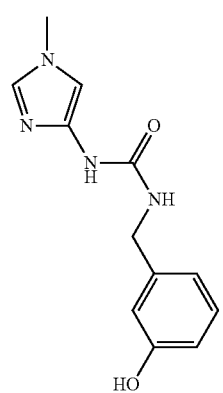 |

TABLE 1-continued
| 220 | 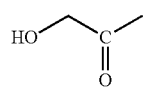 | 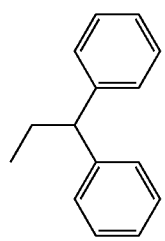 | 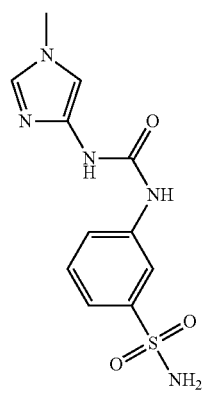 |
| --- | --- | --- | --- |
| 221 | 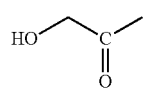 | 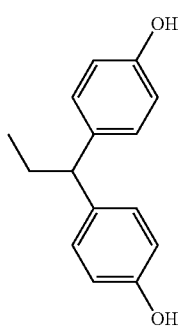 | 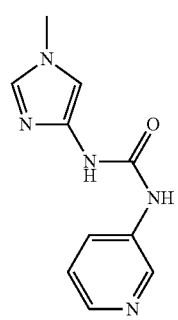 |
| 222 | 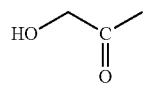 | 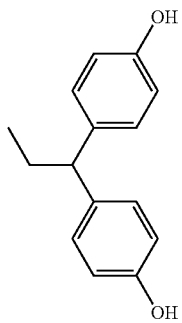 | 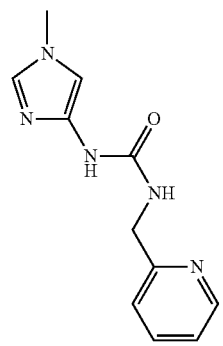 |
| 223 | 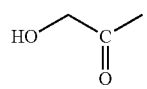 | 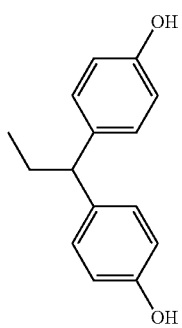 | 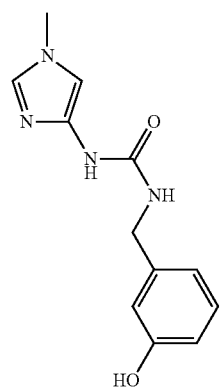 |

TABLE 1-continued
| | | | |
|---|---|---|---|
| 224 | 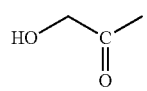 | 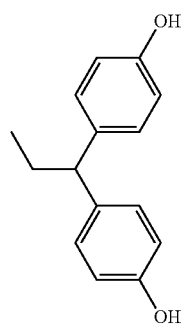 | 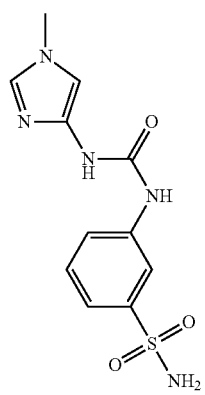 |
| 225 | 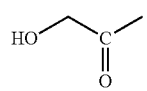 | 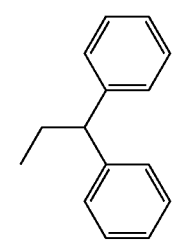 | 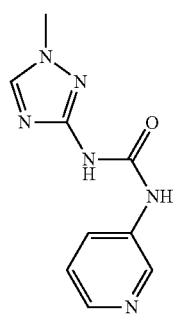 |
| 226 | 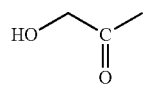 | 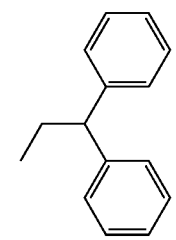 | 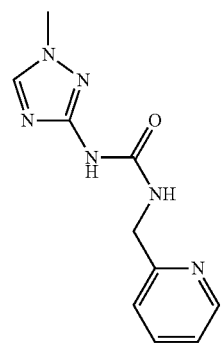 |
| 227 | 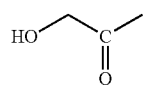 | 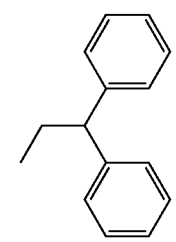 | 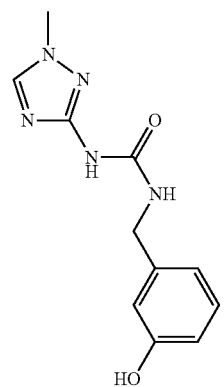 |

| 228 | 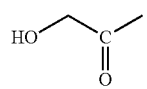 | 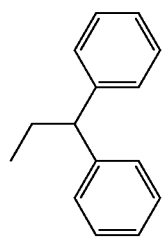 | 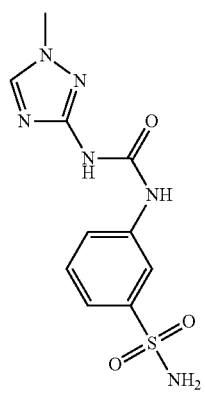 |
| --- | --- | --- | --- |
| 229 | 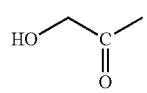 | 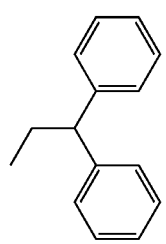 |  |
| 230 | 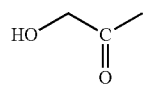 | 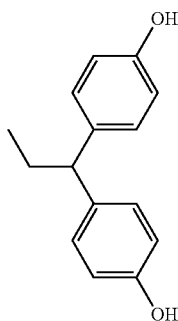 | 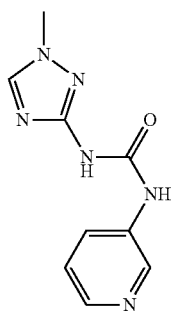 |
| 231 | 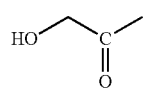 | 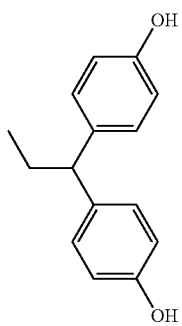 | 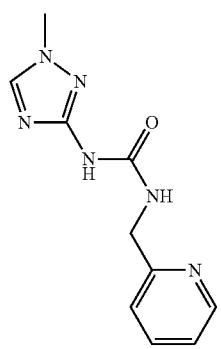 |

TABLE 1-continued
| | | | |
|---|---|---|---|
| 232 | 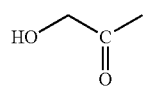 | 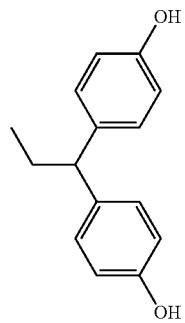 | 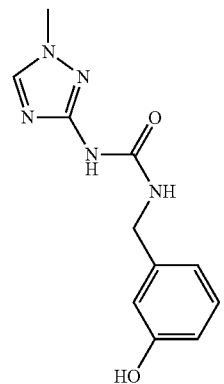 |
| 233 | 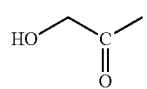 | 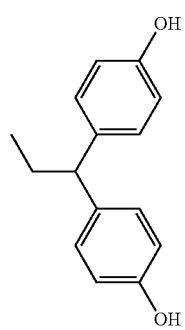 | 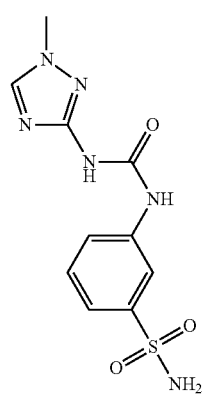 |
| 234 | 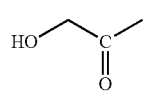 | 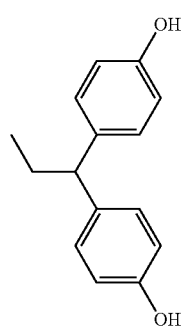 | 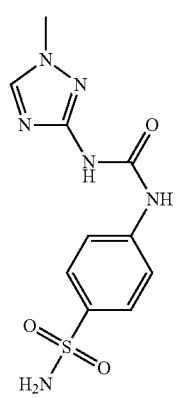 |
| 235 | 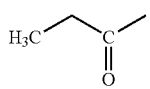 | 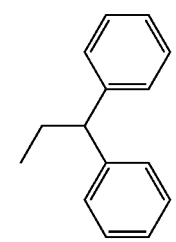 | 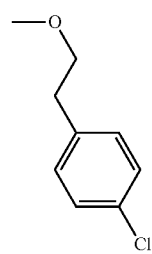 |

TABLE 1-continued

| Example | R1 | R2 | R3 |
|---|---|---|---|
| 236 | (ethyl methyl ketone) | 1,1-diphenylpropyl | methyl 4-(prop-2-yn-1-yl)cyclohexane-1-carboxylate |
| Example | R1 | R2 | R3 |
| 237 | 1-(pyridin-2-yl)ethan-1-one | 1,1-diphenylpropyl | 1-((1-methylpyrrolidin-3-yl))-3-(pyridin-3-yl)urea |
| 238 | 1-(tetrahydro-2H-pyran-4-yl)ethan-1-one | 1,1-diphenylpropyl | 1-((1-methylpyrrolidin-3-yl))-3-(pyridin-3-yl)urea |
| 239 | 4-methoxybutan-2-one | 1,1-diphenylpropyl | 1-((1-methylpyrrolidin-3-yl))-3-(pyridin-3-yl)urea |
| 240 | 1-(isoxazol-5-yl)ethan-1-one | 1,1-diphenylpropyl | 1-((1-methylpyrrolidin-3-yl))-3-(pyridin-3-yl)urea |

TABLE 1-continued
| | | | |
|---|---|---|---|
| 241 | 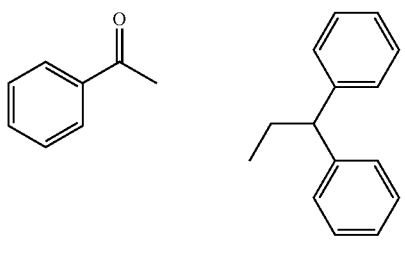 | | |
| 242 | 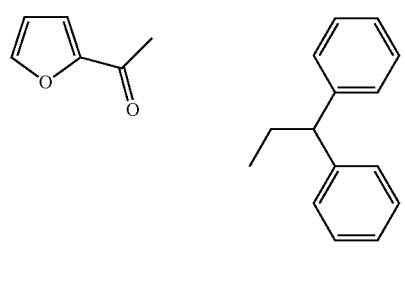 | | |
| 243 | 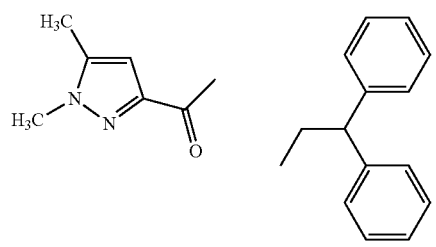 | | |
| 244 | 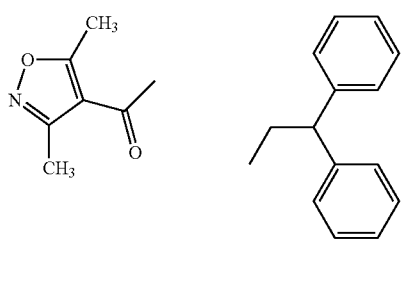 | | |
| 245 | 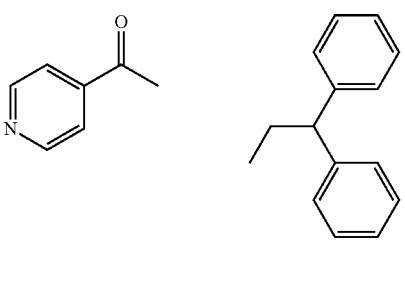 | | |

TABLE 1-continued
| | | | |
|---|---|---|---|
| 246 | 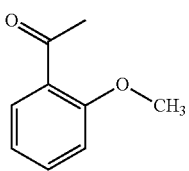 | 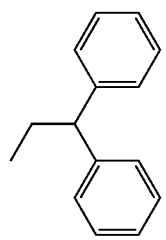 | 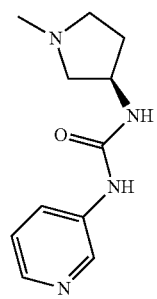 |
| 247 | 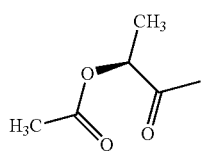 | 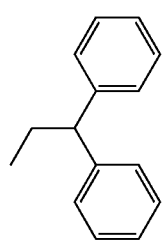 | 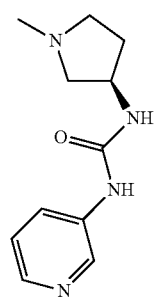 |
| 248 | 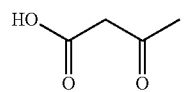 | 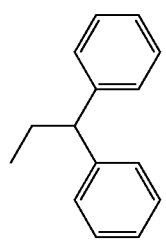 | 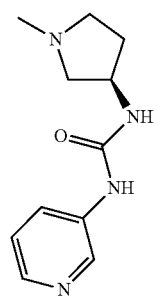 |
| 249 | 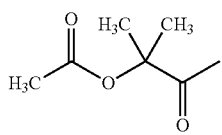 | 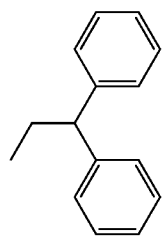 | 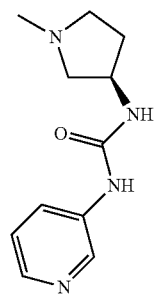 |
| 250 | 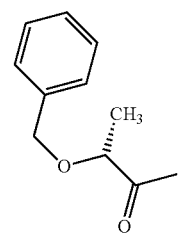 | 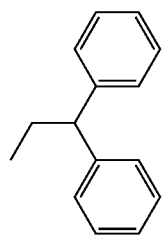 | 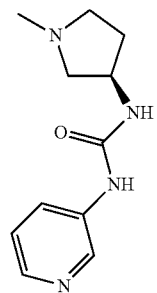 |

US 8,318,750 B2
TABLE 1-continued
| | | | |
|---|---|---|---|
| 251 | 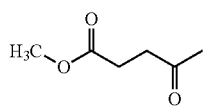 | 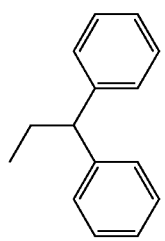 | 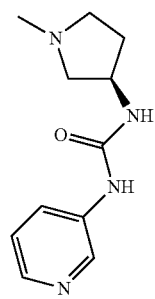 |
| 252 | 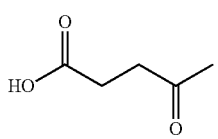 | 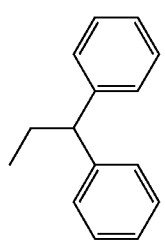 | 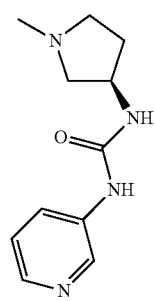 |
| 253 | 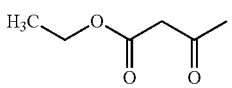 | 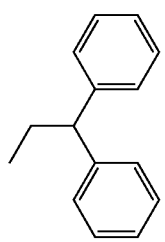 | 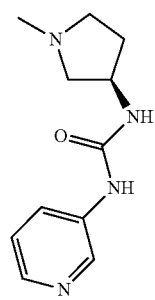 |
| 254 | 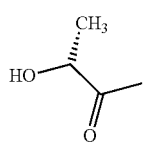 | 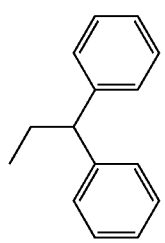 | 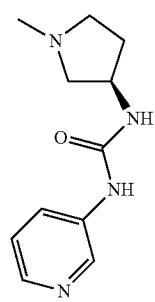 |
| 255 | 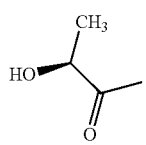 | 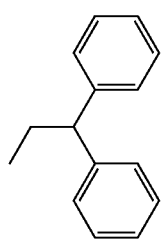 | 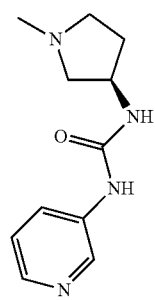 |

US 8,318,750 B2
TABLE 1-continued
| 256 | 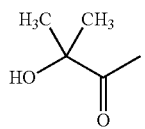 | 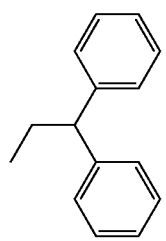 | 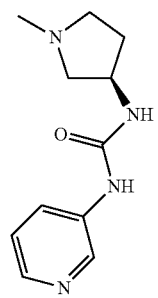 |
| 257 | 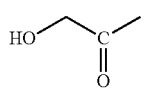 | 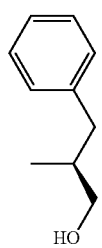 | 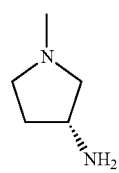 |
| 258 | 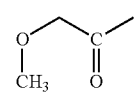 | 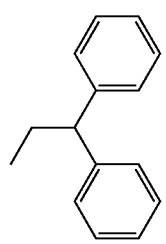 | 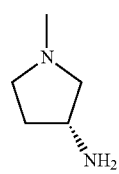 |
| 259 | 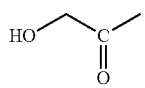 | 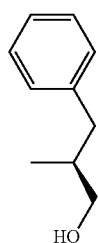 | 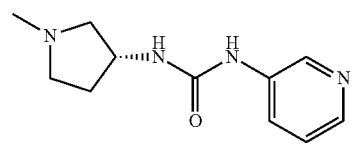 |
| 260 | 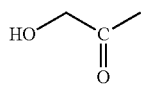 | 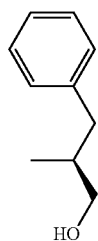 | 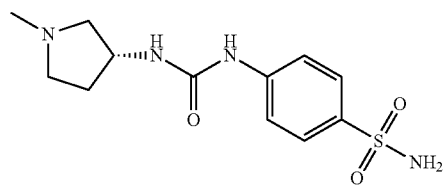 |
| 261 | 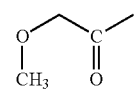 | 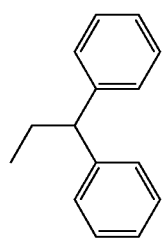 | 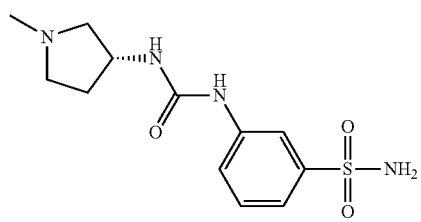 |

TABLE 1-continued

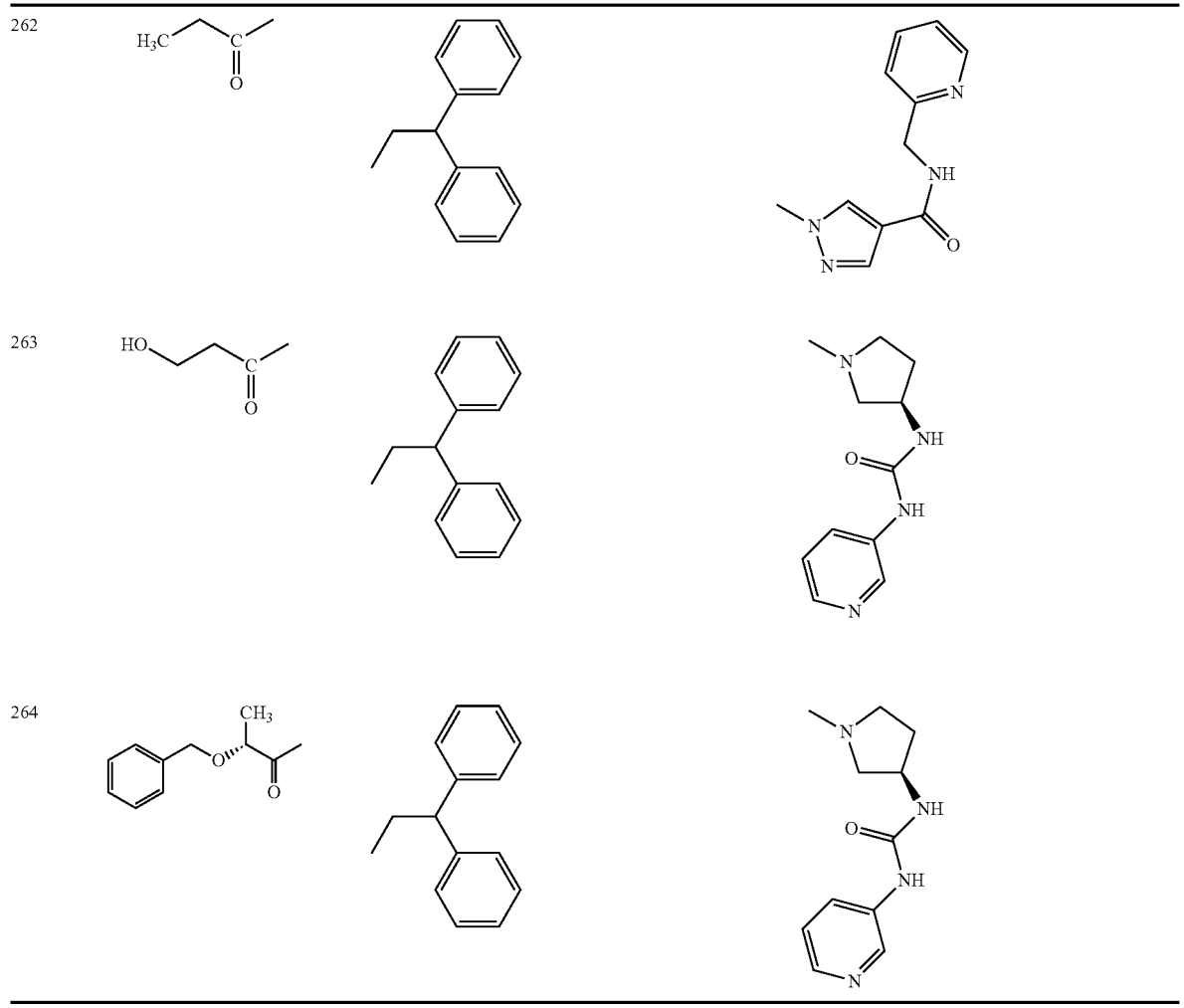

Preparation of Intermediate Compounds

Abbreviations used are as follows: CDI is 1,1'-carbonyldiimidazole, DCM is dichloromethane, DIPEA is diisopropylethylamine, DMAP is 4-dimethylaminopyridine, DMF is dimethyl-formamide, DMSO is dimethylsulfoxide, LCMS is liquid chromatographic mass spectroscopy, TEA is triethylamine, TFA is trifluoroacetic acid, THF is tetrahydrofuran, EtOH is ethanol, IPA is iso-propylalcohol and TLC is thin-layer chromatography.

Intermediate A 1-(R)-Pyrrolidin-3-yl-3-(3,4,5,6-tetrahydro-2H-[1,2']bipyridinyl-4-yl)-urea hydrochloride A1: Imidazole-1-carboxylic acid (3,4,5,6-tetrahydro-2H-[1,2']bipyridinyl-4-yl)-amide A suspension comprising CDI (2.29 g, 14 mmol) and triethylamine (3.8 ml, 27 mmol) in dry DCM (20 ml) is treated portionwise over 5 minutes with 3,4,5,6-tetrahydro-2H-[1,2'] bipyridinyl-4-ylamine dihydrochloride (prepared using the procedure described in international patent application WO 01/94368) (2.88 g, 13 mmol). The reaction mixture is stirred at room temperature for 4.5 hours to yield the title compound as a 0.43 M solution in DCM.

A2: (R)-3-[3-(3,4,5,6-Tetrahydro-2H-[1,2']bipyridinyl-4-yl)-ureido]-pyrrolidine-1-carboxylic acid tert-butyl ester trifluoroacetate To a solution of imidazole-1-carboxylic acid (3,4,5,6-tetrahydro-2H-[1,2']bipyridinyl-4-yl)-amide (18 ml of a 10 mg/ml solution in DCM)(A1) is added (R)-3-amino-1-N-Boc-pyrrolidine (136 mg, 0.74 mmol) in iso-propanol (3 ml). The reaction mixture is stirred at room temperature overnight and then diluted with DCM (25 ml). This mixture is washed with 0.1 M HCl, water, brine, dried (MgSO$_4$) and concentrated in vacuo. Purification of the crude residue by C-18 reverse phase column chromatography eluting with acetonitrile:water:TFA (0.1%) (gradient of 0 to 100% acetonitrile) yields the title compound.

A3: 1-(R)-Pyrrolidin-3-yl-3-(3,4,5,6-tetrahydro-2H-[1,2']bipyridinyl-4-yl)-urea hydrochloride A solution of (R)-3-[3-(3,4,5,6-tetrahydro-2H-[1,2']bipyridinyl-4-yl)-ureido]-pyrrolidine-1-carboxylic acid tert-butyl ester trifluoroacetate (0.2 g, 0.51 mmol) in 1.25 M HCl in MeOH (10 ml) is stirred at room temperature over night. The solvent was removed in vacuo to yield the title compound.

Intermediate B

1,3-Di(R)-pyrrolidin-3-yl-urea

B1: 1,3-Bis-((R)-1-benzyl-pyrrolidin-3-yl)-urea

A solution comprising (R)-1-benzyl-pyrrolidin-3-ylamine (5.0 g, 28.4 mmol) in DCM (10 ml) is treated with CDI (2.3 g, 14.2 mmol) and the reaction mixture is stirred at room temperature for 48 hours. The solvent is removed in vacuo and the resulting residue is dissolved in ethyl acetate. This portion is washed with water followed by brine, dried ($MgSO_4$) and concentrated in vacuo to yield the title compound as pale orange solid.

B2: 1,3-Di(R)-pyrrolidin-3-yl-urea

To a solution of 1,3-bis-((R)-1-benzyl-pyrrolidin-3-yl)-urea (5.34 g, 14.1 mmol) in ethanol (80 ml) under an inert atmosphere of Argon is added palladium hydroxide on carbon (1.07 g). The reaction mixture is purged with Argon and placed under an atmosphere of hydrogen for two days after which time, the mixture is filtered and the catalyst washed with ethanol. The organic portions are combined and concentrated in vacuo to yield the title compound as a white solid.

Intermediate C

Imidazole-1-carboxylic acid (3,4,5,6-tetrahydro-2H-[1,2']bipyridinyl-4-yl)-amide A stirred solution of CDI (1.1 g, 6.77 mmol) in DCM (100 ml) is treated with 3,4,5,6-tetrahydro-2H-[1,2']bipyridinyl-4-ylamine (WO 9965895 EP 21973) (1 g, 5.64 mmol in 50 ml of DCM) added dropwise over 30 minutes. The reaction mixture is stirred at room temperature for 15 minutes to yield the title compound as a 10 mg/ml solution in DCM. The compound is used in solution in subsequent reactions. This solution consists of the imidazole-urea (Intermediate C) together with variable amounts of the corresponding isocyanate and imidazole. This solution is used in the subsequent steps since the imidazole-urea intermediate and isocyanate intermediate are equally suitable as precursors to ureas.

Intermediate D

(2S,3S,4R,5R)-5-[2-Amino-6-(2,2-diphenyl-ethylamino)-purin-9-yl]-3,4-dihydroxy-tetrahydro-furan-2-carboxylic acid ethylamide

Step D1: (3aS,4S,6R,6aR)-6-[2-Chloro-6-(2,2-diphenyl-ethylamino)-purin-9-yl]-2,2-dimethyl-tetrahydro-furo[3,4-d][1,3]dioxole-4-carboxylic acid ethylamide The title compound is prepared by the procedure of Preparation of aminopurine-b-D-ribofuranuronamide derivatives as antiinflammatories. Di Ayres, Barry Edward; Gregson, Michael; Ewan, George Blanch; Keeling, Suzanne Elaine; Bell, Richard. (Glaxo Group Limited, UK). PCT Int. Appl. (1996), 49 pp. WO 9602553.

Step D2: (2S,3S,4R,5R)-5-[2-Chloro-6-(2,2-diphenyl-ethylamino)-purin-9-yl]-3,4-dihydroxy-tetrahydro-furan-2-carboxylic acid ethylamide A solution of (3aS,4S,6R,6aR)-6-[2-Chloro-6-(2,2-diphenyl-ethylamino)-purin-9-yl]-2,2-dimethyl-tetrahydro-furo[3,4-d][1,3]dioxole-4-carboxylic acid ethylamide (Step D1) in TFA/water (2:1) is stirred at RT overnight. The reaction mixture is concentrated in vacuo to afford the titled compound.

Intermediate E

(2S,3S,4R,5R)-5-[2-((R)-3-Amino-pyrrolidin-1-yl)-6-(2,2-diphenyl-ethylamino)-purin-9-yl]-3,4-dihydroxy-tetrahydro-furan-2-carboxylic acid ethylamide trifluoroacetate

Step E1: (2S,3S,4R,5R)-5-[6-(2,2-Diphenyl-ethylamino)-2-(R)-3-BOC-amino-pyrrolidin-1-yl)-purin-9-yl]-3,4-dihydroxy-tetrahydro-furan-2-carboxylic acid ethylamide (2S,3S,4R,5R)-5-[2-Chloro-6-(2,2-diphenyl-ethylamino)-purin-9-yl]-3,4-dihydroxy-tetrahydro-furan-2-carboxylic acid ethylamide (Intermediate D) (1 g, 1.91 mmol), (3R)-3-(BOC-amino)pyrrolidine (1.068 g, 5.74 mmol) and sodium iodide (287 mg, 1.91 mmol) is dissolved in acetonitrile (10 ml) and NMP (0.5 ml). The reaction mixture is heated using microwave radiation at 160° C. for 30 minutes in the Personal Chemistry Emrys™ Optimizer microwave reactor. The reaction mixture is concentrated in vacuo and purified by C-18 reverse phase column chromatography eluting with acetonitrile:water (0.1% TFA) (gradient 0-100% acetonitrile) to afford the titled compound.

Step E2: (2S,3S,4R,5R)-5-[2-((R)-3-Amino-pyrrolidin-1-yl)-6-(2,2-diphenyl-ethylamino)-purin-9-yl]-3,4-dihydroxy-tetrahydro-furan-2-carboxylic acid ethylamide trifluoroacetate (2S,3S,4R,5R)-5-[6-(2,2-Diphenyl-ethylamino)-2-((R)-3-BOC-amino-pyrrolidin-1-yl)-purin-9-yl]-3,4-dihydroxy-tetrahydro-furan-2-carboxylic acid ethylamide (step E1) is dissolved in DCM and TFA and stirred at RT overnight. The reaction mixture is concentrated in vacuo to afford the titled compound.

Intermediate F

[4-(2-Amino-ethyl)-imidazol-1-yl]-acetic acid cyclohexyl ester

F1: [4-(2-Amino-ethyl)-imidazol-1-yl]-acetic acid methyl ester sulphate

A solution comprising [4-(2-amino-ethyl)-imidazol-1-yl]-acetic acid (prepared according to the procedure of Jain, Rahul; Cohen, Louis A. Regiospecific alkylation of histidine and histamine at N-1. Tetrahedron (1996), 52(15), 5363-70) (7.6 g, 44.8 mmol) in methanol (100 ml) is treated with concentrated sulphuric acid (3 drops) and heated to reflux for 18 hours. Molecular sieves are added to the reaction mixture which is refluxed for a further 3 days. The mixture is filtered and concentrated in vacuo. The solid is taken up in water and basified to pH10 using sodium hydroxide. The solution is extracted with DCM using a continuous liquid-liquid extraction system to yield the title product.

F2: [4-(2-Amino-ethyl)-imidazol-1-yl]-acetic acid cyclohexyl ester sulphate

[4-(2-Amino-ethyl)-imidazol-1-yl]-acetic acid methyl ester sulphate (1 g, 3.6 mmol) is suspended in cyclohexanol (50 ml) and treated with concentrated sulphuric acid (5 drops). The reaction mixture is heated to 110° C. for 4 hours and concentrated in vacuo. The residue is dissolved in saturated sodium bicarbonate solution and the mixture is concentrated in vacuo. The resulting solid is triturated with methanol, filtered and the filtrate is reduced in vacuo. The crude solid is dissolved in water, washed with DCM and the aqueous portion is concentrated in vacuo to yield the title product.

Intermediate G

[(1S,2R,3S,4R)-4-(2,6-Dichloro-purin-9-yl)-2,3-dihydroxy-cyclopentyl]-propionyl-carbamic acid tert-butyl ester G1: (1S,4R)-4-(2,6-Dichloro-purin-9-yl)-cyclopent-2-enol 2,6-Dichloropurine (10 g, 52.90 mmol), (1S,4R)-cis 4-acetoxy-2-cyclopenten-1-ol (10 g. 70.40 mmol), tris(dibenzylideneacetone)dipalladium(0) (3.20 g, 3.50 mmol) and polymer supported triphenylphosphine (3 mmol/g, 11.60 g, 35.00 mmol) are placed in an oven-dried flask under an atmosphere of argon. Dry deoxygenated THF (80 ml) is added and the reaction mixture is stirred gently for 5 minutes. Triethylamine (20 ml) is added and the reaction mixture is stirred at 50° C. The reaction is shown to be complete by LCMS after 1 hour. The reaction mixture is allowed to cool, filtered and the solvent is removed in vacuo. The title compound is obtained after purification by flash column chromatography (silica, dichloromethane/methanol 25:1). $^1$H nmr (CDCl$_3$, 400 MHz); 8.30 (s, 1H), 6.40 (m, 1H), 5.90 (m, 1H), 5.50 (m, 1H), 4.95 (m, 1H), 3.05 (m, 1H), 2.10 (m, 1H), MS (ES+) m/e 271 (MH$^+$).

G2: Carbonic acid (1S,4R)-4-(2,6-dichloro-purin-9-yl)-cyclopent-2-enyl ester ethyl ester (1S,4R)-4-(2,6-Dichloro-purin-9-yl)-cyclopent-2-enol (9.5 g, 35.05 mmol) is placed in an oven-dried flask under an atmosphere of argon. Dry THF (200 mL) is added followed by dry pyridine (5.54 g, 70.1 mmol). Ethyl chloroformate (15.21 g, 140.2 mmol) is added slowly so that the temperature does not rise above 40° C. and the reaction mixture is stirred at room temperature. The reaction is shown to be complete by LCMS after 1 hour. The solvent is removed in vacuo and the residue is partitioned between dichloromethane (200 mL) and water (200 mL). The organic layer is washed with water (150 ml) and brine (150 ml), dried over MgSO$_4$, filtered and the solvent is removed in vacuo. The title compound is obtained after crystallisation from methanol. $^1$H nmr (CDCl$_3$, 400 MHz); 8.20 (s, 1H), 6.45 (m, 1H), 6.25 (m, 1H), 5.75 (m, 1H), 5.70 (m, 1H), 4.25 (q, 2H), 3.20 (m, 1H), 2.05 (m, 1H), 1.35 (t, 3H), MS (ES+) m/e 343 (MH$^+$).

G3: [(1S,4R)-4-(2,6-Dichloro-purin-9-yl)-cyclopent-2-enyl]-propionyl-carbamic acid tert-butyl ester Carbonic acid (1S,4R)-4-(2,6-dichloro-purin-9-yl)-cyclopent-2-enyl ester ethyl ester (1.00 g, 2.92 mmol), propionyl-carbamic acid tert-butyl ester (Intermediate W) (0.55 g, 3.21 mmol) and triphenylphosphine (0.115 g, 0.44 mmol) are placed under an inert atmosphere of Argon. THF (10 ml) is added followed by tris(dibenzylideneacetone)dipalladium(0) (0.13 g, 0.15 mmol). The reaction mixture is stirred at 50° C. for 1 hour. The solvent is removed in vacuo and purification by chromatography on silica eluting with EtOAc/hexane (1:4) affords the title product. $^1$H nmr (CDCl$_3$, 400 MHz); 8.70 (s, 1H), 6.15 (m, 1H), 5.85 (m, 1H), 5.80 (m, 1H), 5.60 (m, 1H), 3.15 (m, 1H), 2.75 (q, 2H), 2.10 (m, 1H), 1.55 (s, 9H), 1.15 (t, 3H), MS (ES+) m/e 426 (MH$^+$).

G4: [(1S,2R,3S,4R)-4-(2,6-Dichloro-purin-9-yl)-2,3-dihydroxy-cyclopentyl]-propionyl-carbamic acid tert-butyl ester

[(1S,4R)-4-(2,6-dichloro-purin-9-yl)-cyclopent-2-enyl]-propionyl-carbamic acid tert-butyl ester (11.37 g, 26.7 mmol), methanesulfonamide (2.54 g, 26.7 mmol) and AD-mix-α (55 g) are placed in a flash of water (100 ml) and t-butanol (100 ml). Osmium tetroxide (4% in water) is added and the reaction mixture is stirred vigorously at room temperature overnight. Sodium sulfite (40 g) is added and the mixture is stirred at room temperature for a further hour and then partitioned between EtOAc and water. The organic portion is separated, dried (MgSO$_4$) and concentrated in vacuo. The crude product is purified by chromatography on silica eluting with DCM:MeOH (25:1 increasing to 10:1) to afford the title compound.

Intermediate H

4-[(Imidazole-1-carbonyl)-amino]-piperidine-1-carboxylic acid (3,4,5,6-tetrahydro-2H-[1,2']bipyridinyl-4-yl)-amide H1: [1-(3,4,5,6-Tetrahydro-2H-[1,2']bipyridinyl-4-ylcarbamoyl)-piperidin-4-yl]-carbamic acid tert-butyl ester To a suspension of 4-N-Boc-amino-piperidine (0.396 g, 1.85 mmol) in iso-propanol (5 ml) is added imidazole-1-carboxylic acid (3,4,5,6-tetrahydro-2H-[1,2']bipyridinyl-4-yl)-amide (50 ml of a 10 mg/ml solution in DCM, 1.85 mmol) and the reaction mixture is stirred at room temperature overnight. The solvent is removed in vacuo and recrystallisation of the solid from methanol yields the title product.

H2: 4-Amino-piperidine-1-carboxylic acid (3,4,5,6-tetrahydro-2H-[1,2']bipyridinyl-4-yl)-amide dihydrochloride

[1-(3,4,5,6-Tetrahydro-2H-[1,2']bipyridinyl-4-ylcarbamoyl)-piperidin-4-yl]-carbamic acid tert-butyl ester (0.45 g, 1.12 mmol) is treated with 4 M HCl (in dioxane)(2.5 ml) and methanol (1 ml, co-solvent) and the reaction mixture is allowed to stir at room temperature for 1 hour. The solvent is removed in vacuo and the resulting solid is dried in a vacuum oven to yield the title product.

H3: 4-[(Imidazole-1-carbonyl)-amino]-piperidine-1-carboxylic acid (3,4,5,6-tetrahydro-2H-[1,2']bipyridinyl-4-yl)-amide The title product is prepared analogously to imidazole-1-carboxylic acid (3,4,5,6-tetrahydro-2H-[1,2']bipyridinyl-4-yl)-amide (Intermediate A1) by replacing 3,4,5,6-tetrahydro-2H-[1,2']bipyridinyl-4-ylamine dihydrochloride with 4-amino-piperidine-1-carboxylic acid (3,4,5,6-tetrahydro-2H-[1,2']bipyridinyl-4-yl)-amide dihydrochloride (Intermediate H2).

Intermediate I

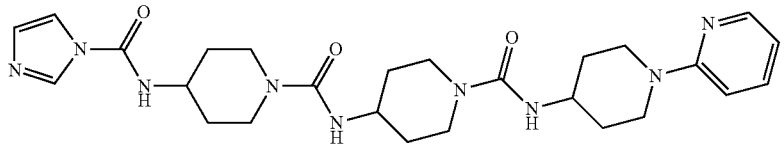

This compound is prepared analogously to 4-[(imidazole-1-carbonyl)-amino]-piperidine-1-carboxylic acid (3,4,5,6-tetrahydro-2H-[1,2']bipyridinyl-4-yl)-amide (Intermediate H) by replacing imidazole-1-carboxylic acid (3,4,5,6-tetrahydro-2H-[1,2']bipyridinyl-4-yl)-amide with 4-[(imidazole-1-carbonyl)-amino]-piperidine-1-carboxylic acid (3,4,5,6-tetrahydro-2H-[1,2']bipyridinyl-4-yl)-amide.

Intermediate J

N-{(1S,2R,3S,4R)-4-[2-Chloro-6-(2,2-diphenyl-ethylamino)-purin-9-yl]-2,3-dihydroxy-cyclopentyl}-propionamide J1: (1S,4R)-4-(2,6-Dichloro-purin-9-yl)-cyclopent-2-enol 2,6-Dichloropurine (10 g, 52.90 mmol), (1S,4R)-cis 4-acetoxy-2-cyclopenten-1-ol (10 g. 70.40 mmol), tris(dibenzylideneacetone)dipalladium(0) (3.20 g, 3.50 mmol) and polymer supported triphenylphosphine (3 mmol/g, 11.60 g, 35.00 mmol) are placed in an oven-dried flask under an atmosphere of argon. Dry deoxygenated THF (80 ml) is added and the reaction mixture is stirred gently for 5 minutes. Triethylamine (20 ml) is added and the reaction mixture is stirred at 50° C. The reaction is shown to be complete by LCMS after 1 hour. The reaction mixture is allowed to cool, filtered and the solvent is removed in vacuo. The title compound is obtained after purification by flash column chromatography (silica, dichloromethane/methanol 25:1). $^1$H nmr (CDCl$_3$, 400 MHz); 8.30 (s, 1H), 6.40 (m, 1H), 5.90 (m, 1H), 5.50 (m, 1H), 4.95 (m, 1H), 3.05 (m, 1H), 2.10 (m, 1H), MS (ES+) m/e 271 (MH$^+$).

J2: Carbonic acid (1S,4R)-4-(2,6-dichloro-purin-9-yl)-cyclopent-2-enyl ester ethyl ester (1S,4R)-4-(2,6-Dichloro-purin-9-yl)-cyclopent-2-enol (9.5 g, 35.05 mmol) is placed in an oven-dried flask under an atmosphere of argon. Dry THF (200 mL) is added followed by dry pyridine (5.54 g, 70.1 mmol). Ethyl chloroformate (15.21 g, 140.2 mmol) is added slowly so that the temperature does not rise above 40° C. and the reaction mixture is stirred at room temperature. The reaction is shown to be complete by LCMS after 1 hour. The solvent is removed in vacuo and the residue is partitioned between dichloromethane (200 mL) and water (200 mL). The organic layer is washed with water (150 ml) and brine (150 ml), dried over MgSO$_4$, filtered and the solvent is removed in vacuo. The title compound is obtained after crystallisation from methanol. $^1$H nmr (CDCl$_3$, 400 MHz); 8.20 (s, 1H), 6.45 (m, 1H), 6.25 (m, 1H), 5.75 (m, 1H), 5.70 (m, 1H), 4.25 (q, 2H), 3.20 (m, 1H), 2.05 (m, 1H), 1.35 (t, 3H), MS (ES+) m/e 343 (MH$^+$).

J3: Di-Boc-[(1S,4R)-4-(2,6-dichloro-purin-9-yl)-cyclopent-2-enyl]-amine

Carbonic acid (1S,4R)-4-(2,6-dichloro-purin-9-yl)-cyclopent-2-enyl ester ethyl ester (2.5 g, 7.29 mmol), di-t-butyl iminodicarboxylate (1.74 g, 8.02 mmol), tris(dibenzylideneacetone)dipalladium(0) (0.33 g, 0.36 mmol) and triphenylphosphine (0.29 g, 1.09 mmol) are placed in an oven-dried flask under an atmosphere of argon. Dry deoxygenated THF (30 ml) is added and the reaction mixture is stirred at room temperature. The reaction is shown to be complete by LCMS after 3 hours. The solvent is removed in vacuo and the title compound is obtained after purification by flash column chromatography (silica, ethyl acetate/isohexane 4:1) $^1$H nmr (CDCl$_3$, 400 MHz); 8.70 (s, 1H), 6.20 (m, 1H), 5.85 (m, 1H), 5.80 (m, 1H), 5.40 (m, 1H), 3.20 (m, 1H), 2.15 (m, 1H), 1.55 (s, 18H), MS (ES+) m/e 470 (MH$^+$).

J4: (1S,2R,3S,5R)-3-(Di-Boc-amino)-5-(2,6-dichloro-purin-9-yl)-cyclopentane-1,2-diol The title compound is prepared from di-Boc-[(1S,4R)-4-(2,6-dichloro-purin-9-yl)-cyclopent-2-enyl]-amine using a procedure analogous to that use to prepare (1R,2S,3R,5S)-3-(6-{[bis-(4-methoxy-phenyl)-methyl]-amino}-2-chloro-purin-9-yl)-5-(di-Boc-amino)-cyclopentane-1,2-diol (Intermediate in the preparation of Intermediate ZA). $^1$H nmr (CDCl$_3$, 400 MHz); 8.35 (s, 1H), 4.80 (m, 1H), 4.70 (m, 1H), 4.50 (m, 1H), 3.85 (m, 1H), 3.75 (m, 1H), 3.10 (m, 1H), 2.75 (m, 1H), 2.55 (m, 1H), 1.55 (s, 18H), MS (ES+) m/e 504 (MH$^+$).

J5: (1S,2R,3S,5R)-3-Amino-5-(2,6-dichloro-purin-9-yl)-cyclopentane-1,2-diol trifluoroacetate A solution of (1S,2R,3S,5R)-3-(Di-Boc-amino)-5-(2,6-dichloro-purin-9-yl)-cyclopentane-1,2-diol (0.550 g, 1.09 mmol) in DCM (4 ml) is treated with TFA (2 ml) and stirred at room temperature for 2 hours. The solvent is removed in vacuo and afford the title product which is used in the next step without further purification. MS (ES+) m/e 304 (MH$^+$).

J6: N-[(1S,2R,3S,4R)-4-(2,6-Dichloro-purin-9-yl)-2,3-dihydroxy-cyclopentyl]-propionamide A solution of 1S,2R,3S,5R)-3-amino-5-(2,6-dichloro-purin-9-yl)-cyclopentane-1,2-diol trifluoroacetate (0.304 g, 1.00 mmol) in THF (10 ml) is treated with DIPEA (0.387 g, 3.00 mmol) followed by propionyl chloride (0.093 g, 1.00 mmol). The reaction mixture is stirred at room temperature for 2 hours. The solvent is removed in vacuo and the title compound is obtained after purification by reverse phase column chromatography (Isolute™ C18, 0-100% acetonitrile in water −0.1% TFA). MS (ES+) m/e 360 (MH$^+$).

J7: N-{(1S,2R,3S,4R)-4-[2-Chloro-6-(2,2-diphenyl-ethylamino)-purin-9-yl]-2,3-dihydroxy-cyclopentyl}-propionamide N-[(1S,2R,3S,4R)-4-(2,6-Dichloro-purin-9-yl)-2,3-dihydroxy-cyclopentyl]-propionamide (160 mg, 0.44 mmol) is dissolved in THF (5 ml) under an atmosphere of argon. Diisopropylamine (69 mg, 0.53 mmol) is added followed by 2,2-diphenylethylamine (96 mg, 0.49 mmol) and the reaction mixture is stirred at 50° C. The reaction is shown to be complete by LCMS after 2 hours. The solvent is removed in vacuo and the title compound is obtained after purification by reverse phase column chromatography (Isolute™ C18, 0-100% acetonitrile in water −0.1% TFA). $^1$H nmr (MeOD, 400 MHz); 8.00 (s, 1H), 7.40-7.15 (m, 10H), 4.75 (m, 1H), 4.60 (m, 1H), 4.50 (m, 1H), 4.20 (m, 3H), 3.95 (m, 1H), 2.85 (m, 1H), 2.40 (q, 2H), 2.10 (m, 1H), 1.20 (t, 3H), MS (ES+) m/e 521 (MH$^+$).

The final compound of Intermediate J may also be prepared using the following process:

JJ1: {2-Chloro-9-[(1R,4S)-4-(di-Boc-amino)-cyclopent-2-enyl]-9H-purin-6-yl}-(2,2-diphenyl-ethyl)-amine (1S,2R,3S,5R)-3-(Di-Boc-amino)-5-(2,6-dichloro-purin-9-yl)-cyclopentane-1,2-diol (13.0 g, 27.66 mmol) is dissolved in THF (250 ml) under an atmosphere of argon. Diisopropylamine (4.28 g, 33.19 mmol) is added followed by 2,2-diphenylethylamine (6.0 g, 30.43 mmol) and the reaction mixture is stirred at 50° C. The reaction is shown to be complete by LCMS after 18 hours. The solvent is removed in vacuo and the reaction mixture is partitioned between dichloromethane (250 ml) and 0.1M HCl (250 ml). The organic layer is washed with water (200 ml) and brine (200 ml), dried over MgSO$_4$, filtered and the solvent is removed in vacuo to give the title compound. $^1$H nmr (CDCl$_3$, 400 MHz); 8.05 (s, 1H), 7.30-7.10 (m, 10H), 6.00 (m, 1H), 5.70 (m, 2H), 5.60 (m, 1H), 5.20 (m, 1H), 4.30 (m, 1H), 4.20 (m, 1H), 3.65 (m, 1H), 3.05 (m, 1H), 2.00 (m, 1H), 1.70 (m, 1H), 1.40 (s, 18H), MS (ES+) m/e 631 (MH$^+$).

JJ2: (1R,2S,3R,5S)-3-[2-Chloro-6-(2,2-diphenyl-ethylamino)-purin-9-yl]-5-(di-Boc-amino)-cyclopentane-1,2-diol A solution of {2-Chloro-9-[(1R,4S)-4-(di-Boc-amino)-cyclopent-2-enyl]-9H-purin-6-yl}-(2,2-diphenyl-ethyl)-amine (2.9 g, 4.6 mmol) in THF (60 ml) is treated with 4-methyl morpholine N-oxide (1.1 g, 9.3 mmol) and osmium tetroxide (4% solution in water) (6 ml) and the mixture is stirred at room temperature for 48 hours. The solvent is removed under reduced pressure and the residue is purified by column chromatography on silica gel eluting with a gradient system of methanol:dichloromethane (0:100 by volume) gradually changing to methanol:dichloromethane (4:96 by volume) to afford the title compound. LCMS (electrospray): m/z [MH$^+$] 665.34

JJ3: (1S,2R,3S,5R)-3-Amino-5-[2-chloro-6-(2,2-diphenyl-ethylamino)-purin-9-yl]-cyclopentane-1,2-diol trifluoroacetate (1R,2S,3R,5S)-3-[2-Chloro-6-(2,2-diphenyl-ethylamino)-purin-9-yl]-5-(di-Boc-amino)-cyclopentane-1,2-diol (10.3 g, 15.50 mmol) is dissolved in dichloromethane (50 ml). TFA (25 ml) is added and the reaction mixture is stirred at room temperature. The reaction is shown to be complete by LCMS after 2 hours. The solvent is removed in vacuo to give the title compound. $^1$H nmr (MeOD, 400 MHz); 7.90 (s, 1H), 7.30-7.10 (m, 10H), 4.65 (m, 1H), 4.50 (m, 1H), 4.40 (m, 1H), 4.20 (m, 1H), 4.10 (m, 2H), 3.50 (m, 1H), 2.75 (m, 1H), 2.15 (m, 1H), MS (ES+) m/e 465 (MH$^+$).

JJ4: N-{(1S,2R,3S,4R)-4-[2-Chloro-6-(2,2-diphenyl-ethylamino)-purin-9-yl]-2,3-dihydroxy-cyclopentyl}-propionamide (1S,2R,3S,5R)-3-Amino-5-[2-chloro-6-(2,2-diphenyl-ethylamino)-purin-9-yl]-cyclopentane-1,2-diol trifluoroacetate (9.50 g, 16.42 mmol) and diisopropylethylamine (6.36 g, 49.27 mmol) are placed in a flask with dry THF (150 ml). Propionyl chloride (1.52 g, 16.42 mmol) is added dropwise and the reaction mixture is stirred at room temperature. The reaction is shown to be complete by LCMS after 1 hour. The solvent is removed in vacuo and the residue is partitioned between dichloromethane (250 ml) and water (250 ml). The organic layer is washed with water (200 ml) and brine (200 ml), dried over MgSO$_4$, filtered and the solvent is removed in vacuo. The solid is recrystallised from 1,2-dichloroethane to give the title compound. $^1$H nmr (MeOD, 400 MHz); 8.00 (s, 1H), 7.40-7.15 (m, 10H), 4.75 (m, 1H), 4.60 (m, 1H), 4.50 (m, 1H), 4.20 (m, 3H), 3.95 (m, 1H), 2.85 (m, 1H), 2.40 (q, 2H), 2.10 (m, 1H), 1.20 (t, 3H), MS (ES+) m/e 521 (MH$^+$).

Intermediate K

Cyclobutanecarboxylic acid {(1S,2R,3S,4R)-4-[2-chloro-6-(2,2-diphenyl-ethylamino)-purin-9-yl]-2,3-dihydroxy-cyclopentyl}-amide A solution of (1S,2R,3S,5R)-3-amino-5-[2-chloro-6-(2,2-diphenyl-ethylamino)-purin-9-yl]-cyclopentane-1,2-diol hydrochloride (Intermediate JJ3) (100 mg, 0.2 mmol) in dry THF (1 ml) is treated with diisopropylethylamine (0.17 ml, 1 mmol) and cyclobutanecarboxylic acid chloride (0.023 ml, 0.2 mmol) and the mixture is stirred at room temperature for 48 hours. The solvent is removed under reduced pressure. The residue is purified by reverse-phase chromatography eluting with a gradient system of acetonitrile (0.1% TFA): water (0.1% TFA) (0:100 by volume) gradually changing to acetonitrile (0.1% TFA): water (0.1% TFA) (100:0 by volume) to afford the title compound (51 mg). LCMS (electrospray): m/z [MH$^+$] 547.26. $^1$H nmr (MeOD, 400 MHz); 8.00 (s, 1H), 7.40-7.25 (m, 8H), 7.20-7.15 (m, 2H), 4.70 (m, 1H), 4.50 (m, 2H), 4.20 (m, 2H), 3.95 (m, 1H), 2.85 (m, 1H), 2.30 (m, 2H), 2.20 (m, 2H), 2.05 (m, 2H), 1.90 (m, 1H).

Intermediate L

{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-carbamic acid benzyl ester

L1: Preparation of Intermediate L1

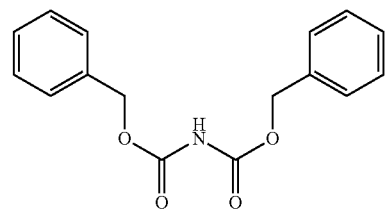

A cooled (0° C.) solution of benzyl carbamate (4.0 g, 27 mmol) in THF (100 ml) under an inert atmosphere of Argon is treated with potassium iodide (3.2 g of a 35% w/w dispersion in oil, 28 mmol) portionwise over 10 minutes. The reaction mixture is allowed to warm to room temperature over 30 minutes after which time benzyl chloroformate (5.0 g, 29 mmol) is added. After stirring at room temperature for 2 hours, the reaction is quenched with water (20 ml). The THF is removed in vacuo and the resulting mixture is partioned between EtOAc and 2M HCl. The organic portion is separated and washed with brine, dried (MgSO$_4$) and concentrated in vacuo. The resulting oil is purified by chromatography on silica eluting with 1:3 EtOAc/iso-hexane to yield a product which is recrystallised from DCM/iso-hexane to afford the title product.

L2: Preparation of Intermediate L2

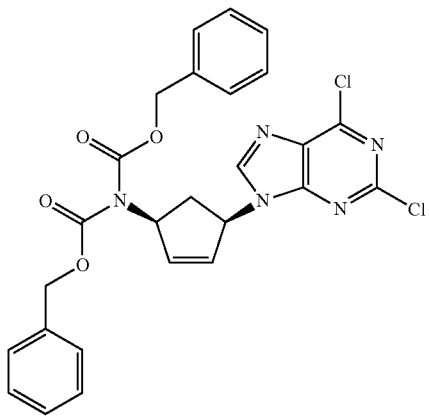

A solution comprising carbonic acid (1S,4R)-4-(2,6-dichloro-purin-9-yl)-cyclopent-2-enyl ester ethyl ester (Intermediate J2) (2.0 g, 5.83 mmol), Intermediate L1 (2.2 g, 7.58 mmol) and triphenyl phosphine (229 mg, 0.9 mmol) in THF (20 ml) is stirred at room temperature for 30 minutes. Tris(dibenzylideneacetone)dipalladium (0) (238 mg, 0.3 mmol) is added and the resulting mixture is stirred at room temperature for 1.5 hours. The solvent is removed in vacuo and the crude product is purified by chromatography on silica eluting with MeOH/DCM (gradient of 0 to 1% MeOH) to yield the title compound.

L3: Preparation of Intermediate L3

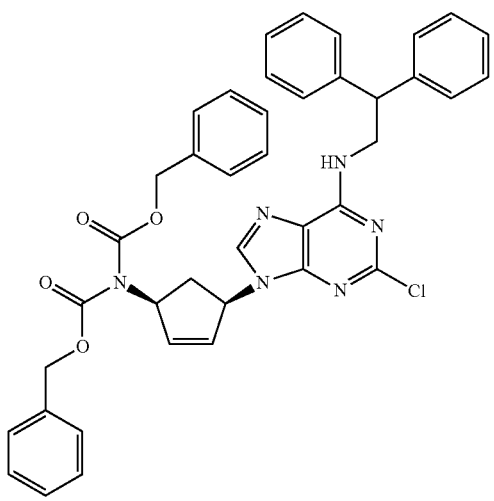

This compound is prepared analogously to 2-chloro-9-[(1R,4S)-4-(di-Boc-amino)-cyclopent-2-enyl]-9H-purin-6-yl}-(2,2-diphenyl-ethyl)-amine (Intermediate JJ1) by replacing (1S,2R,3S,5R)-3-(Di-Boc-amino)-5-(2,6-dichloro-purin-9-yl)-cyclopentane-1,2-diol (Intermediate J4) with Intermediate L2.

L4: Preparation of intermediate L4

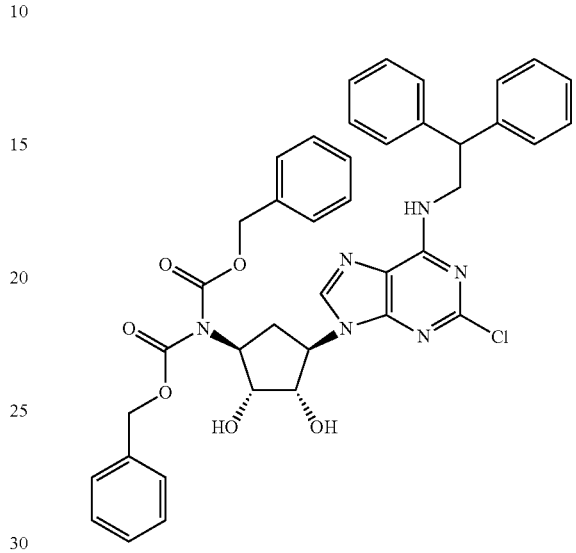

This compound is prepared analogously to (1R,2S,3R,5S)-3-[2-chloro-6-(2,2-diphenyl-ethylamino)-purin-9-yl]-5-(di-Boc-amino)-cyclopentane-1,2-diol (Intermediate JJ2) by replacing {2-Chloro-9-[(1R,4S)-4-(di-Boc-amino)-cyclopent-2-enyl]-9H-purin-6-yl}-(2,2-diphenyl-ethyl)-amine with Intermediate L3.

L5: {(R)-1-[9-((1R,2S,3R,4S)-4-Benzyloxycarbonylamino-2,3-dihydroxy-cyclopentyl)-6-(2,2-diphenyl-ethylamino)-9H-purin-2-yl]-pyrrolidin-3-yl}-carbamic acid tert-butyl ester A suspension of Intermediate L4 (1.03 g, 1.4 mmol) and (3R)-(+)-3-(Boc-amino)pyrrolidine (1.03 g, 5.5 mmol) in acetonitrile (2 ml) is treated with sodium iodide (ca. 2 mg) and then heated using microwave radiation in a Personal Chemistry Emrys™ Optimizer microwave reactor at 160° C. After 1 hour, the solvent is removed in vacuo and the crude residue is pardoned between DCM and 0.2 M HCl. The organic layer is separated and the aqueous portion is extracted with DCM. The combined organic extracts are washed with saturated sodium bicarbonate solution, water, brine, dried (MgSO$_4$) and concentrated in vacuo to afford the title compound as a brown oil. MS (ES+) m/e 745 (MH$^+$).

L6: {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester A solution of {(R)-1-[9-((1R,2S,3R,4S)-4-benzyloxycarbonylamino-2,3-dihydroxy-cyclopentyl)-6-(2,2-diphenyl-ethylamino)-9H-purin-2-yl]-pyrrolidin-3-yl}-carbamic acid tert-butyl ester (Intermediate L5) (1.24 g, 1.7 mmol) in MeOH (3 ml) is treated with 4M HCl in dioxane (5 ml) and stirred at room temperature for 2 hours. The solvent is removed in vacuo and purification is carried out by reverse phase column chromatography (Isolute™ C18, 0-100% acetonitrile in water −0.1% HCl). The fractions are collected and the MeCN is removed in vacuo. The remaining aqueous portion is basified with saturated sodium bicarbonate solution and extracted with DCM. The combined organic extracted are dried (MgSO$_4$) and concentrated in vacuo to afford the title product. MS (ES+) m/e 649 (MH$^+$).

Intermediate M

N-{(3aR,4S,6R,6aS)-6-[2-((R)-3-Amino-pyrrolidin-1-yl)-6-(2,2-diphenyl-ethylamino)-purin-9-yl]-2,2-dimethyl-tetrahydro-cyclopenta[1,3]dioxol-4-yl}-propionamide M1: {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid benzyl ester A solution of (R)-pyrrolidin-3-yl-carbamic acid benzyl ester hydrochloride (0.88 g, 3.45 mmol) in DCM is free-based using sodium hydrogen carbonate solution to yield (R)-pyrrolidin-3-yl-carbamic acid benzyl ester (0.487 g, 2.22 mmol). This amine is added to N-{(1S,2R,3S,4R)-4-[2-chloro-6-(2,2-diphenyl-ethylamino)-purin-9-yl]-2,3-dihydroxy-cyclopentyl}-propionamide (Intermediate J) (0.5 g, 0.96 mmol) and TEA (0.224 g, 2.22 mmol) and then dissolved in NMP (7 ml). The reaction mixture is heated using microwave radiation in a Personal Chemistry Emrys™ Optimizer microwave reactor at 190° C. for 1 hour. The resulting mixture is purified by chromatography on silica eluting with 5% MeOH in DCM to yield the title compound.

M2: {(R)-1-[9-((3aS,4R,6S,6aR)-2,2-Dimethyl-6-propionylamino-tetrahydro-cyclopenta[1,3]dioxol-4-yl)-6-(2,2-diphenyl-ethylamino)-9H-purin-2-yl]-pyrrolidin-3-yl}-carbamic acid benzyl ester A solution of {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-carbamic acid benzyl ester (0.63 g, 0.89 mmol) in acetone (10 ml) and 2,2-dimethyloxypropane (5 ml) is treated with toluenesulfonic acid (ca.60 mg) and then stirred at room temperature overnight. The mixture is basified using ammonium hydroxide and the solvent is removed in vacuo. The crude product is partitioned between DCM and water and the organic portion is washed with brine, dried over MgSO$_4$, filtered and the solvent is removed in vacuo to give the title compound. [MH+ 745].

M3: N-{(3aR,4S,6R,6aS)-6-[2-((R)-3-Amino-pyrrolidin-1-yl)-6-(2,2-diphenyl-ethylamino)-purin-9-yl]-2,2-dimethyl-tetrahydro-cyclopenta[1,3]dioxol-4-yl}-propionamide To a solution of {(R)-1-[9-((3aS,4R,6S,6aR)-2,2-dimethyl-6-propionylamino-tetrahydro-cyclopenta[1,3]dioxol-4-yl)-6-(2,2-diphenyl-ethylamino)-9H-purin-2-yl]-pyrrolidin-3-yl}-carbamic acid benzyl ester (0.598 g, 0.79 mmol) in ethanol (7.5 ml) under an inert atmosphere of Argon is added palladium hydroxide on carbon (10 mg). The reaction mixture is purged with Argon and placed under an atmosphere of hydrogen overnight. The mixture is filtered and purified by chromatography on silica eluting with 5% MeOH in DCM to yield the title compound. [MH+ 611].

Intermediate N (R)-[1,3']Bipyrrolidinyl

N1: (R)-1'-Benzyl-[1,3']bipyrrolidinyl

An ice-cooled solution of 2,5-dimethoxytetrahydrofuran (19.11 ml, 0.147 mol) and 6M sulphuric acid (37.2 ml) in THF (200 ml) is treated dropwise with (R)-(1)-benzyl-3-aminopyrrolidine (10 g, 0.057 mol) 6M sulphuric acid (37.2 ml) in THF (150 ml) and sodium borohydride pellets (8.62 g, 0.227 mol) simultaneously, ensuring the temperature remains below 10° C. The reaction mixture is allowed to warm to room temperature and water (10 ml) is added to aid dissolution of the sodium hydroxide pellets. After stirring at room temperature for 12 days, the mixture is cooled with the use on an ice-bath and water is added (500 ml). The solution is basified by addition of sodium hydroxide pellets (pH<10) and then filtered under vacuum. The filtrate is extracted with diethyl ether and DCM and the organic portions are combined and concentrated in vacuo. The crude residue is sonicated in diethyl ether and filtered under vacuum. The filtrate is reduced in vacuo again and the resulting crude is dissolved in MeCN (8 ml) and purified by reverse phase column chromatography (Isolute™ C18, 0-100% MeCN in water −0.1% TFA) to yield the title product.

N2: (R)-[1,3']Bipyrrolidinyl

A solution of (R)-1'-benzyl-[1,3']bipyrrolidinyl (0.517 g, 2.24 mmol) in methanol (25 ml) under an atmosphere of Argon is treated with palladium hydroxide on carbon (0.1 g). The reaction mixture is placed under an atmosphere of hydrogen and stirred at room temperature overnight and then filtered through Celite™. The filtrate is concentrated in vacuo to yield the title product as a dark orange oil.

Intermediate O (R)-N-Pyrrolidin-3-yl-isonicotinamide

O1: (R)-3-[(Pyridine-4-carbonyl)-amino]-pyrrolidine-1-carboxylic acid tert-butyl ester A cooled (0° C.) stirred solution of (R)-3-amino-pyrrolidine-1-carboxylic acid tert-butyl ester (1.0 g, 5.36 mmol) and TEA (1.5 ml, 11.0 mmol) in THF (10 ml) is treated dropwise over 1 minute with pyridine-4 carbonyl chloride hydrochloride (0.935 g, 5.25 mmol). After 5 minutes, the reaction mixture is allowed to warm to room temperature and stirred overnight. The resulting mixture is diluted with EtOAc and washed twice with saturated sodium bicarbonate solution followed by brine. The organic portion is dried (MgSO$_4$) and concentrated in vacuo. The crude product is purified by recrystallisation from EtOAc/iso-hexane to afford the title product. [MH+ 292].

O2: (R)-N-Pyrrolidin-3-yl-isonicotinamide

A solution of (R)-3-[(pyridine-4-carbonyl)-amino]-pyrrolidine-1-carboxylic acid tert-butyl ester (1.38 g, 4.74 mmol) in MeOH (6 ml) is treated with 2M HCl (5 ml) and left to stand at room temperature overnight. The resulting mixture is diluted with MeOH and added to 12 ml of Dowex resin (50W×2-200). After 30 minutes, the resin is washed with water until neutral and then further washed off with MeOH and 2% ammonia. The solvent is removed in vacuo to afford the title compound as a crystalline solid. [MH+ 192].

Intermediate P

5-Methyl-isoxazole-3-carboxylic acid (R)-pyrrolidin-3-ylamide

TEA (0.42 ml, 3.0 mmol) is added to a cooled (−10° C.) solution of 5-methyl isoxazole-3-carbonyl chloride (0.44 g, 2.95 mmol) in THF (5 ml). To this turbid mixture is added dropwise, (R)-3-amino-1-N-pyrrolidine (0.5 g, 2.68 mmol) in THF (2 ml) and the reaction mixture is allowed to warm to room temperature over 30 minutes. After standing at room temperature overnight, the reaction mixture is diluted with EtOAc (30 ml) and washed with water (2×5 ml), brine, dried ($MgSO_4$) and concentrated in vacuo. The resulting oil is dissolved in MeOH (5 ml) is treated dropwise with 6M HCl (1.15 ml). After standing at room temperature for 4 days, the reaction mixture is concentrated in vacuo and co-evaporated with MeOH/EtOAc. The crude residue is triturated with EtOAc to afford the title compound. [MH+ 196].

Intermediate Q

N-{(1S,2R,3S,4R)-4-[2-Chloro-6-(2,2-diphenyl-ethylamino)-purin-9-yl]-2,3-dihydroxy-cyclopentyl}-2-hydroxy-acetamide Q1: Acetic acid {(1S,2R,3S,4R)-4-[2-chloro-6-(2,2-diphenyl-ethylamino)-purin-9-yl]-2,3-dihydroxy-cyclopentylcarbamoyl}-methyl ester A suspension of (1S,2R,3S,5R)-3-amino-5-[2-chloro-6-(2,2-diphenyl-ethylamino)-purin-9-yl]-cyclopentane-1,2-diol dihydrochloride (Intermediate JJ3) (250 mg, 0.46 mmol) in dry THF (10 ml) is treated with TEA (0.188 g, 1.86 mmol) followed by acetoxyacetylchloride (0.064 g, 0.46 mmol) and then stirred at room temperature for 30 minutes. The solvent is removed in vacuo and the solvent is partitioned between DCM and 0.1M HCl. The organic portion is separated and washed with brine, dried ($MgSO_4$) and concentrated in vacuo to afford the title product.

Q2: N-{(1S,2R,3S,4R)-4-[2-Chloro-6-(2,2-diphenyl-ethylamino)-purin-9-yl]-2,3-dihydroxy-cyclopentyl}-2-hydroxy-acetamide To a suspension of acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (0.2 g, 0.35 mmol) in MeOH (10 ml) is added potassium carbonate (0.098 g, 0.7 mmol) and the reaction mixture is stirred at room temperature for 1 hour. The solvent is removed in vacuo and the solvent is partitioned between DCM and water. The organic portion is separated, dried ($MgSO_4$) and concentrated in vacuo to afford the title product.

Intermediate R

3-Isocyanato-benzenesulfonamide

To a vigorously stirred solution of 3-aminobenzenesulphonamide (1 g, 5.8 mmol) in dry dioxane (25 ml) is added trichloromethyl chloroformate (1.72 g, 8.7 mmol) and the reaction mixture is heated to reflux for 3 hours. The solvent is removed in vacuo to yield the title product which is used without further purification.

Intermediate S

4-Isocyanato-benzenesulfonamide

This compound is prepared analogously to Intermediate R by replacing 3-aminobenzenesulphonamide with 4-aminobenzenesulphonamide.

Intermediate T

{(1S,2R,3S,4R)-4-[2-Chloro-6-(2,2-diphenyl-ethylamino)-purin-9-yl]-2,3-dihydroxy-cyclopentyl}-carbamic acid methyl ester This compound is prepared analogously to cyclobutanecarboxylic acid {(1S,2R,3S,4R)-4-[2-chloro-6-(2,2-diphenyl-ethylamino)-purin-9-yl]-2,3-dihydroxy-cyclopentyl}-amide (Intermediate K) by replacing cyclobutanecarboxylic acid chloride with methylchloroformate.

Intermediate UA (3-Hydroxy-benzyl)-carbamic acid phenyl ester

3-Hydroxybenzylamine (200 mg, 1.62 mmol) and Sodium hydrogen carbonate (273 mg, 3.25 mmol) suspended in water/DCM (4 ml, 1:1) is treated with phenyl chloroformate (0.204 ml, 1.62 mmol). After stirring at RT overnight, the reaction mixture is diluted with more DCM/water and the organic phase is separated. The organic portion is concentrated in vacuo to afford the titled compound. (MH+ 244)

Intermediate UB

Pyridin-3-yl-carbamic acid phenyl ester

Phenyl chloroformate (0.733 ml, 5.84 mmol) is suspended in pyridine/DCM (3 ml, 2:1). The solution is stirred at 0° C., and 3-aminopyridine (500 mg, 5.31 mmol) dissolved in DCM (1 ml) is added drop-wise. The reaction mixture is at 0° C. for 1 hour. The solvent is removed in vacuo and the residue is dissolved in ethyl acetate. This organic portion is washed with 0.1M HCl and then concentrated in vacuo to afford the titled compound. (MH+ 215).

Intermediates UC-UE

These compounds namely,
(3-Sulfamoyl-phenyl)-carbamic acid phenyl ester (Intermediate UC)
(4-Sulfamoyl-phenyl)-carbamic acid phenyl ester (Intermediate UD)
Pyridin-2-ylmethyl-carbamic acid phenyl ester (Intermediate UE)
Are prepared analogously to Intermediate UB by replacing 3-aminopyridine with the appropriate amine.

Intermediate VA 3-((R)-3-Pyrrolidin-3-ylureido)-benzenesulfonamide

VA1: 3-[3-((R)-1-Benzyl-pyrrolidin-3-yl)-ureido]-benzenesulfonamide

A solution of (R)-N-benzyl-3-aminopyrrolidine (14.9 g, 0.084 mol) in methanol (100 mL) is added to a suspension of (3-sulfamoyl-phenyl)-carbamic acid phenyl ester (25 g, 0.084 mol). The resulting pale orange solution is stirred at mild reflux (DrySyn @ 80° C.) for two hours, then allowed to cool to room temperature, before the volatile components are removed under reduced pressure. The orange syrup is purified by flash column chromatography (silica; DCM/methanol 10:1) to give a beige foamed solid.

VA2: 3-((R)-3-Pyrrolidin-3-ylureido)-benzene sulfonamide

A solution of 3-[3-((R)-1-benzyl-pyrrolidin-3-yl)-ureido]-benzenesulfonamide (25 g, 0.067 mol) in ethanol (250 mL) is purged with nitrogen, and palladium hydroxide (2.5 g, 20% w/w) is added. The suspension is purged with hydrogen and stirred under a positive pressure of hydrogen for 24 hours. Filtration though Celite® (filter material) and removal of solvent under reduced pressure gives the product as a colourless waxy solid.

Intermediate VB

1-Pyridin-3-yl-3-(R)-pyrrolidin-3-yl-urea

VB1: 1-((R)-1-Benzyl-pyrrolidin-3-yl)-3-pyridin-3-yl-urea

A solution of pyridin-3-yl-carbamic acid phenyl ester (1.6 g) in dry THF (20 ml) is treated with (R)-1-benzyl-pyrrolidin-3-ylamine (1.9 g, 1.05 eq) and then heated using microwave radiation at 110° C. for 1000 s. The solvent is removed in vacuo and purification of the crude product by chromatography on silica eluting with DCM followed by EtOAc and EtOH affords the title compound as an oil. (MH+ 297).

VB2: 1-Pyridin-3-yl-3-(R)-pyrrolidin-3-yl-urea

The titled compound is prepared from 1-((R)-1-benzyl-pyrrolidin-3-yl)-3-pyridin-3-yl-urea analogously to 3-((R)-3-pyrrolidin-3-ylureido)-benzenesulfonamide (Step VA1).

Intermediate VC

1-Pyridin-3-yl-3-(R)-pyrrolidin-3-yl-urea

This compound is prepared from (4-sulfamoyl-phenyl)-carbamic acid phenyl ester (Intermediate UD).analogously to Intermediate VA.

Intermediate VD

N-{(1S,2R,3S,4R)-4-[6-((S)-1-Benzyl-2-hydroxy-ethylamino)-2-chloro-purin-9-yl]-2,3-dihydroxy-cyclopentyl}-2-hydroxy-acetamide This compound is prepared analogously to (N-((1S,2R,3S,4R)-4-{6-[2,2-Bis-(4-hydroxy-phenyl)-ethylamino]-2-[(R)-3-(3-pyridin-3-yl-ureido)-pyrrolidin-1-yl]-purin-9-yl}-2,3-dihydroxy-cyclopentyl)-2-hydroxy-acetamide trifluoroacetate (Example 7 step 3) by replacing 4,4'-(2-aminoethylidene)bis-phenol (Example 7 step1) with (S)-2-amino-3-phenyl-propan-1-ol.

Intermediate W

Propionyl-carbamic Acid Tert-butyl Ester

The title compound is prepared from propyl-carbamic acid tert-butyl ester using the procedure described by Ken-ichi Takana et al in *Chem. Pharm. Bull.* 1988, 36, 3125. $^1$H nmr (CDCl$_3$, 400 MHz); 7.25 (br s, 1H), 2.75 (q, 2H), 1.50 (s, 9H), 1.15 (t, 3H).

Intermediate X

Bis-(4-methoxy-phenyl)-methanone oxime 4,4'-Dimethoxybenzophenone (25 g, 103 mmol) is suspended in ethanol (150 ml) and pyridine (30 ml). Hydroxylamine hydrochloride (21.50 g, 310 mmol) is added and the reaction mixture is refluxed. The reaction is shown to be complete by TLC after 3 hours. The reaction mixture is allowed to cool and the solvent is removed in vacuo. The residue is partitioned between ethyl acetate (500 ml) and water (500 ml). The organic layer dried is over MgSO$_4$, filtered and the solvent removed in vacuo. The title compound is obtained following crystallisation from ethylacetate/cyclohexane. $^1$H nmr (CDCl$_3$, 400 MHz); 7.70 (s, 1H), 7.40 (d of d, 4H), 6.95 (d, 2H), 6.85 (d, 2H), 3.85 (s, 3H), 3.80 (s, 3H).

Intermediate Y

C,C-Bis-(4-methoxy-phenyl)-methylamine

Bis-(4-methoxy-phenyl)-methanone oxime (20 g, 77.82 mmol) is suspended in ammonia 0.880 (450 ml) and ethanol (90 ml). Ammonium acetate (3.00 g, 38.91 mmol) is added followed by the portionwise addition of zinc dust (25.29 g, 389.10 mmol). Once the addition is complete the reaction mixture is slowly heated to 50° C. When the effervescence has ceased the reaction mixture is refluxed. The reaction is shown to be complete by TLC after 4 hours. The reaction mixture is allowed to cool and ethyl acetate is added (250 ml). The reaction mixture is filtered through Celite™ and the phases are separated. The organic layer dried is over MgSO$_4$, filtered and the solvent removed in vacuo to give the title compound. $^1$H nmr (CDCl$_3$, 400 MHz); 7.25 (d, 4H), 6.80 (d, 4H), 5.10 (s, 1H), 3.75 (s, 6H).

Intermediate Z

Biphenyl-2-yl-carbamic acid 1-[2-((R)-3-amino-pyrrolidin-1-yl)-2-oxo-ethyl]-piperidin-4-yl ester Z1: {(R)-1-[2-(4-Hydroxy-piperidin-1-yl)-acetyl]-pyrrolidin-3-yl}-carbamic acid tert-butyl ester To a solution of (R)-pyrrolidin-3-yl-carbamic acid tert-butyl ester (1.5 g, 8.1 mmol) in THF (150 ml) is added TEA (2.3 ml, 16.1 mmol) followed by dropwise addition of chloroacetyl chloride (0.67 ml, 8.5 mmol). The reaction mixture is allowed to stir at room temperature for 2 hours and then treated TEA (2.3 ml, 16.1 mmol) followed by 4-piperidinol (4.07 g, 40.3 mmol). After stirring at 50° C. for 18 hours, the solvent is removed in vacuo and purification of the crude residue by reverse phase column chromatography (Isolute™ C18, 0-100% MeOH in water –0.1% TFA) to yield the title product. [MH+ 328.19].

Z2: ((R)-1-{2-[4-(Biphenyl-2-ylcarbamoyloxy)-piperidin-1-yl]-acetyl}-pyrrolidin-3-yl)-carbamic acid tert-butyl ester {(R)-1-[2-(4-Hydroxy-piperidin-1-yl)-acetyl]-pyrrolidin-3-yl}-carbamic acid tert-butyl ester (Intermediate Z1) (520 mg, 1.6 mmol) and 2-biphenylisocyanate (930 mg, 2.65 mmol) are dissolved in NMP (2 ml) and heated to 70° C. overnight. Purification is carried out by reverse phase column chromatography (Isolute™ C18, 0-100% MeOH in water −0.1% TFA). The fractions containing the product are concentrated in vacuo to remove the acetonitrile and the aqueous is treated with saturated sodium bicarbonate solution. The product is extracted with DCM and the combined organic portions are concentrated in vacuo to afford the title product. [MH+ 523.24].

Z3: Biphenyl-2-yl-carbamic acid 1-[2-((R)-3-amino-pyrrolidin-1-yl)-2-oxo-ethyl]-piperidin-4-yl ester A solution of ((R)-1-{2-[4-(biphenyl-2-ylcarbamoyloxy)-piperidin-1-yl]-acetyl}-pyrrolidin-3-yl)-carbamic acid tert-butyl ester (Intermediate Z2) (1.17 g, 2.24 mmol) in DCM (10 ml) is treated with TFA (5 ml) and stirred at room temperature for 2 hours. The solution is basified by addition of saturated sodium bicarbonate solution and then extracted with DCM. The combined organic portions are washed with water, brine, dried (MgSO$_4$) and concentrated in vacuo to yield the title product. [MH+ 423.20].

Intermediate ZA

N-[(1S,2R,3S,4R)-4-(6-Amino-2-chloro-purin-9-yl)-2,3-dihydroxy-cyclopentyl]-propionamide trifluoroacetate Bis-(4-methoxy-phenyl)-methyl]-(2-chloro-9H-purin-6-yl)-amine 2,6-Dichloropurine (9.50 g, 50.29 mmol) is dissolved in THF (200 ml) under an atmosphere of argon. Diisopropylamine (7.14 g, 55.32 mmol) is added followed by C,C-bis-(4-methoxy-phenyl)-methylamine (see preparation of intermediates) (12.22 g, 50.29 mmol) and the reaction mixture is stirred at 50° C. The reaction is shown to be complete by LCMS after 5 days. The solvent is removed in vacuo and replaced with MeOH (250 mL). The resulting precipitate is filtered off and dried to give the title compound. $^1$H nmr (d$_6$-DMSO, 400 MHz); 8.20 (br s, 1H), 7.25 (d, 4H), 6.90 (d, 4H), 3.75 (s, 6H), 3.15 (m, 1H), MS (ES+) m/e 396 (MH$^+$).

(1S,4R)-4-(6-{[Bis-(4-methoxy-phenyl)-methyl]-amino}-2-chloro-purin-9-yl)-cyclopent-2-enol Bis-(4-methoxy-phenyl)-methyl]-(2-chloro-9H-purin-6-yl)-amine (13 g, 32.87 mmol) is placed in an oven-dried flask under an atmosphere of argon. Dry deoxygenated THF (100 ml) and dry DMSO (2 ml) are added and the suspension is cooled on an ice-bath. Sodium hydride 95% (0.79 g, 32.87 mmol) is then slowly added and the solution is stirred at room temperature for 30 minutes. (1S,4R)-cis 4-Acetoxy-2-cyclopenten-1-ol (4.9 g. 34.5 mmol) and triphenylphosphine (1.36 g, 5.17 mmol) are placed in an oven-dried flask under an atmosphere of argon. Dry deoxygenated THF (50 ml) is added. This solution is added to the anion solution via syringe. Tetrakis(triphenylphosphine)palladium(0) (2 g, 1.73 mmol) is then added and the mixture is stirred at 50° C. The reaction is shown to be complete by LCMS after 2 hours. The reaction mixture is allowed to cool and the solvent is removed in vacuo. The residue is taken up in methanol (50 ml) and the resulting precipitate is filtered off and dried to give the title compound. $^1$H nmr (CDCl$_3$, 400 MHz); 9.10 (m, 1H), 8.10 (m, 1H), 7.30 (d, 4H), 6.90 (d, 4H), 6.55 (d, 1H), 6.20 (m, 1H), 5.95 (m, 1H), 5.40 (m, 1H), 5.30 (d, 1H), 4.70 (m, 1H), 3.70 (s, 6H), 2.90 (m, 1H), 1.70 (m, 1H), MS (ES+) m/e 478 (MH$^+$).

Carbonic acid (1S,4R)-4-(6-{[bis-(4-methoxy-phenyl)-methyl]-amino}-2-chloro-purin-9-yl)-cyclopent-2-enyl ester ethyl ester (1S,4R)-4-(6-{[Bis-(4-methoxy-phenyl)-methyl]-amino}-2-chloro-purin-9-yl)-cyclopent-2-enol (8.00 g, 16.75 mmol) is placed in an oven-dried flask under an atmosphere of argon. Dry pyridine (80 ml) is added followed by diisopropylamine (16 ml). A catalytic amount of DMAP is added followed by 3-oxy-benzotriazole-1-carboxylic acid ethyl ester (6.94 g, 33.50 mmol, see preparation of intermediates). The reaction mixture is stirred at room temperature. The reaction is shown to be complete by TLC after 18 hours. The solvent is removed in vacuo and the residue is partitioned between ethyl acetate (500 ml) and 2M HCl (200 ml). The organic layer is washed with water (150 ml) and brine (150 ml), dried over MgSO$_4$, filtered and the solvent is removed in vacuo. The title compound is obtained after purification by flash column chromatography (silica, dichloromethane/methanol 50:1). $^1$H nmr (CDCl$_3$, 400 MHz); 7.80 (s, 1H), 7.25 (d of d, 4H), 6.85 (d of d, 4H), 6.65 (m, 1H), 6.50 (m, 1H), 6.35 (m, 1H), 6.15 (m, 1H), 5.65 (m, 2H), 4.25 (q, 2H), 3.80 (s, 6H), 3.10 (m, 1H), 1.95 (m, 1H), 1.35 (t, 3H).

[Bis-(4-methoxy-phenyl)-methyl]-{2-chloro-9-[(1R,4S)-4-(di-Boc-amino)-cyclopent-2-enyl]-9H-purin-6-yl}-amine Carbonic acid (1S,4R)-4-(6-{[bis-(4-methoxy-phenyl)-methyl]-amino}-2-chloro-purin-9-yl)-cyclopent-2-enyl ester ethyl ester (2.00 g, 3.64 mmol), di-t-butyl iminodicarboxylate (0.87 g, 4.00 mmol) and triphenylphosphine (0.14 g, 0.55 mmol) are placed in an oven-dried flask under an atmosphere of argon. Dry deoxygenated THF (20 ml) is added followed by tetrakis(triphenylphosphine)palladium(0) (0.21 g, 0.18 mmol) and the mixture is stirred at room temperature. The reaction is shown to be complete by LCMS after 3 hours. The solvent is removed in vacuo and the title compound is obtained after purification by flash column chromatography (silica, iso-hexane/ethyl acetate 4:1). 1H nmr (CDCl$_3$, 400 MHz); 8.20 (s, 1H), 7.25 (d, 4H), 6.85 (d, 4H), 6.60 (m, 1H), 6.35 (m, 1H), 6.10 (m, 1H), 5.80 (m, 1H), 5.65 (m, 1H), 5.35 (m, 1H), 3.80 (s, 6H), 3.15 (m, 1H), 2.10 (m, 1H), 1.55 (s, 18H).

(1R,2S,3R,5S)-3-(6-{[Bis-(4-methoxy-phenyl)-methyl]-amino}-2-chloro-purin-9-yl)-5-(di-Boc-amino)-cyclopentane-1,2-diol

[Bis-(4-methoxy-phenyl)-methyl]-{2-chloro-9-[(1R,4S)-4-(di-Boc-amino)-cyclopent-2-enyl]-9H-purin-6-yl}-amine (0.75 g, 1.11 mmol) is dissolved in THF (15 ml). N-Methylmorpholine N-oxide (0.26 g, 2.22 mmol) is added followed by osmium tetroxide (1.5 ml, 4% in water). The reaction mixture is stirred at room temperature. The reaction is shown to be complete by LCMS after 18 hours. The solvent is removed in vacuo and the title compound is obtained after purification by flash column chromatography (silica, dichloromethane/methanol 50:1). $^1$H nmr (CDCl$_3$, 400 MHz); 7.75 (s, 1H), 7.25 (m, 4H), 6.85 (m, 4H), 6.60 (m, 2H), 5.70 (m, 1H), 4.70 (m, 2H), 4.60 (m, 1H), 4.45 (m, 1H), 3.80 (s, 6H), 3.70 (m, 1H), 3.40 (m, 1H), 3.25 (m, 1H), 2.65 (m, 1H), 2.50 (m, 1H), 1.55 (s, 18H).

(1S,2R,3S,5R)-3-Amino-5-(6-amino-2-chloro-purin-9-yl)-cyclopentane-1,2-diol trifluoroacetate (1R,2S,3R,5S)-3-(6-{[Bis-(4-methoxy-phenyl)-methyl]-amino}-2-chloro-purin-9-yl)-5-(di-Boc-amino)-cyclopentane-1,2-diol (600 mg, 0.84 mmol) is dissolved in dichloromethane (4 ml). TFA (2 ml) is added and the reaction mixture is stirred at room temperature. The reaction is shown to be complete by LCMS after 18 hours. The solvent is removed in vacuo and the title compound is obtained after purification by reverse phase column chromatography (Isolute™ C18, 0-100% acetonitrile in water −0.1% TFA). $^1$H nmr (MeOD, 400 MHz); 8.10 (s, 1H), 4.80 (m, 1H), 4.60 (m, 1H), 4.30 (m, 1H), 3.60 (m, 1H), 2.85 (m, 1H), 2.30 (m, 1H). MS (ES+) m/e 285 (MH$^+$).

N-[(1S,2R,3S,4R)-4-(6-Amino-2-chloro-purin-9-yl)-2,3-dihydroxy-cyclopentyl]-propionamide trifluoroacetate (1S,2R,3S,5R)-3-Amino-5-(6-amino-2-chloro-purin-9-yl)-cyclopentane-1,2-diol trifluoroacetate (intermediate for preparing Example 1) (20 mg, 39 μmol) and diisopropylethylamine (25 mg, 190 μmol) are placed in a flask with dry THF (1 ml). Propionyl chloride (3.6 mg, 39 μmol) is added and the reaction mixture is stirred at room temperature. The reaction is shown to be complete by LCMS after 3 hours. The solvent is removed in vacuo and the title compound is obtained, which can be purified by reverse phase column chromatography (Isolute™ C18, 0-100% acetonitrile in water −0.1% TFA). $^1$H nmr (MeOD, 400 MHz); 8.10 (s, 1H), 4.75 (m, 1H), 4.60 (m, 1H), 4.20 (m, 1H), 4.00 (m, 1H), 3.75 (m, 1H), 3.25 (m, 1H), 2.85 (m, 1H), 2.40 (q, 2H), 2.10 (m, 1H), 1.20 (t, 3H), MS (ES+) m/e 341 (MH$^+$).

Intermediate ZB

Pyridin-3-yl-carbamic acid phenyl ester

A solution of pyridine (2 ml) in DCM (10 ml) is treated with phenylchloroformate (1.83 g, 11.7 mmol). To this solution is added 3-aminopyridine (1.0 g, 10.6 mmol) in DCM (8 ml) which results in an exotherm of 20° C. The reaction mixture is stirred at room temperature for 2 hours and then concentrated in vacuo. The residue is partitioned between EtOAc and water and the organic portion is separated. This organic portion is washed with water, saturated sodium bicarbonate solution, dried (MgSO$_4$) and concentrated in vacuo to afford the title compound as a white solid. (MH+ 215.13)

Intermediate ZC

Pyridin-2-ylmethyl-carbamic acid phenyl ester

The title compound is prepared analogously to pyridin-3-yl-carbamic acid phenyl ester, by substituting C-pyridin-2-yl-methylamine for 3-aminopyridine.

Intermediate ZD

(3-Hydroxy-benzyl)-carbamic acid phenyl ester

The title compound is prepared analogously to pyridin-3-yl-carbamic acid phenyl ester, by substituting 3-aminomethyl-phenol for 3-aminopyridine.

Intermediate ZE

(4-Sulfamoyl-phenyl)-carbamic acid phenyl ester

The title compound is prepared analogously to pyridin-3-yl-carbamic acid phenyl ester, by substituting 4-amino-benzenesulfonamide for 3-aminopyridine.

Intermediate ZF

(3-Sulfamoyl-phenyl)-carbamic acid phenyl ester

The title compound is prepared analogously to pyridin-3-yl-carbamic acid phenyl ester, by substituting 3-amino-benzenesulfonamide for 3-aminopyridine.

Intermediate ZG

N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-3-hydroxy-propionamide

ZG1: 3-tert-Butoxy-N-[(1S,2R,3S,4R)-4-(2,6-dichloro-purin-9-yl)-2,3-dihydroxy-cyclopentyl]-propionamide The title compound is prepared as described for (R)-2-benzyloxy-N-[(1S,2R,3S,4R)-4-(2,6-dichloro-purin-9-yl)-2,3-dihydroxy-cyclopentyl]-propionamide (Example 181, Step 1), by replacing (R)-2-benzyloxy-propionic acid with 3-tert-butoxypropionic acid.

ZG2: 3-tent-Butoxy-N-{(1S,2R,3S,4R)-4-[2-chloro-6-(2,2-diphenyl-ethylamino)-purin-9-yl]-2,3-dihydroxy-cyclopentyl}-propionamide The title compound is prepared analogously to N-{(1S,2R,3S,4R)-4-[2-chloro-6-(2,2-diphenyl-ethylamino)-purin-9-yl]-2,3-dihydroxy-cyclopentyl}-propionamide (Intermediate J7), by substituting 3-tert-butoxy-N-[(1S,2R,3S,4R)-4-(2,6-dichloro-purin-9-yl)-2,3-dihydroxy-cyclopentyl]-propionamide (Intermediate ZG1) for N-[(1S,2R,3S,4R)-4-(2,6-dichloro-purin-9-yl)-2,3-dihydroxy-cyclopentyl]-propionamide.

ZG3: {(R)-1-[9-[(1R,2S,3R,4S)-4-(3-tert-Butoxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester The title compound is prepared analogously to {(R)-1-[9-[(1R,2S,3R,4S)-4-((R)-2-benzyloxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester (Example 181, step 3), by substituting 3-tert-butoxy-N-{(1S,2R,3S,4R)-4-[2-chloro-6-(2,2-diphenyl-ethylamino)-purin-9-yl]-2,3-dihydroxy-cyclopentyl}-propionamide (Intermediate ZG2) for (R)-2-benzyloxy-N-{(1S,2R,3S,4R)-4-[2-chloro-6-(2,2-diphenyl-ethylamino)-purin-9-yl]-2,3-dihydroxy-cyclopentyl}-propionamide (Example 181, step 2).

ZG4: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-3-hydroxy-propionamide The title compound is prepared analogously to (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4), by substituting {(R)-1-[9-[(1R,2S,3R,4S)-4-(3-tert-butoxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester (Intermediate ZG3) for {(R)-1-[9-[(1R,2S,3R,4S)-4-(R)-2-Benzyloxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester (Example 181, step 3).

Intermediate ZH

N-((1S,2R,3S,4R)-4-{2-((R)-3-Amino-pyrrolidin-1-yl)-6-[2,2-bis-(4-hydroxy-phenyl)-ethylamino]-purin-9-yl}-2,3-dihydroxy-cyclopentyl)-3-hydroxy-propionamide The title compound is prepared analogously to N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-3-hydroxy-propionamide (Intermediate ZG), by substituting 4,4'-(2-aminoethylidene)bis-phenol (prepared as described by Schelkun, R. M. et al. Bioorg. Med. Chem. Lett. (1999), 9(16), pp 2447-2452) for 2,2-diphenyl-ethylamine.

Intermediate ZI

2-Amino-1,1-bis-(4-chloro-phenyl)-ethanol

The title compound is prepared by combining 4,4'-dichlorobenzophenone (5 g, 20 mmol) and zinc iodide (480 mg, 1.49 mmol) in DCM (100 mL). Trimethylsilyl cyanide (2.17 g, 21.9 mmol) is added, and the reaction is stirred at room temperature for 18 hours. The reaction is washed with water (100 mL) and dried over magnesium sulfate, before filtering and removal of the solvent under reduced pressure. The residue is redissolved in dry THF (40 mL), 1.0M borane in THF (40 mL) is added, and the reaction is stirred at reflux for 24 hours. After cooling, the volatile components are removed under reduced pressure, the residue is taken up in methanol (100 mL). Concentrated hydrochloric acid is added, and the reaction is refluxed for a further 2 hours, before once more removing the volatile components under reduced pressure, to give the title compound as a hydrochloride salt.

Intermediate ZJ

Acetic acid [(1S,2R,3S,4R)-4-(2,6-dichloro-purin-9-yl)-2,3-dihydroxy-cyclopentyl-carbamoyl]-methyl ester The title compound is prepared analogously to Intermediate J6, from Intermediate J5, replacing propionyl chloride with acetoxyacetylchloride.

Intermediate ZK

Acetic acid ((1S,2R,3S,4R)-4-{6-[2,2-bis-(4-hydroxy-phenyl)-ethylamino]-2-chloro-purin-9-yl}-2,3-dihydroxy-cyclopentylcarbamoyl)-methyl ester Acetic acid [(1S,2R,3S,4R)-4-(2,6-dichloro-purin-9-yl)-2,3-dihydroxy-cyclopentyl-carbamoyl]-methyl ester (Intermediate ZJ; 1 equivalent) and 4,4'-(2-aminoethylidene)bis-phenol (1.1 equivalents; prepared as described by Schelkun, R. M. et al. Bioorg. Chem. Lett. (1999), 9(16), pp 2447-2452) are combined in dry THF and treated with DIPEA (1.2 equivalents) and stirred at 50° C. overnight. The reaction is diluted with ethyl acetate and washed consecutively with water (×2) and brine, before drying over magnesium sulfate, filtering and removal of the volatile components under reduced pressure to afford the title compound.

Intermediate ZL

Acetic acid ((1S,2R,3S,4R)-4-{6-[2,2-bis-(4-chloro-phenyl)-2-hydroxy-ethylamino]-2-chloro-purin-9-yl}-2,3-dihydroxy-cyclopentylcarbamoyl)-methyl ester The title compound is prepared analogously to acetic acid ((1S,2R,3S,4R)-4-{6-[2,2-bis-(4-hydroxy-phenyl)-ethylamino]-2-chloro-purin-9-yl}-2,3-dihydroxy-cyclopentylcarbamoyl)-methyl ester (Intermediate ZK), by substituting 2-amino-1,1-bis-(4-chloro-phenyl)-ethanol (Intermediate ZI) for 4,4'-(2-aminoethylidene)bis-phenol.

Intermediate ZM

Acetic acid {(1S,2R,3S,4R)-4-[2-chloro-6-((S)-1-hydroxymethyl-2-phenyl-ethylamino)-purin-9-yl]-2,3-dihydroxy-cyclopentylcarbamoyl}-methyl ester The title compound is prepared by combining acetic acid [(1S,2R,3S,4R)-4-(2,6-dichloro-purin-9-yl)-2,3-dihydroxy-cyclopentyl-carbamoyl]-methyl ester (1 equivalent) and (S)-2-amino-3-phenyl-propan-1-ol 1 equivalent) in dichloromethane with triethylamine (1.1 equivalents) and stirring overnight. The reaction is diluted with dichloromethane, and washed consecutively with 0.1M hydrochloric acid, water and brine, before drying over magnesium sulfate. Filtration and removal of the volatile components under reduced pressure, affords the title compound.

Intermediate ZN

Acetic acid ((1S,2R,3S,4R)-4-{2-chloro-6-[(S)-1-hydroxymethyl-2-(4-hydroxy-phenyl)-ethylamino]-purin-9-yl}-2,3-dihydroxy-cyclopentylcarbamoyl)-methyl ester The title compound is prepared analogously to acetic acid {(1S,2R,3S,4R)-4-[2-chloro-6-((S)-1-hydroxymethyl-2-phenyl-ethylamino)-purin-9-yl]-2,3-dihydroxy-cyclopentylcarbamoyl}-methyl ester (intermediate ZM), by substituting 4-((S)-2-amino-3-hydroxy-propyl)-phenol for (S)-2-amino-3-phenyl-propan-1-ol.

Intermediate ZO

N-((1S,2R,3S,4R)-4-{2-((R)-3-Amino-pyrrolidin-1-yl)-6-[2,2-bis-(4-chloro-phenyl)-2-hydroxy-ethylamino]-purin-9-yl}-2,3-dihydroxy-cyclopentyl)-2-hydroxy-acetamide ZO1: Acetic acid {(1S,2R,3S,4R)-4-[6-[2,2-bis-(4-chloro-phenyl)-2-hydroxy-ethylamino]-2-((R)-3-tert-butoxycarbonylamino-pyrrolidin-1-yl)-purin-9-yl]-2,3-dihydroxy-cyclopentylcarbamoyl}-methyl ester A suspension of acetic acid ((1S,2R,3S,4R)-4-{6-[2,2-bis-(4-chloro-phenyl)-2-hydroxy-ethylamino]-2-chloro-purin-9-yl}-2,3-dihydroxy-cyclopentylcarbamoyl)-methyl ester (intermediate ZL; 1 equivalent) and (3R)-(+)-3-(Boc-amino) pyrrolidine (4 equivalents) in acetonitrile is treated with a catalytic amount of sodium iodide and then heated using microwave radiation in a Personal Chemistry Emrys™ Opti- ZO2: N-((1S,2R,3S,4R)-4-{2-((R)-3-Amino-pyrrolidin-1-yl)-6-[2,2-bis-(4-chloro-phenyl)-2-hydroxy-ethylamino]-purin-9-yl}-2,3-dihydroxy-cyclopentyl)-2-hydroxy-acetamide A solution of acetic acid {(1S,2R,3S,4R)-4-[6-[2,2-bis-(4-chloro-phenyl)-2-hydroxy-ethylamino]-2-((R)-3-tert-butoxycarbonylamino-pyrrolidin-1-yl)-purin-9-yl]-2,3-dihydroxy-cyclopentylcarbamoyl}-methyl ester (Intermediate Z01) in MeOH (~0.5M) is treated with an equal volume of 4M HCl in dioxane and stirred at room temperature for 2 hours. The solvent is removed in vacuo and purification is carried out by column chromatography/crystallisation to afford the title compound.

Intermediate ZP

N-{(1S,2R,3S,4R)-4-[2-(4-Amino-pyrazol-1-yl)-6-(2,2-diphenyl-ethylamino)-purin-9-yl]-2,3-dihydroxy-cyclopentyl}-2-hydroxy-acetamide ZP1: N-{(1S,2R,3S,4R)-4-[6-(2,2-Diphenyl-ethylamino)-2-hydrazino-purin-9-yl]-2,3-dihydroxy-cyclopentyl}-2-hydroxy-acetamide The title compound was prepared analogously to N-[(1S,2R,3S,4R)-4-(6-{[bis-(4-methoxy-phenyl)-methyl]-amino}-2-hydrazino-purin-9-yl)-2,3-dihydroxy-cyclopentyl]-propionamide (Example 168, step 2), by substituting acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1) for N-[(1S,2R,3S,4R)-4-(6-{[Bis-(4-methoxy-phenyl)-methyl]-amino}-2-chloro-purin-9-yl)-2,3-dihydroxy-cyclopentyl]-propionamide (example 168, step1).

ZP2: N-{(1S,2R,3S,4R)-4-[6-(2,2-Diphenyl-ethylamino)-2-(4-nitro-pyrazol-1-yl)-purin-9-yl]-2,3-dihydroxy-cyclopentyl}-2-hydroxy-acetamide The title compound is prepared analogously to 1-[6-{[bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid ethyl ester (example 168, step 3), by reaction of N-{(1S,2R,3S,4R)-4-[6-(2,2-diphenyl-ethylamino)-2-hydrazino-purin-9-yl]-2,3-dihydroxy-cyclopentyl}-2-hydroxy-acetamide (Intermediate ZP1) and sodium nitromalonaldehyde (prepared as described by Fanta P. E. Org. Syntheses, Coll. Vol. 4 (1963), pp 844-845).

ZP3: N-{(1S,2R,3S,4R)-4-[2-(4-Amino-pyrazol-1-yl)-6-(2,2-diphenyl-ethylamino)-purin-9-yl]-2,3-dihydroxy-cyclopentyl}-2-hydroxy-acetamide The title compound is prepared by dissolving N-{(1S,2R,3S,4R)-4-[6-(2,2-Diphenyl-ethylamino)-2-(4-nitro-pyrazol-1-yl)-purin-9-yl]-2,3-dihydroxy-cyclopentyl}-2-hydroxy-acetamide (Intermediate ZP2) in methanol (~1.0M), adding a 2:1 mixture by weight of activated carbon and ferric chloride and an excess of hydrazine monohydrate, and stirring the resulting mixture at 65° C. for four hours. Filtration through Celite™, removal of the volatile components under reduced pressure, and purification by column chromatography/crystallisation, affords the title compound.

Intermediate ZQ

N-((1S,2R,3S,4R)-4-{2-(4-Amino-pyrazol-1-yl)-6-[2,2-bis-(4-hydroxy-phenyl)-ethylamino]-purin-9-yl}-2,3-dihydroxy-cyclopentyl)-2-hydroxy-acetamide The title compound is prepared analogously to N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP), by substituting acetic acid ((1S,2R,3S,4R)-4-{6-[2,2-bis-(4-hydroxy-phenyl)-ethylamino]-2-chloro-purin-9-yl}-2,3-dihydroxy-cyclopentylcarbamoyl)-methyl ester (Intermediate ZK) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1).

Intermediate ZR

N-{(1S,2R,3S,4R)-4-[2-(4-Amino-pyrazol-1-yl)-6-(2,2-diphenyl-ethylamino)-purin-9-yl]-2,3-dihydroxy-cyclopentyl}-propionamide The title compound is prepared analogously to N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP), by substituting N-{(1S,2R,3S,4R)-4-[2-chloro-6-(2,2-diphenyl-ethylamino)-purin-9-yl]-2,3-dihydroxy-cyclopentyl}-propionamide (Intermediate J) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1).

Intermediate ZS

1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid ethyl ester The title compound is prepared analogously to 1-[6-{[bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid ethyl ester (example 168, step3), substituting N-{(1S,2R,3S,4R)-4-[6-(2,2-diphenyl-ethylamino)-2-hydrazino-purin-9-yl]-2,3-dihydroxy-cyclopentyl}-2-hydroxy-acetamide (Intermediate ZP1) for N-[(1S,2R,3S,4R)-4-(6-{[Bis-(4-methoxy-phenyl)-methyl]-amino}-2-hydrazino-purin-9-yl)-2,3-dihydroxy-cyclopentyl]-propionamide (Example 168, step 2).

Intermediate ZT

N-{(1S,2R,3S,4R)-4-[2-(4-Amino-pyrazol-1-yl)-6-((S)-1-hydroxymethyl-2-phenyl-ethylamino)-purin-9-yl]-2,3-dihydroxy-cyclopentyl}-2-hydroxy-acetamide The title compound is prepared analogously to N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP), by substituting acetic acid {(1S,2R,3S,4R)-4-[2-chloro-6-((S)-1-hydroxymethyl- 2-phenyl-ethylamino)-purin-9-yl]-2,3-dihydroxy-cyclopentylcarbamoyl}-methyl ester (Intermediate ZM) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1).

Intermediate ZU

N-{(1S,2R,3S,4R)-4-[2-(4-Amino-imidazol-1-yl)-6-(2,2-diphenyl-ethylamino)-purin-9-yl]-2,3-dihydroxy-cyclopentyl}-2-hydroxy-acetamide ZU1: N-{(1S,2R,3S,4R)-4-[6-(2,2-Diphenyl-ethylamino)-2-(4-nitro-imidazol-1-yl)-purin-9-yl]-2,3-dihydroxy-cyclopentyl}-2-hydroxy-acetamide The title compound is prepared by dissolving acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1) in N-methyl-2-pyrrolidinone, followed by potassium carbonate (5 equivalents) and 4-nitro-1H-imidazole (10 equivalents). The mixture is heated by microwave irradiation to 150° C. for two hours, then diluted with ethyl acetate and washed consecutively with water (×2) and brine, before drying over magnesium sulfate. Filtration, removal of the volatile components under reduced pressure and purification by flash column chromatography/crystallisation affords the title compound.

ZU2: N-{(1S,2R,3S,4R)-4-[2-(4-Amino-imidazol-1-yl)-6-(2,2-diphenyl-ethylamino)-purin-9-yl]-2,3-dihydroxy-cyclopentyl}-2-hydroxy-acetamide The title compound is prepared analogously to N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP3), by substituting N-{(1S,2R,3S,4R)-4-[6-(2,2-Diphenyl-ethylamino)-2-(4-nitro-imidazol-1-yl)-purin-9-yl]-2,3-dihydroxy-cyclopentyl}-2-hydroxy-acetamide (Intermediate ZU1) for N-{(1S,2R,3S,4R)-4-[6-(2,2-Diphenyl-ethylamino)-2-(4-nitro-pyrazol-1-yl)-purin-9-yl]-2,3-dihydroxy-cyclopentyl}-2-hydroxy-acetamide (Intermediate ZP2).

Intermediate ZV

N-((1S,2R,3S,4R)-4-{2-(4-Amino-imidazol-1-yl)-6-[2,2-bis-(4-hydroxy-phenyl)-ethylamino]-purin-9-yl}-2,3-dihydroxy-cyclopentyl)-2-hydroxy-acetamide The title compound is prepared analogously to N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU) by substituting acetic acid ((1S,2R,3S,4R)-4-{6-[2,2-bis-(4-hydroxy-phenyl)-ethylamino]-2-chloro-purin-9-yl}-2,3-dihydroxy-cyclopentylcarbamoyl)-methyl ester (Intermediate ZK) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1) in step ZU1.

Intermediate ZW

N-{(1S,2R,3S,4R)-4-[2-(3-Amino-[1,2,4]triazol-1-yl)-6-(2,2-diphenyl-ethylamino)-purin-9-yl]-2,3-dihydroxy-cyclopentyl}-2-hydroxy-acetamide The title compound is prepared analogously to N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU) from {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1) by substituting 3-nitro-1H-[1,2,4]triazole for 4-nitro-1H-imidazole in step ZU1.

Intermediate ZX

N-((1S,2R,3S,4R)-4-{2-(3-Amino-[1,2,4]triazol-1-yl)-6-[2,2-bis-(4-hydroxy-phenyl)-ethylamino]-purin-9-yl}-2,3-dihydroxy-cyclopentyl)-2-hydroxy-acetamide The title compound is prepared analogously to N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU) by substituting acetic acid ((1S,2R,3S,4R)-4-{6-[2,2-bis-(4-hydroxy-phenyl)-ethylamino]-2-chloro-purin-9-yl}-2,3-dihydroxy-cyclopentylcarbamoyl)-methyl ester (Intermediate ZK) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1) and 3-nitro-1H-[1,2,4]triazole for 4-nitro-1H-imidazole in step ZU1.

Intermediate ZY (2S,3S,4R,5R)-5-[2-Chloro-6-(2,2-diphenyl-ethylamino)-purin-9-yl]-3,4-dihydroxy-tetrahydro-furan-2-carboxylic acid ethylamide The title compound is prepared as described in WO 9602553.

Preparation of Specific Examples

Example 1

N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-hydroxy-acetamide trifluoroacetate Step 1: 2-Benzyloxy-N-{(1S,2R,3S,4R)-4-[2-chloro-6-(2,2-diphenyl-ethylamino)-purin-9-yl]-2,3-dihydroxy-cyclopentyl}-acetamide The title compound is prepared analogously to N-{(1S,2R,3S,4R)-4-[2-chloro-6-(2,2-diphenyl-ethylamino)-purin-9-yl]-2,3-dihydroxy-cyclopentyl}-propionamide (Intermediate J) by replacing propionyl chloride with benzyloxy-acetyl chloride.

Step 2: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-benzyloxy-acetamide trifluoroacetate A solution of 2-benzyloxy-N-{(1S,2R,3S,4R)-4-[2-chloro-6-(2,2-diphenyl-ethylamino)-purin-9-yl]-2,3-dihydroxy-cyclopentyl}-acetamide (80 mg, 0.13 mmol) in NMP:MeCN (1 ml of a 1:1 mixture) is treated with sodium iodide (6 mg, 0.04 mmol) followed by (3R)-3-aminopyrrolidine (34 mg, 0.4 mmol). The reaction mixture is heated using microwave radiation in a Personal Chemistry Emrys™ Optimizer microwave reactor at 200° C. The reaction is shown to be complete by LCMS after 30 minutes. The title compound is obtained after purification by reverse phase column chromatography (Isolute™ C18, 0-100% acetonitrile in water −0.1% TFA).

Step 3: N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-hydroxy-acetamide trifluoroacetate A solution of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (0.022 g, 0.03 mmol) in ethanol (2 ml) under an atmosphere of Argon is treated with palladium hydroxide on carbon (0.05 g, 20% w/w carbon). The reaction mixture is placed under an atmosphere of hydrogen and stirred at room temperature for 30 hours and then filtered through Celite™. The filtrate is concentrated in vacuo and purification of the crude by reverse phase column chromatography (Isolute™ C18, 0-100% acetonitrile in water −0.1% TFA) yields the title product. (MH+ 573.4)

Example 2

N-[(1S,2R,3S,4R)-4-(6-(2,2-Diphenyl-ethylamino)-2-{(R)-3-[3-(3-hydroxy-benzyl)-ureido]-pyrrolidin-1-yl}-purin-9-yl)-2,3-dihydroxy-cyclopentyl]-2-hydroxy-acetamide To a stirred solution of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-hydroxy-acetamide trifluoroacetate (Example 1) (1.1 g, 2 mmol) in NMP (2 ml) and MeOH (10 ml) is added dropwise phenyl chloroformate (0.47 g, 3 mmol). The reaction mixture is allowed to stir at room temperature for 3 hours and then treated with 3-hydroxybenzylamine (0.55 g, 4.45 mmol) and stirred for a further 2 hours at 80° C. Purification of the product by C-18 reverse phase column chromatography eluting with acetonitrile:water:TFA (0.1%) (gradient of 0 to 100% acetonitrile) yields the title compound. (MH+ 722.31)

Example 3

((1S,2R,3S,4R)-4-{6-(2,2-Diphenyl-ethyl]amino)-2-[(R)-3-(3-pyridin-2-ylmethyl-ureido)-pyrrolidin-1-yl]-purin-9-yl}-2,3-dihydroxy-cyclopentyl)-carbamic acid benzyl ester This compound is prepared analogously to Example 2 by replacing N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-hydroxy-acetamide trifluoroacetate with {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester (Intermediate L). (MH+ 783.3)

Example 4

N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-2-hydroxy-acetamide hydrochloride A solution comprising N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-hydroxy-acetamide trifluoroacetate (Example 1) (0.5 g, 0.87 mmol) and pyridin-3-yl-carbamic acid phenyl ester (Intermediate ZB) (0.198 g, 0.87 mmol) in NMP (1 ml) is stirred at 100° C. for 1 hour. The solvent is removed in vacuo and the title compound is obtained after purification by reverse phase column chromatography (Isolute™ C18, 0-100% acetonitrile in water −0.1% HCl). (MH+ 707.65)

Example 5

N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-2-hydroxy-acetamide hydrochloride This compound is prepared analogously to Example 4 by replacing pyridin-3-yl-carbamic acid phenyl ester (Intermediate ZB) with (3-sulfamoyl-phenyl)-carbamic acid phenyl ester (EP 365484). (MH+ 707.65)

Example 6

N-[(1S,2R,3S,4R)-4-(6-(2,2-Diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-2-hydroxy-acetamide hydrochloride This compound is prepared analogously to Example 4 by replacing pyridin-3-yl-carbamic acid phenyl ester (Intermediate ZB) with (4-sulfamoyl-phenyl)-carbamic acid phenyl ester (JP 2002283758). (MH+ 771.60)

Example 7

N-[(1S,2R,3S,4R)-4-(6-[2,2-Bis-(4-hydroxy-phenyl)-ethylamino]-2-{(R)-3-[3-(3-hydroxy-benzyl)-ureido]-pyrrolidin-1-yl}-purin-9-yl)-2,3-dihydroxy-cyclopentyl]-2-hydroxy-acetamide Step 1

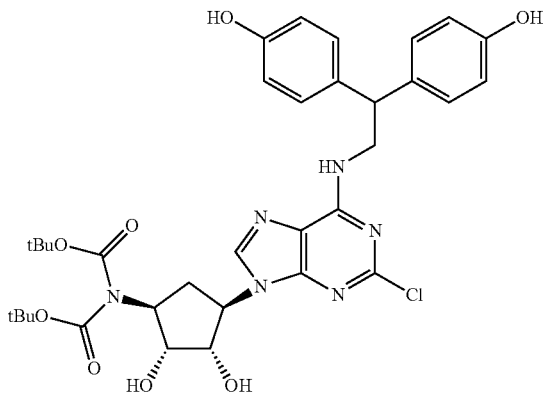

A reaction mixture comprising (1S,2R,3S,5R)-3-(Di-Boc-amino)-5-(2,6-dichloro-purin-9-yl)-cyclopentane-1,2-diol (Intermediate J4) (3.00 g, 5.95 mmol) and 4,4'-(2-aminoethylidene)bis-phenol (prepared according to the preparation of R. M. Schelkun et al. Bioorg. Med. Chem. Lett. 9 (1999) 2447-2452.) (1.5 g, 6.54 mmol) in dry THF (20 ml) is treated with DIPEA (1.2 ml, 7.14 mmol) and stirred at 50° C. overnight. The solvent is removed in vacuo and the residue is partitioned between DCM and 2M HCl. The organic portion is separated, dried (Mg SO₄) and concentrated in vacuo to afford the title compound.

Step 2: (1S,2R,3S,5R)-3-Amino-5-{6-[2,2-bis-(4-hydroxy-phenyl)-ethylamino]-2-chloro-purin-9-yl}-cyclopentane-1,2-diol A solution of Example 7 step 1 (3.45 g, 5.80 mmol) in methanol (7 ml) is treated with 4M HCl in dioxane (3 ml) and the reaction mixture is stirred at room temperature overnight. The solvent is removed in vacuo and the residue is partitioned between saturated sodium bicarbonate solution and DCM. The organic portion is separated, dried (MgSO₄) and concentrated in vacuo to afford the title compound.

Step 3: N-((1S,2R,3S,4R)-4-{6-[2,2-Bis-(4-hydroxy-phenyl)-ethylamino]-2-[(R)-3-(3-pyridin-3-yl-ureido)-pyrrolidin-1-yl]-purin-9-yl}-2,3-dihydroxy-cyclopentyl)-2-hydroxy-acetamide trifluoroacetate A mixture comprising (1S,2R,3S,5R)-3-amino-5-{6-[2,2-bis-(4-hydroxy-phenyl)-ethylamino]-2-chloro-purin-9-yl}-cyclopentane-1,2-diol (1.03 g, 1.93 mmol) and potassium carbonate (1.34 g, 9.65 mmol) in DMF (5 ml) is treated with acetoxyacetyl chloride (0.499 g, 4.63 mmol) and TEA (0.78 g, 7.72 mmol) and stirred at room temperature overnight. The solvent is removed in vacuo and the residue is dissolved in methanol and 5M KOH. The resulting mixture is filtered to removed the undissolved potassium carbonate and then concentrated in vacuo. Purification of the residue by preparative HPLC eluting with acetonitrile:water:TFA (0.1%) (gradient of 5 to 100% acetonitrile) yields the title compound. (MH+ 555.42).

Step 4: ((R)-1-{6-[2,2-Bis-(4-hydroxy-phenyl)-ethylamino]-9-[(1R,2S,3R,4S)-2,3-dihydroxy-4-(2-hydroxy-acetylamino)-cyclopentyl]-9H-purin-2-yl}-pyrrolidin-3-yl)-carbamic acid tert-butyl ester hydrochloride A mixture comprising N-((1S,2R,3S,4R)-4-{6-[2,2-Bis-(4-hydroxy-phenyl)-ethylamino]-2-[(R)-3-(3-pyridin-3-yl-ureido)-pyrrolidin-1-yl]-purin-9-yl}-2,3-dihydroxy-cyclopentyl)-2-hydroxy-acetamide trifluoroacetate (475 mg, 0.71 mmol), (R)-pyrrolidin-3-yl-carbamic acid tert-butyl ester (0.529 g, 2.84 mmol) and sodium iodide (106 mg, 0.71 mmol) in acetonitrile (0.5 ml) is heated using microwave radiation in a Personal Chemistry Emrys™ Optimizer microwave reactor at 160° C. The reaction is shown to be complete by LCMS after 30 minutes. The title compound is obtained after purification by reverse phase column chromatography (Isolute™ C18, 0-100% acetonitrile in water −0.1% HCl).

Step 5: N-((1S,2R,3S,4R)-4-{2-((R)-3-Amino-pyrrolidin-1-yl)-6-[2,2-bis-(4-hydroxy-phenyl)-ethylamino]-purin-9-yl}-2,3-dihydroxy-cyclopentyl)-2-hydroxy-acetamide hydrochloride This compound is prepared analogously to (1S,2R,3S,5R)-3-amino-5-{6-[2,2-bis-(4-hydroxy-phenyl)-ethylamino]-2-chloro-purin-9-yl}-cyclopentane-1,2-diol (step 2)

Step 6: N-[(1S,2R,3S,4R)-4-(6-[2,2-Bis-(4-hydroxy-phenyl)-ethylamino]-2-{(R)-3-[3-(3-hydroxy-benzyl)-ureido]-pyrrolidin-1-yl}-purin-9-yl)-2,3-dihydroxy-cyclopentyl]-2-hydroxy-acetamide A solution comprising N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-2-hydroxy-acetamide hydrochloride (15 mg, 0.02 mmol) and (3-hydroxy-benzyl)-carbamic acid phenyl ester (prepared according to the method of McDonnell M. E. et al Biioorganic and Medicinal Chemistry Letters 14 (2004) 531-534) (6 mg, 0.026 mmol) in MeOH (0.5 ml) is treated with TEA (33 μl, 0.23 mmol) and then heated at 100° C. for 30 minutes. Purification of the crude product by preparative HPLC eluting with acetonitrile:water:TFA (0.1%) (gradient of 10 to 100% acetonitrile) yields the title compound. (MH+ 803.46)

Examples 8-10

These compounds namely,

N-[(1S,2R,3S,4R)-4-(6-[2,2-Bis-(4-hydroxy-phenyl)-ethylamino]-2-{(R)-3-[3-(3-sulfamoyl-phenyl)-ureido]-pyrrolidin-1-yl}-purin-9-yl)-2,3-dihydroxy-cyclopentyl]-2-hydroxy-acetamide trifluoroacetate(MH+ 803.46) (Example 8), N-[(1S,2R,3S,4R)-4-(6-[2,2-Bis-(4-hydroxy-phenyl)-ethylamino]-2-{(R)-3-[3-(4-sulfamoyl-phenyl)-ureido]-pyrrolidin-1-yl}-purin-9-yl)-2,3-dihydroxy-cyclopentyl]-2-hydroxy-acetamide trifluoroacetate (MH+ 803.45) (Example 9) and N-((1S,2R,3S,4R)-4-{6-[2,2-Bis-(4-hydroxy-phenyl)-ethylamino]-2-[(R)-3-(3-pyridin-2-ylmethyl-ureido)-pyrrolidin-1-yl]-purin-9-yl}-2,3-dihydroxy-cyclopentyl)-2-hydroxy-acetamide trifluoroacetate (MH+ 739.36) (Example 10) are prepared analagously to Example 6 by replacing (2-hydroxy-benzyl)-carbamic acid phenyl ester with (2-sulfamoyl-benzyl)-carbamic acid phenyl ester, (3-sulfamoyl-benzyl)-carbamic acid phenyl ester and pyridin-2-ylmethyl-carbamic acid phenyl ester respectively. These carbamic acid phenyl esters are prepared according to the method of McDonnell M. E. et al. Biioorganic and Medicinal Chemistry Letters 14 (2004) 531-534.

Example 11

((1S,2R,3S,4R)-4-[6-(2,2-Diphenyl-ethyl]amino)-2-[(R)-3-(3-pyridin-2-ylmethyl-ureido)-pyrrolidin-1-yl]-purin-9-yl}-2,3-dihydroxy-cyclopentyl)-carbamic acid methyl ester trifluoroacetate Step 1: ((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-carbamic acid benzyl ester A solution of {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester (Intermediate L) (0.2 g, 0.31 mmol) in NMP/THF (3 ml of a 1:2 mixture) is treated with TEA (0.05 g, 0.46 mmol) followed by chloroformic acid phenyl ester (0.053 g, 0.34 mmol). The reaction mixture is stirred at room temperature for 2 hours and then treated with 2-amino methylpyridine (0.076 g, 0.62 mmol). The mixture is heated to 50° C. overnight and then the solvent is removed in vacuo. Purification by C-18 reverse phase column chromatography eluting with acetonitrile:water:HCl (0.1%) (gradient of 0 to 100% acetonitrile) affords the product in acetonitrile which is subsequently washed with saturated sodium bicarbonate solution and extracted with DCM (3 times). The combined organic portions are dried (MgSO₄) and concentrated in vacuo to afford the title compound. (MH+ 783.3)

Step 2: 1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-2-ylmethyl-urea A solution of ((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-carbamic acid benzyl ester (0.13 g, 166 μmol) in ethanol (9 ml) under an inert atmosphere of Argon is treated with Palladium (10% on charcoal) (44 mg). The reaction mixture is placed under an atmosphere of hydrogen and stirred at room temperature overnight and then filtered through Celite™. The filtrate is concentrated in vacuo to afford the title compound. (MH+ 649.89)

Step 3: ((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-carbamic acid methyl ester trifluoroacetate A solution of 1-{(R)-1-[9-((1R,2S,3R,4S)-4-amino-2,3-dihydroxy-cyclopentyl)-6-(2,2-diphenyl-ethylamino)-9H-purin-2-yl]-pyrrolidin-3-yl}-3-pyridin-2-ylmethyl-urea (17 mg, 26 μmol) in THF (1 ml) is treated with TEA (5 mg, 50 μmol) followed by methyl chloroformate (2.7 mg, 29 μmol). The reaction mixture is stirred at room temperature overnight and purification of the crude mixture by preparative LC-MS affords the title compound. (MH+ 707.49)

Example 12

[(1S,2R,3S,4R)-4-(6-(2,2-Diphenyl-ethylamino)-2-{2-[3-(3,4,5,6-tetrahydro-2H-[1,2]bipyridinyl-4-yl)-ureido]-ethylcarbamoyl}-purin-9-yl)-2,3-dihydroxy-cyclopentyl]-carbamic acid tert-butyl ester

Step 1: 9-[(1R,4S)-4-(tert-Butoxycarbonyl-propionyl-amino)-cyclopent-2-enyl]-6-(2,2-diphenyl-ethylamino)-9H-purine-2-carboxylic acid methyl ester This compound is prepared analogously to Di-Boc-[(1S,4R)-4-(2,6-dichloro-purin-9-yl)-cyclopent-2-enyl]-amine (Intermediate J3) by replacing di-t-butyl iminodicarboxylate with propionyl-carbamic acid tert-butyl ester.

Step 2: 9-[(1R,2S,3R,4S)-4-(tert-butoxycarbonyl-propionyl-amino)-2,3-dihydroxy-cyclopentyl]-6-(2,2-diphenyl-ethylamino)-9H-purine-2-carboxylic acid methyl ester To a stirred suspension comprising 9-[(1R,4S)-4-(tert-butoxycarbonyl-propionyl-amino)-cyclopent-2-enyl]-6-(2,2-diphenyl-ethylamino)-9H-purine-2-carboxylic acid methyl ester (6.6 g, 10.82 mmol), methane sulphonamide (1.03 g, 10.82 mmol) and AD-mix-α (16.23 g) in t-butanol (40 ml) and water (40 ml) is added osmium tetroxide (3 ml of a 4% solution in water). The reaction mixture is stirred vigorously for 36 hours. The reaction mixture is partitioned between ethyl acetate and water and the organic portion is dried (MgSO$_4$) and concentrated in vacuo. The title product is precipitated from methanol. Further product is derived from the mother liquor by chromatography on silica eluting with DCM:methanol (25:1).

Step 3: {(1S,2R,3S,4R)-4-[2-(2-Amino-ethylcarbamoyl)-6-(2,2-diphenyl-ethylamino)-purin-9-yl]-2,3-dihydroxy-cyclopentyl}-carbamic acid tert-butyl ester A solution comprising 9-[(1R,2S,3R,4S)-4-(tert-butoxycarbonyl-propionyl-amino)-2,3-dihydroxy-cyclopentyl]-6-(2,2-diphenyl-ethylamino)-9H-purine-2-carboxylic acid methyl ester (3.00 g, 4.66 mmol) in ethylenediamine (5 ml, 75 mmol) is heated at 90° C. for 1 hour. After cooling to room temperature, the ethylenediamine is removed in vacuo and purification by C-18 reverse phase column chromatography eluting with water (100%) followed by MeOH (100%) yields the title compound.

Step 4: [(1S,2R,3S,4R)-4-(6-(2,2-Diphenyl-ethylamino)-2-{2-[3-(3,4,5,6-tetrahydro-2H-[1,2]bipyridinyl-4-yl)-ureido]-ethylcarbamoyl}-purin-9-yl)-2,3-dihydroxy-cyclopentyl]-carbamic acid tert-butyl ester To a suspension of {(1S,2R,3S,4R)-4-[2-(2-amino-ethylcarbamoyl)-6-(2,2-diphenyl-ethylamino)-purin-9-yl]-2,3-dihydroxy-cyclopentyl}-carbamic acid tert-butyl ester (2.5 g, 4.05 mmol) in IPA (10 ml) is added imidazole-1-carboxylic acid (3,4,5,6-tetrahydro-2H-[1,2]bipyridinyl-4-yl)-amide (Intermediate C) (151 ml of a 10 mg/ml solution in DCM, 5.56 mmol) and the reaction mixture is stirred at room temperature overnight. The solvent is removed in vacuo and the crude product is purified by chromatography on silica eluting with DCM/MeOH (25:1 increasing to 15:1). The resulting solid is further purified by dissolving in DCM and washing the solution with water, drying (MgSO$_4$) and concentrating in vacuo to afford the title product. (MH+ 820.7)

Example 13

[(1S,2R,3S,4R)-4-(6-(2,2-diphenyl-ethylamino)-2-{2-[3-(3,4,5,6-tetrahydro-2H-[1,2]bipyridinyl-4-yl)-ureido]-ethylcarbamoyl}-purin-9-yl)-2,3-dihydroxy-cyclopentyl]-carbamic acid methyl ester trifluoroacetate

Step 1: 9-((1R,2S,3R,4S)-4-Amino-2,3-dihydroxy-cyclopentyl)-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide dihydrochloride The title compound is prepared analogously to (1S,2R,3S,5R)-3-Amino-5-{6-[2,2-bis-(4-hydroxy-phenyl)-ethylamino]-2-chloro-purin-9-yl}-cyclopentane-1,2-diol (example 7 step 2) by replacing N-((1S,2R,3S,4R)-4-{6-[2,2-Bis-(4-hydroxy-phenyl)-ethylamino]-2-chloro-purin-9-yl}-2,3-dihydroxy-cyclopentyl)-propionamide hydrochloride with (1S,2R,3S,4R)-4-(6-(2,2-Diphenyl-ethylamino)-2-{2-[3-(3,4,5,6-tetrahydro-2H-[1,2']bipyridinyl-4-yl)-ureido]-ethylcarbamoyl}-purin-9-yl)-2,3-dihydroxy-cyclopentyl]-carbamic acid tert-butyl ester (Example 12).

Step 2: [(1S,2R,3S,4R)-4-(6-(2,2-diphenyl-ethylamino)-2-{2-[3-(3,4,5,6-tetrahydro-2H-[1,2]bipyridinyl-4-yl)-ureido]-ethylcarbamoyl}-purin-9-yl)-2,3-dihydroxy-cyclopentyl]-carbamic acid methyl ester trifluoroacetate A mixture comprising 9-((1R,2S,3R,4S)-4-amino-2,3-dihydroxy-cyclopentyl)-6-(2,2-diphenyl-ethylamino)-9H-purine-2-carboxylic acid {2-[3-(3,4,5,6-tetrahydro-2H-[1,2]bipyridinyl-4-yl)-ureido]-ethyl}-amide dihydrochloride (20 mg, 25 µmol), TEA (12.7 mg, 125 µmol) in THF (2 ml) is treated with methyl chloroformate (6.0 mg, 63 µmol) and left to stir at room temperature overnight. The solvent is removed in vacuo and purification of the crude product by reverse phase column chromatography (Isolute™ C18, 0-100% acetonitrile in water −0.1% TFA) yields the title product. (MH+ 778.6)

Example 14

9-[(1R,2S,3R,4S)-2,3-Dihydroxy-4-(2-hydroxy-acetylamino)-cyclopentyl]-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide trifluoroacetate Step 1: Acetic acid [(1S,2R,3S,4R)-4-(6-(2,2-diphenyl-ethylamino)-2-{2-[3-(3,4,5,6-tetrahydro-2H-[1,2']bipyridinyl-4-yl)-ureido]-ethylcarbamoyl}-purin-9-yl)-2,3-dihydroxy-cyclopentylcarbamoyl]-methyl ester trifluoroacetate This compound is prepared analogously to Example 13 by replacing methyl chloroformate with acetoxyacetyl chloride.

Step 2: 9-[(1R,2S,3R,4S)-2,3-Dihydroxy-4-(2-hydroxy-acetylamino)-cyclopentyl]-6-(2,2-diphenyl-ethylamino)-9H-purine-2-carboxylic acid {2-[3-(3,4,5,6-tetrahydro-2H-[1,2]bipyridinyl-4-yl)-ureido]-ethyl}-amide trifluoroacetate A solution of acetic acid [(1S,2R,3S,4R)-4-(6-(2,2-diphenyl-ethylamino)-2-{2-[3-(3,4,5,6-tetrahydro-2H-[1,2]bipyridinyl-4-yl)-ureido]-ethylcarbamoyl}-purin-9-yl)-2,3-dihydroxy-cyclopentylcarbamoyl]-methyl ester trifluoroacetate (0.015 g, 16 µmol) in methanol (1 ml) is treated with potassium carbonate (0.01 g, 10 µmol) and the reaction mixture is allowed to stir at room temperature for 1 hour. The solvent is removed in vacuo and purification of the crude by reverse phase column chromatography (Isolute™ C18, 0-100% acetonitrile in water −0.1% TFA) yields the title product. (MH+ 778.6)

Example 15

N-((1S,2R,3S,4R)-4-{6-(2,2-Diphenyl-ethylamino)-2-[(R)-3-((R)-3-pyrrolidin-3-ylureido)-pyrrolidin-1-yl]-purin-9-yl}-2,3-dihydroxy-cyclopentyl)-2-hydroxy-acetamide N-{(1S,2R,3S,4R)-4-[2-chloro-6-(2,2-diphenyl-ethylamino)-purin-9-yl]-2,3-dihydroxy-cyclopentyl}-2-hydroxy-acetamide (Intermediate Q) (60 mg, 0.11 mmol) and 1,3-di(R)-pyrrolidin-3-yl-urea (Intermediate B) (91 mg, 0.46 mmol) in dry DMSO (0.2 ml) is stirred at 100° C. for 2 hours. Purification of the resulting mixture by C-18 reverse phase column chromatography eluting with acetonitrile:water:TFA (0.1%) (gradient of 20 to 70% acetonitrile) yields the product which is treated with saturated sodium bicarbonate solution and passed through the C-18 reverse phase column again. The column is washed first with water followed by MeOH (with 1% ammonia) to elute the product which is concentrated in vacuo to afford the title compound. (MH+ 685.2)

Example 16

N-[(1S,2R,3S,4R)-4-(6-(2,2-Diphenyl-ethylamino)-2-{(R)-3-[3-(3,4,5,6-tetrahydro-2H-[1,2']bipyridinyl-4-yl)-ureido]-pyrrolidin-1-yl}-purin-9-yl)-2,3-dihydroxy-cyclopentyl]-2-hydroxy-acetamide The title compound is prepared analogously to N-((1S,2R,3S,4R)-4-{6-(2,2-Diphenyl-ethylamino)-2-[(R)-3-((R)-3-pyrrolidin-3-ylureido)-pyrrolidin-1-yl]-purin-9-yl}-2,3-dihydroxy-cyclopentyl)-2-hydroxy-acetamide (Example 15) by replacing 1,3-di(R)-pyrrolidin-3-yl-urea (Intermediate B) with 1-(R)-pyrrolidin-3-yl-3-(3,4,5,6-tetrahydro-2H-[1,2']bipyridinyl-4-yl)-urea hydrochloride (Intermediate A). (MH+ 388.8)

Example 17

4-[(R)-3-(3-{(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-ureido)-pyrrolidine-1-carbonyl]-benzoic acid trifluoroacetate Step 1: N-((1S,2R,3S,4R)-4-{6-(2,2-Diphenyl-ethylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate The title compound is prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate Example 1 (Step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-{(1S,2R,3S,4R)-4-[2-chloro-6-(2,2-diphenyl-ethylamino)-purin-9-yl]-2,3-dihydroxy-cyclopentyl}-propionamide (Intermediate J) and by replacing (3R)-3-aminopyrrolidine with 1,3-di(R)-pyrrolidin-3-yl-urea (Intermediate B).

Step 2: 4-[(R)-3-(3-{(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-ureido)-pyrrolidine-1-carbonyl]-benzoic acid trifluoroacetate A solution of N-((1S,2R,3S,4R)-4-{6-(2,2-diphenyl-ethylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate (step 1) (0.02 g, 29 µmol) DIPEA (0.0075 g, 58 µmol) in NMP (0.2 ml) is treated with a solution of terephthaloyl chloride (0.006 g, 14.5 µmol) in NMP (0.1 ml). After stirring at room temperature for 1 hour the reaction mixture is purified by C-18 reverse phase column chromatography eluting with acetonitrile:water:TFA (0.1%) (gradient of 0 to 100% acetonitrile) to yield the title compound. (MH+ 831.6)

Example 18

N-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-6-morpholin-4-yl-nicotinamide trifluoroacetate Step 1: {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester trifluoroacetate A reaction mixture comprising N-{(1S,2R,3S,4R)-4-[2-chloro-6-(2,2-diphenyl-ethylamino)-purin-9-yl]-2,3-dihydroxy-cyclopentyl}-propionamide (Intermediate J) (2.5 g, 4.80 mmol) and (3R)-(+)-(3-Boc-amino)pyrrolidine (2.5 g, 13.6 mmol) in DMSO (8 ml) is heated at 100° C. overnight. The resulting mixture is purified by reverse phase column chromatography (Isolute™ C18, 0-100% MeOH in water –0.1% TFA) to yield the title product.

Step 2: N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester trifluoroacetate (3.22 g, 4.80 mmol) is dissolved in 1.25 M HCl in MeOH (60 ml, 75 mmol) and left to stir at room temperature overnight. The solvent is removed in vacuo and the crude product is dissolved in a minimal volume of EtOH/saturated sodium carbonate solution and purified by reverse phase column chromatography (Isolute™ C18, 0-100% MeOH in water) to yield the title product.

Step 3: N-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-6-morpholin-4-yl-nicotinamide trifluoroacetate A solution of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (22.8 mg, 0.04 mmol) in THF (1 ml) is treated with TEA (7.3 mg, 0.072 mmol) and then added to 6-morpholinonicotinoyl chloride (8.2 mg, 0.036 mmol). The reaction mixture is shaken and then allowed to stand at room temperature overnight. The solvent is removed in vacuo and purification by C-18 reverse phase column chromatography eluting with acetonitrile:water:TFA (0.1%) (gradient of 0 to 100% acetonitrile) yields the title compound. (MH+ 761.4)

Example 19

N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-propionamide trifluoroacetate A suspension of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (0.12 mg, 230 µmol) and sodium hydrogencarbonate (27 mg, 253 µmol) in DMSO (300 µl) is treated with phenyl chlorocarbonate (36 mg, 230 µmol) and then stirred at room temperature for 3 hours. This reaction mixture is added to 2-picolylamine (4.1 mg, 38 µmol) and stirred at 80° C. for 5 hours. Purification of the crude product by C-18 reverse phase column chromatography eluting with acetonitrile:water:TFA (0.1%) (gradient of 0 to 100% acetonitrile) to yield the title compound. (MH+ 705.4)

Example 20

N-((1S,2R,3S,4R)-4-{6-(2,2-diphenyl-ethylamino)-2-[(R)-3-(3-pyridin-4-ylmethyl-ureido)-pyrrolidin-1-yl]-purin-9-yl}-2,3-dihydroxy-cyclopentyl)-propionamide trifluoroacetate Step 1: Imidazole-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide A mixture comprising N-{(3aR,4S,6R,6aS)-6-[2-((R)-3-amino-pyrrolidin-1-yl)-6-(2,2-diphenyl-ethylamino)-purin-9-yl]-2,2-dimethyl-tetrahydro-cyclopenta[1,3]dioxol-4-yl}-propionamide (Intermediate M) (0.24 g, 394 µmol) and CDI (0.275 g, 1.7 mmol) in dry DCM (6 ml) is stirred at room temperature for 3 hours. The resulting solution is purified by chromatography on silica eluting with 100% DCM changing to 5% MeOH in DCM to afford the title compound as a yellow oil. The oil consists of the imidazole-urea intermediate together with variable amounts of the corresponding isocyanate and imidazole which are equally suitable as precursors to ureas.

Step 2: N-((1S,2R,3S,4R)-4-{6-(2,2-diphenyl-ethylamino)-2-[(R)-3-(3-pyridin-4-ylmethyl-ureido)-pyrrolidin-1-yl]-purin-9-yl}-2,3-dihydroxy-cyclopentyl)-propionamide trifluoroacetate Pyridylmethylamine (4.3 mg, 40 µmol) is treated with a solution of imidazole-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide (25 mg, 40 µmol) in DCM (1 ml) and the reaction mixture is stirred at room temperature overnight. The solvent is removed in vacuo and the residue is treated with TFA (0.5 ml) and water (0.5 ml). After stirring at room temperature for 3 hours, the reaction mixture is concentrated in vacuo and the resulting crude is purified by mass directed preparative LC-MS eluting with acetonitrile: water: trifluoroacetic acid to afford the title compound. (MH+ 705.4)

Example 21

N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-propionamide trifluoroacetate This compound is prepared analogously to Example 20 by replacing 4-pyridylmethylamine with 3-hydroxybenzylamine. (MH+ 720.4)

Example 22

N-{(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-6-morpholin-4-yl-nicotinamide hydrochloride

Step 1: N-((1S,2R,3S,4R)-4-{6-[2,2-Bis-(4-hydroxy-phenyl)-ethylamino]-2-chloro-purin-9-yl}-2,3-dihydroxy-cyclopentyl)-propionamide hydrochloride A reaction mixture comprising [(1S,2R,3S,4R)-4-(2,6-dichloro-purin-9-yl)-2,3-dihydroxy-cyclopentyl]-propionyl-carbamic acid tert-butyl ester (Intermediate G) (2.00 g, 4.35 mmol) and 4,4'-(2-aminoethylidene)bis-phenol (prepared by the procedure of R. M. Schelkun et al. Bioorg. Med. Chem. Lett. 9 (1999) 2447-2452.) (1.19 g, 5.20 mmol) in dry THF (40 ml) is treated with DIPEA (0.67 g, 5.20 mmol) and stirred at room temperature for 2 days. The solvent is removed in vacuo and the title compound is obtained after purification by reverse phase column chromatography (Isolute™ C18, 20-70% acetonitrile in water −0.1% HCl).

Step 2: 2R,3S,4R)-4-{6-[2,2-Bis-(4-hydroxy-phenyl)-ethylamino]-2-chloro-purin-9-yl}-2,3-dihydroxy-cyclopentyl)-propionamide This compound is prepared analogously to (1S,2R,3S,5R)-3-mino-5-{6-[2,2-bis-(4-hydroxy-phenyl)-ethylamino]-2-chloro-purin-9-yl}-cyclopentane-1,2-diol (Example 7 step 2).

Step 3: {(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-carbamic acid tert-butyl ester trifluoroacetate This compound is prepared analogously to ((R)-1-{6-[2,2-Bis-(4-hydroxy-phenyl)-ethylamino]-9-[(1R,2S,3R,4S)-2,3-dihydroxy-4-(2-hydroxy-acetylamino)-cyclopentyl]-9H-purin-2-yl}-pyrrolidin-3-yl)-carbamic acid tert-butyl ester hydrochloride (Example 7 step 4).

Step 4: N-((1S,2R,3S,4R)-4-{2-((R)-3-Amino-pyrrolidin-1-yl)-6-[2,2-bis-(4-hydroxy-phenyl)-ethylamino]-purin-9-yl}-2,3-dihydroxy-cyclopentyl)-propionamide A solution of {(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-carbamic acid tert-butyl ester trifluoroacetate (0.4 g, 0.57 mmol) in DCM (5 ml) and TFA (2.5 ml) is stirred at room temperature for 2 hours. The solvent is removed in vacuo to afford the title compound.

Step 5: N-{(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-6-morpholin-4-yl-nicotinamide hydrochloride A suspension of N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-propionamide (20 mg, 33 µmol) in dry THF is treated with NMP (0.5 ml) followed by TEA (13.4 mg, 0.13 mmol) and 6-morpholi-nonicotinoyl chloride (8.3 mg, 37 µmol). The reaction mixture is stirred at room temperature for 30 minutes and then the solvent is removed in vacuo. Purification by C-18 reverse phase column chromatography eluting with acetonitrile:water:HCl (0.1%) (gradient of 0 to 100% acetonitrile) yields the title compound. (MH+ 793.4)

Example 23

N-((1S,2R,3S,4R)-4-{6-[2,2-Bis-(4-hydroxy-phenyl)-ethylamino]-2-[(R)-3-(3-pyridin-2-ylmethyl-ureido)-pyrrolidin-1-yl]-purin-9-yl}-2,3-dihydroxy-cyclopentyl)-propionamide hydrochloride

Step 1: {(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-carbamic acid phenyl ester A mixture comprising N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-propionamide (Example 22 step 4) (50 mg, 83 µmol) and potassium carbonate (46 mg, 332 µmol) in NMP (1 ml) is treated with phenylchlorofomate and stirred at room temperature for 90 minutes. This mixture was used in the next step without purification.

Step 2: N-((1S,2R,3S,4R)-4-{6-[2,2-Bis-(4-hydroxy-phenyl)-ethylamino]-2-[(R)-3-(3-pyridin-2-ylmethyl-ureido)-pyrrolidin-1-yl]-purin-9-yl}-2,3-dihydroxy-cyclopentyl)-propionamide hydrochloride A mixture comprising {(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-carbamic acid phenyl ester (12 mg, 16 µmol) and 2-(aminomethyl)pyridine (5.4 mg, 50 µmol) in NMP (0.5 ml) is heated to 100° C. for 2 hours. After cooling to room temperature, purification by C-18 reverse phase column chromatography eluting with acetonitrile:water:HCl (0.1%) (gradient of 0 to 100% acetonitrile) yields the title compound. (MH+ 737.5)

Example 24

N-[(1S,2R,3S,4R)-4-(6-[2,2-Bis-(4-hydroxy-phenyl)-ethylamino]-2-{(R)-3-[3-(3-hydroxy-benzyl)-ureido]-pyrrolidin-1-yl}-purin-9-yl)-2,3-dihydroxy-cyclopentyl]-propionamide hydrochloride This compound is prepared analogously to N-((1S,2R,3S,4R)-4-{6-[2,2-Bis-(4-hydroxy-phenyl)-ethylamino]-2-[(R)-3-(3-pyridin-2-ylmethyl-ureido)-pyrrolidin-1-yl]-purin-9-yl}-2,3-dihydroxy-cyclopentyl)-propionamide hydrochloride (Example 23) by replacing 2-(aminomethyl)pyridine with the appropriate amine. (MH+ 752.5)

Example 25

N-((1S,2R,3S,4R)-4-[6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxyacetamide A solution of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-hydroxy-acetamide trifluoroacetate (0.2 g, 0.28 mmol) in dry THF (10 ml) is treated with TEA (113 mg, 1.12 mmol) followed by 3-isocyanato-pyridine (38 mg, 0.31 mmol). The reaction mixture is heated at 50° C. overnight. The solvent is removed in vacuo and purification by reverse phase column chromatography (Isolute™ C18, 10-50% acetonitrile in water −0.1% TFA) affords the product. The product is further purified by dissolving in MeOH and treating with saturated sodium bicarbonate solution. The mixture is passed through a pre-washed (400 ml MeOH followed by 400 ml water) eluting with 0.5% ammonia 880: water (100 ml) followed by water (400 ml) and finally MeOH to afford the title compound. (MH+ 693.4)

Example 26

((1S,2R,3S,4R)-4-[6-(2,2-Diphenyl-ethyl]amino)-2-(R)-3-(3-pyridin-3-yl-ureido)-pyrrolidin-1-yl]-purin-9-yl}-2,3-dihydroxy-cyclopentyl)-carbamic acid methyl ester hydrochloride Step 1: ((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-carbamic acid benzyl ester trifluoroacetate A solution comprising {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester (Intermediate L) (0.1 g, 0.15 mmol), pyridine-3-isocyanate (0.02 g, 0.17 mmol) and TEA (0.017 g, 0.17 mmol) in THF (2 ml) is stirred at room temperature overnight. The solvent is removed in vacuo and purification is carried out by reverse phase column chromatography (Isolute™ C18, 0-100% acetonitrile in water −0.1% TFA). The fractions are collected and the MeCN is removed in vacuo. The remaining aqueous portion is basified with saturated sodium bicarbonate solution and extracted with DCM. The combined organic extracted are dried (MgSO₄) and concentrated in vacuo to afford the title product. MS (ES+) m/e 769 (MH⁺).

Step 2: 1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-3-yl-urea To a solution of ((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-carbamic acid benzyl ester trifluoroacetate (step 1) (35 mg, 46 μmol) in ethanol (1 ml) under an inert atmosphere of argon is added 10% palladium on carbon (10 mg). The reaction mixture is purged with argon and placed under a positive atmosphere of hydrogen overnight after which time, the mixture is filtered through celite and the catalyst washed with ethanol. The organic portions are combined and concentrated in vacuo to yield the title compound. MS (ES+) m/e 635 (MH⁺).

Step 3: ((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-carbamic acid methyl ester hydrochloride This compound is prepared analogously to Example 11 by replacing 1-{(R)-1-[9-((1R,2S,3R,4S)-4-amino-2,3-dihydroxy-cyclopentyl)-6-(2,2-diphenyl-ethylamino)-9H-purin-2-yl]-pyrrolidin-3-yl}-3-pyridin-2-ylmethyl-urea with 1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-3-yl-urea. (MH+ 693.5)

Example 27

N-[(1S,2R,3S,4R)-4-(6-(2,2-diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-propionamide hydrochloride A suspension of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (20 mg, 0.035 mmol) and 3-isocyanato-benzenesulfonamide (Intermediate S) (17.7 mg, 0.095 mmol) in THF (1 ml) and DMF (1 ml) is stirred at room temperature overnight. The solvent is removed in vacuo and purification by reverse phase column chromatography (Isolute™ C18, 0-100% acetonitrile in water −0.1% HCl) affords the title compound. (MH+ 769.5)

Example 28

N-[(1S,2R,3S,4R)-4-(6-(2,2-diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-propionamide hydrochloride This compound is prepared analogously to Example 27 with the appropriate isocyanate. (MH+ 769.5)

Example 29

1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-2-ylmethyl-urea Step 1: ((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-carbamic acid benzyl ester A solution of {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester (Intermediate L) (0.2 g, 0.31 mmol) in NMP/THF (3 ml of a 1:2 mixture) is treated with TEA (0.05 g, 0.46 mmol) followed by chloroformic acid phenyl ester (0.053 g, 0.34 mmol). The reaction mixture is stirred at room temperature for 2 hours and then treated with 2-amino methylpyridine (0.076 g, 0.62 mmol). The mixture is heated to 50° C. overnight and then the solvent is removed in vacuo. Purification by C-18 reverse phase column chromatography eluting with acetonitrile:water:HCl (0.1%) (gradient of 0 to 100% acetonitrile) affords the product in acetonitrile which is subsequently washed with saturated sodium bicarbonate solution and extracted with DCM (3 times). The combined organic portions are dried (MgSO₄) and concentrated in vacuo to afford the title compound. (MH+ 783.3)

Step 2: 1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-2-ylmethyl-urea A solution of ((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-carbamic acid benzyl ester (0.13 g, 166 μmol) in ethanol (9 ml) under an inert atmosphere of Argon is treated with Palladium (10% on charcoal) (44 mg). The reaction mixture is placed under an atmosphere of hydrogen and stirred at room temperature overnight and then filtered through Celite™. The filtrate is concentrated in vacuo to afford the title compound. (MH+ 649.89)

Example 30-32

These compounds namely,
N-((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-acetamide trifluoroacetate (MH+ 691.5) (Example 30),
Cyclopropanecarboxylic acid ((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-amide trifluoroacetate (MH+ 717.5) (Example 31) and
cyclobutanecarboxylic acid ((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-amide trifluoroacetate (MH+ 731.5) (Example 32)
are prepared analogously (Example 11) by replacing methyl chloroformate with the appropriate acid chloride.

Example 33

N-((1S,2R,3S,4R)-4-{6-(2,2-Diphenyl-ethylamino)-2-[(R)-3-(N'-cyano-N"-pyridin-3-ylmethyl-guanidino)-pyrrolidin-1-yl]-purin-9-yl}-2,3-dihydroxy-cyclopentyl)-propionamide Step 1: (1S,2R,3S,4R)-4-{6-(2,2-Diphenyl-ethylamino)-2-[(R)-3-(3-cyano-2-phenyl-isoureido)-pyrrolidin-1-yl]-purin-9-yl}-2,3-dihydroxy-cyclopentanecarboxylic acid ethylamide A solution of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (50 mg) and diphenyl cyanocarbodiimidate (21 mg) in dry DCM (2 ml) is treated with TEA (13 µl) and then stirred at room temperature for 5 hours. The solvent is removed in vacuo and the resulting residue is partitioned between EtOAc and water. The organic portion is separated, dried (Na$_2$SO$_2$) and concentrated in vacuo to afford the crude product which is purified by preparative HPLC to afford the title compound. (MH+ 715).

Step 2: N-((1S,2R,3S,4R)-4-{6-(2,2-Diphenyl-ethylamino)-2-[(R)-3-(N'-cyano-N"-pyridin-3-ylmethyl-guanidino)-pyrrolidin-1-yl]-purin-9-yl}-2,3-dihydroxy-cyclopentyl)-propionamide A mixture comprising 1S,2R,3S,4R)-4-{6-(2,2-diphenyl-ethylamino)-2-[(R)-3-(3-cyano-2-phenyl-isoureido)-pyrrolidin-1-yl]-purin-9-yl}-2,3-dihydroxy-cyclopentanecarboxylic acid ethylamide (80 mg, 0.11 mmol) and 2-(aminomethyl) pyridine (35 µl, 0.33 mmol) in absolute ethanol (1 ml) is using microwave radiation in a Personal Chemistry Emrys™ Optimizer microwave reactor at 100° C. for 2500 s followed by 120° C. for 1 hour. The solvent is removed in vacuo and purification is carried out by preparative HPLC. The fractions are combined, treated with saturated sodium bicarbonate solution and then extracted with ethyl acetate (3×). The organic portions are dried (Na$_2$SO$_4$) and concentrated in vacuo to afford the title compound. (MH+ 729)

Example 34

((1S,2R,3S,4R)-4-[6-(2,2-Diphenyl-ethyl]amino)-2-[(R)-3-((R)-3-pyrrolidin-3-ylureido)-pyrrolidin-1-yl]-purin-9-yl}-2,3-dihydroxy-cyclopentyl)-carbamic acid methyl ester This compound is prepared analogously to {(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-carbamic acid tert-butyl ester trifluoroacetate (Example 18 step 1) by replacing N-{(1S,2R,3S,4R)-4-[2-chloro-6-(2,2-diphenyl-ethylamino)-purin-9-yl]-2,3-dihydroxy-cyclopentyl}-propionamide (Intermediate J) with {(1S,2R,3S,4R)-4-[2-chloro-6-(2,2-diphenyl-ethylamino)-purin-9-yl]-2,3-dihydroxy-cyclopentyl}-carbamic acid methyl ester (Intermediate T) and by replacing (3R)-(+)-(3-Boc-amino) pyrrolidine with 1,3-di(R)-pyrrolidin-3-yl-urea (Intermediate B). (MH+ 685.2)

Example 35

N-((1S,2R,3S,4R)-4-{6-(2,2-Diphenyl-ethylamino)-2-[(R)-3-(3-phenyl-ureido)-pyrrolidin-1-yl]-purin-9-yl}-2,3-dihydroxy-cyclopentyl)-propionamide hydrochloride This compound is prepared analogously to Example 27 by replacing 3-isocyanato-benzenesulfonamide (Intermediate S) with phenyl isocyanate. (MH+ 690.9)

Example 36

4-[(R)-3-(3-{(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-ureido)-pyrrolidine-1-carbonyl]-benzoic acid methyl ester This compound is prepared analogously to Example 17 by replacing terephthaloyl chloride with methyl-4-chlorocarbonyl benzoate. Purification is carried out by C-18 reverse phase column chromatography eluting with acetonitrile:water:HCl (0.1%) (gradient of 20 to 100% acetonitrile) to yield the title compound. (MH+ 845.58)

Example 37

N-((1S,2R,3S,4R)-4-{6-(2,2-Diphenyl-ethylamino)-2-[(R)-3-(3-pyridin-3-ylmethyl-ureido)-pyrrolidin-1-yl]-purin-9-yl}-2,3-dihydroxy-cyclopentyl)-propionamide trifluoroacetate A suspension of N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (20 mg, 38 µmol) and sodium hydrogencarbonate (4.5 mg, 42 µmol) in DMSO (300 µl) is treated with phenyl chloroformate (36 mg, 230 µmol) and then stirred at room temperature for 3 hours. This reaction mixture is added to 3-picolylamine (4.1 mg, 38 µmol) and stirred at 80° C. for 5 hours. Purification of the crude product by C-18 reverse phase column chromatography eluting with acetonitrile:water:TFA (0.1%) (gradient of 0 to 100% acetonitrile) to yield the title compound. (MH+ 705.4)

Example 38

((1S,2R,3S,4R)-4-[6-(2,2-Diphenyl-ethyl]amino)-2-[(R)-3-(3-pyridin-3-yl-ureido)-pyrrolidin-1-yl]-purin-9-yl}-2,3-dihydroxy-cyclopentyl)-carbamic acid benzyl ester trifluoroacetate A solution comprising {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester (Intermediate L) (0.1 g, 0.15 mmol), pyridine-3-isocyanate (0.02 g, 0.17 mmol) and TEA (0.017 g, 0.17 mmol) in THF (2 ml) is stirred at room temperature overnight. The solvent is removed in vacuo and purification is carried out by reverse phase column chromatography (Isolute™ C18, 0-100% acetonitrile in water −0.1% TFA). The fractions are collected and the MeCN is removed in vacuo. The remaining aqueous portion is basified with saturated sodium bicarbonate solution and extracted with DCM. The combined organic extracted are dried (MgSO$_4$) and concentrated in vacuo to afford the title product. (MH+ 769.5)

Example 39

N-[(1S,2R,3S,4R)-4-(6-(2,2-Diphenyl-ethylamino)-2-{(R)-3-[3-(3-hydroxy-phenyl)-ureido]-pyrrolidin-1-yl}-purin-9-yl)-2,3-dihydroxy-cyclopentyl]-propionamide trifluoroacetate Step 1: Imidazole-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide A mixture comprising N-{(3aR,4S,6R,6aS)-6-[2-((R)-3-amino-pyrrolidin-1-yl)-6-(2,2-diphenyl-ethylamino)-purin-9-yl]-2,2-dimethyl-tetrahydro-cyclopenta[1,3]dioxol-4-yl}-propionamide (Intermediate M) (0.24 g, 394 µmol) and CDI (0.275 g, 1.7 mmol) in dry DCM (6 ml) is stirred at room temperature for 3 hours. The resulting solution is purified by chromatography on silica eluting with 100% DCM changing to 5% MeOH in DCM to afford the title compound as a yellow oil. The oil consists of the imidazole-urea intermediate together with variable amounts of the corresponding isocyanate and imidazole which are equally suitable as precursors to ureas.

Step 2: N-[(1S,2R,3S,4R)-4-(6-(2,2-Diphenyl-ethylamino)-2-{(R)-3-[3-(3-hydroxyphenyl)-ureido]-pyrrolidin-1-yl}-purin-9-yl)-2,3-dihydroxy-cyclopentyl]-propionamide trifluoroacetate 3-Aminophenol (4.3 mg, 40 µmol) is treated with a solution of imidazole-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide (25 mg, 40 µmol) in DCM (1 ml) and the reaction mixture is stirred at room temperature overnight. The solvent is removed in vacuo and the residue is treated with TFA (0.5 ml) and water (0.5 ml). After stirring at room temperature for 3 hours, the reaction mixture is concentrated in vacuo and the resulting crude is purified by mass directed preparative LC-MS eluting with acetonitrile: water: trifluoroacetic acid to afford the title compound. (MH+ 706.4)

Example 40

N-{(1S,2R,3S,4R)-4-[2-[(R)-3-(4-Acetylamino-benzenesulfonylamino)-pyrrolidin-1-yl]-6-(2,2-diphenyl-ethylamino)-purin-9-yl]-2,3-dihydroxy-cyclopentyl}-propionamide trifluoroacetate N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (23 mg, 40 µmol) is treated with a solution of 4-acetamidobenzenesulfonyl chloride (9.5 mg, 0.039 mmol) in NMP (0.5 ml) and stirred at room temperature overnight. Purification by preparative LCMS affords the title compound. (MH+ 768.50)

Example 41

N-{(1S,2R,3S,4R)-4-[2-[(R)-3-(4,5-Dihydro-1H-imidazol-2-ylamino)-pyrrolidin-1-yl]-6-(2,2-diphenyl-ethylamino)-purin-9-yl]-2,3-dihydroxy-cyclopentyl}-propionamide A mixture comprising N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (30 mg, 0.053 mmol) and 4,5-dihydro-1H-imidazole-2-thiol hydroiodide (24 mg, 0.106 mmol) in absolute ethanol (2 ml) is treated with DMAP (catalytic amount) and TEA (29 µl, 0.212 mmol). The resulting mixture is heated using microwave radiation in a Personal Chemistry Emrys™ Optimizer microwave reactor at 150° C. for 4000 s. The solvent is removed in vacuo and purification of the crude product by preparative HPLC ((30-95% acetonitrile in water −0.1% TFA) affords the title compound. (MH+ 639.63)

Example 42

N-{(1S,2R,3S,4R)-4-[2-{N'-[1-Cyclohexyl-methylidene]-hydrazino}-6-(2,2-diphenyl-ethylamino)-purin-9-yl]-2,3-dihydroxy-cyclopentyl}-propionamide Step 1: N-{(1S,2R,3S,4R)-4-[6-(2,2-Diphenyl-ethylamino)-2-hydrazino-purin-9-yl]-2,3-dihydroxy-cyclopentyl}-propionamide N-{(1S,2R,3S,4R)-4-[2-Chloro-6-(2,2-diphenyl-ethylamino)-purin-9-yl]-2,3-dihydroxy-cyclopentyl}-propionamide (Intermediate J) (1.0 g, 1.91 mmol) and hydrazine monohydrate (12 ml) is stirred for 72 h and then isopropyl alcohol (10 ml) is added. The solvent is removed in vacuo and the residue is water (10 ml) and stirred for 12 h. The fine solid obtained is filtered, washed with water and dried in vacuo to afford the product. LC-MS (0.1% formic acid, acetonitrile) (MH+ 517)

Step 2: N-{(1S,2R,3S,4R)-4-[2-{N'-[1-Cyclohexyl-methylidene]-hydrazino}-6-(2,2-diphenyl-ethylamino)-purin-9-yl]-2,3-dihydroxy-cyclopentyl}-propionamide To a solution of N-{4-[6-(2,2-diphenyl-ethylamino)-2-hydrazino-purin-9-yl]-2,3-dihydroxy-cyclopentyl}-propionamide (step 1) (0.1 g, 0.19 mmol) in dry methanol (5 ml) is added cyclohexane carboxaldehyde (0.026 g, 0.23 mmol). The reaction mixture is heated at reflux for 12 h. The reaction mixture is concentrated in vacuo purification by preparative TLC affords the title compound. LC-MS (0.1% formic acid, acetonitrile): (MH+ 611.45)

Example 43

1-{(R)-1-[9-((1R,2S,3R,4S)-2,3-Dihydroxy-4-propylamino-cyclopentyl)-6-(2,2-diphenyl-ethylamino)-9H-purin-2-yl]-pyrrolidin-3-yl}-3-pyridin-3-yl-urea hydrochloride A solution of 1-{(R)-1-[9-((1R,2S,3R,4S)-4-amino-2,3-dihydroxy-cyclopentyl)-6-(2,2-diphenyl-ethylamino)-9H-purin-2-yl]-pyrrolidin-3-yl}-3-pyridin-3-yl-urea (Example 26 step 2) (17 mg, 26 mmol) in DCE (1 ml) is treated with propanaldehyde (1.5 mg, 26 mmol) and placed under an atmosphere of argon. Sodium triacetoxyborohydride (10 mg, 51 µmol) is added and the reaction mixture is stirred at room temperature overnight. The mixture is quenched with 2M NaOH (5 drops) and the solvent is removed in vacuo. The residue is purified by C-18 reverse phase column chromatography eluting with acetonitrile:water:HCl (0.1%) (gradient of 20 to 100% acetonitrile) to yield the title compound. (MH+ 677.14)

Example 44

N-[(1S,2R,3S,4R)-4-(6-Amino-2-{N'[1-cyclohexyl-methylidene]hydrazino}-purin-9-yl)-2,3-dihydroxy-cyclopentyl]propionamide This compound is prepared analogously to Example 42 by replacing N-{(1S,2R,3S,4R)-4-[2-chloro-6-(2,2-diphenyl-ethylamino)-purin-9-yl]-2,3-dihydroxy-cyclopentyl}-propionamide (Intermediate J) with N-[(1S,2R,3S,4R)-4-(6-amino-2-chloro-purin-9-yl)-2,3-dihydroxy-cyclopentyl]-propionamide trifluoroacetate (Intermediate ZA). (MH+ 431.33)

Example 45

(R)-3-(3-{(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-ureido)-pyrrolidine-1-carboxylic acid pyridin-3-ylamide hydrochloride This compound is prepared analogously to Example 23 by replacing {(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-carbamic acid phenyl ester with N-((1S,2R,3S,4R)-4-{6-(2,2-diphenyl-ethylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate (Example 17 step 1) and by replacing (aminomethyl)pyridine with pyridin-3-yl-carbamic acid phenyl ester (Intermediate ZB). (MH+ 803.8)

Examples 46-47

These compounds namely,
9-[(1R,2S,3R,4S)-4-(3,3-dimethyl-ureido)-2,3-dihydroxy-cyclopentyl]-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide trifluoroacetate (MH+ 791.6) (Example 46) and acetic acid [(1S,2R,3S,4R)-4-(6-(2,2-diphenyl-ethylamino)-2-{2-[3-(3,4,5,6-tetrahydro-2H-[1,2']bipyridinyl-4-yl)-ureido]-ethylcarbamoyl}-purin-9-yl)-2,3-dihydroxy-cyclopentylcarbamoyl]-methyl ester trifluoroacetate (Example 47) are prepared analogously to Example 13 by replacing methyl chloroformate with either dimethylcarbamyl chloride or acetoxyacetyl chloride respectively.

Example 48

9-((1R,2S,3R,4S)-2,3-Dihydroxy-4-propionylamino-cyclopentyl)-6-(2,2-diphenyl-ethylamino)-9H-purine-2-carboxylic acid (2-methanesulfonylamino-ethyl)-amide Step 1:
6-(2,2-Diphenyl-ethylamino)-9H-purine-2-carboxylic acid methyl ester 6-(2,2-Diphenyl-ethylamino)-9H-purine-2-carboxylic acid methyl ester hydrochloride (prepared using the procedure described in international patent application WO 2001/94368) (35 g, 85.3 mmol) is placed in a flask under an atmosphere of argon. Dry CHCl$_3$ (300 ml) and N,O-bis(trimethylsilyl)acetamide (61 ml) are added and the reaction mixture is refluxed for 1 hour. The reaction mixture is allowed to cool and any volatiles removed in vacuo. To the resulting oil is added MeOH (300 ml). The resulting white solid is filtered and washed with MeOH (2×200 ml) and then dried in a vacuum oven to give the title compound. $^1$H NMR (DMSO, 400 MHz).

Step 2: 6-(2,2-Diphenyl-ethylamino)-9-((1R,4S)-4-hydroxy-cyclopent-2-enyl)-9H-purine-2-carboxylic acid methyl ester To 6-(2,2-diphenyl-ethylamino)-9H-purine-2-carboxylic acid methyl ester (5 g 13.4 mmol) under an atmosphere of argon is added dry deoxygenated tetrahydrofuran (100 ml) and dry dimethyl sulfoxide (2 ml). Sodium hydride 95% (0.32 g, 13.4 mmol) is then added and the solution is stirred at 40° C. Separately to (1S,4R)-cis 4-Acetoxy-2-cyclopenten-1-ol (1.89 g. 13.4 mmol), triphenylphosphine (0.53 g, 2.0 mmol) and tris(dibenzylideneacetone)dipalladium(0) (0.69 g, 0.67 mmol) is added dry deoxygenated tetrahydrofuran (20 ml) and the mixture stirred at room temperature for 10 minutes. This solution is added to the anion solution via syringe and the resulting mixture is then stirred at 80° C. The reaction is shown to be complete by LCMS after 2 hours. The reaction mixture is allowed to cool, methanol is added and a solid is filtered. The filtrate is concentrated in vacuo and the title compound is obtained by precipitation from dichloromethane/hexane. $^1$H NMR (MeOD, 400 MHz); 8.15 (s, 1H), 7.40-7.15 (m, 10H), 6.20 (m, 1H), 5.95 (m, 1H), 5.50 (m, 2H), 4.75 (m, 2H), 4.55 (m, 1H), 4.10 (m 2H), 3.90 (s, 2H), 3.80 (s, 1H), 2.9 (m, 1H), 1.75 (m, 1H).

Step 3: 6-(2,2-Diphenyl-ethylamino)-9-((1R,4S)-4-ethoxycarbonyloxy-cyclopent-2-enyl)-9H-purine-2-carboxylic acid methyl ester 6-(2,2-Diphenyl-ethylamino)-9-((1R,4S)-4-hydroxy-cyclopent-2-enyl)-9H-purine-2-carboxylic acid methyl ester (2.80 g, 6.14 mmol) is placed in an oven-dried flask under an atmosphere of argon. Dry tetrahydrofuran (30 ml) is added followed by dry pyridine (0.97 g, 12.3 mmol). Ethyl chloroformate (2.66 g, 24.6 mmol) is added slowly and the reaction mixture is stirred at room temperature. The reaction is shown to be complete by LCMS after 3 hours. The solvent is removed in vacuo and the residue is partitioned between dichloromethane (200 ml) and 1M HCl (2×200 ml). The organic layer is washed with water (2×100 ml) and brine (2×100 ml), dried over MgSO$_4$, filtered and the solvent is removed in vacuo. The title compound is obtained after purification by flash column chromatography (silica, 4% MeOH in dichloromethane). MS (ES+) m/e 528.3 (MH$^+$).

Step 4: 9-((1R,4S)-4-Di-tert-butoxycarbonylamino-cyclopent-2-enyl)-6-(2,2-diphenyl-ethylamino)-9H-purine-2-carboxylic acid methyl ester 6-(2,2-Diphenyl-ethylamino)-9-((1R,4S)-4-ethoxycarbonyloxy-cyclopent-2-enyl)-9H-purine-2-carboxylic acid methyl ester (2.2 g, 4.2 mmol) is dissolved in deoxygenated tetrahydrofuran. The resultant solution is stirred under an atmosphere of argon at room temperature. Di-t-butyl iminodicarboxylate (0.9 g, 4.2 mmol), triphenylphosphine (0.16 g, 0.63 mmol) and triethylamine (0.42 g, 4.2 mmol) are added followed by tris(dibenzylideneacetone)dipalladium(0) (0.22 g, 0.21 mmol). The reaction mixture is then stirred at 45° C. for 4 hours, allowed to cool to room temperature, methanol is added and the reaction mixture filtered. The filtrate is concentrated in vacuo. The resultant oil is purified by column chromatography (silica, 80% ether in hexane) to yield the title compound, MS (ES+) m/e 536.4 (MH$^+$).

Step 5: 9-((1R,2S,3R,4S)-4-Di-tert-butoxycarbonylamino-2,3-dihydroxy-cyclopentyl)-6-(2,2-diphenyl-ethylamino)-9H-purine-2-carboxylic acid methyl ester The title compound is prepared from 9-((1R,4S)-4-di-tert-butoxycarbonylamino-cyclopent-2-enyl)-6-(2,2-diphenyl-ethylamino)-9H-purine-2-carboxylic acid methyl ester using a procedure analogous to that of (1R,2S,3R,5S)-3-[2-chloro-6-(2,2-diphenyl-ethylamino)-purin-9-yl]-5-(di-Boc-amino)-cyclopentane-1,2-diol (Intermediate B2). MS (ES+) m/e 689.4 (MH$^+$).

Step 6: 9-((1R,2S,3R,4S)-4-Amino-2,3-dihydroxy-cyclopentyl)-6-(2,2-diphenyl-ethylamino)-9H-purine-2-carboxylic acid methyl ester 9-((1R,2S,3R,4S)-4-Di-tert-butoxycarbonylamino-2,3-dihydroxy-cyclopentyl)-6-(2,2-diphenyl-ethylamino)-9H-purine-2-carboxylic acid methyl ester (0.5 g, 0.73 mmol) is dissolved in dioxane and stirred under an atmosphere of argon. 4M HCl in dioxane (3.68 ml, 14.5 mmol) is added and the resultant solution is stirred for 20 hours then concentrated in vacuo. The title compound is obtained by flash column chromatography (Isolute™ C18, 0-100% acetonitrile in water). MS (ES+) m/e 489.3 (MH$^+$).

Step 7: 9-((1R,2S,3R,4S)-2,3-Dihydroxy-4-propionylamino-cyclopentyl)-6-(2,2-diphenyl-ethylamino)-9H-purine-2-carboxylic acid methyl ester 9-((1R,2S,3R,4S)-,4-Amino-2,3-dihydroxy-cyclopentyl)-6-(2,2-diphenyl-ethylamino)-9H-purine-2-carboxylic acid methyl ester hydrochloride (200 mg, 0.36 mmol) is dissolved in tetrahydrofuran (5 ml). Diisopropylethylamine (0.16 ml, 0.9 mmol) is added and the solution is stirred for 10 minutes. Propionyl chloride (33 mg, 0.36 mmol) is added and the reaction mixture is stirred at room temperature for 1 hour. The reaction is quenched with methanol and the title compound is obtained by flash column chromatography (Isolute™ C18, 0-100% acetonitrile in water). MS (ES+) m/e 545.3 (MH$^+$)

Step 8: 9-((1R,2S,3R,4S)-2,3-Dihydroxy-4-propionylamino-cyclopentyl)-6-(2,2-diphenyl-ethylamino)-9H-purine-2-carboxylic acid (2-amino-ethyl)-amide 9-((1R,2S,3R,4S)-2,3-Dihydroxy-4-propionylamino-cyclopentyl)-6-(2,2-diphenyl-ethylamino)-9H-purine-2-carboxylic acid methyl ester (62 mg, 1.0 mmol) is dissolved in ethylene diamine (3.4 ml, 51 mmol) and the solution is stirred at 105° C. The reaction is shown to be complete by LCMS after 45 minutes. The reaction mixture is concentrated in vacuo and the title compound is obtained after purification by reverse phase column chromatography (Isolute™ C18, 0-100% acetonitrile in water). MS (ES+) m/e 573.4 (MH$^+$).

Step 9: 9-((1R,2S,3R,4S)-2,3-Dihydroxy-4-propionylamino-cyclopentyl)-6-(2,2-diphenyl-ethylamino)-9H-purine-2-carboxylic acid (2-methanesulfonylamino-ethyl)-amide A solution of 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide (0.01 g, 0.017 mmol) in chloroform (1 ml) is treated with mesyl chloride (1 ml of a 3 mg/ml solution in chloroform) and TEA (0.003 ml). After stirring at 5° C. for 1 hour, the reaction mixture is diluted with DCM and extracted with 1 M HCl. The organic portion is isolated and concentrated in vacuo to yield the title product. (MH+ 651.5)

Example 49-55

These compounds,
9-((1R,2S,3R,4S)-2,3-dihydroxy-4-propionylamino-cyclopentyl)-6-(2,2-diphenyl-ethylamino)-9H-purine-2-carboxylic acid {2-[3-(3-methoxy-phenyl)-ureido]-ethyl}-amide trifluoroacetate (MH+ 722.4) (Example 49),
9-((1R,2S,3R,4S)-2,3-Dihydroxy-4-propionylamino-cyclopentyl)-6-(2,2-diphenyl-ethylamino)-9H-purine-2-carboxylic acid {2-[3-(3-cyano-phenyl)-ureido]-ethyl}-amide trifluoroacetate (MH+ 717.5) (Example 50),
[3-(2-{[9-((1R,2S,3R,4S)-2,3-Dihydroxy-4-propionylamino-cyclopentyl)-6-(2,2-diphenyl-ethylamino)-9H-purine-2-carbonyl]-amino}-ethyl)-ureido]-acetic acid ethyl ester trifluoroacetate (MH+ 702.5) (Example 51),
9-((1R,2S,3R,4S)-2,3-Dihydroxy-4-propionylamino-cyclopentyl)-6-(2,2-diphenyl-ethylamino)-9H-purine-2-carboxylic acid [2-(3-ethyl-ureido)-ethyl]-amide trifluoroacetate (MH+ 644.5) (Example 52),
9-((1R,2S,3R,4S)-2,3-Dihydroxy-4-propionylamino-cyclopentyl)-6-(2,2-diphenyl-ethylamino)-9H-purine-2-carboxylic acid {2-[3-(4-methoxy-phenyl)-ureido]-ethyl}-amide trifluoroacetate (MH+ 722.5) (Example 53),
9-((1R,2S,3R,4S)-2,3-Dihydroxy-4-propionylamino-cyclopentyl)-6-(2,2-diphenyl-ethylamino)-9H-purine-2-carboxylic acid {2-[3-(4-cyano-phenyl)-ureido]-ethyl}-amide trifluoroacetate (MH+ 717.5) (Example 54) and
4-[3-(2-{[9-((1R,2S,3R,4S)-2,3-Dihydroxy-4-propionylamino-cyclopentyl)-6-(2,2-diphenyl-ethylamino)-9H-purine-2-carbonyl]-amino}-ethyl)-ureido]-benzoic acid methyl ester trifluoroacetate (MH+ 750.4) (Example 55)

are prepared analogously to Example 48 by replacing mesyl chloride (step 9) with the appropriate isocyanate Example 56

N-[(1S,2R,3S,4R)-4-(6-(2,2-Diphenyl-ethylamino)-2-{(R)-3-[3-(4-phenoxy-phenyl)-ureido]-pyrrolidin-1-yl}-purin-9-yl)-2,3-dihydroxy-cyclopentyl]-propionamide trifluoroacetate N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (0.023 g, 40 µmol) is treated with a solution of 4-phenoxyphenyl isocyanate (0.0078 g, 39 µmol) in NMP (0.5 ml). After stirring at room temperature overnight purification is carried out using mass directed preparative LC-MS eluting with acetonitrile: water: trifluoroacetic acid to afford the title compound. (MH+ 782.5)

Examples 57-90

These compounds namely,
N-[(1S,2R,3S,4R)-4-(6-(2,2-diphenyl-ethylamino)-2-{(R)-3-[3-(2-phenoxy-phenyl)-ureido]-pyrrolidin-1-yl}-purin-9-yl)-2,3-dihydroxy-cyclopentyl]-propionamide trifluoroacetate (MH+ 782.5) (Example 57),
N-((1S,2R,3S,4R)-4-{6-(2,2-diphenyl-ethylamino)-2-[(R)-3-(4-trifluoromethyl-benzenesulfonylamino)-pyrrolidin-1-yl]-purin-9-yl}-2,3-dihydroxy-cyclopentyl)-propionamide trifluoroacetate (MH+ 779.4) (Example 58),
N-[(1S,2R,3S,4R)-4-(6-(2,2-diphenyl-ethylamino)-2-{(R)-3-[3-(3,4,5-trimethoxy-phenyl)-ureido]-pyrrolidin-1-yl}-purin-9-yl)-2,3-dihydroxy-cyclopentyl]-propionamide trifluoroacetate (MH+ 780.5) (Example 59),
N-((1S,2R,3S,4R)-4-{6-(2,2-diphenyl-ethylamino)-2-[(R)-3-((E)-2-phenyl-ethenesulfonylamino)-pyrrolidin-1-yl]-purin-9-yl}-2,3-dihydroxy-cyclopentyl)-propionamide trifluoroacetate (MH+ 737.5) (Example 60),
(3-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-ureido)-acetic acid ethyl ester trifluoroacetate (MH+ 700.5) (Example 61),
Cyclopropanecarboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 639.5) (Example 62),
N-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-propionamide trifluoroacetate (MH+ 627.5) (Example 63),
N-{(1S,2R,3S,4R)-4-[2-[(R)-3-(3,3-dimethyl-ureido)-pyrrolidin-1-yl]-6-(2,2-diphenyl-ethylamino)-purin-9-yl]-2,3-dihydroxy-cyclopentyl}-propionamide trifluoroacetate (MH+ 642.5) (Example 64),
N-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-benzamide trifluoroacetate (MH+ 689.5) (Example 65),
N-((1S,2R,3S,4R)-4-{6-(2,2-diphenyl-ethylamino)-2-[(R)-3-(3-isopropyl-ureido)-pyrrolidin-1-yl]-purin-9-yl}-2,3-dihydroxy-cyclopentyl)-propionamide trifluoroacetate (MH+ 656.5) (Example 66),
N-((1S,2R,3S,4R)-4-{6-(2,2-diphenyl-ethylamino)-2-[(R)-3-(3-ethyl-ureido)-pyrrolidin-1-yl]-purin-9-yl}-2,3-dihydroxy-cyclopentyl)-propionamide trifluoroacetate (MH+ 642.5) (Example 67),
{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-carbamic acid benzyl ester trifluoroacetate (MH+ 705.3) (Example 68)
and N-[(1S,2R,3S,4R)-4-(6-(2,2-diphenyl-ethylamino)-2-{(R)-3-[3-(4-hydroxy-phenyl)-ureido]-pyrrolidin-1-yl}-purin-9-yl)-2,3-dihydroxy-cyclopentyl]-propionamide trifluoroacetate (MH+ 745.6) (Example 69),
N-{(1S,2R,3S,4R)-4-[2-{(R)-3-[3-(2,3-dihydro-benzo[1,4]dioxin-6-yl)-ureido]-pyrrolidin-1-yl}-6-(2,2-diphenyl-ethylamino)-purin-9-yl]-2,3-dihydroxy-cyclopentyl}-propionamide trifluoroacetate (MH+ 748.5) (Example 70),
benzo[1,2,5]thiadiazole-5-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 733.4) (Example 71),
quinoxaline-6-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 727.5) (Example 72),
N-{(1S,2R,3S,4R)-4-[2-{(R)-3-[3-(3,4-dihydro-2H-benzo[b][1,4]dioxepin-7-yl)-ureido]-pyrrolidin-1-yl}-6-(2,2-diphenyl-ethylamino)-purin-9-yl]-2,3-dihydroxy-cyclopentyl}-propionamide trifluoroacetate (MH+ 762.5) (Example 73),
N-{(1S,2R,3S,4R)-4-[2-{(R)-3-[3-(4-Cyano-phenyl)-ureido]-pyrrolidin-1-yl}-6-(2,2-diphenyl-ethylamino)-purin-9-yl]-2,3-dihydroxy-cyclopentyl}-propionamide trifluoroacetate (MH+ 715.5) (Example 74),
4-(4-chloro-benzenesulfonyl)-3-methyl-thiophene-2-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 870.5) (Example 75),
3-chloro-4-(propane-2-sulfonyl)-thiophene-2-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 821.4) (Example 76),
N-[(1S,2R,3S,4R)-4-(6-(2,2-diphenyl-ethylamino)-2-{(R)-3-[3-(4-trifluoromethoxy-phenyl)-ureido]-pyrrolidin-1-yl}-purin-9-yl)-2,3-dihydroxy-cyclopentyl]-propionamide trifluoroacetate (MH+ 774.4) (Example 77),
N-[(1S,2R,3S,4R)-4-(6-(2,2-diphenyl-ethylamino)-2-{(R)-3-[3-(3-methylsulfanyl-phenyl)-ureido]-pyrrolidin-1-yl}-purin-9-yl)-2,3-dihydroxy-cyclopentyl]-propionamide trifluoroacetate (MH+ 736.4) (Example 78),
N-[(1S,2R,3S,4R)-4-(6-(2,2-diphenyl-ethylamino)-2-{(R)-3-[3-(4-methylsulfanyl-phenyl)-ureido]-pyrrolidin-1-yl}-purin-9-yl)-2,3-dihydroxy-cyclopentyl]-propionamide trifluoroacetate (MH+ 736.4) (Example 79),
quinoxaline-2-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 727.5) (Example 80),
benzo[1,2,5]thiadiazole-4-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 733.4) (Example 81),
5-(3-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-ureido)-isophthalic acid dimethyl ester trifluoroacetate (MH+ 806.5) (Example 82), N-[(1S,2R,3S,4R)-4-(6-(2,2-diphenyl-ethylamino)-2-{(R)-3-[2-(1H-indol-3-yl)-2-oxo-acetylamino]-pyrrolidin-1-yl}-purin-9-yl)-2,3-dihydroxy-cyclopentyl]-propionamide trifluoroacetate (MH+ 742.5) (Example 83),
pyridine-2-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 676.5) (Example 84),
1-(4-methoxy-phenyl)-5-methyl-1H-pyrazole-4-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 785.5) (Example 85),
3-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-ylcarbamoyl}-piperidine-1-carboxylic acid benzylester trifluoroacetate (MH+ 816.6) (Example 86),
N-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-4-dipropylsulfamoyl-benzamide trifluoroacetate (MH+ 838.4) (Example 87),
1-(4-trifluoromethyl-pyrimidin-2-yl)-piperidine-4-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 828.4) (Example 88),
N-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-nicotinamide trifluoroacetate (MH+ 676.4) (Example 89),
N-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-isonicotinamide trifluoroacetate (MH+ 676.3) (Example 90),
are prepared analogously to N-[(1S,2R,3S,4R)-4-(6-(2,2-diphenyl-ethylamino)-2-{(R)-3-[3-(4-phenoxy-phenyl)-ureido]-pyrrolidin-1-yl}-purin-9-yl)-2,3-dihydroxy-cyclopentyl]-propionamide trifluoroacetate (Example 56) by replacing 4-phenoxyphenyl isocyanate with the appropriate isocyanate or acid chloride. Reactions using acid chlorides also have excess triethylamine added.

Example 91-92

These compounds namely,
N-{(R)-1-[9-((1R,2S,3R,4S)-2,3-dihydroxy-4-propionylamino-cyclopentyl)-6-(1-ethyl-propylamino)-9H-purin-2-yl]-pyrrolidin-3-yl}-isonicotinamide hydrochloride (MH 566.4+) (Example 91) and
N-{(R)-1-[9-((1R,2S,3R,4S)-2,3-dihydroxy-4-propionylamino-cyclopentyl)-6-(3,3-dimethyl-butylamino)-9H-purin-2-yl]-pyrrolidin-3-yl}-isonicotinamide hydrochloride (MH+ 580.5) (Example 92),
are prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (Example 1 step 2) by replacing (3R)-3-aminopyrrolidine with (R)-N-pyrrolidin-3-yl-isonicotinamide (Intermediate O) and by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with the appropriate starting compound. The preparation of the starting compounds are either described herein or can be prepared from [(1S,2R,3S,4R)-4-(2,6-dichloro-purin-9-yl)-2,3-dihydroxy-cyclopentyl]-propionyl-carbamic acid tert-butyl ester (Intermediate G) and the appropriate amine using a procedure analogous to 2R,3S,4R)-4-{6-[2,2-Bis-(4-hydroxy-phenyl)-ethylamino]-2-chloro-purin-9-yl}-2,3-dihydroxy-cyclopentyl)-propionamide (Example 22 steps 1 and 2)

Example 93

5-Methyl-isoxazole-3-carboxylic acid {(R)-1-[9-((1R,2S,3R,4S)-2,3-dihydroxy-4-propionylamino-cyclopentyl)-6-(1-ethyl-propylamino)-9H-purin-2-yl]-pyrrolidin-3-yl}-amide hydrochloride This compound is prepared analogously to N-((1S,2R,3S,4R)-4-{6-(2,2-diphenyl-ethylamino)-2-[(R)-3-((R)-3-pyrrolidin-3-ylureido)-pyrrolidin-1-yl]-purin-9-yl}-2,3-dihydroxy-cyclopentyl)-2-hydroxy-acetamide (Example 15) by replacing N-{(1S,2R,3S,4R)-4-[2-chloro-6-(2,2-diphenyl-ethylamino)-purin-9-yl]-2,3-dihydroxy-cyclopentyl}-2-hydroxy-acetamide (Intermediate Q) with N-{(1S,2R,3S,4R)-4-[2-Chloro-6-(1-ethyl-propylamino)-purin-9-yl]-2,3-dihydroxy-cyclopentyl}-propionamide [prepared from [(1S,2R,3S,4R)-4-(2,6-dichloro-purin-9-yl)-2,3-dihydroxy-cyclopentyl]-propionyl-carbamic acid tert-butyl ester (Intermediate G) and the appropriate amine using a procedure analogous to 2R,3S,4R)-4-{6-[2,2-Bis-(4-hydroxy-phenyl)-ethylamino]-2-chloro-purin-9-yl}-2,3-dihydroxy-cyclopentyl)-propionamide (Example 22 steps 1 and 2)] and by replacing 1,3-di(R)-pyrrolidin-3-yl-urea (Intermediate B) with 5-methyl-isoxazole-3-carboxylic acid (R)-pyrrolidin-3-ylamide (Intermediate P). (MH+ 570.4)

Example 94

Cyclobutanecarboxylic acid {(1S,2R,3S,4R)-4-[2-((R)-1-benzyl-pyrrolidin-3-ylamino)-6-(2,2-diphenyl-ethylamino)-purin-9-yl]-2,3-dihydroxy-cyclopentyl}-amide trifluoroacetate This compound is prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate Example 1 (Step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with cyclobutanecarboxylic acid {(1S,2R,3S,4R)-4-[2-chloro-6-(2,2-diphenyl-ethylamino)-purin-9-yl]-2,3-dihydroxy-cyclopentyl}-amide (Intermediate K) and by replacing (3R)-3-aminopyrrolidine with (R)-1-benzyl-pyrrolidin-3-ylamine. (MH+ 687.5)

Example 95

9-((1R,2S,3R,4S)-2,3-Dihydroxy-4-propionylamino-cyclopentyl)-6-(2,2-diphenyl-ethylamino)-9H-purine-2-carboxylic acid {2-[3-(2-diisopropylamino-ethyl)-ureido]-ethyl}-amide trifluoroacetate To a solution comprising 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide (25 mg, 0.04 mmol) (Example 48 step 8) in toluene (0.8 ml) and IPA (0.4 ml) is added imidazole-1-carboxylic acid (2-diisopropylamino-ethyl)-amide (10 mg, 0.04 mmol) in DCM (0.44 ml). The reaction mixture is stirred at room temperature under an inert atmosphere of Argon overnight and then the solvent is removed in vacuo. Purification of the resulting crude product by reverse phase column chromatography (Isolute™ C18, 0-100% acetonitrile in water –0.1% TFA) yields the title product. (MH+ 372.3)

Example 96-98

These compounds namely,

N-{(1S,2R,3S,4R)-4-[2-((R)-1-benzyl-pyrrolidin-3-ylamino)-6-(2,2-diphenyl-ethylamino)-purin-9-yl]-2,3-dihydroxy-cyclopentyl}-propionamide trifluoroacetate (MH+ 661.6) (Example 96), {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-carbamic acid tert-butyl ester trifluoroacetate (MH+ 661.6) (Example 97) and (R)-3-[9-((1R,2S,3R,4S)-2,3-dihydroxy-4-propionylamino-cyclopentyl)-6-(2,2-diphenyl-ethylamino)-9H-purin-2-ylamino]-pyrrolidine-1-carboxylic acid tert-butyl ester trifluoroacetate (MH+ 671.5) (Example 98), are prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate Example 1 (Step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-{(1S,2R,3S,4R)-4-[2-chloro-6-(2,2-diphenyl-ethylamino)-purin-9-yl]-2,3-dihydroxy-cyclopentyl}-propionamide (Intermediate J) and by replacing (3R)-3-aminopyrrolidine with the appropriate amine.

Example 99

9-((1R,2S,3R,4S)-2,3-Dihydroxy-4-propionylamino-cyclopentyl)-6-(2,2-diphenyl-ethylamino)-9H-purine-2-carboxylic acid (2-propionylamino-ethyl)-amide Step 1: 9-((1R,2S,3R,4S)-4-Di-tert-butoxycarbonylamino-2,3-dihydroxy-cyclopentyl)-6-(2,2-diphenyl-ethylamino)-9H-purine-2-carboxylic acid (2-amino-ethyl)-amide The title compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide (Example 48, step 8) by replacing 9-((1R,2S,3R,4S)-2,3-dihydroxy-4-propionylamino-cyclopentyl)-6-(2,2-diphenyl-ethylamino)-9H-purine-2-carboxylic acid methyl ester with 9-((1R,2S,3R,4S)-4-di-tert-butoxycarbonylamino-2,3-dihydroxy-cyclopentyl)-6-(2,2-diphenyl-ethylamino)-9H-purine-2-carboxylic acid methyl ester (Example 48 step 5).

Step 2: 9-((1R,2S,3R,4S)-4-Amino-2,3-dihydroxy-cyclopentyl)-6-(2,2-diphenyl-ethylamino)-9H-purine-2-carboxylic acid (2-amino-ethyl)-amide hydrochloride The title compound is prepared from 9-((1R,2S,3R,4S)-4-amino-2,3-dihydroxy-cyclopentyl)-6-(2,2-diphenyl-ethylamino)-9H-purine-2-carboxylic acid (2-amino-ethyl)-amide hydrochloride analogously to (1S,2R,3S,5R)-3-amino-5-{6-[2,2-bis-(4-hydroxy-phenyl)-ethylamino]-2-chloro-purin-9-yl}-cyclopentane-1,2-diol (Example 7 step 2).

Step 3: 9-((1R,2S,3R,4S)-2,3-Dihydroxy-4-propionylamino-cyclopentyl)-6-(2,2-diphenyl-ethylamino)-9H-purine-2-carboxylic acid (2-propionylamino-ethyl)-amide The title compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid methyl ester (Example 48 step 7) by replacing 9-((1R,2S,3R,4S)-4-amino-2,3-dihydroxy-cyclopentyl)-6-(2,2-diphenyl-ethylamino)-9H-purine-2-carboxylic acid methyl ester hydrochloride with 9-((1R,2S,3R,4S)-4-amino-2,3-dihydroxy-cyclopentyl)-6-(2,2-diphenyl-ethylamino)-9H-purine-2-carboxylic acid (2-amino-ethyl)-amide hydrochloride. (MH+ 629.5)

Example 100

N-{(1S,2R,3S,4R)-4-[2-(2-Amino-ethylamino)-6-(2,2-diphenyl-ethylamino)-purin-9-yl]-2,3-dihydroxy-cyclopentyl}-propionamide trifluoroacetate The title compound is prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (Example 1 step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-{(1S,2R,3S,4R)-4-[2-chloro-6-(2,2-diphenyl-ethylamino)-purin-9-yl]-2,3-dihydroxy-cyclopentyl}-propionamide (Intermediate J) and by replacing (3R)-3-aminopyrrolidine with ethylene diamine. (MH+ 545.4)

Example 101

9-((1R,2S,3R,4S)-2,3-Dihydroxy-4-propionylamino-cyclopentyl)-6-(2,2-diphenyl-ethylamino)-9H-purine-2-carboxylic acid (2-{3-[1-(3,4,5,6-tetrahydro-2H-[1,2']bipyridinyl-4-ylcarbamoyl)-piperidin-4-yl]-ureido}-ethyl)amide trifluoroacetate Step 1: {(1S,2R,3S,4R)-4-[6-(2,2-Diphenyl-ethylamino)-2-(2-{3-[1-(3,4,5,6-tetrahydro-2H-[1,2']bipyridinyl-4-ylcarbamoyl)-piperidin-4-yl]-ureido}-ethylcarbamoyl)-purin-9-yl]-2,3-dihydroxy-cyclopentyl}-carbamic acid tert-butyl ester The title compound is prepared analogously to [(1S,2R,3S,4R)-4-(6-(2,2-diphenyl-ethylamino)-2-{2-[3-(3,4,5,6-tetrahydro-2H-[1,2']bipyridinyl-4-yl)-ureido]-ethylcarbamoyl}-purin-9-yl)-2,3-dihydroxy-cyclopentyl]-carbamic acid tert-butyl ester (Example 12) by replacing imidazole-1-carboxylic acid (3,4,5,6-tetrahydro-2H-[1,2']bipyridinyl-4-yl)-amide (Intermediate C) with 4-[(imidazole-1-carbonyl)-amino]-piperidine-1-carboxylic acid (3,4,5,6-tetrahydro-2H-[1,2']bipyridinyl-4-yl)-amide (Intermediate H).

Step 2: 9-((1R,2S,3R,4S)-4-Amino-2,3-dihydroxy-cyclopentyl)-6-(2,2-diphenyl-ethylamino)-9H-purine-2-carboxylic acid (2-{3-[1-(3,4,5,6-tetrahydro-2H-[1,2']bipyridinyl-4-ylcarbamoyl)-piperidin-4-yl]-ureido}-ethyl)-amide dihydrochloride A solution of {(1S,2R,3S,4R)-4-[6-(2,2-diphenyl-ethylamino)-2-(2-{3-[1-(3,4,5,6-tetrahydro-2H-[1,2']bipyridinyl-4-ylcarbamoyl)-piperidin-4-yl]-ureido}-ethylcarbamoyl)-purin-9-yl]-2,3-dihydroxy-cyclopentyl}-carbamic acid tert-butyl ester (76.7 mg, 81 μmol) in MeOH (0.5 ml) is treated with 4M HCl in dioxane (0.5 ml). After stirring at room temperature for 1 hour, the solvent is removed in vacuo to afford the title compound which is used crude in the next step.

Step 3: 9-((1R,2S,3R,4S)-2,3-Dihydroxy-4-propionylamino-cyclopentyl)-6-(2,2-diphenyl-ethylamino)-9H-purine-2-carboxylic acid (2-{3-[1-(3,4,5,6-tetrahydro-2H-[1,2']bipyridinyl-4-ylcarbamoyl)-piperidin-4-yl]-ureido}-ethyl)amide trifluoroacetate The title compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid methyl ester (Example 48 step 7) by replacing 9-((1R,2S,3R,4S)-,4-amino-2,3-dihydroxy-cyclopentyl)-6-(2,2-diphenyl-ethylamino)-9H-purine-2-carboxylic acid methyl ester hydrochloride with 9-((1R,2S,3R,4S)-4-amino-2,3-dihydroxy-cyclopentyl)-6-(2,2-diphenyl-ethylamino)-9H-purine-2-carboxylic acid (2-{3-[1-(3,4,5,6-tetrahydro-2H-[1,2']bipyridinyl-4-ylcarbamoyl)-piperidin-4-yl]-ureido}-ethyl)-amide dihydrochloride. (MH+ 451.8)

Example 102-104

These compounds namely,
{1-[9-((1R,2S,3R,4S)-2,3-dihydroxy-4-propionylamino-cyclopentyl)-6-(2,2-diphenyl-ethylamino)-9H-purin-2-yl]-piperidin-4-yl}-carbamic acid tert-butyl ester trifluoroacetate (MH+ 685.6) (Example 102),
N-{(1S,2R,3S,4R)-4-[2-(1-benzyl-piperidin-4-ylamino)-6-(2,2-diphenyl-ethylamino)-purin-9-yl]-2,3-dihydroxy-cyclopentyl}-propionamide trifluoroacetate (MH+ 675.5) (Example 103) and N-{(1S,2R,3S,4R)-4-[2-[1,4]diazepan-1-yl-6-(2,2-diphenyl-ethylamino)-purin-9-yl]-2,3-dihydroxy-cyclopentyl}-propionamide trifluoroacetate (MH+ 585.5) (Example 104)
are prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate Example 1 (Step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-{(1S,2R,3S,4R)-4-[2-chloro-6-(2,2-diphenyl-ethylamino)-purin-9-yl]-2,3-dihydroxy-cyclopentyl}-propionamide (Intermediate J) and by replacing (3R)-3-aminopyrrolidine with the appropriate amine.

Example 105 and 106

These compounds namely,
{(R)-1-[9-[(1R,2S,3R,4S)-4-(cyclobutanecarbonyl-amino)-2,3-dihydroxy-cyclopentyl]-6-(2,2-diphenyl-ethylamino)-9H-purin-2-yl]-pyrrolidin-3-yl}-carbamic acid tert-butyl ester trifluoroacetate (MH+ 697.3) (Example 105) and
(S)-3-[9-[(1R,2S,3R,4S)-4-(cyclobutanecarbonyl-amino)-2,3-dihydroxy-cyclopentyl]-6-(2,2-diphenyl-ethylamino)-9H-purin-2-ylamino]-pyrrolidine-1-carboxylic acid tert-butyl ester trifluoroacetate (MH+ 697.3) (Example 106)
are prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate Example 1 (Step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with cyclobutanecarboxylic acid {(1S,2R,3S,4R)-4-[2-chloro-6-(2,2-diphenyl-ethylamino)-purin-9-yl]-2,3-dihydroxy-cyclopentyl}-amide (Intermediate K) and by replacing (3R)-3-aminopyrrolidine with the appropriate amine.

Example 107

N-{(1S,2R,3S,4R)-4-[6-(2,2-diphenyl-ethylamino)-2-(3,4,5,6-tetrahydro-2H-[1,2]bipyridinyl-4-ylamino)-purin-9-yl}-2,3-dihydroxy-cyclopentyl]-propionamide trifluoroacetate This compound is prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate Example 1 (Step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-{(1S,2R,3S,4R)-4-[2-chloro-6-(2,2-diphenyl-ethylamino)-purin-9-yl]-2,3-dihydroxy-cyclopentyl}-propionamide (Intermediate J) and by replacing (3R)-3-aminopyrrolidine with 3,4,5,6-tetrahydro-2H-[1,2']bipyridinyl-4-ylamine. (MH+ 331.7)

Example 108

4-[3-(2-{[9-((1R,2S,3R,4S)-2,3-Dihydroxy-4-propionylamino-cyclopentyl)-6-(2,2-diphenyl-ethylamino)-9H-purine-2-carbonyl]-amino}-ethyl)-ureido]-piperidine-1-carboxylic acid benzyl ester To a solution of 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide (Example 48 step 8) (0.1 g, 174 mmol) in chloroform (5 ml) is added 4-isocyanato-Z-piperidine (0.045 g, 0.174 mmol) in chloroform (5 ml). The reaction mixture is allowed to stir at room temperature overnight and then methanol is added to quench any residual isocyanate. The solvent is removed in vacuo to yield the title compound. (MH+ 833.5)

Example 109

9-((1R,2S,3R,4S)-2,3-dihydroxy-4-propionylamino-cyclopentyl)-6-(2,2-diphenyl-ethylamino)-9H-purine-2-carboxylic acid {2-[3-(5-methyl-3-phenyl-isoxazol-4-yl)-ureido]-ethyl}-amide trifluoroacetate This compound is prepared analogously to 4-[3-(2-{[9-((1R,2S,3R,4S)-2,3-dihydroxy-4-propionylamino-cyclopentyl)-6-(2,2-diphenyl-ethylamino)-9H-purine-2-carbonyl]-amino}-ethyl)-ureido]-piperidine-1-carboxylic acid benzyl ester (Example 108) by replacing 4-isocyanato-Z-piperidine with 4-isocyanato-5-methyl-3-phenyl-isoxazole. (MH+ 773.5)

Examples 110-112

These compounds namely,
N-{(1S,2R,3S,4R)-4-[2-((R)-3-dimethylamino-pyrrolidin-1-yl)-6-(2,2-diphenyl-ethylamino)-purin-9-yl]-2,3-dihydroxy-cyclopentyl}-propionamide trifluoroacetate (MH+ 599.5) (Example 110),
N-{(1S,2R,3S,4R)-4-[6-(2,2-diphenyl-ethylamino)-2-((R)-3-methylamino-pyrrolidin-1-yl)-purin-9-yl]-2,3-dihydroxy-cyclopentyl}-propionamide trifluoroacetate (MH+ 585.4) (Example 111) and (4-{2-[9-((1R,2S,3R,4S)-2,3-dihydroxy-4-propionylamino-cyclopentyl)-6-(2,2-diphenyl-ethylamino)-9H-purin-2-ylamino]-ethyl}-imidazol-1-yl)-acetic acid trifluoroacetate (MH+ 654.3) (Example 112)
are prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate Example 1 (Step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-{(1S,2R,3S,4R)-4-[2-chloro-6-(2,2-diphenyl-ethylamino)-purin-9-yl]-2,3-dihydroxy-cyclopentyl}-propionamide (Intermediate J) and by replacing (3R)-3-aminopyrrolidine with the appropriate amine.

Example 113

9-((1R,2S,3R,4S)-2,3-dihydroxy-4-propionylamino-cyclopentyl)-6-(2,2-diphenyl-ethylamino)-9H-purine-2-carboxylic acid (2-{3-[1-(4-methoxy-phenylcarbamoyl)-piperidin-4-yl]-ureido}-ethyl)-amide trifluoroacetate Step 1: 9-((1R,2S,3R,4S)-2,3-Dihydroxy-4-propionylamino-cyclopentyl)-6-(2,2-diphenyl-ethylamino)-9H-purine-2-carboxylic acid [2-(3-piperidin-4-yl-ureido)-ethyl]-amide A solution of 4-[3-(2-{[9-((1R,2S,3R,4S)-2,3-dihydroxy-4-propionylamino-cyclopentyl)-6-(2,2-diphenyl-ethylamino)-9H-purine-2-carbonyl]-amino}-ethyl)-ureido]-piperidine-1-carboxylic acid benzyl ester (Example 108) (0.145 g, 0.174 mmol) in methanol (1 ml) under an atmosphere of Argon is treated with palladium hydroxide on carbon (0.054 g, 20% w/w carbon). The reaction mixture is placed under an atmosphere of hydrogen and stirred at room temperature for 72 hours and then filtered. The filtrate is concentrated in vacuo to yield the title compound as a green oil.

Step 2: 9-((1R,2S,3R,4S)-2,3-dihydroxy-4-propionylamino-cyclopentyl)-6-(2,2-diphenyl-ethylamino)-9H-purine-2-carboxylic acid (2-{3-[1-(4-methoxy-phenylcarbamoyl)-piperidin-4-yl]-ureido}-ethyl)-amide trifluoroacetate This compound is prepared analogously to 4-[3-(2-{[9-((1R,2S,3R,4S)-2,3-dihydroxy-4-propionylamino-cyclo-pentyl)-6-(2,2-diphenyl-ethylamino)-9H-purine-2-carbonyl]-amino}-ethyl)-ureido]-piperidine-1-carboxylic acid benzyl ester (Example 108) by replacing 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide with 9-((1R,2S,3R,4S)-2,3-dihydroxy-4-propionylamino-cyclopentyl)-6-(2,2-diphenyl-ethylamino)-9H-purine-2-carboxylic acid [2-(3-piperidin-4-yl-ureido)-ethyl]-amide and by replacing 4-isocyanato-Z-piperidine with 1-isocyanato-4-methoxy-benzene. (MH+ 848.6)

Example 114-115

These compounds namely,
9-((1R,2S,3R,4S)-2,3-dihydroxy-4-propionylamino-cyclopentyl)-6-(2,2-diphenyl-ethylamino)-9H-purine-2-carboxylic acid (2-{3-[1-(4-cyano-phenylcarbamoyl)-piperidin-4-yl]-ureido}-ethyl)-amide trifluoroacetate (MH+ 843.6) (Example 114) and ({4-[3-(2-{[9-((1R,2S,3R,4S)-2,3-dihydroxy-4-propionylamino-cyclopentyl)-6-(2,2-diphenyl-ethylamino)-9H-purine-2-carbonyl]-amino}-ethyl)-ureido]-piperidine-1-carbonyl}-amino)-acetic acid ethyl ester trifluoroacetate (MH+ 828.6) (Example 115)
are prepared analogously to Example 113 by replacing 1-isocyanato-4-methoxy-benzene with the appropriate isocyanate.

Example 116

9-((1R,2S,3R,4S)-2,3-Dihydroxy-4-propionylamino-cyclopentyl)-6-(2,2-diphenyl-ethylamino)-9H-purine-2-carboxylic acid [2-(3-{1-[1-(3,4,5,6-tetrahydro-2H-[1,2]bipyridinyl-4-ylcarbamoyl)-piperidin-4-ylcarbamoyl]-piperidin-4-yl}-ureido)-ethyl]-amide trifluoroacetate The title compound is prepared analogously to 9-((1R,2S,3R,4S)-2,3-dihydroxy-4-propionylamino-cyclopentyl)-6-(2,2-diphenyl-ethylamino)-9H-purine-2-carboxylic acid (2-{3-[1-(3,4,5,6-tetrahydro-2H-[1,2']bipyridinyl-4-ylcarbamoyl)-piperidin-4-yl]-ureido}-ethyl)amide trifluoroacetate (Example 101) by replacing 4-[(imidazole-1-carbonyl)-amino]-piperidine-1-carboxylic acid (3,4,5,6-tetrahydro-2H-[1,2]bipyridinyl-4-yl)-amide with Intermediate I. (MH+ 514.9)

Examples 117-125

These compounds namely,
N-{(1S,2R,3S,4R)-4-[6-[2,2-bis-(4-methoxy-phenyl)-ethylamino]-2-((R)-3-dimethylamino-pyrrolidin-1-yl)-purin-9-yl]-2,3-dihydroxy-cyclopentyl}-propionamide trifluoroacetate (MH+ 659.4) (Example 117),
N-((1S,2R,3S,4R)-4-{2-((R)-3-Dimethylamino-pyrrolidin-1-yl)-6-[2-(4-fluoro-phenyl)-2-phenyl-ethylamino]-purin-9-yl}-2,3-dihydroxy-cyclopentyl)-propionamide trifluoroacetate (MH+ 617.4)(Example 118),
N-{(1S,2R,3S,4R)-4-[2-((R)-3-dimethylamino-pyrrolidin-1-yl)-6-(1-ethyl-propylamino)-purin-9-yl]-2,3-dihydroxy-cyclopentyl}-propionamide trifluoroacetate (MH+ 489.3) (Example 119),
N-((1S,2R,3S,4R)-4-{2-((R)-3-dimethylamino-pyrrolidin-1-yl)-6-[(9H-fluoren-9-ylmethyl)-amino]-purin-9-yl}-2,3-dihydroxy-cyclopentyl)-propionamide trifluoroacetate (MH+ 597.4) (Example 120),
N-{(1S,2R,3S,4R)-4-{2-((R)-3-dimethylamino-pyrrolidin-1-yl)-6-(S)-1-hydroxymethyl-2-phenyl-ethylamino)-purin-9-yl]-2,3-dihydroxy-cyclopentyl}-propionamide trifluoroacetate (MH+ 553.4) (Example 121),
N-((1S,2R,3S,4R)-4-{2-((R)-3-dimethylamino-pyrrolidin-1-yl)-6-[(naphthalen-1-ylmethyl)-amino]-purin-9-yl}-2,3-dihydroxy-cyclopentyl)-propionamide trifluoroacetate (MH+ 559.4) (Example 122),
N-{(1S,2R,3S,4R)-4-[6-[(2'-cyano-biphenyl-4-ylmethyl)-amino]-2-((R)-3-dimethylamino-pyrrolidin-1-yl)-purin-9-yl]-2,3-dihydroxy-cyclopentyl}-propionamide trifluoroacetate (MH+ 610.3) (Example 123),
N-{(1S,2R,3S,4R)-4-[2-((R)-3-dimethylamino-pyrrolidin-1-yl)-6-(3,3-dimethyl-butylamino)-purin-9-yl]-2,3-dihydroxy-cyclopentyl}-propionamide trifluoroacetate (MH+ 503.4) (Example 124) and
N-((1S,2R,3S,4R)-4-{2-((R)-3-dimethylamino-pyrrolidin-1-yl)-6-[2-(4-sulfamoyl-phenyl)-ethylamino]-purin-9-yl}-2,3-dihydroxy-cyclopentyl)-propionamide trifluoroacetate (MH+ 602.3) (Example 125)

are prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (Example 1 step 2) by replacing (3R)-3-aminopyrrolidine with dimethyl-(R)-pyrrolidin-3-yl-amine and by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with the appropriate starting compounds. The preparation of the starting compounds are either described herein or can be prepared from [(1S,2R,3S,4R)-4-(2,6-dichloro-purin-9-yl)-2,3-dihydroxy-cyclopentyl]-propionyl-carbamic acid tert-butyl ester (Intermediate G) and the appropriate amine using a procedure analogous to 2R,3S,4R)-4-{6-[2,2-Bis-(4-hydroxy-phenyl)-ethylamino]-2-chloro-purin-9-yl}-2,3-dihydroxy-cyclopentyl)-propionamide (Example 22 steps 1 and 2)

Example 126

N-{(1S,2R,3S,4R)-4-[2-[(R)-3-(2-acetylamino-4-methyl-thiazole-5-sulfonylamino)-pyrrolidin-1-yl]-6-(2,2-diphenyl-ethylamino)-purin-9-yl]-2,3-dihydroxy-cyclopentyl}-propionamide trifluoroacetate N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-propionamide (Example 18 step 2) (0.023 g, 40 µmol) is treated with a solution of 2-acetamido-4-methyl-5-thiazolesulfonyl chloride (0.0104 g, 39 µmol) in NMP (0.5 ml). After stirring at room temperature overnight purification is carried out using mass directed preparative LC-MS eluting with acetonitrile: water: trifluoroacetic acid to afford the title compound. (MH+ 789.4)

Examples 127-132

These compounds namely,
N-[(1S,2R,3S,4R)-4-(6-(2,2-diphenyl-ethylamino)-2-{(R)-3-[3-(3-phenyl-isoxazol-4-yl)-ureido]-pyrrolidin-1-yl}-purin-9-yl)-2,3-dihydroxy-cyclopentyl]-propionamide trifluoroacetate (MH+ 771.5) (Example 127),
5-pyridin-2-yl-thiophene-2-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 758.4) (Example 128),
4-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-ylcarbamoyl}-piperidine-1-carboxylic acid benzylester trifluoroacetate (MH+ 816.6) (Example 129),
N-[(1S,2R,3S,4R)-4-(6-(2,2-diphenyl-ethylamino)-2-{(R)-3-[3-(3-methyl-5-phenyl-isoxazol-4-yl)-ureido]-pyrrolidin-1-yl}-purin-9-yl)-2,3-dihydroxy-cyclopentyl]-propionamide trifluoroacetate (MH+ 771.5) (Example 130),
1,3-dimethyl-1H-thieno[2,3-c]pyrazole-5-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 749.4) (Example 131),
1-methyl-1H-benzotriazole-5-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 730.5) (Example 132),
are prepared analogously to Example 126 by replacing 2-acetamido-4-methyl-5-thiazolesulfonyl chloride with the appropriate isocyanate or acid chloride. Reactions using acid chlorides also have triethylamine added.

Example 133

N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-formamide hydrochloride Step 1: ((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-carbamic acid benzyl ester trifluoroacetate A solution comprising {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester (Intermediate L) (0.1 g, 0.15 mmol), pyridine-3-isocyanate (0.02 g, 0.17 mmol) and TEA (0.017 g, 0.17 mmol) in THF (2 ml) is stirred at room temperature overnight. The solvent is removed in vacuo and purification is carried out by reverse phase column chromatography (Isolute™ C18, 0-100% acetonitrile in water −0.1% TFA). The fractions are collected and the MeCN is removed in vacuo. The remaining aqueous portion is basified with saturated sodium bicarbonate solution and extracted with DCM.

The combined organic extracted are dried (MgSO$_4$) and concentrated in vacuo to afford the title product. MS (ES+) m/e 769 (MH$^+$).

Step 2: 1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-3-yl-urea To a solution of ((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-carbamic acid benzyl ester trifluoroacetate (35 mg, 46 µmol) in ethanol (1 ml) under an inert atmosphere of Argon is added 10% palladium on carbon (10 mg). The reaction mixture is purged with Argon and placed under a positive atmosphere of hydrogen overnight after which time, the mixture is filtered through celite and the catalyst washed with ethanol. The organic portions are combined and concentrated in vacuo to yield the title compound. MS (ES+) m/e 635 (MH$^+$).

Step 3: N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-formamide hydrochloride Acetic anhydride (1.9 mg, 19 mmol) and formic acid (1.4 mg, 30 mmol) are stirred together for 30 minutes and then added to a solution of 1-{(R)-1-[9-((1R,2S,3R,4S)-4-amino-2,3-dihydroxy-cyclopentyl)-6-(2,2-diphenyl-ethylamino)-9H-purin-2-yl]-pyrrolidin-3-yl}-3-pyridin-3-yl-urea (11 mg, 17 µmol) in THF (0.5 ml). The reaction mixture is stirred at room temperature overnight and purification by reverse phase column chromatography (Isolute™ C18, 0-100% acetonitrile in water −0.1% HCl) affords the title compound. (MH+ 663.5)

Example 134

(R)-3-Dimethylamino-pyrrolidine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate Step 1: Imidazole-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide A mixture comprising N-{(3aR,4S,6R,6aS)-6-[2-((R)-3-amino-pyrrolidin-1-yl)-6-(2,2-diphenyl-ethylamino)-purin-9-yl]-2,2-dimethyl-tetrahydro-cyclopenta[1,3]dioxol-4-yl}-propionamide (Intermediate M) (0.24 g, 394 μmol) and CDI (0.275 g, 1.7 mmol) in dry DCM (6 ml) is stirred at room temperature for 3 hours. The resulting solution is purified by chromatography on silica eluting with 100% DCM changing to 5% MeOH in DCM to afford the title compound as a yellow oil. The oil consists of the imidazole-urea intermediate together with variable amounts of the corresponding isocyanate and imidazole which are equally suitable as precursors to ureas.

Step 2: (R)-3-Dimethylamino-pyrrolidine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate Dimethyl-(R)-pyrrolidin-3-yl-amine (4.6 mg, 40 μmol) is treated with a solution of imidazole-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide (25 mg, 40 μmol) in DCM (1 ml) and the reaction mixture is stirred at room temperature overnight. The solvent is removed in vacuo and the residue is treated with TFA (0.5 ml) and water (0.5 ml). After stirring at room temperature for 3 hours, the reaction mixture is concentrated in vacuo and the resulting crude is purified by mass directed preparative LC-MS eluting with acetonitrile: water: trifluoroacetic acid to afford the title compound. (MH+ 711.5)

Example 135

4-(2-cyano-ethyl)-piperazine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate This compound is prepared analogously to (R)-3-dimethylamino-pyrrolidine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (Example 134) by replacing dimethyl-(R)-pyrrolidin-3-yl-amine with the appropriate amine. (MH+ 697.4)

Example 136-155

These compounds namely,

N-[(1S,2R,3S,4R)-4-(2-((R)-3-dimethylamino-pyrrolidin-1-yl)-6-{[(1R,3S)-2,2-dimethyl-3-(2-methyl-propenyl)-cyclopropylmethyl]-amino}-purin-9-yl)-2,3-dihydroxy-cyclopentyl]-propionamide trifluoroacetate (MH+ 555.6) (Example 136), N-{(1S,2R,3S,4R)-4-[6-((1R,2R)-2-benzyloxy-cyclopentylamino)-2-((R)-3-dimethylamino-pyrrolidin-1-yl)-purin-9-yl]-2,3-dihydroxy-cyclopentyl}-propionamide trifluoroacetate (MH+ 593.5) (Example 137), N-{(1S,2R,3S,4R)-4-[6-((1S,2S)-2-benzyloxy-cyclopentylamino)-2-(R)-3-dimethylamino-pyrrolidin-1-yl)-purin-9-yl]-2,3-dihydroxy-cyclopentyl}-propionamide trifluoroacetate (MH+ 593.5) (Example 138), N-{(1S,2R,3S,4R)-4-[6-((1S,2S)-bicyclopentyl-2-ylamino)-2-((R)-3-dimethylamino-pyrrolidin-1-yl)-purin-9-yl]-2,3-dihydroxy-cyclopentyl}-propionamide trifluoroacetate (MH+ 555.6) (Example 139), N-{(1S,2R,3S,4R)-4-[6-((R)-1-benzyl-pyrrolidin-3-ylamino)-2-((R)-3-dimethylamino-pyrrolidin-1-yl)-purin-9-yl]-2,3-dihydroxy-cyclopentyl}-propionamide trifluoroacetate (MH+ 578.5) (Example 140), N-{(1S,2R,3S,4R)-4-[6-((S)-1-benzyl-pyrrolidin-3-ylamino)-2-((R)-3-dimethylamino-pyrrolidin-1-yl)-purin-9-yl]-2,3-dihydroxy-cyclopentyl}-propionamide trifluoroacetate (MH+ 578.5) (Example 141), N-{(1S,2R,3S,4R)-4-[2-((R)-3-dimethylamino-pyrrolidin-1-yl)-6-(2-piperidin-1-yl-ethylamino)-purin-9-yl]-2,3-dihydroxy-cyclopentyl}-propionamide trifluoroacetate (MH+ 530.5) (Example 142), N-{(1S,2R,3S,4R)-4-[6-[2-(4-benzyl-piperidin-1-yl)-ethylamino]-2-((R)-3-dimethylamino-pyrrolidin-1-yl)-purin-9-yl]-2,3-dihydroxy-cyclopentyl}-propionamide trifluoroacetate (MH+ 620.5) (Example 143), N-{(1S,2R,3S,4R)-4-[2-((R)-3-dimethylamino-pyrrolidin-1-yl)-6-[((S)-2-phenyl-1-pyrrolidin-1-ylmethyl-ethylamino)-purin-9-yl]-2,3-dihydroxy-cyclopentyl}-propionamide trifluoroacetate (MH+ 606.5) (Example 144), N-{(1S,5R,3S,4R)-4-[2-((R)-3-dimethylamino-pyrrolidin-1-yl)-6-(3,4,5,6-tetrahydro-2H-[1,2']bipyridinyl-4-ylamino)-purin-9-yl]-2,3-dihydroxy-cyclopentyl}-propionamide trifluoroacetate (MH+ 579.5) (Example 145), N-{(1S,2R,3S,4R)-4-[2-((R)-3-dimethylamino-pyrrolidin-1-yl)-6-((S)-1-hydroxymethyl-3-methyl-butylamino)-purin-9-yl]-2,3-dihydroxy-cyclopentyl}-propionamide trifluoroacetate (MH+ 519.5) (Example 146), N-{(1S,2R,3S,4R)-4-[2-((R)-3-dimethylamino-pyrrolidin-1-yl)-6-((S)-1-hydroxymethyl-3-methylsulfanyl-propylamino)-purin-9-yl]-2,3-dihydroxy-cyclopentyl}-propionamide trifluoroacetate (MH+ 537.5) (Example 147), N-{(1S,2R,3S,4R)-4-[6-((R)-1-benzyl-2-hydroxy-ethylamino)-2-((R)-3-dimethylamino-pyrrolidin-1-yl)-purin-9-yl]-2,3-dihydroxy-cyclopentyl}-propionamide trifluoroacetate (MH+ 553.5) (Example 148), N-{(1S,2R,3S,4R)-4-[2-((R)-3-dimethylamino-pyrrolidin-1-yl)-6-((1S,2S)-2-hydroxy-1-hydroxymethyl-2-phenyl-ethylamino)-purin-9-yl]-2,3-dihydroxy-cyclopentyl}-propionamide trifluoroacetate (MH+ 569.5) (Example 149), N-((1S,2R,3S,4R)-4-{2-((R)-3-dimethylamino-pyrrolidin-1-yl)-6-[(S)-2-hydroxy-1-(4-hydroxy-benzyl)-ethylamino]-purin-9-yl}-2,3-dihydroxy-cyclopentyl)-propionamide trifluoroacetate (MH+ 569.5) (Example 150), N-((1S,2R,3S,4R)-4-{2-((R)-3-dimethylamino-pyrrolidin-1-yl)-6-[(S)-2-hydroxy-1-(1H-imidazol-4-ylmethyl)-ethylamino]-purin-9-yl}-2,3-dihydroxy-cyclopentyl)-propionamide trifluoroacetate (MH+ 543.5) (Example 151), N-((1S,2R,3S,4R)-4-{2-((R)-3-dimethylamino-pyrrolidin-1-yl)-6-[(S)-2-hydroxy-1-(1H-indol-3-ylmethyl)-ethylamino]-purin-9-yl}-2,3-dihydroxy-cyclopentyl)-propionamide trifluoroacetate (MH+ 592.4) (Example 152), N-{(1S,2R,3S,4R)-4-[6-((S)-1-benzyl-2-methoxy-ethylamino)-2-(R)-3-dimethylamino-pyrrolidin-1-yl)-purin-9-yl]-2,3-dihydroxy-cyclopentyl}-propionamide trifluoroacetate (MH+ 567.4) (Example 153), N-{(1S,2R,3S,4R)-4-[6-[(S)-1-(4-benzyloxy-benzyl)-2-hydroxy-ethylamino]-2-((R)-3-dimethylamino-pyrrolidin-1-yl)-purin-9-yl]-2,3-dihydroxy-cyclopentyl}-propionamide trifluoroacetate (MH+ 659.4) (Example 154) and N-((1S,2R,3S,4R)-4-{2-((R)-3-dimethylamino-pyrrolidin-1-yl)-6-[(1S,2S)-2-hydroxy-1-hydroxymethyl-2-(4-methylsulfanyl-phenyl)-ethylamino]-purin-9-yl}-2,3-dihydroxy-cyclopentyl)-propionamide trifluoroacetate (MH+ 615) (Example 155)

are prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (Example 1 step 2) by replacing (3R)-3-aminopyrrolidine with dimethyl-(R)-pyrrolidin-3-yl-amine and by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with the appropriate starting compounds. The preparation of the starting compounds are either described herein or can be prepared from [(1S,2R,3S,4R)-4-(2,6-dichloro-purin-9-yl)-2,3-dihydroxy-cyclopentyl]-propionyl-carbamic acid tert-butyl ester (Intermediate G) and the appropriate amine using a procedure analogous to 2R,3S,4R)-4-{6-[2,2-Bis-(4-hydroxy-phenyl)-ethylamino]-2-chloro-purin-9-yl}-2,3-dihydroxy-cyclopentyl)-propionamide (Example 22 steps 1 and 2).

Example 156

N-{(R)-1-[6-[2,2-Bis-(4-methoxy-phenyl)-ethylamino]-9-((1R,2S,3R,4S)-2,3-dihydroxy-4-propionylamino-cyclopentyl)-9H-purin-2-yl]-pyrrolidin-3-yl}-isonicotinamide hydrochloride This compound is prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (Example 1 step 2) by replacing (3R)-3-aminopyrrolidine with (R)-N-pyrrolidin-3-yl-isonicotinamide (Intermediate O) and by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-((1S,2R,3S,4R)-4-{6-[2,2-Bis-(4-methoxy-phenyl)-ethylamino]-2-chloro-purin-9-yl}-2,3-dihydroxy-cyclopentyl)-propionamide {prepared from [(1S,2R,3S,4R)-4-(2,6-dichloro-purin-9-yl)-2,3-dihydroxy-cyclopentyl]-propionyl-carbamic acid tert-butyl ester (Intermediate G) and the appropriate amine using a procedure analogous to 2R,3S,4R)-4-{6-[2,2-Bis-(4-hydroxy-phenyl)-ethylamino]-2-chloro-purin-9-yl}-2,3-dihydroxy-cyclopentyl)-propionamide (Example 22 steps 1 and 2)}. (MH+ 736.5)

Example 157

5-Methyl-isoxazole-3-carboxylic acid {(R)-1-[6-[2,2-bis-(4-methoxy-phenyl)-ethylamino]-9-((1R,2S,2R,4S)-2,3-dihydroxy-4-propionylamino-cyclopentyl)-9H-purin-2-yl]-pyrrolidin-3-yl}-amide hydrochloride are prepared analogously to Example 93 by replacing N-{(1S,2R,3S,4R)-4-[2-chloro-6-(1-ethyl-propylamino)-purin-9-yl]-2,3-dihydroxy-cyclopentyl}-propionamide with N-((1S,2R,3S,4R)-4-{6-[2,2-Bis-(4-methoxy-phenyl)-ethylamino]-2-chloro-purin-9-yl}-2,3-dihydroxy-cyclopentyl)-propionamide [prepared from [(1S,2R,3S,4R)-4-(2,6-dichloro-purin-9-yl)-2,3-dihydroxy-cyclopentyl]-propionyl-carbamic acid tert-butyl ester (Intermediate G) and the appropriate amine using a procedure analogous to 2R,3S,4R)-4-{6-[2,2-Bis-(4-hydroxy-phenyl)-ethylamino]-2-chloro-purin-9-yl}-2,3-dihydroxy-cyclopentyl)-propionamide (Example 22 steps 1 and 2)]. (MH+ 740.5)

Example 158

N-{(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-isonicotinamide hydrochloride A mixture comprising N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-propionamide (Example 22 step 4) (20 mg, 33 μmol) in THF (0.5 ml) and NMP (0.5 ml) is treated with TEA (13 mg, 0.13 mmol) followed by isonicotinoyl chloride hydrochloride (16 mg, 83 μmol). After stirring at room temperature for 2 hours, the solvent is removed in vacuo and purification by C-18 reverse phase column chromatography eluting with acetonitrile:water:HCl (0.1%) (gradient of 0 to 100% acetonitrile) yields the title compound. (MH+ 708.4)

Example 159

1-Methyl-1H-benzotriazole-5-carboxylic acid {(R)-1-[6-[2,2-bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-amide hydrochloride This compound is prepared analogously to N-{(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-isonicotinamide hydrochloride (Example 158) by replacing isonicotinoyl chloride hydrochloride with 1-methyl-1H-1,2,3-benzotriazole-5-carbonyl chloride. (MH+ 762.4)

Example 160-162

These compounds namely,

N-((1S,2R,3S,4R)-4-{6-[2,2-Bis-(4-hydroxy-phenyl)-ethylamino]-2-[(R)-3-(3-pyridin-3-ylmethyl-ureido)-pyrrolidin-1-yl]-purin-9-yl}-2,3-dihydroxy-cyclopentyl)-propionamide hydrochloride (MH+ 737.5) (Example 160), N-((1S,2R,3S,4R)-4-{6-[2,2-Bis-(4-hydroxy-phenyl)-ethylamino]-2-[(R)-3-(3-pyridin-4-ylmethyl-ureido)-pyrrolidin-1-yl]-purin-9-yl}-2,3-dihydroxy-cyclopentyl)-propionamide hydrochloride (MH+ 737.2) (Example 161), N-((1S,2R,3S,4R)-4-{6-[2,2-Bis-(4-hydroxy-phenyl)-ethylamino]-2-[(R)-3-(3-pyridin-4-ylmethyl-ureido)-pyrrolidin-1-yl]-purin-9-yl}-2,3-dihydroxy-cyclopentyl)-propionamide hydrochloride (MH+ 740.5) (Example 162), are prepared analogously to N-((1S,2R,3S,4R)-4-{6-[2,2-Bis-(4-hydroxy-phenyl)-ethylamino]-2-[(R)-3-(3-pyridin-2-ylmethyl-ureido)-pyrrolidin-1-yl]-purin-9-yl}-2,3-dihydroxy-cyclopentyl)-propionamide hydrochloride (Example 23) by replacing 2-(aminomethyl)pyridine with the appropriate amine.

Example 163

2-Amino-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-acetamide hydrochloride A solution of 1-{(R)-1-[9-((1R,2S,3R,4S)-4-amino-2,3-dihydroxy-cyclopentyl)-6-(2,2-diphenyl-ethylamino)-9H-purin-2-yl]-pyrrolidin-3-yl}-3-pyridin-3-yl-urea (Example 26 step 2) (17 mg, 26 µmol) in THF (1 ml) is treated with tert-butoxycarbonylamino-acetic acid 2,5-dioxo-pyrrolidin-1-yl ester (9 mg, 29 µmol) and stirred at room temperature overnight. The resulting solution is treated with 1.25 M HCl in EtOH (1 ml) and stirred at room temperature for 2 days. Purification by C-18 reverse phase column chromatography eluting with acetonitrile:water:HCl (0.1%) (gradient of 0 to 100% acetonitrile) yields the title compound. (MH+ 691.99)

Example 164

N-{(1S,2R,3S,4R)-4-[(R)-2-[1,3']Bipyrrolidinyl-1'-yl-6-(2,2-diphenyl-ethylamino)-purin-9-yl]-2,3-dihydroxy-cyclopentyl}-propionamide hydrochloride The title compound is prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (Example 1 step 2) by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-{(1S,2R,3S,4R)-4-[2-chloro-6-(2,2-diphenyl-ethylamino)-purin-9-yl]-2,3-dihydroxy-cyclopentyl}-propionamide (Intermediate J) and by replacing (3R)-3-aminopyrrolidine with (R)-[1,3']bipyrrolidinyl (Intermediate N). (MH+ 625.4)

Example 165

N-[(1S,2R,3S,4R)-4-(6-(2,2-Diphenyl-ethylamino)-2-{2-[3-(3,4,5,6-tetrahydro-2H-[1,2]bipyridinyl-4-yl)-ureido]-ethylamino}-purin-9-yl)-2,3-dihydroxy-cyclopentyl]-propionamide trifluoroacetate A solution of N-{(1S,2R,3S,4R)-4-[2-(2-amino-ethylamino)-6-(2,2-diphenyl-ethylamino)-purin-9-yl]-2,3-dihydroxy-cyclopentyl}-propionamide trifluoroacetate (Example 100) (27 mg, 37 µmol) in IPA (0.5 ml) is treated with imidazole-1-carboxylic acid (3,4,5,6-tetrahydro-2H-[1,2']bipyridinyl-4-yl)-amide (Intermediate C) (1.1 ml of a 10 mg/ml solution in DCM, 40 µmol). After stirring at room temperature for 7 days, the solvent is removed in vacuo and purification of the residue by C-18 reverse phase column chromatography eluting with acetonitrile:water:TFA (0.1%) (gradient of 0 to 100% acetonitrile) yields the title compound. (MH+ 748.6)

Example 166

Biphenyl-2-yl-carbamic acid 1-{2-[(R)-3-(3-{(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-ureido)-pyrrolidin-1-yl]-2-oxo-ethyl}-piperidin-4-yl ester trifluoroacetate This compound is prepared analogously to (R)-3-dimethylamino-pyrrolidine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (Example 134) by replacing dimethyl-(R)-pyrrolidin-3-yl-amine with Intermediate Z. (MH+/2 510.62)

Example 167

N-[(1S,2R,3S,4R)-4-(6-(2,2-Diphenyl-ethylamino)-2-{(R)-3-[3-(2-methyl-5-phenyl-furan-3-yl)-ureido]-pyrrolidin-1-yl}-purin-9-yl)-2,3-dihydroxy-cyclopentyl]-propionamide This compound is prepared analogously to (Example 126) by replacing 2-acetamido-4-methyl-5-thiazolesulfonyl chloride with 3-isocyanato-2-methyl-5-phenyl-furan and by changing the solvent to THF. (MH+ 770.48)

Example 168

1-[6-Amino-9-((1R,2S,3R,4S)-2,3-dihydroxy-4-propionylamino-cyclopentyl)-9H-purin-2-yl]-1H-pyrazole-4-carboxylic acid ethyl ester Step 1: N-[(1S,2R,3S,4R)-4-(6-{[Bis-(4-methoxy-phenyl)-methyl]-amino}-2-chloro-purin-9-yl)-2,3-dihydroxy-cyclopentyl]-propionamide To a solution of N-[(1S,2R,3S,4R)-4-(2,6-dichloro-purin-9-yl)-2,3-dihydroxy-cyclopentyl]-propionamide(Intermediate J7) (2.6 g, 7.22 mmol) in dry THF (26 ml) is added C,C-Bis-(4-methoxy-phenyl)-methylamine (Intermediate Y) (3.5 g, 14.44 mmol). The mixture is heated at 50° C. for 12 hours and then concentrated in vacuo. The residue is dissolved in chloroform and washed sequentially with 1.5N HCl, water and saturated aqueous brine solution. The organic phase is dried over anhydrous sodium sulphate and concentrated in vacuo. The crude product is purified by chromatography on silica (60-120 mesh) eluting with 2% methanol in chloroform to afford the title product. LC-MS (0.1% formic acid, acetonitrile): (MH+ 567)

Step 2: N-[(1S,2R,3S,4R)-4-(6-{[Bis-(4-methoxy-phenyl)-methyl]-amino}-2-hydrazino-purin-9-yl)-2,3-dihydroxy-cyclopentyl]-propionamide A mixture comprising N-[(1S,2R,3S,4R)-4-(6-{[Bis-(4-methoxy-phenyl)-methyl]-amino}-2-chloro-purin-9-yl)-2,3-dihydroxy-cyclopentyl]-propionamide (1.6 g, 2.82 mmol), and hydrazine monohydrate (14 ml) is stirred at room temperature for 72 h. Then isopropyl alcohol (10 ml) is added and the solvent was decanted off to afford a gummy mixture. It is dissolved in water (10 ml) and stirred for 12 h. The fine solid obtained is filtered, washed with water and dried in vacuo to afford the title product which is used in the next step without further purification. LC-MS (0.1% formic acid, acetonitrile): (MH+ 563).

Step 3: 1-[6-{[Bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid ethyl ester To a solution of N-[(1S,2R,3S,4R)-4-(6-{[Bis-(4-methoxy-phenyl)-methyl]-amino}-2-hydrazino-purin-9-yl)-2,3-dihydroxy-cyclopentyl]-propionamide (0.1 g, 0.177 mmol) in dry ethyl alcohol (5 ml) is added 2-formyl-3-oxo-propionic acid ethyl ester (synthesised from ethyl-3,3-diethoxy-propionoate, as described in: Bertz S. H., Dabbagh G. and Cotte P.; J. Org. Chem. (1982) 47, pp 2216-2217) (0.033 g, 0.231 mmol). The reaction mixture is heated at reflux for 8 hours then concentrated in vacuo. The crude residue is purified by chromatography on silica (60-120 mesh) eluting with 3% methanol in chloroform to afford the title compound. LC-MS (0.1% formic acid, acetonitrile): (MH+ 671).

Step 4: 1-[6-Amino-9-((1R,2S,3R,4S)-2,3-dihydroxy-4-propionylamino-cyclopentyl)-9H-purin-2-yl]-1H-pyrazole-4-carboxylic acid ethyl ester A cooled (0° C.) solution of 1-[6-{[Bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid ethyl ester (0.1 g, 0.149 mmol) in dry dichloromethane (4 ml) is treated dropwise with TFA (2 ml). The mixture is stirred at room temperature for 12 h and then concentrated in vacuo. The residue is co-evaporated with chloroform three times to remove excess trifluoro acetic acid and purification of the residued by preparative HPLC affords the title compound. LC-MS (0.1% formic acid, acetonitrile): (MH+ 445.3).

Example 169

Isoxazole-5-carboxylic acid {(1S,2R,3S,4R)-4-[2-chloro-6-(2,2-diphenyl-ethylamino)-purin-9-yl]-2,3-dihydroxy-cyclopentyl}-amide This compound is prepared analogously to N-{(1S,2R,3S,4R)-4-[2-chloro-6-(2,2-diphenyl-ethylamino)-purin-9-yl]-2,3-dihydroxy-cyclopentyl}-propionamide (Intermediate JJ4) by replacing propionyl chloride with isoxazole-5-carbonyl chloride. (MH+ 560.28)

Example 170

N-{(1S,2R,3S,4R)-4-[6-Amino-2-(4-q uinolin-4-yl-pyrazol-1-yl)-purin-9-yl]-2,3-dihydroxy-cyclopentyl}-propionamide This compound is prepared analogously to Example 168 by replacing 2-formyl-3-oxopropionic acid ethyl ester with 2-(4-quinolyl)-maloaldehyde. (MH+ 500.3)

Example 171

N-[(1S,2R,3S,4R)-4-[6-(2,2-Diphenyl-ethylamino)-2-(4-pyridin-2-yl-pyrazol-1-yl)-purin-9-yl]-2,3-dihydroxy-cyclopentyl]-propionamide This compound is prepared analogously to Example 42 by replacing cyclohexane carboxaldehyde with 2-pyridinyl-propanedial. The reaction is carried out in ethanol. (MH+ 630.40)

Example 172

N-{(1S,2R,3S,4R)-4-[6-(2,2-Diphenyl-ethylamino)-2-(4-pyridin-4-yl-pyrazol-1-yl)-purin-9-yl]-2,3-dihydroxy-cyclopentyl}-propionamide This compound is prepared analogously to Example 42 by replacing cyclohexane carboxaldehyde with 4-pyridinyl-propanedial. The reaction is carried out in ethanol. (MH+ 630.41)

Example 173

1-[9-((1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid methylamide Step 1: 1-[9-((1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid ethyl ester This compound is prepared analogously to 1-[6-{[Bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid ethyl ester (Example 168 step 3) by replacing N-[(1S,2R,3S,4R)-4-(6-{[Bis-(4-methoxy-phenyl)-methyl]-amino}-2-hydrazino-purin-9-yl)-2,3-dihydroxy-cyclopentyl]-propionamide with N-{(1S,2R,3S,4R)-4-[6-(2,2-diphenyl-ethylamino)-2-hydrazino-purin-9-yl]-2,3-dihydroxy-cyclopentyl}-propionamide.

Step 2: 1-[9-((1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid methylamide A mixture of 1-[9-((1R,2S,3R,4S)-2,3-dihydroxy-4-propionylamino-cyclopentyl)-6-(2,2-diphenyl-ethylamino)-9H-purin-2-yl]-1H-pyrazole-4-carboxylic acid ethyl ester (0.07 g, 0.112 mmol) and 40% aqueous methyl amine solution (3 ml) is heated to 65° C. for 12 h. The reaction mixture is concentrated in vacuo and purification of the crude residue by chromatography on silica eluting with 4% methanol in chloroform yields the title compound.
LC-MS (0.1% formic acid, acetonitrile): (MH+ 610.41)

Example 174

1-[6-Amino-9-((1R,2S,3R,4S)-2,3-dihydroxy-4-propionylamino-cyclopentyl)-9H-purin-2-yl]-1H-pyrazole-4-carboxylic acid methylamide Step 1: 1-[6-{[Bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid methylamide A mixture of 1-[6-{[Bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid ethyl ester (Example 168, step 3) (0.2 g, 0.298 mmol) and 40% aqueous methyl amine solution (5 ml) is heated to 65° C. for 12 h. The reaction mixture concentrated in vacuo and purification of the crude residue by chromatography on silica eluting with 3% methanol in chloroform yields the title compound. LC-MS (0.1% formic acid, acetonitrile): 656 (MH+).

Step 2: 1-[6-Amino-9-((1R,2S,3R,4S)-2,3-dihydroxy-4-propionylamino-cyclopentyl)-9H-purin-2-yl]-1H-pyrazole-4-carboxylic acid methylamide A cooled (0° C.) solution of 1-[6-{[Bis-(4-methoxy-phenyl)-methyl]-amino}-9-((1R,2S,3R,4S)-2,3-dihydroxy-4-propionylamino-cyclopentyl)-9H-purin-2-yl]-1H-pyrazole-4-carboxylic acid methylamide (0.08 g, 0.122 mmol) in dry dichloromethane (4 ml) is treated slowly with trifluoroacetic acid (2 ml). The reaction mixture is stirred at room temperature for 48 h and then concentrated in vacuo. The residue was co-evaporated with chloroform three times to remove excess trifluoro acetic acid and purification of the crude product by preparative HPLC affords the title compound. LC-MS (0.1% formic acid, acetonitrile): (MH+ 430.28)

Example 175

N-((1S,2R,3S,4R)-4-{6-[2,2-Bis-(4-hydroxy-phenyl)-ethylamino]-2-[(R)-3-(3-pyridin-3-yl-ureido)-pyrrolidin-1-yl]-purin-9-yl}-2,3-dihydroxy-cyclopentyl)-2-hydroxy-acetamide trifluoroacetate This compound is prepared analogously to Example 23 by replacing {(R)-1-[6-[2,2-Bis-(4-hydroxy-phenyl)-ethylamino]-9-((1R,2S,3R,4S)-2,3-dihydroxy-4-propionylamino-cyclopentyl)-9H-purin-2-yl]-pyrrolidin-3-yl}-carbamic acid phenyl ester with N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-2-hydroxy-acetamide hydrochloride (Example 7 step 5) and by replacing 2-(aminomethyl)pyridine with pyridin-3-yl-carbamic acid phenyl ester (Intermediate ZB). (MH+ 725.32)

Example 176

4-{[(R)-3-(3-{(R)-1-[9-((1R,2S,3R,4S)-2,3-Dihydroxy-4-propionylamino-cyclopentyl)-6-(2,2-diphenyl-ethylamino)-9H-purin-2-yl]-pyrrolidin-3-yl}-ureido)-pyrrolidine-1-carbonyl]-amino}-piperidine-1-carboxylic acid benzyl ester trifluoroacetate The title compound is prepared analogously to 4-[3-(2-{[9-((1R,2S,3R,4S)-2,3-dihydroxy-4-propionylamino-cyclopentyl)-6-(2,2-diphenyl-ethylamino)-9H-purine-2-carbonyl]-amino}-ethyl)-ureido]-piperidine-1-carboxylic acid benzyl ester (Example 108) by replacing 9-((1R,2S,3R,4S)-2,3-dihydroxy-4-propionylamino-cyclopentyl)-6-(2,2-diphenyl-ethylamino)-9H-purine-2-carboxylic acid (2-amino-ethyl)-amide with N-((1S,2R,3S,4R)-4-{6-(2,2-diphenyl-ethylamino)-2-[(R)-3-((R)-3-pyrrolidin-3-ylureido)-pyrrolidin-1-yl]-purin-9-yl}-2,3-dihydroxy-cyclopentyl)-propionamide trifluoroacetate (Example 17 step 1). (MH+ 943.4)

Example 177

N-((1S,2R,3S,4R)-4-{2-[((S)-1-benzyl-pyrrolidin-3-yl)-methyl-amino]-6-[2-(4-fluoro-phenyl)-2-phenyl-ethylamino]-purin-9-yl}-2,3-dihydroxy-cyclopentyl)-propionamide trifluoroacetate This compound is prepared analogously to N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-acetamide trifluoroacetate (Example 1 step 2) by replacing (3R)-3-(Boc-amino)pyrrolidine with ((S)-1-benzyl-pyrrolidin-3-yl)-methyl-amine and by replacing 2-benzyloxy-N-{(1S,2R,3S,4R)-4-[2-chloro-6-(2,2-diphenyl-ethylamino)-purin-9-yl]-2,3-dihydroxy-cyclopentyl}-acetamide with N-((1S,2R,3S,4R)-4-{2-chloro-6-[2-(4-fluoro-phenyl)-2-phenyl-ethylamino]-purin-9-yl}-2,3-dihydroxy-cyclopentyl)-propionamide trifluoroacetate [prepared from [(1S,2R,3S,4R)-4-(2,6-dichloro-purin-9-yl)-2,3-dihydroxy-cyclopentyl]-propionyl-carbamic acid tert-butyl ester (Intermediate G) and the appropriate amine using a procedure analogous to 2R,3S,4R)-4-{6-[2,2-Bis-(4-hydroxy-phenyl)-ethylamino]-2-chloro-purin-9-yl}-2,3-dihydroxy-cyclopentyl)-propionamide (Example 22 steps 1 and 2)]. (MH+ 693.5)

Example 178

N-{(1S,2R,3S,4R)-4-[2-{(R)-3-[3-(4-Benzyloxy-phenyl)-ureido]-pyrrolidin-1-yl}-6-(2,2-diphenyl-ethylamino)-purin-9-yl]-2,3-dihydroxy-cyclopentyl}-propionamide trifluoroacetate This compound is prepared analogously to Example 126 by replacing 2-acetamido-4-methyl-5-thiazolesulfonyl chloride with 1-benzyloxy-4-isocyanato-benzene. (MH+ 796.49)

Example 179-180

These compounds namely,
(R)-3-amino-pyrrolidine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 677.5) (Example 179) and
(S)-3-amino-pyrrolidine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (MH+ 683.4) (Example 180)
are prepared analogously to (R)-3-dimethylamino-pyrrolidine-1-carboxylic acid {(R)-1-[9-((1R,2S,3R,4S)-2,3-dihydroxy-4-propionylamino-cyclopentyl)-6-(2,2-diphenyl-ethylamino)-9H-purin-2-yl]-pyrrolidin-3-yl}-amide trifluoroacetate (Example 134) by replacing dimethyl-(R)-pyrrolidin-3-yl-amine with the appropriate amine.

Example 181

(R)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-propionamide Step 1: (R)-2-Benzyloxy-N-[(1S,2R,3S,4R)-4-(2,6-dichloro-purin-9-yl)-2,3-dihydroxy-cyclopentyl]-propionamide The title compound is prepared by dissolving (R)-2-benzyloxy-propionic acid (1 equivalent) in dichloromethane with 1,3-dicyclohexylcarbodiimide (1 equivalent) and a catalytic amount of 4-dimethylaminopyridine, stirring for five minutes, then adding (1S,2R,3S,5R)-3-amino-5-(2,6-dichloro-purin-9-yl)-cyclopentane-1,2-diol (Intermediate J5; 1-equivalent) in dichloromethane. The reaction is stirred at room temperature until determined to be complete, the solvent is removed under reduced pressure, and the title compound purified by column chromatography/crystallisation.

Step 2: (R)-2-Benzyloxy-N-{(1S,2R,3S,4R)-4-[2-chloro-6-(2,2-diphenyl-ethylamino)-purin-9-yl]-2,3-dihydroxy-cyclopentyl}-propionamide The title compound is prepared analogously to N-{(1S,2R,3S,4R)-4-[2-chloro-6-(2,2-diphenyl-ethylamino)-purin-9-yl]-2,3-dihydroxy-cyclopentyl}-propionamide (Intermediate J7), by substituting acetic acid (R)-2-benzyloxy-N-[(1S, 2R,3S,4R)-4-(2,6-dichloro-purin-9-yl)-2,3-dihydroxy-cyclopentyl]-propionamide for N-[(1S,2R,3S,4R)-4-(2,6-dichloro-purin-9-yl)-2,3-dihydroxy-cyclopentyl]-propionamide.

Step 3: {(R)-1-[9-[(1R,2S,3R,4S)-4-((R)-2-Benzyloxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester A suspension of (R)-2-benzyloxy-N-{(1S,2R,3S,4R)-4-[2-chloro-6-(2,2-diphenyl-ethylamino)-purin-9-yl]-2,3-dihydroxy-cyclopentyl}-propionamide (1 equivalent) and (3R)-(+)-3-(Boc-amino)pyrrolidine (4 equivalents) in acetonitrile is treated with a catalytic amount of sodium iodide and then heated using microwave radiation in a Personal Chemistry Emrys™ Optimizer microwave reactor at 160° C. After 1 hour, the solvent is removed in vacuo; purification by column chromatography/crystallisation affords the title compound.

Step 4: (R)-N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-benzyloxy-propionamide A solution of {(R)-1-[9-[(1R,2S,3R,4S)-4-(R)-2-Benzyloxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester in MeOH (~0.5M) is treated with an equal volume of 4M HCl in dioxane and stirred at room temperature for 2 hours. The solvent is removed in vacuo and purification is carried out by column chromatography/crystallisation to afford the title compound.

Step 5: (R)-2-Benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide A solution comprising (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (1 equivalent) and pyridin-3-yl-carbamic acid phenyl ester (Intermediate ZB) (1 equivalent) in NMP is stirred at 100° C. for 1 hour. The solvent is removed in vacuo and the title compound is obtained after purification by column chromatography/crystallisation.

Step 6: (R)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-propionamide To a stirred solution of (R)-2-Benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide in ethanol is added 10 equivalents of ammonium formate and 20 mol % of 10% palladium on carbon. The mixture is stirred at 80° C. for five hours, allowed to cool and filtered through Celite™. Removal of the solvent under reduced pressure affords the title compound.

Example 182

(S)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-propionamide

Step 1: Acetic acid (S)-1-[(1S,2R,3S,4R)-4-(2,6-dichloro-purin-9-yl)-2,3-dihydroxy-cyclopentylcarbamoyl]-ethyl ester The title compound is prepared analogously to Intermediate J6, from Intermediate J5, replacing propionyl chloride with acetic acid (S)-1-chlorocarbonyl-ethyl ester.

Step 2: Acetic acid (S)-1-{(1S,2R,3S,4R)-4-[2-chloro-6-(2,2-diphenyl-ethylamino)-purin-9-yl]-2,3-dihydroxy-cyclopentylcarbamoyl}-ethyl ester The title compound is prepared analogously to N-{(1S,2R,3S,4R)-4-[2-chloro-6-(2,2-diphenyl-ethylamino)-purin-9-yl]-2,3-dihydroxy-cyclopentyl}-propionamide (Intermediate J7), by substituting acetic acid (S)-1-[(1S,2R,3S,4R)-4-(2,6-dichloro-purin-9-yl)-2,3-dihydroxy-cyclopentylcarbamoyl]-ethyl ester (Example 182, step 1) for N-[(1S,2R,3S,4R)-4-(2,6-dichloro-purin-9-yl)-2,3-dihydroxy-cyclopentyl]-propionamide.

Step 3: Acetic acid (S)-1-{(1S,2R,3S,4R)-4-[2-((R)-3-tert-butoxycarbonylamino-pyrrolidin-1-yl)-6-(2,2-diphenyl-ethylamino)-purin-9-yl]-2,3-dihydroxy-cyclopentylcarbamoyl}-ethyl ester The title compound is prepared analogously to {(R)-1-[9-[(1R,2S,3R,4S)-4-((R)-2-benzyloxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester (Example 181, step 3), by substituting acetic acid (S)-1-{(1S,2R,3S,4R)-4-[2-chloro-6-(2,2-diphenyl-ethylamino)-purin-9-yl]-2,3-dihydroxy-cyclopentylcarbamoyl}-ethyl ester (Example 182, step 2) for (R)-2-benzyloxy-N-{(1S,2R,3S,4R)-4-[2-chloro-6-(2,2-diphenyl-ethylamino)-purin-9-yl]-2,3-dihydroxy-cyclopentyl}-propionamide (Example 181, step 2).

Step 4: (S)-N-{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-2-hydroxy-propionamide The title compound is prepared analogously to (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4), by substituting acetic acid (S)-1-{(1S,2R,3S,4R)-4-[2-((R)-3-tert-butoxycarbonylamino-pyrrolidin-1-yl)-6-(2,2-diphenyl-ethylamino)-purin-9-yl]-2,3-dihydroxy-cyclopentylcarbamoyl}-ethyl ester (Example 182, step 3) for {(R)-1-[9-[(1R,2S,3R,4S)-4-((R)-2-benzyloxy-propionylamino)-2,3-dihydroxy-cyclopentyl]-6-(2,2-diphenyl-ethylamino)-9H-purin-2-yl]-pyrrolidin-3-yl}-carbamic acid tert-butyl ester (Example 181, step 3).

Step 5: (S)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-propionamide The title compound was prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting (S)-N-{(1S,2R,3S, 4R)-4-[2-((R)-3-amino-pyrrolidin-1-yl)-6-(2,2-diphenyl-ethylamino)-purin-9-yl]-2,3-dihydroxy-cyclopentyl}-2-hydroxy-propionamide (Example 182, step 4) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 183

N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-3-hydroxy-propionamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 184

N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide The title compound was prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4) and pyridin-2-ylmethyl-carbamic acid (Intermediate ZC) for pyridin-3-yl-carbamic acid phenyl ester (Intermediate ZB).

Example 185

N-(1S,2R,3S,4R)-4-(6-(2,2-Diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide The title compound was prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4) and (3-Hydroxy-benzyl)-carbamic acid phenyl ester (Intermediate ZD) for pyridin-3-yl-carbamic acid phenyl ester (Intermediate ZB).

Example 186

N-[(1S,2R,3S,4R)-4-(6-(2,2-Diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide The title compound was prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4) and (4-Sulfamoyl-phenyl)-carbamic acid phenyl ester (Intermediate ZE) for pyridin-3-yl-carbamic acid phenyl ester (Intermediate ZB).

Example 187

N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide The title compound was prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4) and (3-Sulfamoyl-phenyl)-carbamic acid phenyl ester (Intermediate ZF) for pyridin-3-yl-carbamic acid phenyl ester (Intermediate ZB).

Example 188

N-[(1S,2R,3S,4R)-4-(6-[2,2-Bis-(4-hydroxy-phenyl)-ethylamino]-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide The title compound is prepared analogously to N-[(1S,2R,3S,4R)-4-(6-(2,2-Diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide (Example 186), by substituting N-((1S,2R,3S,4R)-4-{2-((R)-3-amino-pyrrolidin-1-yl)-6-(2,2-bis-(4-hydroxy-phenyl)-ethylamino]-purin-9-yl}-2,3-dihydroxy-cyclopentyl)-3-hydroxy-propionamide (Intermediate ZH) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 189

N-((1S,2R,3S,4R)-4-{6-(2,2-Bis-(4-hydroxy-phenyl)-ethylamino]-2-[(R)-3-(3-pyridin-2-ylmethyl-ureido)-pyrrolidin-1-yl]-purin-9-yl}-2,3-dihydroxy-cyclopentyl)-3-hydroxy-propionamide The title compound is prepared analogously to N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-((1S,2R,3S,4R)-4-{2-((R)-3-amino-pyrrolidin-1-yl)-6-(2,2-bis-(4-hydroxy-phenyl)-ethylamino]-purin-9-yl}-2,3-dihydroxy-cyclopentyl)-3-hydroxy-propionamide (Intermediate ZH) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 190

N-[(1S,2R,3S,4R)-4-(6-[2,2-Bis-(4-hydroxy-phenyl)-ethylamino]-2-{(R)-3-[3-(3-hydroxy-benzyl)-ureido]-pyrrolidin-1-yl}-purin-9-yl)-2,3-dihydroxy-cyclopentyl]-3-hydroxy-propionamide The title compound is prepared analogously to N-[(1S,2R,3S,4R)-4-(6-(2,2-Diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-3-hydroxy-propionamide (Intermediate ZH) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 191

N-[(1S,2R,3S,4R)-4-(6-[2,2-Bis-(4-hydroxy-phenyl)-ethylamino]-2-{(R)-3-[3-(3-sulfamoyl-benzyl)-ureido]-pyrrolidin-1-yl}-purin-9-yl)-2,3-dihydroxy-cyclopentyl]-3-hydroxy-propionamide The title compound is prepared analogously to N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide (Example 187), by substituting N-((1S,2R,3S,4R)-4-{2-((R)-3-amino-pyrrolidin-1-yl)-6-(2,2-bis-(4-hydroxy-phenyl)-ethylamino]-purin-9-yl}-2,3-dihydroxy-cyclopentyl)-3-hydroxy-propionamide (Intermediate ZH) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 192

N-((1S,2R,3S,4R)-2,3-Dihydroxy-4-{6-(2-hydroxy-2,2-diphenyl-ethylamino)-2-[(R)-3-(3-pyridin-3-yl-ureido)-pyrrolidin-1-yl]-purin-9-yl}-cyclopentyl)-2-hydroxy-acetamide Step 1: N-((1S,2R,3S,4R)-4-{6-(2,2-Bis-(4-chloro-phenyl)-2-hydroxy-ethylamino]-2-[(R)-3-(3-pyridin-3-yl-ureido)-pyrrolidin-1-yl]-purin-9-yl}-2,3-dihydroxy-cyclopentyl)-2-hydroxy-acetamide A solution comprising: N-((1S,2R,3S,4R)-4-{2-((R)-3-Amino-pyrrolidin-1-yl)-6-[2,2-bis-(4-chloro-phenyl)-2-hydroxy-ethylamino]-purin-9-yl}-2,3-dihydroxy-cyclopentyl)-2-hydroxy-acetamide (Intermediate ZO; 1 equivalent) and pyridin-3-yl-carbamic acid phenyl ester (Intermediate ZB; 1 equivalent) in NMP is stirred at 100° C. for 1 hour. The solvent is removed in vacuo and the title compound is obtained after purification by column chromatography/crystallisation.

Step 2: N-((1S,2R,3S,4R)-2,3-Dihydroxy-4-{6-(2-hydroxy-2,2-diphenyl-ethylamino)-2-[(R)-3-(3-pyridin-3-yl-ureido)-pyrrolidin-1-yl]-purin-9-yl}-cyclopentyl)-2-hydroxy-acetamide To a stirred solution of N-((1S,2R,3S,4R)-4-{6-[2,2-Bis-(4-chloro-phenyl)-2-hydroxy-ethylamino]-2-[(R)-3-(3-pyridin-3-yl-ureido)-pyrrolidin-1-yl]-purin-9-yl}-2,3-dihydroxy-cyclopentyl)-2-hydroxy-acetamide in ethanol is added 10 equivalents of ammonium formate and 20 mol % of 10% palladium on carbon. The mixture is stirred at 80° C. for five hours, allowed to cool and filtered through Celite™. Removal of the solvent under reduced pressure affords the title compound.

Example 193

N-{(1S,2R,3S,4R)-2,3-Dihydroxy-4-[2-{(R)-3-[3-(3-hydroxy-benzyl)-ureido]-pyrrolidin-1-yl}-6-(2-hydroxy-2,2-diphenyl-ethylamino)-purin-9-yl]-cyclopentyl}-2-hydroxy-acetamide The title compound is prepared analogously to N-((1S,2R,3S,4R)-2,3-dihydroxy-4-{6-(2-hydroxy-2,2-diphenyl-ethylamino)-2-[(R)-3-(3-pyridin-3-yl-ureido)-pyrrolidin-1-yl]-purin-9-yl}-cyclopentyl)-2-hydroxy-acetamide (Example 192), by substituting (3-hydroxy-benzyl)-carbamic acid phenyl ester (Intermediate ZD) for pyridin-3-yl-carbamic acid phenyl ester (Intermediate ZB).

Example 194

N-((1S,2R,3S,4R)-2,3-Dihydroxy-4-{6-((S)-1-hydroxymethyl-2-phenyl-ethylamino)-2-[(R)-3-(3-pyridin-3-yl-ureido)-pyrrolidin-1-yl]-purin-9-yl}-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting Acetic acid {(1S,2R,3S,4R)-4-[2-chloro-6-((S)-1-hydroxymethyl-2-phenyl-ethylamino)-purin-9-yl]-2,3-dihydroxy-cyclopentylcarbamoyl}-methyl ester (intermediate ZM) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 195

N-((1S,2R,3S,4R)-2,3-Dihydroxy-4-{6-[(S)-1-hydroxymethyl-2-(4-hydroxy-phenyl)-ethylamino]-2-[(R)-3-(3-pyridin-3-yl-ureido)-pyrrolidin-1-yl]-purin-9-yl}-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting Acetic acid {(1S,2R,3S,4R)-4-[2-chloro-6-((S)-1-hydroxymethyl-2-(4-hydroxy-phenyl)-ethylamino)-purin-9-yl]-2,3-dihydroxy-cyclopentylcarbamoyl}-methyl ester (Intermediate ZN) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 196

N-((1S,2R,3S,4R)-2,3-Dihydroxy-4-{2-{(R)-3-[3-(3-hydroxy-benzyl)-ureido]-pyrrolidin-1-yl}-6-[(S)-1-hydroxymethyl-2-(4-hydroxy-phenyl)-ethylamino]-purin-9-yl}-cyclopentyl)-2-hydroxy-acetamide The title compound is prepared analogously to N-((1S,2R,3S,4R)-2,3-Dihydroxy-4-{6-[(S)-1-hydroxymethyl-2-(4-hydroxy-phenyl)-ethylamino]-2-[(R)-3-(3-pyridin-3-yl-ureido)-pyrrolidin-1-yl]-purin-9-yl}-cyclopentyl)-2-hydroxy-acetamide (Example 195), by substituting (3-hydroxy-benzyl)-carbamic acid phenyl ester (Intermediate ZD) for pyridin-3-yl-carbamic acid phenyl ester (Intermediate ZB).

Example 197

N-((1S,2R,3S,4R)-4-{6-(2,2-Diphenyl-ethylamino)-2-[4-(3-pyridin-3-yl-ureido)-pyrazol-1-yl]-purin-9-yl}-2,3-dihydroxy-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 198

N-((1S,2R,3S,4R)-4-{6-(2,2-Diphenyl-ethylamino)-2-[4-(3-pyridin-2-ylmethyl-ureido)-pyrazol-1-yl]-purin-9-yl}-2,3-dihydroxy-cyclopentyl)-2-hydroxy-acetamide The title compound is prepared analogously to N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 199

N-[(1S,2R,3S,4R)-4-(6-(2,2-Diphenyl-ethylamino)-2-{4-[3-(3-hydroxy-benzyl)-ureido]-pyrazol-1-yl}-purin-9-yl)-2,3-dihydroxy-cyclopentyl]-2-hydroxy-acetamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 200

N-[(1S,2R,3S,4R)-4-(6-(2,2-Diphenyl-ethylamino)-2-{4-[3-(3-sulfamoyl-phenyl)-ureido]-pyrazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide (Example 187), by substituting N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 201

N-[(1S,2R,3S,4R)-4-(6-(2,2-Diphenyl-ethylamino)-2-{4-[3-(4-sulfamoyl-phenyl)-ureido]-pyrazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide (Example 186), by substituting N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 202

N-((1S,2R,3S,4R)-4-{6-[2,2-Bis-(4-hydroxy-phenyl)-ethylamino]-2-[4-(3-pyridin-3-yl-ureido)-pyrazol-1-yl]-purin-9-yl}-2,3-dihydroxy-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-((1S,2R,3S,4R)-4-{2-(4-amino-pyrazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZQ) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 203

N-((1S,2R,3S,4R)-4-{6-[2,2-Bis-(4-hydroxy-phenyl)-ethylamino]-2-[4-(3-pyridin-2-ylmethyl-ureido)-pyrazol-1-yl]-purin-9-yl}-2,3-dihydroxy-cyclopentyl)-2-hydroxy-acetamide The title compound is prepared analogously to N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-((1S,2R,3S,4R)-4-{2-(4-amino-pyrazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZQ) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 204

N-[(1S,2R,3S,4R)-4-(6-[2,2-Bis-(4-hydroxy-phenyl)-ethylamino]-2-{4-[3-(3-hydroxy-benzyl)-ureido]-pyrazol-1-yl}-purin-9-yl)-2,3-dihydroxy-cyclopentyl]-2-hydroxy-acetamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-((1S,2R,3S,4R)-4-{2-(4-amino-pyrazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZQ) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 205

N-[(1S,2R,3S,4R)-4-(6-[2,2-Bis-(4-hydroxy-phenyl)-ethylamino]-2-{4-[3-(3-sulfamoyl-phenyl)-ureido]-pyrazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide (Example 187), by substituting N-((1S,2R,3S,4R)-4-{2-(4-amino-pyrazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZQ) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 206

N-[(1S,2R,3S,4R)-4-(6-[2,2-Bis-(4-hydroxy-phenyl)-ethylamino]-2-{4-[3-(4-sulfamoyl-phenyl)-ureido]-pyrazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide (Example 186), by substituting N-((1S,2R,3S,4R)-4-{2-(4-amino-pyrazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZQ) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 207

N-[(1S,2R,3S,4R)-4-(6-(2,2-Diphenyl-ethylamino)-2-{4-[3-(3-hydroxy-benzyl)-ureido]-pyrazol-1-yl}-purin-9-yl)-2,3-dihydroxy-cyclopentyl]-propionamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-{(1S,2R,3S,4R)-4-[2-(4-amino-pyrazol-1-yl)-6-(2,2-diphenyl-ethylamino)-purin-9-yl]-2,3-dihydroxy-cyclopentyl}-propionamide (Intermediate ZR) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 208

N-((1S,2R,3S,4R)-4-{6-(2,2-Diphenyl-ethylamino)-2-[4-(3-pyridin-2-ylmethyl-ureido)-pyrazol-1-yl]-purin-9-yl}-2,3-dihydroxy-cyclopentyl)-propionamide The title compound is prepared analogously to N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-{(1S,2R,3S,4R)-4-[2-(4-amino-pyrazol-1-yl)-6-(2,2-diphenyl-ethylamino)-purin-9-yl]-2,3-dihydroxy-cyclopentyl}-propionamide (Intermediate ZR) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 209

1-[9-((1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid 3-hydroxy-benzylamide The title compound is prepared analogously to 1-[9-((1R,2S,3R,4S)-2,3-dihydroxy-4-propionylamino-cyclopentyl)-6-(2,2-diphenyl-ethylamino)-9H-purin-2-yl]-1H-pyrazole-4-carboxylic acid methylamide (Example 173), by substituting 3-hydroxybenzylamine for methylamine.

Example 210

1-[9-[((1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid (pyridin-2-yl]methyl)-amide The title compound is prepared analogously to 1-[9-((1R,2S,3R,4S)-2,3-dihydroxy-4-propionylamino-cyclopentyl)-6-(2,2-diphenyl-ethylamino)-9H-purin-2-yl]-1H-pyrazole-4-carboxylic acid methylamide (Example 173), by substituting C-pyridin-2-yl-methylamine for methylamine.

Example 211

1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid (pyridin-2-ylmethyl)-amide The title compound is prepared analogously to 1-[9-((1R,2S,3R,4S)-2,3-dihydroxy-4-propionylamino-cyclopentyl)-6-(2,2-diphenyl-ethylamino)-9H-purin-2-yl]-1H-pyrazole-4-carboxylic acid methylamide (Example 173), by substituting 1-[9-[(1R,2S,3R,4S)-2,3-dihydroxy-4-(2-hydroxy-acetylamino)-cyclopentyl]-6-(2,2-diphenyl-ethylamino)-9H-purin-2-yl]-1H-pyrazole-4-carboxylic acid ethyl ester (Intermediate ZS) for 1-[9-((1R,2S,3R,4S)-2,3-dihydroxy-4-propionylamino-cyclopentyl)-6-(2,2-diphenyl-ethylamino)-9H-purin-2-yl]-1H-pyrazole-4-carboxylic acid ethyl ester (Example 173, step 1) and C-pyridin-2-yl-methylamine for methylamine.

Example 212

1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid 3-hydroxy-benzylamide The title compound is prepared analogously to 1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid (pyridin-2-ylmethyl)-amide (Example 211), by substituting 3-hydroxybenzylamine for C-pyridin-2-yl-methylamine.

Example 213

1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid (3-sulfamoyl-phenyl)-amide The title compound is prepared analogously to 1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid (pyridin-2-ylmethyl)-amide (Example 211), by substituting 3-amino-benzenesulfonamide for C-pyridin-2-yl-methylamine.

Example 214

1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid (4-sulfamoyl-phenyl)-amide The title compound is prepared analogously to 1-[9-[(1R,2S,3R,4S)-2,3-Dihydroxy-4-(2-hydroxy-acetylamino)-cyclopentyl]-6-(2,2-diphenyl-ethylamino)-9H-purin-2-yl]-1H-pyrazole-4-carboxylic acid (pyridin-2-ylmethyl)-amide (Example 211), by substituting 4-amino-benzenesulfonamide for C-pyridin-2-yl-methylamine.

Example 215

N-{(1S,2R,3S,4R)-2,3-Dihydroxy-4-[2-{4-[3-(3-hydroxy-benzyl)-ureido]-pyrazol-1-yl}-6-((S)-1-hydroxymethyl-2-phenyl-ethylamino)-purin-9-yl]-cyclopentyl}-2-hydroxy-acetamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-{(1S,2R,3S,4R)-4-[2-(4-amino-pyrazol-1-yl)-6-(S)-1-hydroxymethyl-2-phenyl-ethylamino)-purin-9-yl]-2,3-dihydroxy-cyclopentyl}-2-hydroxy-acetamide (intermediate ZT) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 216

N-[(1S,2R,3S,4R)-2,3-Dihydroxy-4-(6-((S)-1-hydroxymethyl-2-phenyl-ethylamino)-2-{4-[3-(4-sulfamoyl-phenyl)-ureido]pyrazol-1-yl}-purin-9-yl)-cyclopentyl]-2-hydroxy-acetamide The title compound is prepared analogously to N-[(1S,2R,3S,4R)-4-(6-(2,2-diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide (Example 186), by substituting N-{(1S,2R,3S,4R)-4-[2-(4-amino-pyrazol-1-yl)-6-(S)-1-hydroxymethyl-2-phenyl-ethylamino)-purin-9-yl]-2,3-dihydroxy-cyclopentyl}-2-hydroxy-acetamide (intermediate ZT) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 217

N-((1S,2R,3S,4R)-4-{6-(2,2-Diphenyl-ethylamino)-2-[4-(3-pyridin-3-yl-ureido)-imidazol-1-yl]-purin-9-yl}-2,3-dihydroxy-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 218

N-((1S,2R,3S,4R)-4-{6-(2,2-Diphenyl-ethylamino)-2-[4-(3-pyridin-2-ylmethyl-ureido)-imidazol-1-yl]-purin-9-yl}-2,3-dihydroxy-cyclopentyl}-2-hydroxy-acetamide The title compound is prepared analogously to N-((1S,2R,3S,4R)-4-{6-(2,2-diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 219

N-[(1S,2R,3S,4R)-4-(6-(2,2-Diphenyl-ethylamino)-2-{4-[3-(3-hydroxy-benzyl)-ureido]-imidazol-1-yl}-purin-9-yl)-2,3-dihydroxy-cyclopentyl]-2-hydroxy-acetamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 220

N-[(1S,2R,3S,4R)-4-(6-(2,2-Diphenyl-ethylamino)-2-{4-[3-(3-sulfamoyl-phenyl)-ureido]-imidazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide (Example 187), by substituting N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 221

N-((1S,2R,3S,4R)-4-{6-[2,2-Bis-(4-hydroxy-phenyl)-ethylamino]-2-[4-(3-pyridin-3-yl-ureido)-imidazol-1-yl]-purin-9-yl}-2,3-dihydroxy-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-((1S,2R,3S,4R)-4-{2-(4-Amino-imidazol-1-yl)-6-[2,2-bis-(4-hydroxy-phenyl)-ethylamino]-purin-9-yl}-2,3-dihydroxy-cyclopentyl)-2-hydroxy-acetamide (intermediate ZV) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 222

N-((1S,2R,3S,4R)-4-{6-[2,2-Bis-(4-hydroxy-phenyl)-ethylamino]-2-[4-(3-pyridin-2-ylmethyl-ureido)-imidazol-1-yl]-purin-9-yl}-2,3-dihydroxy-cyclopentyl)-2-hydroxy-acetamide The title compound is prepared analogously to N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-((1S,2R,3S,4R)-4-{2-(4-amino-imidazol-1-yl)-6-[2,2-bis-(4-hydroxy-phenyl)-ethylamino]-purin-9-yl}-2,3-dihydroxy-cyclopentyl)-2-hydroxy-acetamide (intermediate ZV) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 223

N-[(1S,2R,3S,4R)-4-(6-[2,2-Bis-(4-hydroxy-phenyl)-ethylamino]-2-{4-[3-(3-hydroxy-benzyl)-ureido]-imidazol-1-yl}-purin-9-yl)-2,3-dihydroxy-cyclopentyl]-2-hydroxy-acetamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-((1S,2R,3S,4R)-4-{2-(4-Amino-imidazol-1-yl)-6-[2,2-bis-(4-hydroxy-phenyl)-ethylamino]-purin-9-yl}-2,3-dihydroxy-cyclopentyl)-2-hydroxy-acetamide (intermediate ZV) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 224

N-[(1S,2R,3S,4R)-4-(6-[2,2-Bis-(4-hydroxy-phenyl)-ethylamino]-2-{4-[3-(3-sulfamoyl-phenyl)-ureido]-imidazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide (Example 187), by substituting N-((1S,2R,3S,4R)-4-{2-(4-amino-imidazol-1-yl)-6-[2,2-bis-(4-hydroxy-phenyl)-ethylamino]-purin-9-yl}-2,3-dihydroxy-cyclopentyl)-2-hydroxy-acetamide (intermediate ZV) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 225

N-((1S,2R,3S,4R)-4-{6-(2,2-Diphenyl-ethylamino)-2-[3-(3-pyridin-3-yl-ureido)-[1,2,4]triazol-1-yl]-purin-9-yl}-2,3-dihydroxy-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-{(1S,2R,3S,4R)-4-[2-(3-Amino-[1,2,4]triazol-1-yl)-6-(2,2-diphenyl-ethylamino)-purin-9-yl]-2,3-dihydroxy-cyclopentyl}-2-hydroxy-acetamide (Intermediate ZW) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 226

N-((1S,2R,3S,4R)-4-{6-(2,2-Diphenyl-ethylamino)-2-[3-(3-pyridin-2-ylmethyl-ureido)-[1,2,4]triazol-1-yl]-purin-9-yl}-2,3-dihydroxy-cyclopentyl)-2-hydroxy-acetamide The title compound is prepared analogously to N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-{(1S,2R,3S,4R)-4-[2-(3-Amino-[1,2,4]triazol-1-yl)-6-(2,2-diphenyl-ethylamino)-purin-9-yl]-2,3-dihydroxy-cyclopentyl}-2-hydroxy-acetamide (Intermediate ZW) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 227

N-[(1S,2R,3S,4R)-4-(6-(2,2-Diphenyl-ethylamino)-2-{3-[3-(3-hydroxy-benzyl)-ureido]-[1,2,4]triazol-1-yl}-purin-9-yl)-2,3-dihydroxy-cyclopentyl]-2-hydroxy-acetamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-{(1S,2R,3S,4R)-4-[2-(3-Amino-[1,2,4]triazol-1-yl)-6-(2,2-diphenyl-ethylamino)-purin-9-yl]-2,3-dihydroxy-cyclopentyl}-2-hydroxy-acetamide (Intermediate ZW) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 228

N-[(1S,2R,3S,4R)-4-(6-(2,2-Diphenyl-ethylamino)-2-{3-[3-(3-sulfamoyl-phenyl)-ureido]-[1,2,4]triazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide (Example 187), by substituting N-{(1S,2R,3S,4R)-4-[2-(3-Amino-[1,2,4]triazol-1-yl)-6-(2,2-diphenyl-ethylamino)-purin-9-yl]-2,3-dihydroxy-cyclopentyl}-2-hydroxy-acetamide (Intermediate ZW) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 229

N-[(1S,2R,3S,4R)-4-(6-(2,2-Diphenyl-ethylamino)-2-{3-[3-(4-sulfamoyl-phenyl)-ureido]-[1,2,4]triazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide (Example 186), by substituting N-{(1S,2R,3S,4R)-4-[2-(3-Amino-[1,2,4]triazol-1-yl)-6-(2,2-diphenyl-ethylamino)-purin-9-yl]-2,3-dihydroxy-cyclopentyl}-2-hydroxy-acetamide (Intermediate ZW) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 230

N-((1S,2R,3S,4R)-4-{6-[2,2-Bis-(4-hydroxy-phenyl)-ethylamino]-2-[3-(3-pyridin-3-yl-ureido)-[1,2,4]triazol-1-yl]-purin-9-yl}-2,3-dihydroxy-cyclopentyl)-2-hydroxy-acetamide The title compound is prepared analogously to (R)-2-benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide (Example 181, step 5), by substituting N-((1S,2R,3S,4R)-4-{2-(3-Amino-[1,2,4]triazol-1-yl)-6-[2,2-bis-(4-hydroxy-phenyl)-ethylamino]-purin-9-yl}-2,3-dihydroxy-cyclopentyl)-2-hydroxy-acetamide (intermediate ZX) for (R)-N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-2-benzyloxy-propionamide (Example 181, step 4).

Example 231

N-((1S,2R,3S,4R)-4-{6-[2,2-Bis-(4-hydroxy-phenyl)-ethylamino]-2-[3-(3-pyridin-2-ylmethyl-ureido)-[1,2,4]triazol-1-yl]-purin-9-yl}-2,3-dihydroxy-cyclopentyl)-2-hydroxy-acetamide The title compound is prepared analogously to N-((1S,2R,3S,4R)-4-{6-(2,2-Diphenyl-ethylamino)-2-[(R)-3-(3-pyridin-2-ylmethyl-ureido)-pyrrolidin-1-yl]-purin-9-yl}-2,3-dihydroxy-cyclopentyl)-3-hydroxy-propionamide (Example 184), by substituting N-((1S,2R,3S,4R)-4-{2-(3-Amino-[1,2,4]triazol-1-yl)-6-[2,2-bis-(4-hydroxy-phenyl)-ethylamino]-purin-9-yl}-2,3-dihydroxy-cyclopentyl)-2-hydroxy-acetamide (intermediate ZX) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 232

N-[(1S,2R,3S,4R)-4-(6-[2,2-Bis-(4-hydroxy-phenyl)-ethylamino]-2-{3-[3-(3-hydroxy-benzyl)-ureido]-[1,2,4]triazol-1-yl}-purin-9-yl)-2,3-dihydroxy-cyclopentyl]-2-hydroxy-acetamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting N-((1S,2R,3S,4R)-4-{2-(3-Amino-[1,2,4]triazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZX) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 233

N-[(1S,2R,3S,4R)-4-(6-[2,2-Bis-(4-hydroxy-phenyl)-ethylamino]-2-{3-[3-(3-sulfamoyl-phenyl)-ureido]-[1,2,4]triazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-3-hydroxy-propionamide (Example 187), by substituting N-((1S,2R,3S,4R)-4-{2-(3-amino-[1,2,4]triazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZX) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 234

N-[(1S,2R,3S,4R)-4-(6-[2,2-Bis-(4-hydroxy-phenyl)-ethylamino]-2-{3-[3-(4-sulfamoyl-phenyl)-ureido]-[1,2,4]triazol-1-yl}-purin-9-yl)-2,3-dihydroxy-cyclopentyl]-2-hydroxy-acetamide The title compound is prepared analogously to N-[(1S,2R,3S,4R)-4-(6-(2,2-Diphenyl-ethylamino)-2-{(R)-3-[3-(4-sulfamoyl-phenyl)-ureido]-pyrrolidin-1-yl}-purin-9-yl)-2,3-dihydroxy-cyclopentyl]-3-hydroxy-propionamide (Example 186), by substituting N-((1S,2R,3S,4R)-4-{2-(3-amino-[1,2,4]triazol-1-yl)-6-[2,2-bis-(4-hydroxy-phenyl)-ethylamino]-purin-9-yl}-2,3-dihydroxy-cyclopentyl)-2-hydroxy-acetamide (Intermediate ZX) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 235

N-{(1S,2R,3S,4R)-4-[2-[2-(4-Chloro-phenyl)-ethoxy]-6-(2,2-diphenyl-ethylamino)-purin-9-yl]-2,3-dihydroxy-cyclopentyl}-propionamide Step 1: N-{(3aR,4S,6R,6aS)-6-[2-Chloro-6-(2,2-diphenyl-ethylamino)-purin-9-yl]-2,2-dimethyl-tetrahydro-cyclopenta[1,3]dioxol-4-yl}-propionamide The title compound is prepared by dissolving N-{(1S,2R,3S,4R)-4-[2-chloro-6-(2,2-diphenyl-ethylamino)-purin-9-yl]-2,3-dihydroxy-cyclopentyl}-propionamide (Intermediate J) in a 2:1 mixture of acetone and 2,2-dimethoxypropane with a catalytic amount of toluene-4-sulfonic acid, and stirring at room temperature overnight. The volatile components are removed under reduced pressure to afford the title compound.

Step 2: N-{(3aR,4S,6R,6aS)-6-[2-[2-(4-Chloro-phenyl)-ethoxy]-6-(2,2-diphenyl-ethylamino)-purin-9-yl]-2,2-dimethyl-tetrahydro-cyclopenta[1,3]dioxol-4-yl}-propionamide The title compound is prepared by adding N-{(3aR,4S,6R,6aS)-6-[2-Chloro-6-(2,2-diphenyl-ethylamino)-purin-9-yl]-2,2-dimethyl-tetrahydro-cyclopenta[1,3]dioxol-4-yl}-propionamide (example 235, step 1) to a premixed solution of sodium hydride (60% in oil) and 2-(4-chloro-phenyl)-ethanol (1 equivalent) in dry THF. The reaction is stirred at 50° C. for 48 hours, before quenching residual sodium hydride with excess aqueous ammonium chloride. The reaction mixture id then partioned between ethyl acetate and water; the organic phase is washed consecutively with water and brine before drying over magnesium sulfate. Filtration and removal of the volatile components under reduced pressure yields the crude product; purification by column chromatography/crystallisation affords the title compound.

Step 3: N-{(1S,2R,3S,4R)-4-[2-[2-(4-Chloro-phenyl)-ethoxy]-6-(2,2-diphenyl-ethylamino)-purin-9-yl]-2,3-dihydroxy-cyclopentyl}-propionamide The title compound is prepared by dissolving N-{(3aR,4S,6R,6aS)-6-[2-[2-(4-Chloro-phenyl)-ethoxy]-6-(2,2-diphenyl-ethylamino)-purin-9-yl]-2,2-dimethyl-tetrahydro-cyclopenta[1,3]dioxol-4-yl}-propionamide (Example 235, Step 2) in THF, adding an equal volume of 1.0M hydrochloric acid, and stirring at room temperature for 48 hours, before diluting with water, and extracting into ethyl acetate. The organic phase is dried over magnesium sulfate, filtered and the volatile components removed under reduced pressure, to yield the title compound.

Example 236

4-{3-[9-((1R,2S,3R,4S)-2,3-Dihydroxy-4-propionylamino-cyclopentyl)-6-(2,2-diphenyl-ethylamino)-9H-purin-2-yl]-prop-2-ynyl}-cyclohexanecarboxylic acid methyl ester The title compound is prepared by combining N-{(1S,2R,3S,4R)-4-[2-chloro-6-(2,2-diphenyl-ethylamino)-purin-9-yl]-2,3-dihydroxy-cyclopentyl}-propionamide (intermediate J), 4-prop-2-ynyl-cyclohexanecarboxylic acid methyl ester (prepared as described by Rieger J. M., Brown M. L., Sullivan G. W., Linden J. and Macdonald T. L.'; *J. Med. Chem*.(2001), 44, 531-539), copper (I) iodide, triphenylphosphine and dichlorobis(triphenylphosphine)palladium(II) in a 2:1 mixture of triethylamine/DMF, and heating by microwave irradiation for 3600 seconds at 120° C. Purification by column chromatography affords the title compound.

Example 237

(2S,3S,4R,5R)-5-(6-(2,2-Diphenyl-ethylamino)-2-{4-[3-(3-hydroxy-benzyl)-ureido]-pyrazol-1-yl}-purin-9-yl)-3,4-dihydroxy-tetrahydro-furan-2-carboxylic acid ethylamide Step 1: (2S,3S,4R,5R)-5-[2-(4-Amino-pyrazol-1-yl)-6-(2,2-diphenyl-ethylamino)-purin-9-yl]-3,4-dihydroxy-tetrahydro-furan-2-carboxylic acid ethylamide The title compound is prepared analogously to N-{(1S,2R,3S,4R)-4-[2-(4-amino-pyrazol-1-yl)-6-(2,2-diphenyl-ethylamino)-purin-9-yl]-2,3-dihydroxy-cyclopentyl}-2-hydroxy-acetamide (Intermediate ZP), by substituting (2S,3S,4R,5R)-5-[2-chloro-6-(2,2-diphenyl-ethylamino)-purin-9-yl]-3,4-dihydroxy-tetrahydro-furan-2-carboxylic acid ethylamide (Intermediate ZY) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1) in step ZP1.

Step 2: (2S,3S,4R,5R)-5-(6-(2,2-Diphenyl-ethylamino)-2-{4-[3-(3-hydroxy-benzyl)-ureido]-pyrazol-1-yl}-purin-9-yl)-3,4-dihydroxy-tetrahydro-furan-2-carboxylic acid ethylamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting (2S,3S,4R,5R)-5-[2-(4-Amino-pyrazol-1-yl)-6-(2,2-diphenyl-ethylamino)-purin-9-yl]-3,4-dihydroxy-tetrahydro-furan-2-carboxylic acid ethylamide (Example 237, step 1) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 238

(2S,3S,4R,5R)-5-(6-(2,2-Diphenyl-ethylamino)-2-{4-[3-(3-hydroxy-benzyl)-ureido]-imidazol-1-yl}-purin-9-yl)-3,4-dihydroxy-tetrahydro-furan-2-carboxylic acid ethylamide Step 1: (2S,3S,4R,5R)-5-[2-(4-Amino-imidazol-1-yl)-6-(2,2-diphenyl-ethylamino)-purin-9-yl]-3,4-dihydroxy-tetrahydro-furan-2-carboxylic acid ethylamide The title compound is prepared analogously to N-{(1S,2R,3S,4R)-4-[2-(4-amino-imidazol-1-yl)-6-(2,2-diphenyl-ethylamino)-purin-9-yl]-2,3-dihydroxy-cyclopentyl}-2-hydroxy-acetamide (Intermediate ZU), by substituting (2S,3S,4R,5R)-5-[2-chloro-6-(2,2-diphenyl-ethylamino)-purin-9-yl]-3,4-dihydroxy-tetrahydro-furan-2-carboxylic acid ethylamide (Intermediate ZY) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1) in step ZU1.

Step 2: (2S,3S,4R,5R)-5-(6-(2,2-Diphenyl-ethylamino)-2-{4-[3-(3-hydroxy-benzyl)-ureido]-imidazol-1-yl}-purin-9-yl)-3,4-dihydroxy-tetrahydro-furan-2-carboxylic acid ethylamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting (2S,3S,4R,5R)-5-[2-(4-amino-imidazol-1-yl)-6-(2,2-diphenyl-ethylamino)-purin-9-yl]-3,4-dihydroxy-tetrahydro-furan-2-carboxylic acid ethylamide (Example 238, step 1) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 239

(2S,3S,4R,5R)-5-(6-(2,2-Diphenyl-ethylamino)-2-{3-[3-(3-hydroxy-benzyl)-ureido]-[1,2,4]triazol-1-yl}-purin-9-yl)-3,4-dihydroxy-tetrahydro-furan-2-carboxylic acid ethylamide Step 1: (2S,3S,4R,5R)-5-[2-(3-Amino-[1,2,4]triazol-1-yl)-6-(2,2-diphenyl-ethylamino)-purin-9-yl]-3,4-dihydroxy-tetrahydro-furan-2-carboxylic acid ethylamide The title compound is prepared analogously to N-{(1S,2R,3S,4R)-4-[2-(3-Amino-[1,2,4]triazol-1-yl)-6-(2,2-diphenyl-ethylamino)-purin-9-yl]-2,3-dihydroxy-cyclopentyl}-2-hydroxy-acetamide (intermediate ZW), by substituting (2S,3S,4R,5R)-5-[2-chloro-6-(2,2-diphenyl-ethylamino)-purin-9-yl]-3,4-dihydroxy-tetrahydro-furan-2-carboxylic acid ethylamide (Intermediate ZY) for acetic acid {(1S,2R,3S,4R)-4-[2-chloro-6-(2,2-diphenyl-ethylamino)-purin-9-yl]-2,3-dihydroxy-cyclopentylcarbamoyl}-methyl ester (Intermediate Q1).

Step 2: (2S,3S,4R,5R)-5-(6-(2,2-Diphenyl-ethylamino)-2-{3-[3-(3-hydroxy-benzyl)-ureido]-[1,2,4]-triazol-1-yl}-purin-9-yl)-3,4-dihydroxy-tetrahydro-furan-2-carboxylic acid ethylamide The title compound is prepared analogously to N-[(1S,2R,3S,4R)-4-(6-(2,2-diphenyl-ethylamino)-2-{(R)-3-[3-(3-hydroxy-benzyl)-ureido]-pyrrolidin-1-yl}-purin-9-yl)-2,3-dihydroxy-cyclopentyl]-3-hydroxy-propionamide (Example 185), by substituting (2S,3S,4R,5R)-5-[2-(3-amino-[1,2,4]triazol-1-yl)-6-(2,2-diphenyl-ethylamino)-purin-9-yl]-3,4-dihydroxy-tetrahydro-furan-2-carboxylic acid ethylamide (Example 239, step 1) for N-{(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-3-hydroxy-propionamide (Intermediate ZG).

Example 240

(2S,3S,4R,5R)-5-(6-(2,2-Diphenyl-ethylamino)-2-{(R)-3-[3-(3-hydroxy-benzyl)-ureido]-pyrrolidin-1-yl}-purin-9-yl)-3,4-dihydroxy-tetrahydro-furan-2-carboxylic acid ethylamide (2S,3S,4R,5R)-5-[2-((R)-3-Amino-pyrrolidin-1-yl)-6-(2,2-diphenyl-ethylamino)-purin-9-yl]-3,4-dihydroxy-tetrahydro-furan-2-carboxylic acid ethylamide trifluoroacetate (Intermediate E) and (3-Hydroxy-benzyl)-carbamic acid phenyl ester (Intermediate UA) are dissolved in methanol and TEA. The reaction mixture is heated using microwave radiation at 100° C. for 30 minutes in the Personal Chemistry Emrys™ Optimizer microwave reactor. The reaction mixture is concentrated in vacuo and purified by C-18 reverse phase column chromatography eluting with acetonitrile:water (0.1% TFA) (gradient 0-100% acetonitrile) to afford the titled compound.

Example 241

(2S,3S,4R,5R)-5-(6-(2,2-Diphenyl-ethylamino)-2-{(R)-3-[3-(4-sulfamoyl-phenyl)-ureido]-pyrrolidin-1-yl}-purin-9-yl)-3,4-dihydroxy-tetrahydro-furan-2-carboxylic acid ethylamide This compound is prepared analogously to Example 240 by replacing (3-Hydroxy-benzyl)-carbamic acid phenyl ester (Intermediate UA) with (4-Sulfamoyl-phenyl)-carbamic acid phenyl ester (Intermediate UD).

Example 242

(2S,3S,4R,5R)-5-(6-(2,2-Diphenyl-ethylamino)-2-{(R)-3-[3-(3-sulfamoyl-phenyl)-ureido]-pyrrolidin-1-yl}-purin-9-yl)-3,4-dihydroxy-tetrahydro-furan-2-carboxylic acid ethylamide This compound is prepared analogously to Example 240 by replacing (3-Hydroxy-benzyl)-carbamic acid phenyl ester (Intermediate UA) with (3-Sulfamoyl-phenyl)-carbamic acid phenyl ester (Intermediate UC).

Example 243

(2S,3S,4R,5R)-5-{6-(2,2-Diphenyl-ethylamino)-2-[(R)-3-(3-pyridin-2-ylmethyl-ureido)-pyrrolidin-1-yl]-purin-9-yl}-3,4-dihydroxy-tetrahydro-furan-2-carboxylic acid ethylamide This compound is prepared analogously to Example 240 by replacing (3-Hydroxy-benzyl)-carbamic acid phenyl ester (Intermediate UA) with Pyridin-2-ylmethyl-carbamic acid phenyl ester (Intermediate UE).

Example 244

(2S,3S,4R,5R)-5-[2-{(R)-3-[3,4-Dioxo-2-(pyridin-3-ylamino)-cyclobut-1-enylamino]-pyrrolidin-1-yl}-6-(2,2-diphenyl-ethylamino)-purin-9-yl]-3,4-dihydroxy-tetrahydro-furan-2-carboxylic acid ethylamide Step 244a: (2S,3S,4R,5R)-5-{6-(2,2-Diphenyl-ethylamino)-2-[(R)-3-(2-methoxy-3,4-dioxo-cyclobut-1-enylamino)-pyrrolidin-1-yl]-purin-9-yl}-3,4-dihydroxy-tetrahydro-furan-2-carboxylic acid ethylamide A mixture comprising (2S,3S,4R,5R)-5-[2-((R)-3-Amino-pyrrolidin-1-yl)-6-(2,2-diphenyl-ethylamino)-purin-9-yl]-3,4-dihydroxy-tetrahydro-furan-2-carboxylic acid ethylamide trifluoroacetate (Intermediate E) and 3,4-dimethoxy-3-cyclobutene-1,2-dione in absolute EtOH and cat.DMAP is heated using microwave radiation in a Personal Chemistry Emrys™ Optimizer microwave reactor at 120° C. for 1 hour. The solvent is removed in vacuo and the resulting crude product partitioned between ethyl acetate and water. The organic portion is separated, dried ($Na_2SO_4$) and concentrated in vacuo. Purification by column chromatography on silica gel eluting with EtOAc/iso-hexane (30-100% EtOAc) affords the titled compound.

Step 244b: (2S,3S,4R,5R)-5-{6-(2,2-Diphenyl-ethylamino)-2-[(R)-3-(2-methoxy-3,4-dioxo-cyclobut-1-enylamino)-pyrrolidin-1-yl]-purin-9-yl}-3,4-dihydroxy-tetrahydro-furan-2-carboxylic acid ethylamide A mixture comprising (2S,3S,4R,5R)-5-{6-(2,2-Diphenyl-ethylamino)-2-[(R)-3-(2-methoxy-3,4-dioxo-cyclobut-1-enylamino)-pyrrolidin-1-yl]-purin-9-yl}-3,4-dihydroxy-tetrahydro-furan-2-carboxylic acid ethylamide (step 244a) in absolute EtOH and catalytic amount of TsOH is heated using microwave radiation in a Personal Chemistry Emrys™ Optimizer microwave reactor at 150° C. for 4000 seconds. The solvent is removed in vacuo and the resulting crude product partitioned between ethyl acetate and water. The organic portion is separated, dried ($Na_2SO_4$) and concentrated in vacuo. Purification by C-18 reverse phase column chromatography eluting with acetonitrile:water (0.1% TFA) (gradient 0-100% acetonitrile) to afford the titled compound.

Example 245

(2S,3S,4R,5R)-5-(6-(2,2-Diphenyl-ethylamino)-2-{(R)-3-[2-(3-hydroxy-benzylamino)-3,4-dioxo-cyclobut-1-enylamino]-pyrrolidin-1-yl}-purin-9-yl)-3,4-dihydroxy-tetrahydro-furan-2-carboxylic acid ethylamide This compound is prepared analogously to Example 244 by replacing 3-aminopyridine with 3-hydroxybenzylamine.

Example 246-253

These compounds are prepared from the product of Example 26 step 2 following an analogous procedure to Example 26 step 3, replacing methyl chloroformate with the appropriate acid chloride or anhydride.

Example 254

(R)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-propionamide Step 1: (R)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-phenoxy-propionamide HATU (61 mg, 0.16 mmol) and R-(+)-2-benzyloxypropionic acid (32 mg, 0.16 mmol) are dissolved in DMF (5 ml) and after stirring for 5 minutes, the solution is treated with 1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-3-yl-urea (Example 26 step 2) (0.1 g, 0.16 mmol) in DMF (0.5 ml). DIPEA (56 µl, 0.32 mmol) is added and the resulting solution is stirred for 2 hours. The mixture is then treated with sat. $Na_2CO_3$ and 1 ml MeOH and then partitioned between EtOAc and water. The organic portion is separated and concentrated in vacuo. The resulting crude product is purified by reverse phase column chromatography (Isolute™ C18, 0-100% acetonitrile in water –0.1% HCl) to afford the title product.

Step 2: (R)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-propionamide A solution of (R)-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-2-phenoxy-propionamide (83 mg, 0.104 mmol) in EtOH (20 ml) and THF (5 ml) under an inert atmosphere is treated with palladium hydroxide (20% w/w on carbon, 32 mg) followed by acetic acid (2 ml). The reaction mixture is placed under an atmosphere of hydrogen for two weeks after which time, the mixture is filtered and concentrated in vacuo. The resulting crude product is washed with EtOH (3 times), filtered and then concentrated in vacuo. The residue is dissolved in MeOH (2 ml) and purification by reverse phase column chromatography (Isolute™ C18, 0-100% acetonitrile in water –0.1% $NH_3$) affords the title compound as a white solid. (MH+ 707.4)

Example 255

(S)-N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-propionamide A mixture comprising 1-{(R)-1-[9-((1R,2S,3R,4S)-4-amino-2,3-dihydroxy-cyclopentyl)-6-(2,2-diphenyl-ethylamino)-9H-purin-2-yl]-pyrrolidin-3-yl}-3-pyridin-3-yl-urea (Example 26 step 2) (0.1 g, 0.16 mmol) and TEA (24 μA, 0.18 mmol) in THF (7 ml) at room temperature is treated with (S)-(−)-2-acetoxy-propionyl chloride (24 mg, 0.16 mmol) in MeCN (1 ml) at (0° C.) over 1 minute. The mixture is allowed to stir at room temperature for 18 h and then treated with sat. Na₂CO₃ (1 ml) and MeOH (1 ml) and then stirred for a further 2 days. The solvent is removed in vacuo and purification by reverse phase column chromatography (Isolute™ C18, 0-100% acetonitrile in water −0.3% NH₃) affords the title compound as a white solid. (MH+ 707.7)

Example 256

N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-2-hydroxy-2-methyl-propionamide This compound is prepared analogously to Example 255 by replacing (S)-(−)-2-acetoxy-propionyl chloride with 2-acetoxy isobutyryl chloride. The ester hydrolysis is carried out in the presence of 1M NaOH in MeOH. (MH+ 721.5)

Example 257

N-{(1S,2R,3S,4R)-4-[2-((R)-3-Amino-pyrrolidin-1-yl)-6-((S)-1-hydroxymethyl-2-phenyl-ethylamino)-purin-9-yl]-2,3-dihydroxy-cyclopentyl}-2-hydroxy-acetamide This compound is prepared from N-{(1S,2R,3S,4R)-4-[6-((S)-1-benzyl-2-hydroxy-ethylamino)-2-chloro-purin-9-yl]-2,3-dihydroxy-cyclopentyl}-2-hydroxy-acetamide (Intermediate VD) analogously to N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-2-hydroxy-acetamide hydrochloride (Example 7 step 5). (MH+ 527.26)

Example 258

{(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-carbamic acid methyl ester trifluoroacetate This compound is prepared from {(1S,2R,3S,4R)-4-[2-chloro-6-(2,2-diphenyl-ethylamino)-purin-9-yl]-2,3-dihydroxy-cyclopentyl}-carbamic acid methyl ester (Intermediate T) analogously to N-((1S,2R,3S,4R)-4-{2-((R)-3-amino-pyrrolidin-1-yl)-6-[2,2-bis-(4-hydroxy-phenyl)-ethylamino]-purin-9-yl}-2,3-dihydroxy-cyclopentyl)-2-hydroxy-acetamide hydrochloride (Example 7 step 5). (MH+ 572.21)

Examples 259-261

These compounds namely,
N-((1S,2R,3S,4R)-4-{6-((S)-1-Benzyl-2-hydroxy-ethylamino)-2-[(R)-3-(3-pyridin-3-yl-ureido)-pyrrolidin-1-yl]-purin-9-yl}-2,3-dihydroxy-cyclopentyl)-2-hydroxy-acetamide (MH+ 647.01) (Example 259),
N-[(1S,2R,3S,4R)-4-(6-((S)-1-Benzyl-2-hydroxy-ethylamino)-2-{(R)-3-[3-(4-sulfamoyl-phenyl)-ureido]-pyrrolidin-1-yl}-purin-9-yl)-2,3-dihydroxy-cyclopentyl]-2-hydroxy-acetamide (MH+ 724.99) (Example 260) and
[(1S,2R,3S,4R)-4-(6-(2,2-Diphenyl-ethylamino)-2-{(R)-3-[3-(3-sulfamoyl-phenyl)-ureido]-pyrrolidin-1-yl}-purin-9-yl)-2,3-dihydroxy-cyclopentyl]-carbamic acid methyl ester (MH+ 771.34) (Example 261)
are prepared from the appropriate starting compounds and corresponding pyrrolidinyl-urea (preparations described herein) analogously to Example 15.

Example 262

1-[9-(1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid (pyridin-2-ylmethyl)-amide Step 1: 1-[9-((1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid QBA289

A solution comprising 1-[9-((1R,2S,3R,4S)-2,3-dihydroxy-4-propionylamino-cyclopentyl)-6-(2,2-diphenyl-ethylamino)-9H-purin-2-yl]-1H-pyrazole-4-carboxylic acid ethyl ester (Example 173 step 1) (0.4 g, 0.64 mmol) in water (3 ml) is treated with 1M KOH in MeOH (6 ml) and stirred at room temperature for 48 h. The solvent is removed in vacuo and the resulting crude product is dissolved in water (5 ml) and acidified to pH 3-4 with 1.5N HCl. The solution is extracted with EtOAc and the organic portion is dried over sodium sulphate and concentrated in vacuo. Purification by chromatography on silica eluting with 5% MeOH in chloroform affords the title compound.

Step 2: 1-[9-((1R,2S,3R,4S)-2,3-Dihydroxy-4-propionylamino-cyclopentyl)-6-(2,2-diphenyl-ethylamino)-9H-purin-2-yl]-1H-pyrazole-4-carboxylic acid (pyridin-2-ylmethyl)-amide A mixture comprising 1-[9-((1R,2S,3R,4S)-2,3-dihydroxy-4-propionylamino-cyclopentyl)-6-(2,2-diphenyl-ethylamino)-9H-purin-2-yl]-1H-pyrazole-4-carboxylic acid (0.06 g, 0.01 mmol) in dry DCM (10 ml) is treated with 2-aminomethylpyridine (0.021 g, 0.2 mmol) followed by HOBt (0.027 g, 0.2 mmol), 1-[Bis(dimethylamino)methylene]-1H-benzotriazoliumhexafluorophosphate-3-oxide HBTU (0.076 g, 0.2 mmol), N-methyl morpholine (0.02 g, 0.2 mmol) and DMAP (1 ml). The resulting mixture is stirred at room temperature for 24 h and then concentrated in vacuo. The resulting residue purified by preparative TLC eluting with 10% MeOH in chloroform to afford the title compound. (MH+ 687.1)

Example 263

N-((1S,2R,3S,4R)-4-{6-(2,2-Diphenyl-ethylamino)-2-[(R)-3-(3-pyridin-3-yl-ureido)-pyrrolidin-1-yl]-purin-9-yl}-2,3-dihydroxy-cyclopentyl)-3-hydroxy-propionamide hydrochloride This compound is prepared analogously to (R)-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-2-phenoxy-propionamide (Example 254 step 1) by replacing R-(+)-2-benzyloxypropionic acid with 3-tert-butoxypropionic acid. (MH+ 707.4)

Example 264

(R)-2-Benzyloxy-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-propionamide hydrochloride This compound is prepared analogously to (R)-N-((1S,2R,3S,4R)-4-{6-(2,2-diphenyl-ethylamino)-2-[(R)-3-(3-pyridin-3-yl-ureido)-pyrrolidin-1-yl]-purin-9-yl}-2,3-dihydroxy-cyclopentyl)-2-phenoxy-propionamide (Example 254 step 1) by replacing R-(+)-2-benzyloxypropionic acid with (R)-2-benzyloxy-propionic acid. (MH+ 797.7)

The invention claimed is:
1. A compound of formula (I), or stereoisomers or pharmaceutically acceptable salts thereof,

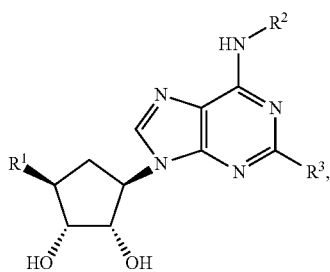

(I)

wherein
$R^1$ is selected from NH—$C_1$-$C_8$-alkyl, NHC(O)$C_1$-$C_8$ hydroxyalkyl, NHC(O)$C_1$-$C_8$ aminoalkyl, NHCO$_2$$C_1$-$C_8$-alkyl, NHCO$_2$$C_2$-$C_8$ hydroxyalkyl, NHC(O)-3- to 12-membered heterocyclic group containing from 1 to 4 heteroatoms selected from the group consisting of oxygen, nitrogen and sulfur, that group being optionally substituted, by $C_1$-$C_8$-alkyl, NHC(O )-$C_6$-$C_{10}$-aryl optionally substituted by $C_1$-$C_8$-alkyl or O—$C_1$-$C_8$-alkyl, NH—$C_1$-$C_8$-alkoxycarbonyl optionally substituted by $C_6$-$C_{10}$-aryl, and NHC(O)-$C_1$-$C_8$-alkyl substituted by halo, COOH or $C_1$-$C_8$-alkoxycarbonyl;
$R^2$ is $C_1$-$C_8$-alkyl substituted by OH, or by $C_6$-$C_{10}$-aryl optionally substituted by OH;
$R^3$ is a N-bonded 3- to 12-membered heterocyclic group containing from 1 to 4 ring nitrogen atoms and optionally containing from 1 to 4 other heteroatoms selected from the group consisting of oxygen and sulfur, that heterocyclic group being optionally substituted by $NR^{4f}C(O)NR^{4g}R^{4h}$, $NR^{4a}R^{4b}$, $NHC(O)R^{4q}$ and $NHC(=NR^{4m})N(R^{4n})R^{4o}$;
$R^{4a}$, $R^{4f}$ and $R^{4h}$ are, independently, H, $C_1$-$C_8$-alkyl or $C_6$-$C_{10}$-aryl;
$R^{4b}$ is H, $C_1$-$C_8$-alkyl, $C_6$-$C_{10}$-aryl, or a 3- to 12-membered heterocyclic group containing at least one ring heteroatom selected from the group consisting of nitrogen, oxygen and sulfur, optionally substituted by 0-3$R^5$;
$R^{4g}$ is $C_1$-$C_8$-alkyl optionally subsituted by a 3- to 12-membered heterocyclic group containing at least one ring heteroatom selected from the group consisting of nitrogen, oxygen and sulfur, optionally substituted with SO$_2$$R^{10}$, CN, or 0-3$R^5$, or
$R^{4g}$ is a $C_6$-$C_{10}$-aryl optionally substituted by OH, $C_1$-$C_8$-alkyl, O—$C_1$-$C_8$-alkyl, SO$_2$$R^{10}$ or -halogen, or
$R^{4g}$ is a $C_7$-$C_{14}$-aralkyl optionally substituted by OH, O—$C_1$-$C_8$-alkyl, halogen, $C_6$-$C_{10}$-aryl, SO$_2$$R^{10}$, CN, —C(=NH)NH2, or O—$C_6$-$C_{10}$-aryl, or
$R^{4g}$ is a 3- to 12-membered heterocyclic group containing at least one ring heteroatom selected from the group consisting of nitrogen, oxygen and sulfur, optionally substituted by 0-3$R^5$;
$R^{4m}$ is H or CN;
$R^{4n}$ is H or $C_1$-$C_8$ alkyl;
$R^{4o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with SO$_2$$R^{10}$, CN, or 0-3$R^5$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl SO$_2$$R^{10}$ or -halogen;
$R^4q$ is $C_6$-$C_{10}$-aryl optionally substituted by OH, C(=NH)NH$_2$, or SO$_2$NH$_2$, or a 3- to 12-membered heterocyclic group containing at least one ring heteroatom selected from the group consisting of nitrogen, oxygen and sulfur optionally substituted by 0-3$R^5$ or a 3- to 12-membered heterocyclic group containing at least one ring heteroatom selected from the group consisting of nitrogen, oxygen and sulfur, optionally substituted by 0-3$R^5$;
$R^5$ is selected from
(i) OH,
(ii) $C_1$-$C_8$-alkyl optionally substituted by OH, CN, SO$_2$$R^{10}$ or halogen,
(iii) $C_7$-$C_{14}$-aralkyl optionally substituted with OH, O—$C_1$-$C_8$-alkyl, $C_6$-$C_{10}$-aryl, or O—$C_6$
(iv) -$C_{10}$-aryl,
(v) $C_1$-$C_8$-alkoxy,
(vi) $C_6$-$C_{10}$-aryl optionally substituted by OH, $C_1$-$C_8$-alkyl, O—$C_1$-$C_8$-alkyl or -halogen,
(vii) O—$C_6$-$C_{10}$-aryl optionally substituted by OH,
(viii) $C_1$-$C_8$-alkyl,
(ix) O—$C_1$-$C_8$-alkyl optionally substituted by halogen,
(x) $NR^{5a}R^{5b}$,
(xi) $NHC(O)R^{5c}$,
(xii) $NHS(O)_2R^{5d}$,
(xiii) $NHS(O)_2R^{5e}$,
(xiv) $NR^{5f}C(O)NR^{5g}R^{5h}$,
(xv) $NR^{5i}C(O)OR^{5J}$,
(xvi) $C_1$-$C_8$-alkylcarbonyl,
(xvii) $C_1$-$C_8$-alkoxycarbonyl,
(xviii) di($C_1$-$C_8$-alkyl)aminocarbonyl,
(xix) $COOR^{5k}$,
(xx) $C(O)R^{5l}$,
(xxi) a C(O)-$C_6$-$C_{10}$-aryl optionally substituted by OH, $C_1$-$C_8$-alkyl, O—$C_1$-$C_8$-alkyl, -halogen, or SO$_2$$R^{10}$,
(xxii) $C(O)NHR^{5m}$
and (xxiii) a 3-10-membered heterocyclic group containing at least one ring heteroatom selected from the group consisting of nitrogen, oxygen and sulfur, optionally substituted by 0-3$R^7$;
$R^{5a}$, $R^{5b}$, $R^{5c}$, $R^{5f}$, $R^{5h}$ and $R^{5i}$ are, independently, H, $C_1$-$C_8$-alkyl or $C_6$-$C_{10}$-aryl;
$R^{5d}$, $R^{5e}$, $R^{5g}$, $R^{5j}$ and $R^{5m}$ are, independently, $C_1$-$C_8$-alkyl or a 3- to 12-membered heterocyclic group containing at least one ring heteroatom selected from the group consisting of nitrogen, oxygen and sulfur, optionally substituted by $COOR^8$;

$R^{5k}$ is H, $C_1$-$C_8$-alkyl, $C_6$-$C_{10}$-aryl or a 3- to 12-membered heterocyclic group containing at least one ring heteroatom selected from the group consisting of nitrogen, oxygen and sulfur;

$R^{5l}$ is $C_1$-$C_8$-alkyl, $C_6$-$C_{10}$-aryl or a 3- to 12-membered heterocyclic group containing at least one ring heteroatom selected from the group consisting of nitrogen, oxygen and sulfur, optionally substituted by COOR$^9$;

$R^6$ is COOR$^{6a}$ or a 3- to 12-membered heterocyclic group containing at least one ring heteroatom selected from the group consisting of nitrogen, oxygen and sulfur, optionally substituted by COOR$^{6b}$;

$R^{6a}$, $R^{6b}$, $R^7$, $R^8$ and $R^9$ are selected from H, $C_1$-$C_8$-alkyl and $C_7$-$C_{14}$-aralkyl; and $R^{10}$ is $C_1$-$C_8$-alkyl optionally substituted by
(i) halogen,
(ii) $C_6$-$C_{10}$-aryl optionally substituted by OH, $C_1$-$C_8$-alkyl, O—$C_1$-$C_8$-alkyl or -halogen,
or (iii) NR$^{4a}$R$^{4b}$.

2. A compound of formula (I) according to claim 1, or stereoisomers or pharmaceutically acceptable salts thereof, wherein $R^1$ is selected from NHC(O)$C_1$-$C_8$ hydroxyalkyl and, NHCO$_2$$C_1$-$C_8$-alkyl;

$R^2$ is selected from $C_1$-$C_8$-alkyl optionally substituted by OH, or
$C_6$-$C_{10}$-aryl optionally substituted by OH;

$R^3$ is a N-bonded 3-to 12-membered heterocyclic group containing at least one ring heteroatom selected from the group consisting of nitrogen, oxygen and sulfur, optionally substituted by 0-3R$^4$;

$R^{4a}$ is selected from H and $C_1$-$C_8$ alkyl;

$R^{4b}$ is selected from H, $C_1$-$C_8$ alkyl and 3- to 12-membered heterocyclic group containing at least one ring heteroatom selected from the group consisting of nitrogen, oxygen and sulfur, optionally substituted by 0-3R$^5$;

$R^{4f}$ and $R^{4h}$ are H;

$R^{4g}$ is $C_8$-alkyl optionally substituted by a 3- to 12-membered heterocyclic group containing at least one ring heteroatom selected from the group consisting of nitrogen, oxygen and sulfur, optionally substituted with SO$_2$R$^{10}$, CN, or 0-3R$^5$, or $R^{4g}$ is a $C_6$-$C_{10}$-aryl optionally substituted by OH, $C_1$-$C_8$-alkyl, O—$C_1$-$C_8$-alkyl, SO$_2$R$^{10}$, or -halogen, or $R^{4g}$ is a $C_7$-$C_{14}$-aralkyl optionally substituted by OH, O—$C_1$-$C_8$-alkyl, halogen, $C_6$-$C_{10}$-aryl, SO$_2$R$^{10}$, CN, —C(=NH)NH$_2$, or O—$C_6$-$C_{10}$-aryl, or $R^{4g}$ is a 3- to 12-membered heterocyclic group containing at least one ring heteroatom selected from the group consisting of nitrogen, oxygen and sulfur, optionally substituted by 0-3R$^5$;

$R^{4m}$ is CN;

$R^{4n}$ is H or $C_1$-$C_8$ alkyl;

$R^{4o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with SO$_2$R$^{10}$, CN, or 0-3R$^5$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl SO$_2$R$^{10}$ or-halogen;

$R^{4q}$ is a 3- to 12-membered heterocyclic group containing at least one ring heteroatom selected from the group consisting of nitrogen, oxygen and sulfur optionally substituted by a 3- to 12-membered heterocyclic group containing at least one ring heteroatom selected from the group consisting of nitrogen, oxygen and sulfur, optionally substituted by 0-3R$^5$;

$R^5$ is selected from OH, $C_1$-$C_8$-alkyl optionally substituted by OH, CN, SO$_2$R$^{10}$ or halogen, O—$C_1$-$C_8$-alkyl optionally substituted by halogen, NR$^{5a}$R$^{5b}$, NHC(O)R$^{5c}$, a C(O)-$C_6$-$C_{10}$-aryl optionally substituted by OH, $C_1$-$C_8$-alkyl, O—$C_1$-$C_8$-alkyl, -halogen, or SO$_2$R$^{10}$;

$R^{5a}$, $R^{5b}$, and $R_{5c}$ independently, H, $C_1$-$C_8$-alkyl or $C_6$-$C_{10}$-aryl; and $R^{10}$ is $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or -halogen, or NR$^{4a}$R$^{4b}$.

3. A compound according to claim 1 or stereoisomers or pharmaceutically acceptable salts thereof, wherein the compound is of formula (Ia)
wherein

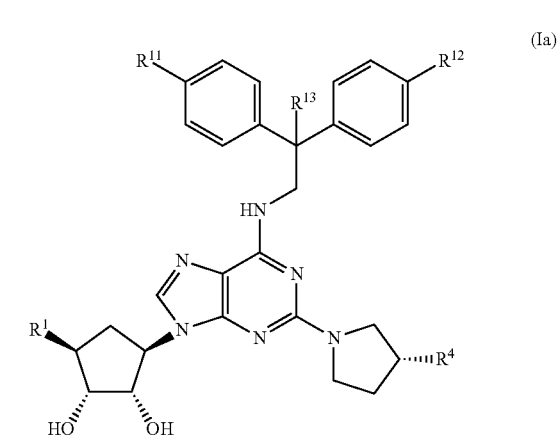

(Ia)

$R^1$ is NH-$C_1$-$C_8$-alkyl or, NHCO$_2$$C_1$-$C_8$-alkyl;

$R^{4a}$ is selected from H and $C_1$-$C_8$ alkyl;

$R^{4b}$ is selected from H, $C_1$-$C_8$ alkyl and 3- to 12-membered heterocyclic group containing at least one ring heteroatom selected from the group consisting of nitrogen, oxygen and sulfur;

$R^{4f}$ and $R^{4h}$ are H;

$R^{4g}$ is $C_1$-$C_8$-alkyl optionally substituted by a 3- to 12-membered heterocyclic group containing at least one ring heteroatom selected from the group consisting of nitrogen, oxygen and sulfur, optionally substituted with CN, or $R^{4g}$ is a $C_6$-$C_{10}$-aryl optionally substituted by OH or SO$_2$R$^{10}$, or $R^{4g}$ is a $C_7$-$C_{14}$-aralkyl optionally substituted by OH -C(=NH)NH$_2$, or $R^{4g}$ is a 3- to 12-membered heterocyclic group containing at least one ring heteroatom selected from the group consisting of nitrogen, oxygen and sulfur, optionally substituted by 0-3R$^5$;

$R^{4m}$ is CN;

$R^{4n}$ is H or $C_1$-$C_8$ alkyl;

$R^{4o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with SO$_2$R$^{10}$, a $C_7$-$C_{14}$-aralkyl optionally substituted with OH, O—$C_1$-$C_8$-alkyl, halogen, $C_6$-$C_{10}$-aryl, or O—$C_6$-$C_{10}$-aryl;

$R^{4q}$ is $C_6$-$C_{10}$-aryl optionally substituted by OH, C(=NH)NH$_2$, or SO$_2$NH$_2$, or a 3- to 12-membered heterocyclic group containing at least one ring heteroatom selected from the group consisting of nitrogen, oxygen and sulfur optionally substituted by a 3- to 12-membered heterocyclic group containing at least one ring heteroatom selected from the group consisting of nitrogen, oxygen and sulfur;

$R^5$ is C(O)-$C_6$-$C_{10}$-aryl optionally substituted by OH, $C_1$-$C_8$-alkyl, O—$C_1$-$C_8$-alkyl, -halogen, or $SO_2R^{10}$;

$R^{10}$ is $NH_2$;

$R^{11}$ and $R^{12}$ are, independently, selected from H, OH, halogen and O—$C_1$-$C_8$-alkyl; and $R^{13}$ is selected from H or OH.

4. A compound of formula (II) or stereoisomers or pharmaceutically acceptable salts thereof,

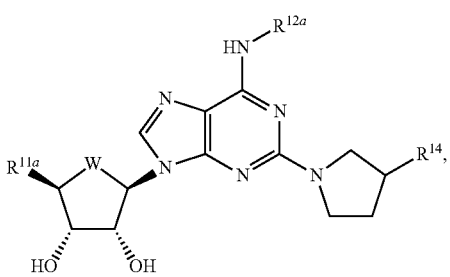

(II)

wherein

W is $CH_2$ or O, with the proviso that when W is O, then $R^{11a}$ is not a N-bonded substituent;

$R^{11a}$ is —$NH_2$, —NH—$C_1$-$C_8$-alkylcarbonyl, —NH—$C_3$-$C_8$-cycloalkylcarbonyl, —$NHSO_2$—$C_1$-$C_8$-alkyl, —NH—$C_7$-$C_{14}$-aralkylcarbonyl or —NHC(=O)—C(=O)—NH—$C_1$-$C_8$-alkyl optionally substituted by $R^{11b}$; or $R^{11a}$ is selected from $CH_2OH$, $CH_2$—O—$C_1$-$C_8$-alkyl, C(O)—O—$C_1$-$C_8$-alkyl, $C(O)NH_2$, and C(O)—NH—$C_1$-$C_8$-alkyl;

$R^{11b}$ is a 3- to 12-membered heterocyclic ring containing at least one ring heteroatom selected from the group consisting of nitrogen, oxygen and sulfur, said 3- to 12-membered heterocyclic ring being optionally substituted by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl or $C_1$-$C_8$-alkoxy optionally substituted by aminocarbonyl;

$R^{12a}$ is $C_1$-$C_8$-alkyl substituted by OH, or by $C_6$-$C_{10}$-aryl optionally substituted by OH;

$R^{14}$ is selected from $NR^{14a}R^{14b}$, $NR^{14f}C(O)NR^{14g}R^{14h}$, $NHC(O)R^{14q}$, and $NHC(=NR^{14m})N(R^{14n})R^{14o}$;

$R^{14a}$, $R^{14c}$, $R^{14f}$, $R^{14h}$ and $R^{14i}$ are, independently, H, $C_1$-$C_8$-alkyl or $C_6$-$C_{10}$-aryl;

$R^{14b}$ is H, $C_1$-$C_8$-alkyl a 3- to 12-membered heterocyclic group containing at least one ring heteroatom selected from the group consisting of nitrogen, oxygen and sulfur, optionally substituted by 0-3$R^{15}$ or $C_6$-$C_{10}$-aryl;

$R^{14g}$ is $C_1$-$C_8$-alkyl optionally substituted by a 3- to 12-membered heterocyclic group containing at least one ring heteroatom selected from the group consisting of nitrogen, oxygen and sulfur, optionally substituted with $SO_2R^{16}$, CN, or 0-3$R^{15}$, or $R^{14g}$ is a $C_6$-$C_{10}$-aryl optionally substituted by OH, $C_1$-$C_8$-alkyl, O—$C_1$-$C_8$-alkyl, $SO_2R^{16}$ or -halogen, or $R^{14g}$ is a $C_7$-$C_{14}$-aralkyl optionally substituted by OH, O—$C_1$-$C_8$-alkyl, halogen, $C_6$-$C_{10}$-aryl, $SO_2R^{16}$, CN, —C(=NH)NH2, or O—$C_6$-$C_{10}$-aryl, or $R^{14g}$ is a 3- to 12-membered heterocyclic group containing at least one ring heteroatom selected from the group consisting of nitrogen, oxygen and sulfur, optionally substituted by 0-3$R^{15}$;

$R^{14m}$ is CN;

$R^{14n}$ is H or $C_1$-$C_8$ alkyl;

$R^{14o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with $SO_2R^{16}$, CN, or 0-3$R^{15}$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^{16}$ or -halogen;

$R^{14p}$ is H, $C_1$-$C_8$-$_{alkyl\ or\ C7}$-$C_{14}$-aralkyl;

$R^{14q}$ is a 3- to 12-membered heterocyclic group containing at least one ring heteroatom selected from the group consisting of nitrogen, oxygen and sulfur optionally substituted by 0-3$R^{15}$ or a 3- to 12-membered heterocyclic group containing at least one ring heteroatom selected from the group consisting of nitrogen, oxygen and sulfur, optionally substituted by 0-3$R^{15}$;

$R^{15}$ is selected from OH, $C_1$-$C_8$-alkyl optionally substituted by OH, CN, $SO_2R^{16}$ or halogen, )—$C_1$-$C_8$-alkyl optionally substituted by halogen, $NR^{15a}R^{15b}$, $NHC(O)R^{15c}$, a C(O)—$C_6$-$C_{10}$-aryl optionally substituted by OH, $C_1$-$C_8$-alkyl, O—$C_1$-$C_8$-alkyl, -halogen, or $SO_2R^{16}$;

$R^{15a}$, $R^{15b}$, and $R^{15c}$ independently, H, $C_1$-$C_8$-alkyl or $C_6$-$C_{10}$-aryl; and $R^{16}$ is $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or halogen, or $NR^{14a}R^{14b}$.

5. A compound of formula (II) according to claim 4 or stereoisomers or pharmaceutically acceptable salts thereof, wherein W is $CH_2$ or O, with the proviso that when W is O, then $R^{11a}$ is not a N-bonded substituent;

$R^{11a}$ is —NH—$C_1$-$C_8$-alkylcarbonyl, —NH—$C_3$-$C_8$-cycloalkylcarbonyl, or C(O)—NH—$C_1$-$C_8$-alkyl;

$R^{12a}$ is $C_1$-$C_8$-alkyl optionally substituted by —OH or- by $C_6$-$C_{10}$-aryl optionally substituted by OH;

$R^{14}$ is selected from $NR^{14f}C(O)NR^{14g}R^{14h}$, $NR^{14a}NR^{14b}$, $NHC(O)R^{14q}$ and $NHC(=NR^{14m})N(R^{14n})R^{14o}$;

$R^{14a}$ is selected from H and $C_1$-$C_8$ alkyl;

$R^{14b}$ is selected from H, $C_1$-$C_8$ alkyl and 3- to 12-membered heterocyclic group containing at least one ring heteroatom selected from the group consisting of nitrogen, oxygen and sulfur, optionally substituted by 0-3$R^{15}$;

$R^{14f}$ and $R^{14h}$ are H;

$R^{14g}$ is $C_1$-$C_8$-alkyl optionally substituted by a 3- to 12-membered heterocyclic group containing at least one ring heteroatom selected from the group consisting of nitrogen, oxygen and sulfur, optionally substituted with $SO_2R^{16}$, CN, or 0-3$R^{15}$, or $R^{14g}$ is a $C_6$-$C_{10}$-aryl optionally substituted by OH, $C_1$-$C_8$-alkyl, O—$C_1$-$C_8$-alkyl, $SO_2R^{16}$, or -halogen, or $R^{14g}$ is a $C_7$-$C_{14}$-aralkyl optionally substituted by OH, O—$C_1$-$C_8$-alkyl, halogen, $C_6$-$C_{10}$-aryl, $SO_2R^{16}$, CN, —C(=NH)$NH_2$, or O—$C_6$-$C_{10}$-aryl, or $R^{14g}$ is a 3- to 12-membered heterocyclic group containing at least one ring heteroatom selected from the group consisting of nitrogen, oxygen and sulfur, optionally substituted by 0-3$R^{15}$;

$R^{14m}$ is CN;

$R^{14n}$ is H or $C_1$-$C_8$ alkyl;

$R^{14o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with $SO_2R^{16}$, CN, or 0-3$R^{15}$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^{16}$ or -halogen;

$R^{14q}$ is a 3- to 12-membered heterocyclic group containing at least one ring heteroatom selected from the group consisting of nitrogen, oxygen and sulfur optionally substituted by a 3- to 10-membered heterocyclic group containing at least one ring heteroatom selected from the group consisting of nitrogen, oxygen and sulfur, optionally substituted by 0-3$R^{15}$;

$R^{15}$ is selected from OH, $C_1$-$C_8$-alkyl optionally substituted by OH, CN, $SO_2R^{16}$ or halogen, O—$C_1$-$C_8$-alkyl optionally substituted by halogen, $NR^{15a}R^{15b}$, NHC(O) $R^{15c}$, a C(O)-$C_6$-$C_{10}$-aryl optionally substituted by OH, $C_1$-$C_8$-alkyl, O—$C_1$-$C_8$-alkyl, -halogen, or $SO_2R^{16}$;

$R^{15a}$, $R^{15b}$, and $R^{15c}$ independently, H, $C_1$-$C_8$-alkyl or $C_6$-$C_{10}$-aryl; and $R^{16}$ is $C_1$-$C_8$-alkyl optionally substituted by halogen, $C_6$-$C_{10}$-aryl optionally substituted by OH, $C_1$-$C_8$-alkyl, O—$C_1$-$C_8$-alkyl or -halogen, or $NR^{14a}R^{14b}$.

6. A compound according to claim 1 in combination with an anti-inflammatory, bronchodilatory, anti-histamine or anti-tussive drug substance.

7. A pharmaceutical composition comprising as active ingredient a compound according to claim 1 together with a pharmaceutically acceptable diluent or carrier.

8. A process for the preparation of compounds of formula (I) as defined in claim 1, or stereoisomers or pharmaceutically acceptable salts thereof, which comprises the steps of:
(i) reacting a compound of formula (Ib)

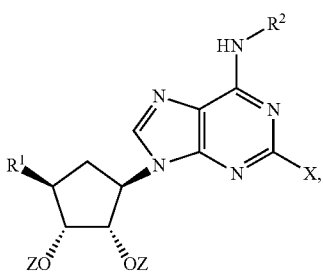

(Ib)

wherein
$R^1$, $R^2$ are as defined in claim 1;
Z is H or a protecting group; and
X is a leaving group, with a compound of formula (Ic)

H—$R^3$ (ic), wherein
$R^3$ is defined in claim 1; and
removing any protecting groups and recovering the resultant compound of formula (I), in free or pharmaceutically acceptable salt form.

9. A process for the preparation of compounds of formula (II) as defined in claim 4, or stereoisomers or pharmaceutically acceptable salts thereof, which comprises the steps of:
(i) reacting a compound of formula (IIa)

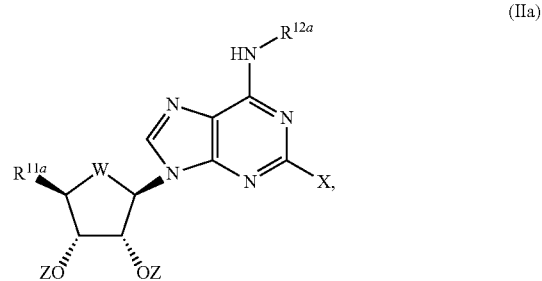

(IIa)

wherein
$R^{11a}$, W and $R^{12a}$ are as defined in claim 4;
Z is H or a protecting group; and
X is a leaving group, with a compound of formula (IIb)

(IIb)

wherein
$R^{14}$ as defined in claim 1; and
removing any protecting groups and recovering the resultant compound of formula (I), in free or pharmaceutically acceptable salt form.

10. A compound according to claim 4 in combination with an anti-inflammatory, bronchodilatory, anti-histamine or anti-tussive drug substance.

11. A pharmaceutical composition comprising as active ingredient a compound according to claim 4, together with a pharmaceutically acceptable diluent or carrier.

* * * * *

UNITED STATES PATENT AND TRADEMARK OFFICE
CERTIFICATE OF CORRECTION

| | | |
|---|---|---|
| PATENT NO. | : 8,318,750 B2 | Page 1 of 1 |
| APPLICATION NO. | : 13/218865 | |
| DATED | : November 27, 2012 | |
| INVENTOR(S) | : Robin Alec Fairhurst et al. | |

It is certified that error appears in the above-identified patent and that said Letters Patent is hereby corrected as shown below:

On the Title Page, Item (73) Assignee should read as follows:

--(73) Assignee: Novartis AG, Basel (CH)--

Signed and Sealed this
Sixth Day of May, 2014

Michelle K. Lee
*Deputy Director of the United States Patent and Trademark Office*